US012415771B2

(12) United States Patent
Knutsen et al.

(10) Patent No.: US 12,415,771 B2
(45) Date of Patent: Sep. 16, 2025

(54) COMPOUNDS FOR THE TREATMENT OF NEUROMUSCULAR DISORDERS

(71) Applicant: NMD PHARMA A/S, Aarhus N (DK)

(72) Inventors: Lars J. S. Knutsen, Essex (GB); Nicholas Kelly, Bagsværd (DK); Martin Brandhøj Skov, Aarhus C (DK); Anders Riisager, Skødstrup (DK); Neerja Saraswat, Winnipeg (CA)

(73) Assignee: NMD PHARMA A/S, Aarhus N (DK)

( * ) Notice: Subject to any disclaimer, the term of this patent is extended or adjusted under 35 U.S.C. 154(b) by 854 days.

(21) Appl. No.: 17/620,294

(22) PCT Filed: Jun. 19, 2020

(86) PCT No.: PCT/EP2020/067072
§ 371 (c)(1),
(2) Date: Dec. 17, 2021

(87) PCT Pub. No.: WO2020/254559
PCT Pub. Date: Dec. 24, 2020

(65) Prior Publication Data
US 2022/0388938 A1    Dec. 8, 2022

(30) Foreign Application Priority Data

Jun. 19, 2019 (EP) .................................... 19181270

(51) Int. Cl.
| C07C 59/70 | (2006.01) |
| A61P 21/00 | (2006.01) |
| C07C 59/68 | (2006.01) |
| C07C 59/72 | (2006.01) |
| C07C 255/54 | (2006.01) |
| C07D 277/24 | (2006.01) |

(52) U.S. Cl.
CPC ............. *C07C 59/70* (2013.01); *A61P 21/00* (2018.01); *C07C 59/68* (2013.01); *C07C 59/72* (2013.01); *C07C 255/54* (2013.01); *C07D 277/24* (2013.01); *C07C 2601/04* (2017.05)

(58) Field of Classification Search
CPC .................................................. C07C 59/70
See application file for complete search history.

(56) References Cited

U.S. PATENT DOCUMENTS

| 10,385,028 B2* | 8/2019 | Knutsen ............... C07D 213/30 |
| 10,934,244 B2 | 3/2021 | Holm Pedersen et al. |
| 11,147,788 B2* | 10/2021 | Knutsen ............... A61K 31/216 |
| 11,591,284 B2* | 2/2023 | Knutsen ............... A61P 21/00 |
| 11,730,714 B2* | 8/2023 | Pedersen ............... A61K 31/216 |
| | | 514/532 |
| 2006/0211765 A1 | 9/2006 | Pairaudeau et al. |

FOREIGN PATENT DOCUMENTS

| CL | 2021001739 A1 | 1/2022 |
| CL | 2021003374 A1 | 9/2022 |
| CL | 2021003388 A1 | 9/2022 |
| CN | 107820425 A | 3/2018 |
| JP | 2018-517760 A | 7/2018 |
| TW | 201927738 A | 7/2019 |
| WO | 2005/105727 A1 | 11/2005 |
| WO | 2006/037982 A2 | 4/2006 |
| WO | 2006/056752 A1 | 6/2006 |
| WO | 2007/039741 A1 | 4/2007 |
| WO | 2007/062678 A1 | 6/2007 |
| WO | 2007/062773 A1 | 6/2007 |
| WO | 2011/133920 A1 | 10/2011 |
| WO | 2016202341 A1 | 12/2016 |
| WO | 2019/115780 A1 | 6/2019 |
| WO | 2020/142742 A1 | 7/2020 |
| WO | 2020/254985 A1 | 12/2020 |
| WO | 2020/257487 A1 | 12/2020 |

OTHER PUBLICATIONS

Examination Report issued on Feb. 27, 2024, by the Taiwanese Patent Office in corresponding Taiwanese Patent Application No. 109120913, with English Translation (12 pgs).
Examination Report issued on Mar. 1, 2024, by the Intellectual Property of India Patent Office in corresponding Indian Patent Application No. 202117048901 (6 pgs).
First Office Action issued on Apr. 30, 2024, by China National Intellectual Property Administration in corresponding Chinese Patent Application No. 2020800445437, with English Translation (10 pgs).
Notice of Reasons for Rejection issued on Jun. 18, 2024, by the Japanese Patent Office in corresponding Japanese Patent Application No. 2021-575325, with English Translation (6 pgs).
Office Action issued Jun. 13, 2023, by the Chile Patent Office in corresponding Chilean Patent Application No. 202103318. (17 pages).
Notification of the Substantive Examination Report issued Sep. 19, 2023, by the Saudi Authority for Intellectual Property (SAIP) in corresponding Saudi Patent Application No. 521431094 and an English translation of the Notification of the Substantive Examination Report. (14 pages).
International Search Report (PCT/ISA/210) and Written Opinion (PCT/ISA/237) mailed on Aug. 21, 2020, by the European Patent Office as the International Searching Authority for International Application No. PCT/EP2020/067072.
Ammar, T., et al., "Understanding the physiology of the asymptomatic diaphragm of the M1592V hyperkalemic periodic paralysis mouse", Journal of General Physiology, 2015, 146(6), pp. 509-525.
Angelini, C., "Spectrum of metabolic myopathies", Biochimica et Biophysica Acta (BBA)—Molecular Basis of Disease, 2015, 1852(4), pp. 615-621.

(Continued)

*Primary Examiner* — Golam M Shameem
(74) *Attorney, Agent, or Firm* — BUCHANAN INGERSOLL & ROONEY PC

(57) ABSTRACT

The present disclosure relates to compounds suitable for treating, ameliorating and/or preventing neuromuscular disorders, including the reversal of drug-induced neuromuscular blockade. The compounds as defined herein can inhibit the ClC-1 ion channel.

19 Claims, 2 Drawing Sheets

(56) References Cited

OTHER PUBLICATIONS

Aromataris, E.C., "Pharmacology of the ClC-1 chloride channel (Doctoral dissertation)", 2009, see https://digital.library.adelaide.edu.au/dspace/bitstream/2440/58973/8/02whole.pdf (179 pages).
Bansagi, B., et al., "Genetic heterogeneity of motor neuropathies", Neurology 88, 2017, No. 13, pp. 1226-1234.
Dowling, J.J., et al., "Myotubular myopathy and the neuromuscular junction: a novel therapeutic approach from mouse models", Disease models & mechanisms, 2012, 5(6), pp. 852-859.
Fletcher, S.N., et al., "Persistent neuromuscular and neurophysiologic abnormalities in long-term survivors of prolonged critical illness", Critical care medicine, 2003, 31(4), pp. 1012-1016.
Garcia, C.C., et al. "Acetylcholinesterase deficiency contributes to neuromuscular junction dysfunction in type 1 diabetic neuropathy", American Journal of Physiology-Endocrinology and Metabolism, 2012, 303(4), pp. E551-E561.
Gilhus, N.E., et al., "Myasthenia gravis: a review of available treatment approaches", Autoimmune diseases, 2011 (7 pages).
Hwee, D.T., et al., "The small-molecule fast skeletal troponin activator, CK-2127107, improves exercise tolerance in a rat model of heart failure", Journal of Pharmacology and Experimental Therapeutics, 2015, 353(1), pp. 159-168.
Kawamura, Y., et al., "Efficacy of a half dose of oral pyridostigmine in the treatment of chronic fatigue syndrome: three case reports", Pathophysiology, 2003, 9(3), pp. 189-194.
Kwieciński, H., et al., "Drug-induced myotonia in human intercostal muscle", Muscle Nerve, Jun. 1988, 11(6), pp. 576-581.
Kwieciński, H., et al., "Membrane currents in human intercostal muscle at varied extracellular potassium", Muscle Nerve, Jul.-Aug. 1984, 7(6), pp. 465-469.
Liantonio, A., et al., "Molecular requisites for drug binding to muscle CLC-1 and renal CLC-K channel revealed by the use of phenoxy-alkyl derivatives of 2-(p-chlorophenoxy) propionic acid", Molecular pharmacology, 2002, 62(2), pp. 265-271.
Liantonio, A., et al., "Investigations of pharmacologic properties of the renal CLC-K1 chloride channel co-expressed with barttin by the use of 2-(p-chlorophenoxy) propionic acid derivatives and other structurally unrelated chloride channels blockers", Journal of the American Society of Nephrology, 2012, 15(1), pp. 13-20.
Liantonio, A., et al., "Structural requisites of 2-(p-chlorophenoxy) propionic acid analogues for activity on native rat skeletal muscle chloride conductance and on heterologously expressed CLC-1", British journal of pharmacology, 2003, 139(7), pp. 1255-1264.
Mehndiratta, MM, et al., "Acetylcholinesterase inhibitor treatment for myasthenia gravis", Cochrane Database Syst Rev., 10, 2014 (19 pages).
Murphy, G.S. and Brull, S.J., "Residual neuromuscular block: lessons unlearned. Part I: definitions, incidence, and adverse physiologic effects of residual neuromuscular block", Anesthesia & Analgesia, 2010, 111(1), pp. 120-128.
Pedersen, TH, et al., "Increased excitability of acidified skeletal muscle: role of chloride conductance", J Gen Physiol, Feb. 2005, 125(2), pp. 237-246.
Pedersen, TH, et al., "Role of physiological ClC-1 Cl-ion channel regulation for the excitability and function of working skeletal muscle", Journal of General Physiology, 2016, 147(4), pp. 291-308.
Pusch, M., et al., "Pharmacological characterization of chloride channels belonging to the ClC family by the use of chiral clofibric acid derivatives", Molecular Pharmacology, 2000, 58(3), pp. 498-507.
Riisager, A., et al., "Determination of cable parameters in skeletal muscle fibres during repetitive firing of action potentials", The Journal of physiology, 2014, 592(20), pp. 4417-4429.
Silva, A., et al., "Antivenom for snake venom-induced neuromuscular paralysis", The Cochrane Database of Systematic Reviews, 2017, 3, Art. No. CD0112604 (12 pages).
Srivastava, A. and Hunter, J.M., "Reversal of neuromuscular block", British journal of anaesthesia, 2009, 103(1), pp. 115-129.
Stevic, Z., et al., "Myasthenic symptoms in a patient with Kennedy's disease", Acta Neurologica Belgica, 2014, 114(1), pp. 71-73.
Titulaer, MJ., et al., "Lambert-Eaton myasthenic syndrome: from clinical characteristics to therapeutic strategies", Lancet Neurol., 2011, 10, pp. 1098-1107.
Trojan, D.A., et al., "Electrophysiology and electrodiagnosis of the post-polio motor unit" Orthopedics, 1991, 14(12), pp. 1353-1361.
Wood, SJ, et al., "Safety factor at the neuromuscular junction", Prog. Neurobiol., 2001, 64, pp. 393-429.
Wu, F., et al., "Bumetanide prevents transient decreases in muscle force in murine hypokalemic periodic paralysis", Neurology, 2013, 80(12), pp. 1110-1116.

* cited by examiner

COMPOUNDS FOR THE TREATMENT OF NEUROMUSCULAR DISORDERS

TECHNICAL FIELD

The present disclosure relates to compounds and their use in treating, ameliorating and/or preventing neuromuscular disorders, including the reversal of drug-induced neuromuscular blockade. The compounds as defined herein can inhibit the CIC-1 ion channel. The disclosure further relates to methods of treating, preventing and/or ameliorating neuromuscular disorders, by administering said composition to a person in need thereof.

BACKGROUND

Walking, breathing, and eye movement are examples of essential everyday physiological activities that are powered by the contractile activity of skeletal muscle. Skeletal muscles are inherently in a resting state and contractile activity occurs exclusively in response to commands from the central nervous system (CNS). Such neuronal commands take the form of action potentials that travel from the brain to the muscle fibres in several steps. The neuromuscular junction (NMJ) is a highly specialized membrane area on muscle fibres where motor neurons come into close contact with the muscle fibres, and it is at the NMJ where neuronal action potentials are transmitted to muscular action potentials in a one-to-one fashion via synaptic transmission.

Neuromuscular transmission refers to the sequence of cellular events at the NMJ whereby an action potential in the lower motor neuron is transmitted to a corresponding action potential in a muscle fibre (Wood S J, Slater C R. Safety factor at the neuromuscular junction. *Prog. Neurobiol.* 2001, 64, 393-429). When a neuronal action potential arrives at the pre-synaptic terminal it triggers influx of $Ca^{2+}$ through voltage gated P/Q-type $Ca^{2+}$ channels in the nerve terminal membrane. This influx causes a rise in cytosolic $Ca^{2+}$ in the nerve terminal that triggers exocytosis of acetylcholine (ACh). Released ACh next diffuses across the synaptic cleft to activate nicotinic ACh receptors in the post-synaptic, muscle fibre membrane. Upon activation, ACh receptors convey an excitatory current flow of $Na^+$ into the muscle fibre, which results in a local depolarization of the muscle fibre at the NMJ that is known as the endplate potential (EPP). If the EPP is sufficiently large, voltage gated $Na^+$ channels in the muscle fibre will activate and an action potential in the muscle fibre will ensue. This action potential then propagates from the NMJ throughout the muscle fibre and triggers release of $Ca^{2+}$ release from the sarcoplasmic reticulum. The released $Ca^{2+}$ activates the contractile proteins within the muscle fibres, thus resulting in contraction of the fibre.

Failure of neuromuscular transmission can arise from both pre-synaptic dysfunction [Lambert Eaton syndrome (Titulaer M J, Lang B, Verschuuren J J. Lambert-Eaton myasthenic syndrome: from clinical characteristics to therapeutic strategies. *Lancet Neurol.* 2011, 10, 1098-107), amyotrophic lateral sclerosis (Killian J M, Wilfong A A, Burnett L, Appel S H, Boland D. Decremental motor responses to repetitive nerve stimulation in ALS. *Muscle Nerve,* 1994, 17, 747-754), spinal muscular atrophy (Wadman R I, Vrancken A F, van den Berg L H, van der Pol W L. Dysfunction of the neuromuscular junction in spinal muscular atrophy types 2 and 3. *Neurology,* 2012, 79, 2050-2055) and as a result of post-synaptic dysfunction as occurs in myasthenia gravis (Le Panse R, Berrih-Aknin S. Autoimmune myasthenia gravis: autoantibody mechanisms and new developments on immune regulation. *Curr Opin Neurol.,* 2013, 26, 569-576)]. Failure to excite and/or propagate action potentials in muscle can also arise from reduced muscle excitability such as in critical illness myopathy (CIM) (Latronico, N., Bolton, C. F. Critical illness polyneuropathy and myopathy: a major cause of muscle weakness and paralysis. *Lancet Neurol.* 2011, 10, 931-941). In Lambert Eaton syndrome, an autoimmune attack against the pre-synaptic P/Q-type $Ca^{2+}$ channels results in markedly reduced $Ca^{2+}$ influx into the nerve terminal during the pre-synaptic action potential and consequently a reduced release of ACh into the synaptic cleft. In myasthenia gravis, the most common finding is an autoimmune attack on the post-synaptic membrane either against the nicotinic ACh receptors or the musk-receptor in the muscle fibre membrane. Congenital forms of myasthenia are also known. Common to disorders with neuromuscular transmission failure (Lambert Eaton syndrome, amyotrophic lateral sclerosis, spinal muscular atrophy and myasthenia gravis) is that the current flow generated by ACh receptor activation is markedly reduced, and EPPs therefore become insufficient to trigger muscle fibre action potentials.

Neuromuscular blocking agents also reduce EPP by antagonizing ACh receptors. In CIM with reduced muscle excitability, the EPP may be of normal amplitude but they are still insufficient to trigger muscle fibre action potentials because the membrane potential threshold for action potential excitation has become more depolarized because of loss of function of voltage gated $Na^+$ channels in the muscle fibres.

While ACh release (Lambert Eaton, amyotrophic lateral sclerosis, spinal muscular atrophy), ACh receptor function (myasthenia gravis, neuromuscular blockade) and function of voltage gated $Na^+$ channels (CIM) are essential components in the synaptic transmission at NMJ, the magnitude of the EPP is also affected by inhibitory currents flowing in the NMJ region of muscle fibres. These currents tend to outbalance excitatory current through ACh receptors and, expectedly, they thereby tend to reduce EPP amplitude. The most important ion channel for carrying such inhibitory membrane currents in muscle fibres is the muscle-specific CIC-1 $Cl^-$ ion channel (Kwieciński H, Lehmann-Horn F, Rüdel R. Membrane currents in human intercostal muscle at varied extracellular potassium. *Muscle Nerve.* 1984, 7, 465-469; Kwieciński H, Lehmann-Horn F, Rüdel R. Drug-induced myotonia in human intercostal muscle. *Muscle Nerve.* 1988, 11, 576-581; Pedersen, T. H., F. de Paoli, and O. B. Nielsen. Increased excitability of acidified skeletal muscle: role of chloride conductance. *J. Gen. Physiol.,* 2005, 125, 237-246).

ACh esterase (AChE) inhibitors are traditionally used in the treatment of myasthenia gravis. This treatment leads to improvement in most patients but it is associated with side effects, some of which are serious (Mehndiratta M M, Pandey S, Kuntzer T. Acetylcholinesterase inhibitor treatment for myasthenia gravis. *Cochrane Database Syst Rev.* 2014, October 13; 10). Because ACh is an import neurotransmitter in the autonomic nervous system, delaying its breakdown can lead to gastric discomfort, diarrhoea, salivation and muscle cramping. Overdosing is a serious concern as it can lead to muscle paralysis and respiratory failure, a situation commonly referred to as cholinergic crisis. Despite the serious side effects of AChE inhibitors, these drugs are today the treatment of choice for a number of disorders involving neuromuscular impairment. In patients where pyridostigmine (a parasympathomimetic and a reversible AChE inhibitor) is insufficient, corticosteroid treatment (prednisone) and immunosuppressive treatment (azathioprine) is used. Plasma exchange can be used to obtain a fast but transient improvement.

Unfortunately, all of the currently employed drug regimens for treatment of myasthenia gravis are associated with deleterious long-term consequences (Howard, J. F. Jr. Adverse drug effects on neuromuscular transmission. *Semin Neurol.* 1990, 10, 89-102) despite research to identify new treatments (Gilhus, N. E. New England Journal of Medicine, 2016, 375, 2570-2581).

The ClC-1 ion channel (Pedersen, T. H., Riisager, A., Vincenzo de Paoli, F., Chen, T-Y, Nielsen, O. B. Role of physiological ClC-1 Cl⁻ ion channel regulation for the excitability and function of working skeletal muscle. *J. Gen. Physiol.* 2016, 147, 291-308) is emerging as a target for potential drugs, although its potential has been largely unrealised.

There have been publications of various ligands at the ClC-1 ion channels, see for example: Liantonio, A., Accardi, A., Carbonara, G., Fracchiolla, G., Loiodice, F., Tortorella P, Traverso S, Guida P, Pierno S, De Luca A, Camerino D C, Pusch M. Molecular requisites for drug binding to muscle ClC-1 and renal ClC-K channel revealed by the use of phenoxy-alkyl derivatives of 2-(p-chlorophenoxy)propionic acid. *Mol. Pharmacol.*, 2002, 62, 265-271 and Liantonio, A. et al., Structural requisites of 2-(p-chlorophenoxy)propionic acid analogues for activity on native rat skeletal muscle chloride conductance and on heterologously expressed ClC-1. *Br. J. Phamacol.*, 2003, 129, 1255-1264.

In the article Liantonio, A., Pusch, M., Picollo, A., Guida, P., De Luca, A., Pierno, S., Fracchiolla, G., Loiodice, F., Tortorella, P., Conte-Camerino, D. Investigations of pharmacologic properties of the renal ClC-K1 chloride channel co-expressed with barttin by the use of 2-(p-chlorophenoxy) propionic acid derivatives and other structurally unrelated chloride hannels blockers. *Journal of the American Society of Nephrology*, 2004, 15, 13-20, ligands for ClC-K1 chloride channels were disclosed.

In the publication Pusch, M., Liantonio, A., Bertorello, L., Accardi, A., De Luca, A., Pierno, S., Tortorella, V., Conte-Camerino, D. Pharmacological characterization of chloride channels belonging to the ClC family by the use of chiral clofibric acid derivatives. *Molecular Pharmacology*, 2000, 58, 498-507, the authors disclosed effects of enantiomers of 2-(p-chlorophenoxy)propionic acid on ClC-1 and ClC-2 ion channels.

In the article Ferorelli, S., Loiodice, F., Tortorella, V., Conte-Camerino, D., De Luca, A. M. Carboxylic acids and skeletal muscle chloride channel conductance: effects on the biological activity induced by the introduction of methyl groups on the aromatic ring of chiral α-(4-chloro-phenoxy) alkanoic acids, *Farmaco*, 2001, 56, 239-246, derivatives of (4-chloro-phenoxy)alkanoic acids were tested for skeletal muscle chloride conductance.

Edoardo Aromataris investigated 4-chlorophenoxyisobutyric acid derivatives in his PhD thesis "Pharmacology of the ClC-1 Chloride Channel"; see: https://digital.library.adelaide.edu.au/dspace/bitstream/2440/58973/8/02whole.pdf In WO 2016/202341, Pedersen et al. reported a series of phenoxypropionic acids and related compounds that appear to block the ClC-1 ion channel for use in treating, ameliorating and/or preventing neuromuscular disorders. However, they possess alternative structural features to those in the current disclosure.

SUMMARY

The present disclosure comprises a series of compounds that can alleviate disorders of the neuromuscular junction through inhibition of ClC-1 channels.

It has been found that a compounds that inhibit ClC-1 ion channels are capable of restoring neuromuscular transmission, as evidenced by the data generated by investigation of the compound set in biological models described herein. These compounds thus constitute a group of potential drugs that can be used to treat and/or ameliorate muscle weakness and/or muscle fatigue in neuromuscular junction disorders caused by disease or by neuromuscular blocking agents.

The present disclosure is directed to ClC-1 ion channel inhibitors with application in the treatment of a range of conditions, such as reversal of block, ALS, and myasthenic conditions, in which muscle activation by the nervous system is compromised and symptoms of weakness and fatigue are prominent.

In one aspect, the disclosure concerns a compound of Formula (I):

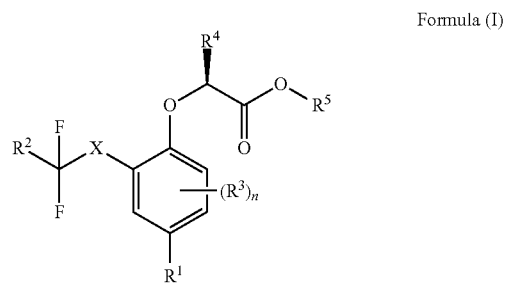

Formula (I)

wherein:

$R^1$ is selected from the group consisting of $C_{1-2}$ alkyl, $C_2$ alkenyl, $C_2$ alkynyl, CN, $CF_3$, $NO_2$, F, Cl, Br, and I;

$R^2$ is selected from the group consisting of $C_{1-5}$ alkyl optionally be substituted with one or more, identical or different, substituents $R^6$, $C_{2-5}$ alkenyl optionally be substituted with one or more, identical or different, substituents $R^6$, $C_{2-5}$ alkynyl optionally be substituted with one or more, identical or different, substituents $R^6$, $C_{3-5}$ cycloalkyl optionally substituted with one or more, identical or different, substituents $R^6$, phenyl optionally substituted with one or more, identical or different, substituents $R^9$, and 5-6 membered aromatic heterocycle optionally substituted with one or more, identical or different, substituents $R^7$;

$R^3$ is selected from the group consisting of deuterium, Cl and F;

$R^4$ is selected from the group consisting of H, deuterium, $C_{1-5}$ alkyl, $C_{2-5}$ alkenyl, $C_{2-5}$ alkynyl, and $C_{3-5}$ cycloalkyl, each of which may be optionally substituted with one or more, identical or different, substituents $R^7$;

$R^5$ is selected from the group consisting of H, $C_{1-5}$ alkyl optionally substituted with one or more, identical or different, substituents $R^8$, $C_{2-5}$ alkenyl optionally substituted with one or more, identical or different, substituents $R^8$, $C_{2-5}$ alkynyl optionally substituted with one or more, identical or different, substituents $R^8$, $C_{3-6}$ cycloalkyl optionally substituted with one or more, identical or different, substituents $R^8$, phenyl optionally substituted with one or more, identical or different, substituents $R^9$, and benzyl optionally substituted with one or more, identical or different, substituents $R^9$;

$R^6$ is independently selected from the group consisting of deuterium, F, —CN, —O—$C_{1-5}$ alkyl, —O—$C_{3-5}$ cycloalkyl, —S—$C_{1-5}$ alkyl, and —S—$C_{3-5}$ cycloalkyl, wherein the —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;

$R^7$ is independently selected from the group consisting deuterium, F, Cl, —CN, $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, wherein the $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;

$R^8$ is independently selected from the group consisting of deuterium and F;

$R^9$ is independently selected from the group consisting of deuterium, methoxy, nitro, cyano, Cl, Br, I, and F;

X is a bond or selected from the group consisting of —O—, —S—, —$CH_2$—, —$CHR^6$—, and —$C(R^6)_2$—; and n is an integer 0, 1, 2, or 3;

or a pharmaceutically acceptable salt, hydrate, polymorph, tautomer, or solvate thereof.

In another aspect, the disclosure concerns a compound as defined herein for use in treating, ameliorating and/or preventing a neuromuscular disorder, and/or for use in reversing and/or ameliorating a neuromuscular blockade. In yet another aspect, the disclosure concerns a composition comprising a compound as defined herein.

DEFINITIONS

Figure 1:
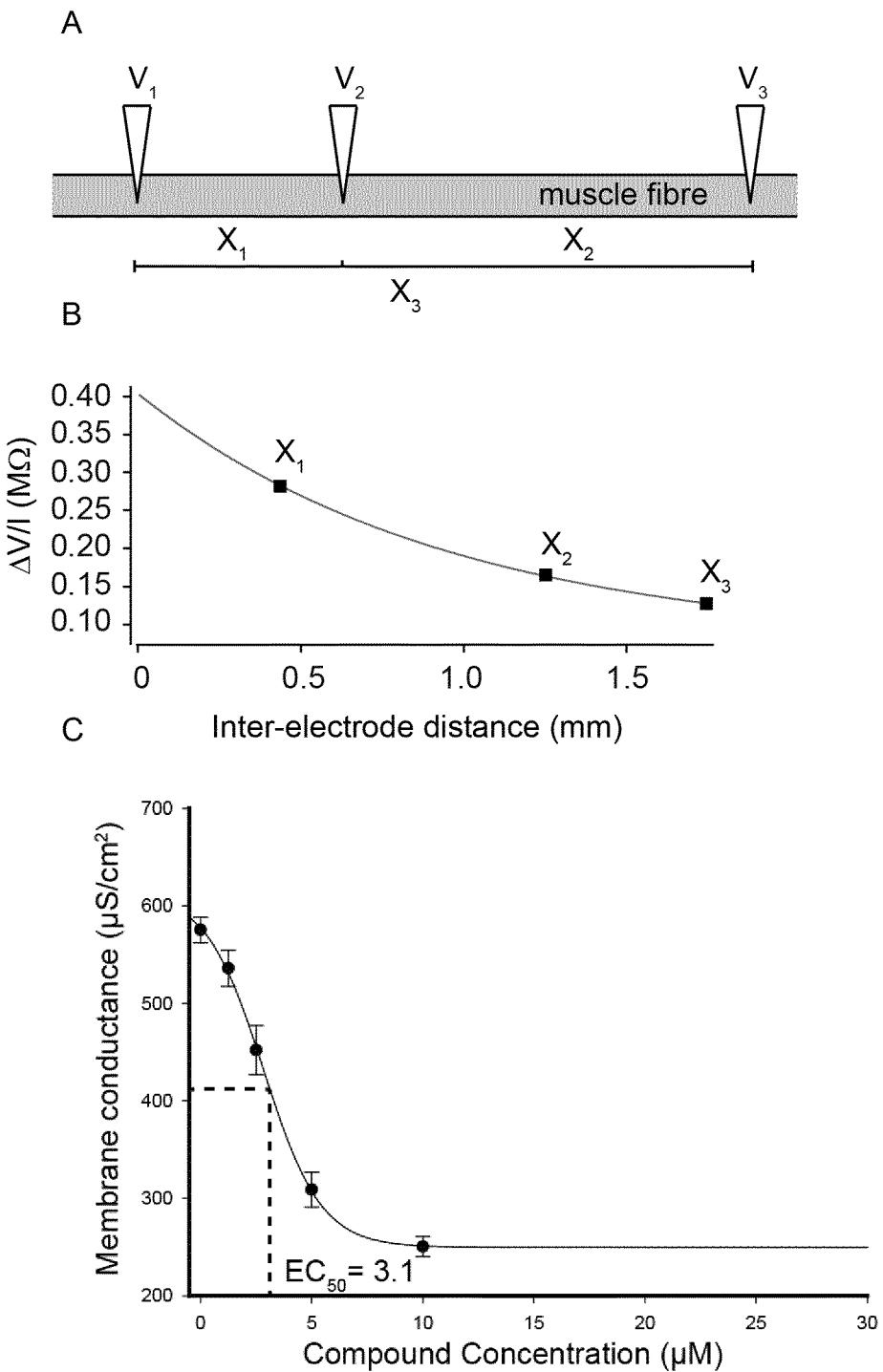
FIG. 1. Panel A shows a schematic representation of the positioning of the three microelectrodes ($V_1$, $V_2$ and $V_3$) when inserted in a single skeletal muscle fibre for $G_m$ determination. Please note that the drawing illustrates only the impaled fibre although it is part of an intact muscle that contains many such fibres. All electrodes recorded the membrane potential of the fibre and the two peripheral electrodes were used to inject current (−30 nA, 50 ms). The electrodes were inserted with known inter-electrode distances ($X_1$, $X_2$ and $X_3$). After insertion, current was passed first via the $V_1$ electrode and then via the $V_3$ electrode. The resulting deflections in the membrane voltage were measured by the other electrodes. The steady state deflections in membrane potential were measured and divided by the magnitude of the injected current (−30 nA) to obtain transfer resistances. These were next plotted against inter-electrode distances, and fitted to an exponential function (Panel B), from which $G_m$ could be calculated using linear cable theory. The approach described in panel A and B, was repeated for several muscle fibres in the muscle during exposure at increasing concentrations of compound A-3, with approx. 10 fibres at each concentration. Average $G_m$ at each concentration was plotted as a function of compound concentration in panel C, and fitted to a 4-parameter sigmoidal function from which the $EC_{50}$ value for the compound was obtained (dashed line)

The terms "$C_{1-2}$ alkyl", "$C_{1-3}$ alkyl" and "$C_{1-5}$ alkyl" refers to a branched or unbranched alkyl group having from one to two, one to three or one to five carbon atoms respectively, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl and pent-3-yl.

The term "$C_2$ alkenyl" and "$C_{2-5}$ alkenyl" refers to a branched or unbranched alkenyl group having two or from two to five carbon atoms respectively, two of which are connected by a double bond, including but not limited to ethenyl, propenyl, isopropenyl, butenyl, isobutenyl, pentenyl and isopentenyl.

The term "$C_2$ alkynyl" and "$C_{2-5}$ alkynyl" refers to a branched or unbranched alkynyl group having two or from two to five carbon atoms respectively, two of which are connected by a triple bond, including but not limited to ethynyl, prop-1-ynyl, prop-2-ynyl, but-1-ynyl, but-2-ynyl, but-3-ynyl, buta-1,3-diynyl, pent-1-ynyl, pent-2-ynyl, pent-3-ynyl, pent-4-ynyl, penta-2,4-diynyl and penta-1,3-diynyl.

The term "$C_{3-5}$ cycloalkyl" and "$C_{3-6}$ cycloalkyl" refers to a group having three to five or three to six carbon atoms respectively including a monocyclic or bicyclic carbocycle, including but not limited to cyclopropyl, cyclobutyl, cyclopentyl and cyclohexyl. Examples of $C_{3-5}$ cycloalkyl wherein one —$CH_2$— is replaced by —O— are oxiran-2-yl, oxetan-2-yl, oxetan-3-yl, oxolan-2-yl and oxolan-3-yl.

The term "5-6 membered aromatic heterocycle" refers to a group having five to six carbon atoms wherein between 1 and 3 carbon atoms in the ring have been replaced with a heteroatom selected from the group comprising nitrogen, sulphur and oxygen. Binding to the heterocycle may be at the position of the heteroatom or via a carbon atom of the heterocycle.

5-membered aromatic heterocycles include but are not limited to furan, thiophene, pyrrole, imidazole, pyrazole, oxazole, thiazole, isoxazole, isothiazole, 1,2,3-triazole, 1,2,4-triazole, 1,2,5-oxadiazole, 1,2,3-oxadiazole, 1,2,4-oxadiazole, 1,3,4-oxadiazole, 1,2,5-thiadiazole, 1,2,3-thiadiazole, 1,2,4-thiadiazole and 1,3,4-thiadiazole. 6-membered aromatic heterocycles include but are not limited to pyridine, pyrazine, pyrimidine and pyridazine.

The term "half-life" as used herein is the time it takes for the compound to lose one-half of its pharmacologic activity. The term "plasma half-life" is the time that it takes the compound to lose one-half of its pharmacologic activity in the blood plasma.

The term "treatment" refers to the combating of a disease or disorder. "Treatment" or "treating," as used herein, includes any desirable effect on the symptoms or pathology of a disease or condition as described herein, and may include even minimal changes or improvements in one or more measurable markers of the disease or condition being treated. "Treatment" or "treating" does not necessarily indicate complete eradication or cure of the disease or condition, or associated symptoms thereof. In some embodiments, the term "treatment" encompasses amelioration and prevention.

The term "amelioration" refers to moderation in the severity of the symptoms of a disease or condition. Improvement in a patient's condition, or the activity of making an effort to correct, or at least make more acceptable, conditions that are difficult to endure related to patient's conditions is considered "ameliorative" treatment.

The term "prevent" or "preventing" refers to precluding, averting, obviating, forestalling, stopping, or hindering something from happening, especially by advance action.

The term "reversal" or "reversing" refers to the ability of a compound to restore nerve-stimulated force in skeletal muscle exposed either ex vivo or in vivo to a non-depolarizing neuromuscular blocking agent or another pharmaceutical that is able to depress neuromuscular transmission The term "non-depolarizing blockers" refers to pharmaceutical agents that antagonize the activation of acetylcholine receptors at the post-synaptic muscle fibre membrane by blocking the acetylcholine binding site on the receptor. These agents are used to block neuromuscular transmission and induce muscle paralysis in connection with surgery.

The term "ester hydrolysing reagent" refers to a chemical reagent which is capable of converting an ester functional group to a carboxylic acid with elimination of the alcohol moiety of the original ester, including but not limited to acid, base, a fluoride source, $PBr_3$, $PCl_3$ and lipase enzymes.

The term "recovery of force in muscle with neuromuscular dysfunction" refers to the ability of a compound to recover contractile force in nerve-stimulated healthy rat muscle after exposure to submaximal concentration of (115 nM) tubocurarine for 90 mins. Recovery of force is quantified as the percentage of the force prior to tubocurarine that is recovered by the compound.

The term "total membrane conductance (Gm)" is the electrophysiological measure of the ability of ions to cross the muscle fibre surface membrane. It reflects the function of ion channels that are active in resting muscle fibres of which ClC-1 is known to contribute around 80% in most animal species.

DETAILED DESCRIPTION

Compounds

It is within the scope of the present disclosure to provide a compound for use in treating, ameliorating and/or preventing neuromuscular disorders that reduce neuromuscular function. As disclosed herein, inhibition of ClC-1 improves or restores neuromuscular function. The compounds of the present disclosure comprise compounds capable of inhibiting the ClC-1 channel thereby improving or restoring neuromuscular function. In one embodiment, the $EC_{50}$ of the compound is <50 µM, such as <40 µM, such as <30 µM, such as <20 µM, such as <15 µM, such as <10 µM, and such as <5 µM. In one embodiment, the recovery of force in muscles with neuromuscular dysfunction is >5%, for example >10%, for example >15%, for example >20%, for example >25%, for example >30% and for example >35%. The recovery of force in muscle can be determined as the amount of force restored in muscle as a percentage of the initial force after a muscle has been exposure to a compound of the present disclosure, for example as described in Example 23.

In one aspect, the disclosure concerns a compound of Formula (I):

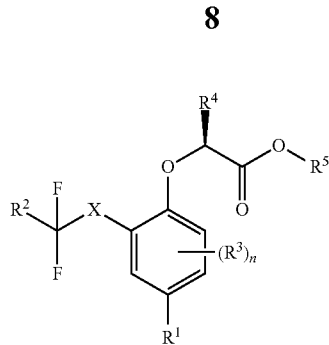

Formula (I)

wherein:
  $R^1$ is selected from the group consisting of $C_{1-2}$ alkyl, $C_2$ alkenyl, $C_2$ alkynyl, CN, $CF_3$, $NO_2$, F, Cl, Br, and I;
  $R^2$ is selected from the group consisting of $C_{1-5}$ alkyl optionally be substituted with one or more, identical or different, substituents $R^6$, $C_{2-5}$ alkenyl optionally be substituted with one or more, identical or different, substituents $R^6$, $C_{2-5}$ alkynyl optionally be substituted with one or more, identical or different, substituents $R^6$, $C_{3-5}$ cycloalkyl optionally substituted with one or more, identical or different, substituents $R^6$, phenyl optionally substituted with one or more, identical or different, substituents $R^9$, and 5-6 membered aromatic heterocycle optionally substituted with one or more, identical or different, substituents $R^7$;
  $R^3$ is selected from the group consisting of deuterium, Cl and F;
  $R^4$ is selected from the group consisting of H, deuterium, $C_{1-5}$ alkyl, $C_{2-5}$ alkenyl, $C_{2-5}$ alkynyl, and $C_{3-5}$ cycloalkyl, each of which may be optionally substituted with one or more, identical or different, substituents $R^7$;
  $R^5$ is selected from the group consisting of H, $C_{1-5}$ alkyl optionally substituted with one or more, identical or different, substituents $R^8$, $C_{2-5}$ alkenyl optionally substituted with one or more, identical or different, substituents $R^8$, $C_{2-5}$ alkynyl optionally substituted with one or more, identical or different, substituents $R^8$, $C_{3-6}$ cycloalkyl optionally substituted with one or more, identical or different, substituents phenyl optionally substituted with one or more, identical or different, substituents $R^9$, and benzyl optionally substituted with one or more, identical or different, substituents $R^9$;
  $R^6$ is independently selected from the group consisting of deuterium, F, —CN, —O—$C_{1-5}$ alkyl, —O—$C_{3-5}$ cycloalkyl, —S—$C_{1-5}$ alkyl, and —S—$C_{3-5}$ cycloalkyl, wherein the —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;
  $R^7$ is independently selected from the group consisting deuterium, F, Cl, —CN, $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, wherein the $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;
  $R^8$ is independently selected from the group consisting of deuterium and F;

$R^9$ is independently selected from the group consisting of deuterium, methoxy, nitro, cyano, Cl, Br, I, and F;

X is a bond or selected from the group consisting of —O—, —S—, —CH$_2$—, —CHR$^6$—, and —C(R$^6$)$_2$—; and n is an integer 0, 1, 2, or 3;

or a pharmaceutically acceptable salt, hydrate, polymorph, tautomer, or solvate thereof.

In one aspect, the disclosure concerns a compound of Formula (I):

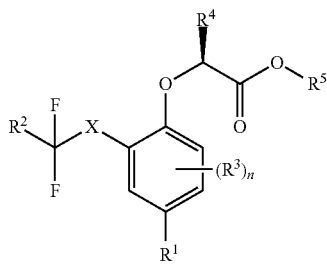

Formula (I)

wherein:
- $R^1$ is selected from the group consisting of F, Cl, Br, and I;
- $R^2$ is selected from the group consisting of C$_{1-5}$ alkyl optionally be substituted with one or more, identical or different, substituents $R^6$, C$_{2-5}$ alkenyl optionally be substituted with one or more, identical or different, substituents $R^6$, C$_{2-5}$ alkynyl optionally be substituted with one or more, identical or different, substituents $R^6$, C$_{3-5}$ cycloalkyl optionally substituted with one or more, identical or different, substituents $R^6$, phenyl optionally substituted with one or more, identical or different, substituents $R^9$, and 5-6 membered aromatic heterocycle optionally substituted with one or more, identical or different, substituents $R^7$;
- $R^3$ is selected from the group consisting of deuterium and F;
- $R^4$ is selected from the group consisting of H, deuterium, C$_{1-5}$ alkyl, C$_{2-5}$ alkenyl, C$_{2-5}$ alkynyl, and C$_{3-5}$ cycloalkyl, each of which may be optionally substituted with one or more, identical or different, substituents $R^7$;
- $R^5$ is selected from the group consisting of H, C$_{1-5}$ alkyl optionally substituted with one or more, identical or different, substituents $R^8$, C$_{2-5}$ alkenyl optionally substituted with one or more, identical or different, substituents $R^8$, C$_{2-5}$ alkynyl optionally substituted with one or more, identical or different, substituents $R^8$, C$_{3-6}$ cycloalkyl optionally substituted with one or more, identical or different, substituents $R^8$, phenyl optionally substituted with one or more, identical or different, substituents $R^9$, and benzyl optionally substituted with one or more, identical or different, substituents $R^9$;
- $R^6$ is independently selected from the group consisting of —O—C$_{1-5}$ alkyl, —O—C$_{3-5}$ cycloalkyl, —S—C$_{1-5}$ alkyl, and —S—C$_{3-5}$ cycloalkyl, each of which may optionally be substituted with one or more, identical or different, substituents $R^8$, deuterium, F and —CN;
- $R^7$ is independently selected from the group consisting C$_{3-5}$ cycloalkyl, —O—C$_{1-5}$ alkyl, —O—C$_{3-5}$ cycloalkyl, —S—C$_{1-5}$ alkyl, and —S—C$_{3-5}$ cycloalkyl, each of which may optionally be substituted with one or more, identical or different, substituents $R^8$, of deuterium, F and —CN;
- $R^8$ is independently selected from the group consisting of deuterium and F;
- $R^9$ is independently selected from the group consisting of deuterium, methoxy, nitro, cyano, Cl, Br, I, and F;

X is a bond or selected from the group consisting of —O—, —S—, —CH$_2$—, —CHR$^6$—, and —C(R$^6$)$_2$—; and n is an integer 0, 1, 2, or 3;

or a pharmaceutically acceptable salt, hydrate, polymorph, tautomer, or solvate thereof.

In one embodiment, $R^1$ is C$_{1-2}$ alkyl. In one embodiment, $R^1$ is C$_2$ alkenyl. In one embodiment, $R^1$ is C$_2$ alkynyl. In one embodiment, $R^1$ is CN. In one embodiment, $R^1$ is CF$_3$. In one embodiment, $R^1$ is NO$_2$. In one embodiment, $R^1$ is Cl or Br. In one embodiment, $R^1$ is C$_1$. In one embodiment, $R^1$ is Br.

In one embodiment, $R^2$ is C$_{1-5}$ alkyl optionally substituted with one or more, identical or different, substituents $R^6$. In one embodiment, $R^2$ is selected from the group consisting of methyl, ethyl, n-propyl and isopropyl. In one embodiment, $R^2$ is selected from the group consisting of methyl, ethyl, n-propyl and isopropyl wherein the methyl, ethyl, n-propyl or isopropyl group is substituted with one or more, identical or different, substituents $R^6$. In one embodiment, $R^2$ is C$_{2-5}$ alkenyl optionally substituted with one or more, identical or different, substituents $R^6$. In one embodiment, $R^2$ is C$_{2-5}$ alkynyl optionally substituted with one or more, identical or different, substituents $R^6$. In one embodiment, $R^2$ is C$_{3-5}$ cycloalkyl optionally substituted with one or more, identical or different, substituents $R^6$. In one embodiment, $R^2$ is phenyl optionally substituted with one or more, identical or different, substituents $R^9$. In one embodiment, $R^2$ is 5-6 membered aromatic heterocycle optionally substituted with one or more, identical or different, substituents $R^7$.

In one embodiment, $R^3$ is deuterium. In one embodiment, $R^3$ is C$_1$. In one embodiment, $R^3$ is F.

In one embodiment, $R^4$ is C$_{1-5}$ alkyl optionally substituted with one or more, identical or different, substituents $R^7$. In one embodiment, $R^4$ is selected from the group consisting of methyl, ethyl, n-propyl and isopropyl. In one embodiment, $R^4$ is selected from the group consisting of methyl, ethyl, n-propyl and isopropyl wherein the methyl, ethyl, n-propyl or isopropyl group is substituted with one or more, identical or different, substituents $R^7$. In one embodiment, $R^4$ is Me. In one embodiment, $R^4$ is —CH$_2$F. In one embodiment, $R^4$ is —CH$_2$—O—C$_{1-5}$ alkyl optionally substituted with one or more, identical or different, substituents $R^7$. In one embodiment, $R^4$ is —CH$_2$—S—C$_{1-5}$ alkyl optionally substituted with one or more, identical or different, substituents $R^7$. In one embodiment, $R^4$ is C$_{2-5}$ alkenyl optionally be substituted with one or more, identical or different, substituents $R^7$. In one embodiment, $R^4$ is C$_{2-5}$ alkynyl optionally be substituted with one or more, identical or different, substituents $R^7$. In one embodiment, $R^4$ is —CH$_2$—C$_{2-4}$ alkynyl optionally substituted with one or more, identical or different, substituents $R^7$. In one embodiment, $R^4$ is C$_{3-5}$ cycloalkyl optionally substituted with one or more, identical or different, substituents $R^7$. In one embodiment, $R^4$ is H. When $R^4$ is H, the carbon to which $R^4$ is bound is not a stereogenic centre.

In one embodiment, $R^5$ is H. In one embodiment, $R^5$ is C$_{1-5}$ alkyl optionally substituted with one or more, identical or different, substituents $R^8$. In one embodiment, $R^5$ is C$_{3-6}$ cycloalkyl optionally substituted with one or more, identical or different, substituents $R^8$. In one embodiment, $R^5$ is phenyl optionally substituted with one or more, identical or different, substituents $R^9$. In one embodiment, $R^5$ is benzyl optionally substituted with one or more, identical or different, substituents $R^9$.

In one embodiment, $R^6$ is deuterium. In one embodiment, $R^6$ is F. In one embodiment, $R^6$ is CN. In one embodiment, $R^6$ is —O—$C_{1-5}$ alkyl optionally substituted with one or more, identical or different, substituents $R^8$. In one embodiment, $R^6$ is —O—$C_{3-5}$ cycloalkyl optionally substituted with one or more, identical or different, substituents $R^8$. In one embodiment, $R^6$ is —S—$C_{1-5}$ alkyl optionally substituted with one or more, identical or different, substituents $R^8$. In one embodiment, $R^6$ is —S—$C_{3-5}$ cycloalkyl optionally substituted with one or more, identical or different, substituents $R^8$.

In one embodiment, $R^7$ is deuterium. In one embodiment, $R^7$ is F. In one embodiment, $R^7$ is $C_l$. In one embodiment, $R^7$ is CN. In one embodiment, $R^7$ is —O—$C_{1-5}$ alkyl optionally substituted with one or more, identical or different, substituents $R^8$. In one embodiment, $R^7$ is —O—$C_{3-5}$ cycloalkyl optionally substituted with one or more, identical or different, substituents $R^8$. In one embodiment, $R^7$ is —S—$C_{1-5}$ alkyl optionally substituted with one or more, identical or different, substituents $R^8$. In one embodiment, $R^7$ is —S—$C_{3-5}$ cycloalkyl optionally substituted with one or more, identical or different, substituents $R^8$. In one embodiment, $R^7$ is $C_{3-5}$ cycloalkyl optionally substituted with one or more, identical or different, substituents $R^8$.

In one embodiment, $R^8$ is deuterium. In one embodiment, $R^8$ is F.

In one embodiment, n is 0. In one embodiment, n is 1. In one embodiment, n is 2. In one embodiment, n is 3.

In one embodiment, X is a bond. In one embodiment, X is —O—. In one embodiment, X is —S—. In one embodiment, X is —$CH_2$—. In one embodiment, X is —$CHR^6$—. In one embodiment, X is —$C(R^6)_2$—.

In one embodiment, $R^1$ is Cl or Br, $R^2$ is selected from the group consisting of methyl, ethyl, n-propyl and isopropyl optionally substituted with one or more, identical or different, substituents $R^7$, and $R^5$ is H.

In one embodiment, the enantiomeric excess of the compounds are >90% e.e, for example>90% e.e, for example>95%. e.e, and for example>98% e.e.

In one embodiment, the disclosure concerns a compound of Formula (II):

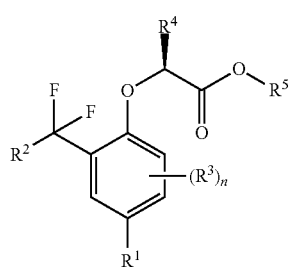

Formula (II)

wherein:
R$^1$ is selected from the group consisting of $C_{1-2}$ alkyl, $C_2$ alkenyl, $C_2$ alkynyl, CN, $CF_3$, $NO_2$, F, Cl, Br, and I;
R$^2$ is selected from the group consisting of $C_{1-5}$ alkyl optionally be substituted with one or more, identical or different, substituents $R^6$, $C_{2-5}$ alkenyl optionally be substituted with one or more, identical or different, substituents $R^6$, $C_{2-5}$ alkynyl optionally be substituted with one or more, identical or different, substituents $R^6$, $C_{3-5}$ cycloalkyl optionally substituted with one or more, identical or different, substituents $R^6$, phenyl optionally substituted with one or more, identical or different, substituents $R^9$, and 5-6 membered aromatic heterocycle optionally substituted with one or more, identical or different, substituents $R^7$;
R$^3$ is selected from the group consisting of deuterium, Cl and F;
R$^4$ is selected from the group consisting of H, deuterium, $C_{1-5}$ alkyl, $C_{2-5}$ alkenyl, $C_{2-5}$ alkynyl, and $C_{3-5}$ cycloalkyl, each of which may be optionally substituted with one or more, identical or different, substituents $R^7$;
R$^5$ is selected from the group consisting of H, $C_{1-5}$ alkyl optionally substituted with one or more, identical or different, substituents $R^8$, $C_{2-5}$ alkenyl optionally substituted with one or more, identical or different, substituents $R^8$, $C_{2-5}$ alkynyl optionally substituted with one or more, identical or different, substituents $R^8$, $C_{3-6}$ cycloalkyl optionally substituted with one or more, identical or different, substituents $R^8$, phenyl optionally substituted with one or more, identical or different, substituents $R^9$, and benzyl optionally substituted with one or more, identical or different, substituents $R^9$;
R$^6$ is independently selected from the group consisting of deuterium, F, —CN, —O—$C_{1-5}$ alkyl, —O—$C_{3-5}$ cycloalkyl, —S—$C_{1-5}$ alkyl, and —S—$C_{3-5}$ cycloalkyl, wherein the —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;
R$^7$ is independently selected from the group consisting deuterium, F, Cl, —CN, $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, wherein the $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;
R$^8$ is independently selected from the group consisting of deuterium and F;
R$^9$ is independently selected from the group consisting of deuterium, methoxy, nitro, cyano, Cl, Br, I, and F; and
n is an integer 0, 1, 2, or 3;
or a pharmaceutically acceptable salt, hydrate, polymorph, tautomer, or solvate thereof.

In one embodiment, the disclosure concerns a compound of Formula (II):

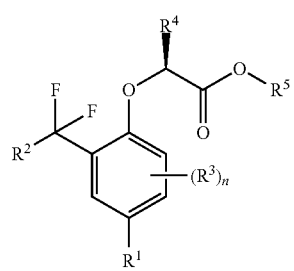

Formula (II)

wherein:
- R¹ is selected from the group consisting of F, Cl, Br, and I;
- R² is selected from the group consisting of $C_{1-5}$ alkyl optionally be substituted with one or more, identical or different, substituents R⁶, $C_{2-5}$ alkenyl optionally be substituted with one or more, identical or different, substituents R⁶, $C_{2-5}$ alkynyl optionally be substituted with one or more, identical or different, substituents R⁶, $C_{3-5}$ cycloalkyl optionally substituted with one or more, identical or different, substituents R⁶, phenyl optionally substituted with one or more, identical or different, substituents R⁹, and 5-6 membered aromatic heterocycle optionally substituted with one or more, identical or different, substituents R⁷;
- R³ is selected from the group consisting of deuterium and F;
- R⁴ is selected from the group consisting of H, deuterium, $C_{1-5}$ alkyl, $C_{2-5}$ alkenyl, $C_{2-5}$ alkynyl, and $C_{3-5}$ cycloalkyl, each of which may be optionally substituted with one or more, identical or different, substituents R⁷;
- R⁵ is selected from the group consisting of H, $C_{1-5}$ alkyl optionally substituted with one or more, identical or different, substituents R⁸, $C_{2-5}$ alkenyl optionally substituted with one or more, identical or different, substituents R⁸, $C_{2-5}$ alkynyl optionally substituted with one or more, identical or different, substituents R⁸, $C_{3-6}$ cycloalkyl optionally substituted with one or more, identical or different, substituents R⁸, phenyl optionally substituted with one or more, identical or different, substituents R⁹, and benzyl optionally substituted with one or more, identical or different, substituents R⁹;
- R⁶ is independently selected from the group consisting of —O—$C_{1-5}$ alkyl, —O—$C_{3-5}$ cycloalkyl, —S—$C_{1-5}$ alkyl, and —S—$C_{3-5}$ cycloalkyl, each of which may optionally be substituted with one or more, identical or different, substituents R⁸, deuterium, F and —CN;
- R⁷ is independently selected from the group consisting $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, each of which may optionally be substituted with one or more, identical or different, substituents R⁸, of deuterium, F and —CN;
- R⁸ is independently selected from the group consisting of deuterium and F;
- R⁹ is independently selected from the group consisting of deuterium, methoxy, nitro, cyano, Cl, Br, I, and F; and
- n is an integer 0, 1, 2, or 3;

or a pharmaceutically acceptable salt, hydrate, polymorph, tautomer, or solvate thereof.

In one embodiment, the disclosure concerns a compound of Formula (II):

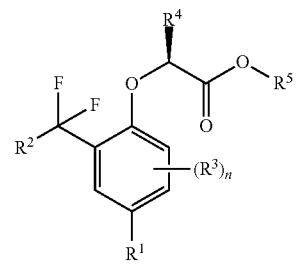

Formula (II)

wherein:
- R¹ is selected from the group consisting of $C_2$ alkenyl, $C_2$ alkynyl, $NO_2$, F, Cl, Br, and I;
- R² is $C_{1-5}$ alkyl optionally be substituted with one or more, identical or different, substituents R⁶;
- R³ is selected from the group consisting of deuterium, Cl and F;
- R⁴ is selected from the group consisting of H, deuterium, $C_{1-5}$ alkyl and $C_{2-5}$ alkynyl each of which may be optionally substituted with one or more, identical or different, substituents R⁷;
- R⁵ is H;
- R⁶ is independently selected from the group consisting of deuterium, F, —CN, —O—$C_{1-5}$ alkyl, —O—$C_{3-5}$ cycloalkyl, —S—$C_{1-5}$ alkyl, and —S—$C_{3-5}$ cycloalkyl, wherein the —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents R⁸;
- R⁷ is independently selected from the group consisting deuterium, F, Cl, —CN, $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, wherein the $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents R⁸;
- R⁸ is independently selected from the group consisting of deuterium and F; and
- n is an integer 0, 1, 2, or 3;

or a pharmaceutically acceptable salt, hydrate, polymorph, tautomer, or solvate thereof.

In one embodiment, the disclosure concerns a compound of Formula (III):

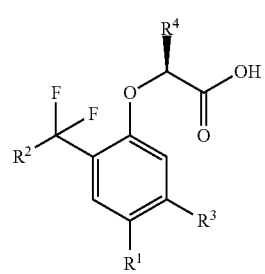

Formula (III)

wherein:
- R¹ is selected from the group consisting of $C_2$ alkenyl, $C_2$ alkynyl, $NO_2$, F, Cl, Br, and I;
- R² is $C_{1-5}$ alkyl optionally be substituted with one or more, identical or different, substituents R⁶;

$R^3$ is selected from the group consisting of H, deuterium, Cl and F;

$R^4$ is selected from the group consisting of H, deuterium, $C_{1-5}$ alkyl and $C_{2-5}$ alkynyl each of which may be optionally substituted with one or more, identical or different, substituents $R^7$;

$R^6$ is independently selected from the group consisting of deuterium, F, —CN, —O—$C_{1-5}$ alkyl, —O—$C_{3-5}$ cycloalkyl, —S—$C_{1-5}$ alkyl, and —S—$C_{3-5}$ cycloalkyl, wherein the —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;

$R^7$ is independently selected from the group consisting deuterium, F, Cl, —CN, $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, wherein the $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$; and $R^8$ is independently selected from the group consisting of deuterium and F;

or a pharmaceutically acceptable salt, hydrate, polymorph, tautomer, or solvate thereof.

In one embodiment, the disclosure concerns a compound of Formula (III):

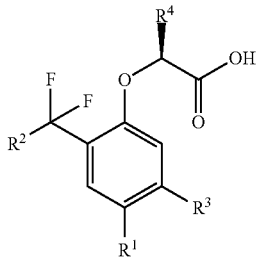

Formula (III)

wherein:

$R^1$ is selected from the group consisting of $C_2$ alkenyl, $C_2$ alkynyl, $NO_2$, F, Cl, Br, and I;

$R^2$ is $C_{1-3}$ alkyl optionally be substituted with one or more, identical or different, substituents $R^8$;

$R^3$ is selected from the group consisting of H, deuterium, Cl and F;

$R^4$ is selected from the group consisting of H, deuterium, $C_{1-3}$ alkyl and $C_{2-3}$ alkynyl each of which may be optionally substituted with one or more, identical or different, substituents $R^8$; and $R^8$ is independently selected from the group consisting of deuterium and F;

or a pharmaceutically acceptable salt, hydrate, polymorph, tautomer, or solvate thereof.

In one embodiment, the compound is selected from the list consisting of (2S)-2-[4-bromo-2-(1,1-difluoroethyl)phenoxy]-3-cyclopropylpropanoic acid;

(2S)-2-[4-bromo-2-(1,1-difluoroethyl)phenoxy]butanoic acid;

(2S)-2-[4-bromo-2-(1,1-difluoropropyl)phenoxy]propanoic acid;

(2S)-2-[4-bromo-2-(1,1-difluoroethyl)phenoxy]propanoic acid;

(2S)-2-[4-chloro-2-(1,1-difluoropropyl)phenoxy]propanoic acid;

2-[4-bromo-2-(1,1-difluoropropyl)phenoxy]acetic acid;

(2S)-2-[4-bromo-2-(1,1-difluoro-2-methylpropyl)phenoxy]propanoic acid;

(2S)-2-{4-bromo-2-[difluoro(phenyl)methyl]phenoxy}propanoic acid;

(2S)-2-[4-bromo-2-(1,1-difluoroethyl)phenoxy]-2-cyclopropylacetic acid;

(2S)-2-[4-bromo-2-(1,1-difluorobutyl)phenoxy]propanoic acid;

(2R)-2-[4-bromo-2-(1,1-difluoropropyl)phenoxy]-3-fluoropropanoic acid;

(2S)-2-[4-bromo-2-(cyclopropyldifluoromethyl)phenoxy]propanoic acid;

(2S)-2-{4-bromo-2-[difluoro(1,3-thiazol-2-yl)methyl]phenoxy}propanoic acid;

(2S)-2-[4-bromo-2-(1,1-difluoroethyl)phenoxy]pent-4-ynoic acid;

(2S)-2-[4-bromo-2-(cyclobutyldifluoromethyl)phenoxy]propanoic acid;

(2R)-2-[4-bromo-2-(1,1-difluoroethyl)phenoxy]-3-fluoropropanoic acid;

(2R)-2-[4-bromo-2-(1,1-difluoropropyl)phenoxy]-3-chloropropanoic acid;

(2S)-2-[4-bromo-2-(1,1-difluoropropyl)phenoxy]pent-4-ynoic acid;

(2S)-2-[4-chloro-2-(1,1-difluoroethyl)phenoxy]pent-4-ynoic acid;

(2S)-2-[2-(1,1-difluoropropyl)-4-iodophenoxy]propanoic acid;

(2S)-2-[4-bromo-2-(1,1-difluoropropyl)phenoxy](2-$^2$H)propanoic acid;

(2R)-2-[4-chloro-2-(1,1-difluoropropyl)phenoxy]-3-fluoropropanoic acid;

(2S)-2-[2-(1,1-difluoropropyl)-4-ethynylphenoxy]propanoic acid;

(2S)-2-[4-bromo-2-(1,1-difluoropropyl)-5-fluorophenoxy]propanoic acid;

(2S)-2-[4-bromo-2-(1,1-difluoropropyl)-6-fluorophenoxy]propanoic acid;

(2S)-2-[4-cyano-2-(1,1-difluoropropyl)phenoxy]propanoic acid;

(2R)-2-[4-chloro-2-(1,1-difluoroethyl)phenoxy]-3-fluoropropanoic acid;

(2S)-2-[4-bromo-2-(1,1-difluoroethyl)-5-fluorophenoxy]propanoic acid;

(2S)-2-[4-bromo-2-(1,1-difluoropropyl)(3,5,6-$^2$H$_3$)phenoxy]propanoic acid;

2-[4-bromo-2-(1,1-difluoropropyl)-5-fluorophenoxy]acetic acid;

(2S)-2-[4-chloro-2-(1,1-difluoropropyl)-5-fluorophenoxy]propanoic acid;

(2S)-2-[2-(1,1-difluoropropyl)-4-(trifluoromethyl)phenoxy]propanoic acid;

(2R)-2-[4-bromo-2-(1,1-difluoropropyl)-5-fluorophenoxy]-3-fluoropropanoic acid;

(2S)-2-[2-(1,1-difluoropropyl)-4-ethenylphenoxy]propanoic acid;

2-[4-bromo-2-(1,1-difluoroethyl)-5-fluorophenoxy]acetic acid;

(2S)-2-[2-(1,1-difluoropropyl)-4-methylphenoxy]propanoic acid;

2-[4-bromo-2-(1,1-difluoro-2-methylpropyl)phenoxy]acetic acid;

2-[4-chloro-2-(1,1-difluoropropyl)-5-fluorophenoxy]acetic acid;

(2S)-2-[2-(1,1-difluoroethyl)-4-ethynylphenoxy]propanoic acid;
(2R)-2-[4-chloro-2-(1,1-difluoropropyl)-5-fluorophenoxy]-3-fluoropropanoic acid;
(2S)-2-[4,5-dichloro-2-(1,1-difluoropropyl)phenoxy]propanoic acid;
(2R)-2-[4-bromo-2-(1,1-difluoroethyl)-5-fluorophenoxy]-3-fluoropropanoic acid;
(2R)-2-[4,5-dichloro-2-(1,1-difluoroethyl)phenoxy]-3-fluoropropanoic acid;
(2S)-2-[4-bromo-2-(1,1-difluoroethyl)phenoxy]-4-fluorobutanoic acid;
(2S)-2-[4-bromo-2-(1,1-difluoro-2-methylpropyl)phenoxy]butanoic acid;
(2S)-2-[2-(1,1-difluoropropyl)-4-ethenyl-5-fluorophenoxy]propanoic acid;
(2S)-2-[4-bromo-2-(1,1-difluoropropyl)-5-fluorophenoxy]butanoic acid;
(2S)-2-[4-chloro-2-(1,1-difluoropropyl)-5-fluorophenoxy]butanoic acid;
(2R)-2-[5-chloro-2-(1,1-difluoropropyl)-4-fluorophenoxy]-3-fluoropropanoic acid;
(2S)-2-[2-(1,1-difluoropropyl)-4-nitrophenoxy]propanoic acid;
(2S)-2-[5-chloro-2-(1,1-difluoropropyl)-4-fluorophenoxy]propanoic acid;
(2S)-2-[4-bromo-2-(1,1-difluoropropyl)phenoxy]-4-methoxybutanoic acid;
(2R)-2-[2-(1,1-difluoropropyl)-4,5-difluorophenoxy]-3-fluoropropanoic acid;
(2S)-2-[2-(1,1-difluoropropyl)-4,5-difluorophenoxy]propanoic acid; and
(2S)-2-[4-bromo-2-(1,1-difluoro-3-methoxypropyl)phenoxy]propanoic acid.

Methods of Treatment

In one aspect, the disclosure relates to the use of compounds of Formula (I) and/or Formula (II) and/or Formula (III) in treating, ameliorating and/or preventing a neuromuscular disorder. In one aspect, the disclosure relates to the use of compounds of Formula (I) and/or Formula (II) and/or Formula (III) in reversing and/or ameliorating a neuromuscular blockade. Thus, in one aspect, the disclosure relates to a compound of Formula (I):

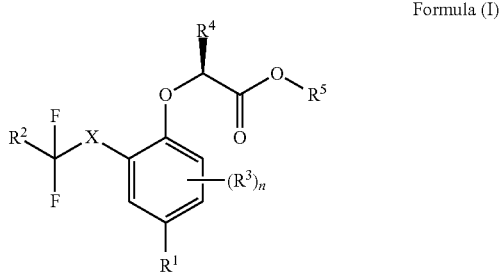

Formula (I)

wherein $R^1$ to $R^9$, n and X are defined as disclosed herein, or a pharmaceutically acceptable salt, hydrate, polymorph, tautomer, or solvate thereof for use in treating, ameliorating and/or preventing a neuromuscular disorder, and/or for use in reversing and/or ameliorating a neuromuscular blockade.

In one embodiment, the disclosure concerns a compound of Formula (II):

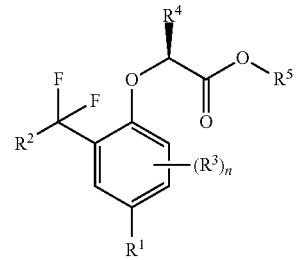

Formula (II)

wherein $R^1$ to $R^9$ and n are defined as disclosed herein, or a pharmaceutically acceptable salt, hydrate, polymorph, tautomer, or solvate thereof for use in treating, ameliorating and/or preventing a neuromuscular disorder, and/or for use in reversing and/or ameliorating a neuromuscular blockade.

In one embodiment, the disclosure concerns a compound of Formula (III):

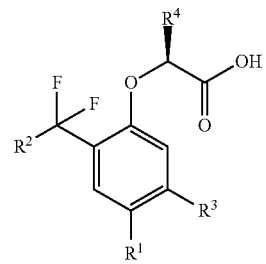

Formula (III)

wherein $R^1$ to $R^8$ and n are defined as disclosed herein, or a pharmaceutically acceptable salt, hydrate, polymorph, tautomer, or solvate thereof for use in treating, ameliorating and/or preventing a neuromuscular disorder, and/or for use in reversing and/or ameliorating a neuromuscular blockade.

In one embodiment, the compound for use in treating, ameliorating and/or preventing a neuromuscular disorder, and/or for use in reversing and/or ameliorating a neuromuscular blockade is selected from the list consisting of
(2S)-2-[4-bromo-2-(1,1-difluoroethyl)phenoxy]-3-cyclopropylpropanoic acid;
(2S)-2-[4-bromo-2-(1,1-difluoroethyl)phenoxy]butanoic acid;
(2S)-2-[4-bromo-2-(1,1-difluoropropyl)phenoxy]propanoic acid;
(2S)-2-[4-bromo-2-(1,1-difluoroethyl)phenoxy]propanoic acid;
(2S)-2-[4-chloro-2-(1,1-difluoropropyl)phenoxy]propanoic acid;
2-[4-bromo-2-(1,1-difluoropropyl)phenoxy]acetic acid;
(2S)-2-[4-bromo-2-(1,1-difluoro-2-methylpropyl)phenoxy]propanoic acid;
(2S)-2-{4-bromo-2-[difluoro(phenyl)methyl]phenoxy}propanoic acid;
(2S)-2-[4-bromo-2-(1,1-difluoroethyl)phenoxy]-2-cyclopropylacetic acid;
(2S)-2-[4-bromo-2-(1,1-difluorobutyl)phenoxy]propanoic acid;
(2R)-2-[4-bromo-2-(1,1-difluoropropyl)phenoxy]-3-fluoropropanoic acid;

(2S)-2-[4-bromo-2-(cyclopropyldifluoromethyl)phenoxy]propanoic acid;
(2S)-2-{4-bromo-2-[difluoro(1,3-thiazol-2-yl)methyl]phenoxy}propanoic acid;
(2S)-2-[4-bromo-2-(1,1-difluoroethyl)phenoxy]pent-4-ynoic acid;
(2S)-2-[4-bromo-2-(cyclobutyldifluoromethyl)phenoxy]propanoic acid;
(2R)-2-[4-bromo-2-(1,1-difluoroethyl)phenoxy]-3-fluoropropanoic acid;
(2R)-2-[4-bromo-2-(1,1-difluoropropyl)phenoxy]-3-chloropropanoic acid;
(2S)-2-[4-bromo-2-(1,1-difluoropropyl)phenoxy]pent-4-ynoic acid;
(2S)-2-[4-chloro-2-(1,1-difluoroethyl)phenoxy]pent-4-ynoic acid;
(2S)-2-[2-(1,1-difluoropropyl)-4-iodophenoxy]propanoic acid;
(2S)-2-[4-bromo-2-(1,1-difluoropropyl)phenoxy](2-$^2$H)propanoic acid;
(2R)-2-[4-chloro-2-(1,1-difluoropropyl)phenoxy]-3-fluoropropanoic acid;
(2S)-2-[2-(1,1-difluoropropyl)-4-ethynylphenoxy]propanoic acid;
(2S)-2-[4-bromo-2-(1,1-difluoropropyl)-5-fluorophenoxy]propanoic acid;
(2S)-2-[4-bromo-2-(1,1-difluoropropyl)-6-fluorophenoxy]propanoic acid;
(2S)-2-[4-cyano-2-(1,1-difluoropropyl)phenoxy]propanoic acid;
(2R)-2-[4-chloro-2-(1,1-difluoroethyl)phenoxy]-3-fluoropropanoic acid;
(2S)-2-[4-bromo-2-(1,1-difluoroethyl)-5-fluorophenoxy]propanoic acid;
(2S)-2-[4-bromo-2-(1,1-difluoropropyl)(3,5,6-$^2$H$_3$)phenoxy]propanoic acid;
2-[4-bromo-2-(1,1-difluoropropyl)-5-fluorophenoxy]acetic acid;
(2S)-2-[4-chloro-2-(1,1-difluoropropyl)-5-fluorophenoxy]propanoic acid;
(2S)-2-[2-(1,1-difluoropropyl)-4-(trifluoromethyl)phenoxy]propanoic acid;
(2R)-2-[4-bromo-2-(1,1-difluoropropyl)-5-fluorophenoxy]-3-fluoropropanoic acid;
(2S)-2-[2-(1,1-difluoropropyl)-4-ethenylphenoxy]propanoic acid;
2-[4-bromo-2-(1,1-difluoroethyl)-5-fluorophenoxy]acetic acid;
(2S)-2-[2-(1,1-difluoropropyl)-4-methylphenoxy]propanoic acid;
2-[4-bromo-2-(1,1-difluoro-2-methylpropyl)phenoxy]acetic acid;
2-[4-chloro-2-(1,1-difluoropropyl)-5-fluorophenoxy]acetic acid;
(2S)-2-[2-(1,1-difluoroethyl)-4-ethynylphenoxy]propanoic acid;
(2R)-2-[4-chloro-2-(1,1-difluoropropyl)-5-fluorophenoxy]-3-fluoropropanoic acid;
(2S)-2-[4,5-dichloro-2-(1,1-difluoropropyl)phenoxy]propanoic acid;
(2R)-2-[4-bromo-2-(1,1-difluoroethyl)-5-fluorophenoxy]-3-fluoropropanoic acid;
(2R)-2-[4,5-dichloro-2-(1,1-difluoroethyl)phenoxy]-3-fluoropropanoic acid;
(2S)-2-[4-bromo-2-(1,1-difluoroethyl)phenoxy]-4-fluorobutanoic acid;
(2S)-2-[4-bromo-2-(1,1-difluoro-2-methylpropyl)phenoxy]butanoic acid;
(2S)-2-[2-(1,1-difluoropropyl)-4-ethenyl-5-fluorophenoxy]propanoic acid;
(2S)-2-[4-bromo-2-(1,1-difluoropropyl)-5-fluorophenoxy]butanoic acid;
(2S)-2-[4-chloro-2-(1,1-difluoropropyl)-5-fluorophenoxy]butanoic acid;
(2R)-2-[5-chloro-2-(1,1-difluoropropyl)-4-fluorophenoxy]-3-fluoropropanoic acid;
(2S)-2-[2-(1,1-difluoropropyl)-4-nitrophenoxy]propanoic acid;
(2S)-2-[5-chloro-2-(1,1-difluoropropyl)-4-fluorophenoxy]propanoic acid;
(2S)-2-[4-bromo-2-(1,1-difluoropropyl)phenoxy]-4-methoxybutanoic acid;
(2R)-2-[2-(1,1-difluoropropyl)-4,5-difluorophenoxy]-3-fluoropropanoic acid;
(2S)-2-[2-(1,1-difluoropropyl)-4,5-difluorophenoxy]propanoic acid; and
(2S)-2-[4-bromo-2-(1,1-difluoro-3-methoxypropyl)phenoxy]propanoic acid.

In one embodiment, the compound or the compound for use according to the present disclosure has been modified in order to increase its half-life when administered to a patient, in particular its plasma half-life.

In one embodiment, the compound or the compound for use according to the present disclosure further comprises a moiety conjugated to said compound, thus generating a moiety-conjugated compound. In one embodiment, said moiety-conjugated compound has a plasma and/or serum half-life being longer than the plasma and/or serum half-life of the non-moiety conjugated compound.

In one embodiment, the moiety conjugated to the compound or compound for use according to the present disclosure, is one or more type(s) of moieties selected from the group consisting of albumin, fatty acids, polyethylene glycol (PEG), acylation groups, antibodies and antibody fragments.

Neuromuscular Disorders

The compound or compound for use of the present disclosure is used for treating, ameliorating and/or preventing a neuromuscular disorder, or reversing neuromuscular blockade caused by non-depolarizing neuromuscular blocker or antibiotic agent.

The inventors of the present disclosure have shown that inhibition of ClC-1 channels strengthens neuromuscular transmission. ClC-1 function may therefore contribute to muscle weakness in conditions of compromised neuromuscular transmission.

Thus, in one embodiment of the present disclosure, the compound or the compound for use as described herein inhibits ClC-1 channels. Thus, it is appreciated that compounds and/or compounds for use of Formula (I) inhibit ClC-1 channels.

The neuromuscular disorder may also include neuromuscular dysfunctions.

Neuromuscular disorders include for example disorders with symptoms of muscle weakness and fatigue. Such disorders may include conditions with reduced neuromuscular transmission safety factor. In one embodiment the neuromuscular disorders are motor neuron disorders. Motor neuron disorders are disorders with reduced safety in the neuromuscular transmission. In one embodiment motor neuron disorders are selected from the group consisting of amyotrophic lateral sclerosis (ALS) (Killian J M, Wilfong A A, Burnett L, Appel S H, Boland D. Decremental motor responses to repetitive nerve stimulation in ALS. *Muscle*

Nerve, 1994, 17, 747-754), spinal muscular atrophy (SMA) (Wadman R I, Vrancken A F, van den Berg L H, van der Pol W L. Dysfunction of the neuromuscular junction in spinal muscular atrophy types 2 and 3. *Neurology*, 2012, 79, 2050-2055), Charcot-Marie Tooth disease (Bansagi B, Griffin H, Whittaker R G, Antoniadi T, Evangelista T, Miller J, Greenslade M, Forester N, Duff J, Bradshaw A, Kleinle S, Boczonadi V, Steele H, Ramesh V, Franko E, Pyle A, Lochmüller H, Chinnery P F, Horvath R. Genetic heterogeneity of motor neuropathies. *Neurology*, 2017, 28; 88(13): 1226-1234), X-linked spinal and bulbar muscular atrophy (Yamada, M., Inaba, A., Shiojiri, T. X-linked spinal and bulbar muscular atrophy with myasthenic symptoms. *Journal of the Neurological Sciences*, 1997, 146, 183-185), Kennedy's disorder (Stevic, Z., Peric, S., Pavlovic, S., Basta, I., Lavrnic, D., Myasthenic symptoms in a patient with Kennedy's disorder. *Acta Neurologica Belgica*, 2014, 114, 71-73), multifocal motor neuropathy (Roberts, M., Willison, H. J., Vincent, A., Newsom-Davis, J. Multifocal motor neuropathy human sera block distal motor nerve conduction in mice. *Ann Neurol.* 1995, 38, 111-118), Guillain-Barré syndrome (Ansar, V., Valadi, N. *Guillain-Barré Syndrome Prim. Care*, 2015, 42, 189-193; poliomyelitis (Trojan, D. A., Gendron, D., Cashman, N. R. Electrophysiology and electrodiagnosis of the post-polio motor unit. Orthopedics, 1991, 14, 1353-1361, and Birk T. J. Poliomyelitis and the post-polio syndrome: exercise capacities and adaptation—current research, future directions, and widespread applicability. *Med. Sci. Sports Exerc.*, 1993, 25, 466-472), post-polio syndrome (Garcia, C. C., Potian, J. G., Hognason, K., Thyagarajan, B., Sultatos, L. G., Souayah, N., Routh, V. H., McArdle, J. J. Acetylcholinesterase deficiency contributes to neuromuscular junction dysfunction in type 1 diabetic neuropathy. *Am. J. Physiol. Endocrinol. Metab.*, 2012, 15, E551-561) and sarcopenia (Gilmore K. J., Morat T., Doherty T. J., Rice C. L., Motor unit number estimation and neuromuscular fidelity in 3 stages of sarcopenia. 2017, 55 (5), 676-684).

Thus, in one embodiment of the present disclosure the neuromuscular disorder is amyotrophic lateral sclerosis (ALS). In another embodiment the neuromuscular disorder is spinal muscular atrophy (SMA). In another embodiment the neuromuscular disorder is Charcot-Marie tooth disease (CMT). In another embodiment the neuromuscular disorder is sarcopenia. In yet another embodiment, the neuromuscular disorder is critical illness myopathy (CIM).

As stated above the neuromuscular disorders include for example disorders with symptoms of muscle weakness and fatigue. Such disorder may for example include diabetes (Burton, A. Take your pyridostigmine: that's an (ethical?) order! *Lancet Neurol.*, 2003, 2, 268).

In one embodiment the compound or the compound for use of the present disclosure is used to prevent neuromuscular disorder. The compound or the compound for use may for example be used prophylactically or as a treatment against nerve gas that is known to cause symptoms of muscle weakness and fatigue (Kawamura, Y., Kihara, M., Nishimoto, K., Taki, M. Efficacy of a half dose of oral pyridostigmine in the treatment of chronic fatigue syndrome: three case reports. *Pathophysiology*, 2003, 9, 189-194). In one disclosure, the compound or the compound for use of the present disclosure is used in the treatment of botulism poisoning (Sellin, L. C., The action of botulinum toxin at the neuromuscular junction, *Med Biol.*, 1981, 59, 11-20. In one disclosure, the compound or the compound for use of the present disclosure is used in the treatment of snake bites (Silva A., Maduwage K., Buckley N. A., Lalloo D. G., de Silva H. J., Isbister G. K., Antivenom for snake venom-induced neuromuscular paralysis, Cochrane Database of Systematic Reviews, 2017, 3, Art. No.: CD012604).

In another embodiment the neuromuscular disorders is chronic fatigue syndrome. Chronic fatigue syndrome (CFS) (Fletcher, S. N., Kennedy, D. D., Ghosh, I. R., Misra, V. P., Kiff, K., Coakley, J. H., Hinds, C. J. Persistent neuromuscular and neurophysiologic abnormalities in long-term survivors of prolonged critical illness. *Crit. Care Med.* 2003, 31, 1012-1016) is the common name for a medical condition characterized by debilitating symptoms, including fatigue that lasts for a minimum of six months in adults. CFS may also be referred to as systemic exertion intolerance disorder (SEID), myalgic encephalomyelitis (ME), post-viral fatigue syndrome (PVFS), chronic fatigue immune dysfunction syndrome (CFIDS), or by several other terms. Symptoms of CFS include malaise after exertion; unrefreshing sleep, widespread muscle and joint pain, physical exhaustion, and muscle weakness.

In another embodiment the neuromuscular disorder is myotubular myopathy (Dowling, J. J. et al, Myotubular myopathy and the neuromuscular junction: a novel therapeutic approach from mouse models, Disease Models & Mechanisms, 2012, 5, 852-859). In another embodiment the neuromuscular disorder is Duchenne muscular dystrophy (van der Pijl, M. M. et al, Characterization of neuromuscular synapse function abnormalities in multiple Duchenne muscular dystrophy mouse models, European Journal of Neuroscience, 2016, 43, 1623-1635.

In a further embodiment the neuromuscular disorder is a critical illness polyneuropathy (Angelini C. Spectrum of metabolic myopathies. *Biochim. Biophys. Acta.*, 2015, 1852, 615-621) or CIM (Latronico, N., Bolton, C. F. Critical illness polyneuropathy and myopathy: a major cause of muscle weakness and paralysis. *Lancet Neurol.* 2011, 10, 931-941). Critical illness polyneuropathy and CIM are overlapping syndromes of widespread muscle weakness and neurological dysfunction developing in critically ill patients.

The neuromuscular disorder may also include metabolic myopathy (Milone, M., Wong, L. J. Diagnosis of mitochondrial myopathies. Mol. Genet. Metab., 2013, 110, 35-41) and mitochondrial myopathy (Srivastava, A., Hunter, J. M. Reversal of neuromuscular block. *Br. J. Anaesth.* 2009, 103, 115-129). Metabolic myopathies result from defects in biochemical metabolism that primarily affects muscle. These may include glycogen storage disorders, lipid storage disorder and 3-phosphocreatine storage disorder. Mitochondrial myopathy is a type of myopathy associated with mitochondrial disorder. Symptoms of mitochondrial myopathies include muscular and neurological problems such as muscle weakness, exercise intolerance, hearing loss and trouble with balance and coordination.

In another embodiment the neuromuscular disorder is periodic paralysis, in particular hypokalemic periodic paralysis which is a disorder of skeletal muscle excitability that presents with recurrent episodes of weakness, often triggered by exercise, stress, or carbohydrate-rich meals (Wu, F., Mi, W., Cannon, S. C., *Neurology*, 2013, 80, 1110-1116 and Suetterlin, K. et at, *Current Opinion Neurology*, 2014, 27, 583-590) or hyperkalemic periodic paralysis which is an inherited autosomal dominant disorder that affects sodium channels in muscle cells and the ability to regulate potassium levels in the blood (Ammat, T. et at, *Journal of General Physiology*, 2015, 146, 509-525).

In an embodiment the neuromuscular disorder is a myasthenic condition. Myasthenic conditions are characterized by muscle weakness and neuromuscular transmission failure. Congenital myasthenia gravis (Finlayson, S., Beeson, D., Palace, J. Congenital myasthenic syndromes: an update. *Pract. Neurol.*, 2013, 13, 80-91) is an inherited neuromuscular disorder caused by defects of several types at the neuromuscular junction.

Myasthenia gravis and Lambert-Eaton syndrome (Titulaer M J, Lang B, Verschuuren J J. Lambert-Eaton myasthenic syndrome: from clinical characteristics to therapeutic strategies. *Lancet Neurol.* 2011, 10, 1098-107) are examples of myasthenic conditions. Myasthenia gravis is either an autoimmune or congenital neuromuscular disorder that leads to fluctuating muscle weakness and fatigue. In the most common cases, muscle weakness is caused by circulating antibodies that block ACh receptors at the postsynaptic neuromuscular junction, inhibiting the excitatory effects of the neurotransmitter ACh on nicotinic ACh-receptors at neuromuscular junctions (Gilhus, N. E., Owe, J. F., Hoff, J. M., Romi, F., Skeie, G. O., Aarli, J. A. Myasthenia Gravis: A Review of Available Treatment Approaches, Autoimmune Diseases, 2011, Article ID 84739). Lambert-Eaton myasthenic syndrome (also known as LEMS, Lambert-Eaton syndrome, or Eaton—Lambert syndrome) is a rare autoimmune disorder that is characterized by muscle weakness of the limbs. It is the result of an autoimmune reaction in which antibodies are formed against presynaptic voltage-gated calcium channels, and likely other nerve terminal proteins, in the neuromuscular junction.

Thus, in one embodiment of the present disclosure the neuromuscular disorder is myasthenia gravis. In another embodiment the neuromuscular disorder is Lambert—Eaton syndrome.

Neuromuscular blockade is used in connection with surgery under general anaesthesia. Reversing agents are used for more rapid and safer recovery of muscle function after such blockade. Complications with excessive muscle weakness after blockade during surgery can result in delayed weaning from mechanical ventilation and respiratory complications after the surgery. These complications can have pronounced effects on outcome of the surgery and future quality of life of patients, there is a need for improved reversing agents (Murphy G S, Brull S J. Residual neuromuscular block: lessons unlearned. Part I: definitions, incidence, and adverse physiologic effects of residual neuromuscular block. Anesth Analg. 2010 111(1):120-8). Thus, in one embodiment, the neuromuscular disorder has been induced by a neuromuscular blocking agent. In one particular embodiment the neuromuscular disorder is muscle weakness caused by neuromuscular blockade after surgery. In another embodiment of the present disclosure the compound or the compound for use is used for reversing and/or ameliorating neuromuscular blockade after surgery. In one embodiment, the neuromuscular blockade is drug induced. In one embodiment the neuromuscular blockade is induced by an antibiotic. In one embodiment the neuromuscular blockade is induced by a non-depolarizing neuromuscular blocker.

Pharmaceutical Formulations

In one embodiment, a composition comprising the compound or the compound for use, according to the present disclosure, is provided. The composition according to the present disclosure is used for treating, ameliorating and/or preventing a neuromuscular disorder, and/or for use in reversing and/or ameliorating a neuromuscular blockade. Thus, the compositions and compounds described herein can be pharmaceutically acceptable. In one embodiment the composition as described herein is in the form of a pharmaceutical formulation. In one embodiment, the composition as described herein further comprises a pharmaceutically acceptable carrier. Examples of potential formulations and preparations are contained, for example, in the Handbook of Pharmaceutical Excipients as well as Remington's Pharmaceutical Sciences.

Combination Therapy

The composition of the present disclosure may comprise further active ingredients/agents or other components to increase the efficiency of the composition. Thus, in one embodiment the composition further comprises at least one further active agent. It is appreciated that the active agent can be suitable for treating, preventing or ameliorating said neuromuscular disorder.

The active agent in certain embodiments can be an acetylcholine esterase inhibitor. Said acetylcholine esterase inhibitor may for example be selected from the group consisting of delta-9-tetrahydrocannabinol, carbamates, physostigmine, neostigmine, pyridostigmine, ambenonium, demecarium, rivastigmine, phenanthrene derivatives, galantamine, piperidines, donepezil, tacrine, edrophonium, huperzine, ladostigil, ungeremine and lactucopicrin.

In certain embodiments, the acetylcholine esterase inhibitor is selected from the group consisting of neostigmine, physostigmine and pyridostigmine. In certain embodiments, the acetylcholine esterase inhibitor is neostigmine or pyridostigmine.

The active agent may also be an immunosuppressive drug. Immunosuppressive drugs are drugs that suppress or reduce the strength of the body's immune system. They are also known as anti-rejection drugs. Immunosuppressive drugs include but are not limited to glucocorticoids, corticosteroids, cytostatics, antibodies and drugs acting on immunophilins. In one embodiment the active agent is prednisone.

The active agent may also be an agent that is used in anti-myotonic treatment. Such agents include for example blockers of voltage gated $Na^+$ channels, and aminoglycosides.

The active agent may also be an agent for reversing a neuromuscular blockade after surgery. Such agents include for example neostigmine or sugammadex (Org 25969, tradename Bridion). The active agent may also be an agent for increasing the $Ca^{2+}$ sensitivity of the contractile filaments in muscle. Such agents include tirasemtiv and CK-2127107 (Hwee, D. T., Kennedy, A. R., Hartman, J. J., Ryans, J., Durham, N., Malik, F. I., Jasper, J. R. The small-molecule fast skeletal troponin activator, CK-2127107, improves exercise tolerance in a rat model of heart failure. Journal of Pharmacology and Experimental Therapeutics, 2015, 353, 159-168).

The active agent may also be an agent for increasing ACh release by blocking voltage-gated $K^+$ channels in the presynaptic terminal. Such agent includes 3,4-aminopyridine.

Methods

In one aspect, the present disclosure relates to a method of treating, preventing and/or ameliorating a neuromuscular disorder, said method comprising administering a therapeutically effective amount of the compound or the compound for use as defined herein to a person in need thereof. In one embodiment, the person is a human being.

In one aspect, the present disclosure relates to a method of reversing and/or ameliorating a neuromuscular blockade, said method comprising administering a therapeutically effective amount of the compound or the compound for use as defined herein to a person in need thereof.

In one aspect, the present disclosure relates to a method for recovery of neuromuscular transmission, said method comprising administering a therapeutically effective amount of the compound or the compound for use as defined herein to a person in need thereof.

The person in need thereof may be a person having a neuromuscular disorder or a person at risk of developing a neuromuscular disorder or a person having symptoms of muscle weakness and/or fatigue. In another embodiment the person in need thereof is a person with reduced neuromuscular transmission safety with prolonged recovery after neuromuscular blockade. Types of neuromuscular disorders are defined herein above. In an embodiment the person has amyotrophic lateral sclerosis, spinal muscular atrophy, myasthenia gravis or Lambert-Eaton syndrome.

A therapeutically effective amount is an amount that produces a therapeutic response or desired effect in the person taking it. Administration routes, formulations and dosages can be determined by persons of skill in the art.

The method of treatment may be combined with other methods that are known to treat, prevent and/or ameliorate neuromuscular disorders. The treatment method may for example be combined with administration of any of the agents mentioned herein above. In one embodiment the treatment is combined with administration of acetylcholine esterase inhibitor such as for example neostigmine or pyridostigmine.

In one embodiment, invention relates to a method for recovery of force in muscles with neuromuscular dysfunction, said method comprising administering a compound or a composition as defined herein to a subject in need thereof. In one embodiment, said recovery of force is >5%, such as >10%, such as >15%, such as >20%, such as >25%, such as >30%, such as >35%. The recovery of force in muscle can be determined as the amount of force restored in muscle as a percentage of the initial force after a muscle has been exposure to a compound of the present disclosure, for example as described in Example 23.

Another aspect of the disclosure relates to use of a compound as defined herein, for the manufacture of a medicament for the treatment, prevention and/or amelioration of a neuromuscular disorder.

Another aspect relates to use of a compound as defined herein, for the manufacture of a medicament or a reversal agent for reversing and/or ameliorating a neuromuscular blockade after surgery.

Method of Manufacturing

In one aspect, the present disclosure relates to methods of manufacturing compounds or compounds for use according to formula (I).

One method for manufacturing the compounds or compounds for use according to the present disclosure comprises the steps of a. reacting a compound having formula (GM.III)

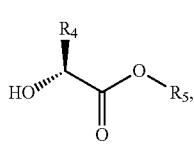

(GM.III)

wherein $R^4$ and $R^5$ are defined herein with a compound having formula (GM.II) under Mitsunobu or similar reaction conditions

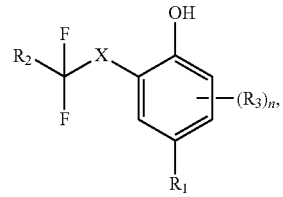

(GM.II)

wherein $R^1$, $R^2$, $R^3$, n and X are as defined herein to generate a compound having formula (GM.IV)

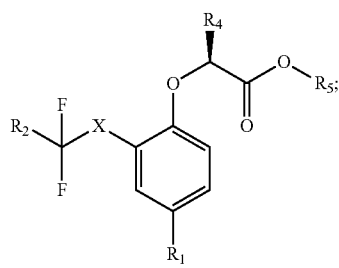

(GM.IV)

and b. reacting the product compound of a) with an ester hydrolysing reagent thus generating a compound as defined herein.

One method for manufacturing the compounds or compounds for use according to the present disclosure comprises the steps of a. reacting a compound having formula (GM.VI)

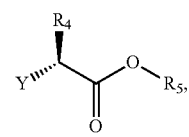

(GM.VI)

wherein $R^4$ and $R^5$ are defined herein and Y is a leaving group (for example a methanesulphonate or a tosylate) with a compound having formula (GM.II) under conditions which involve a suitable base such a sterically hindered amine or an alkali metal carbonate

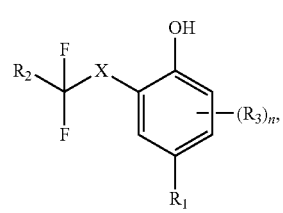

(GM.II)

wherein $R^1$, $R^2$, $R^3$, n and X are as defined herein to generate a compound having formula (GM.IV)

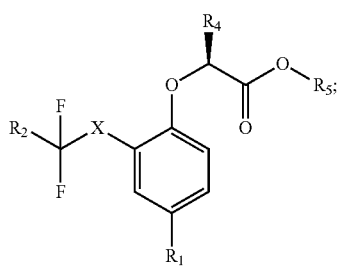
(GM.IV)

and b. reacting the product compound of a) with an ester hydrolysing reagent thus generating a compound as defined herein.

One method for manufacturing the compounds or compounds for use according to the present disclosure comprises the steps of a. reacting a compound having formula (GM.VIII)

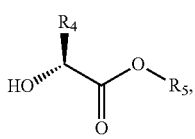
(GM.VIII)

wherein $R^4$ and $R^5$ are defined herein with a compound having formula (GM.VII)

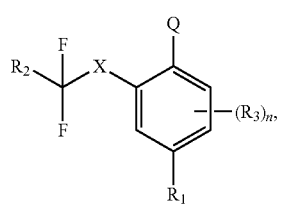
(GM.VII)

wherein $R^1$, $R^2$, $R^3$, n and X are as defined herein and Q is a suitable leaving group such as a halogen such as fluorine or iodine, to generate a compound having formula (GM.IV)

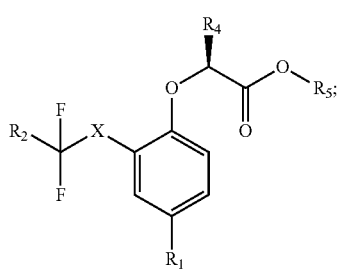
(GM.IV)

and b. reacting the product compound of a) with an ester hydrolysing reagent thus generating a compound as defined herein.

One method for manufacturing the compounds or compounds for use according to the present disclosure comprises the steps of a. reacting a compound having formula (GM.IX)

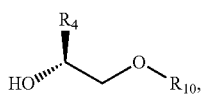
(GM.IX)

wherein $R^4$ is defined herein and $R_{10}$ is a suitable protecting group, such as a silyl-containing moiety, with a compound having formula (GM.II) under Mitsunobu or similar reaction conditions

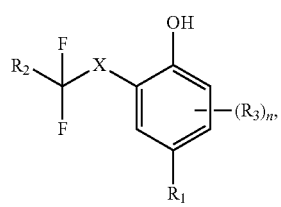
(GM.II)

wherein $R^1$, $R^2$, $R^3$, n and X are as defined herein to generate a compound having formula (GM.X)

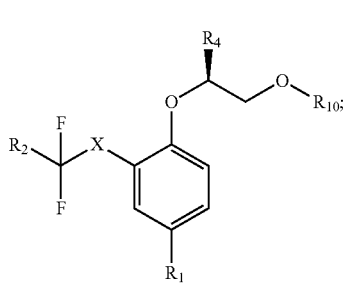
(GM.X)

b. removing the protecting group $R_{10}$ of product compound of a); and c. reacting the product compound of b) with an oxidising reagent thus generating a compound as defined herein.

One method for manufacturing the compounds or compounds for use according to the present disclosure comprises the steps of a. reacting a compound having formula (GM.III)

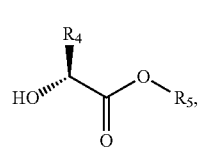
(GM.III)

wherein $R^4$ and $R^5$ are defined herein with a compound having formula (GM.XI)

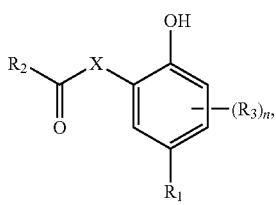

(GM.XI)

wherein $R^1$, $R^2$, $R^3$, n and X are as defined herein to generate a compound having formula (GM.XII)

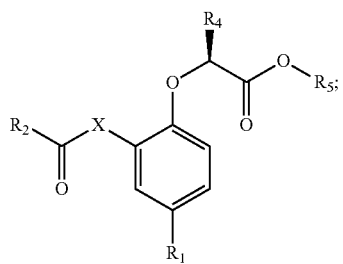

(GM.XII)

b. converting the keto group of product compound of a) into an alkyl-difluoro group; and
c. reacting the product compound of b) with an ester hydrolysing reagent thus generating a compound as defined herein.

One method for manufacturing the compounds or compounds for use according to the present disclosure comprises the steps of
a. reacting a compound having formula (GM.XIII)

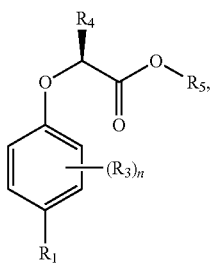

(GM.XIII)

wherein $R^1$, $R^3$, $R^4$, $R^5$ and n are defined herein under acylating conditions to generate a compound having formula (GM.XII)

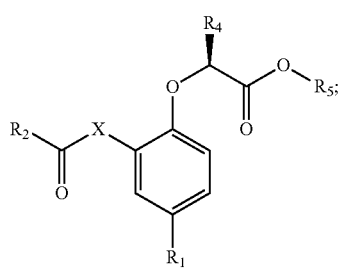

(GM.XII)

b. converting the keto group of product compound of a) into an alkyl-difluoro group wherein X is a bond and $R^2$ is defined herein; and
c. reacting the product compound of b) with an ester hydrolysing reagent thus generating a compound as defined herein.

One method for manufacturing the compounds or compounds for use according to the present disclosure comprises the steps of
a. reacting a compound having formula (GM.IX)

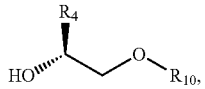

(GM.IX)

wherein $R^4$ and $R^9$ are defined herein with a compound having formula (GM.XV)

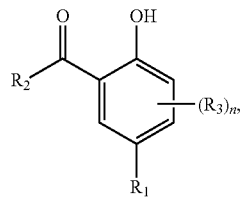

(GM.XV)

wherein $R^1$, $R^2$, $R^3$ and n are defined herein to generate a compound having formula (GM.XIV)

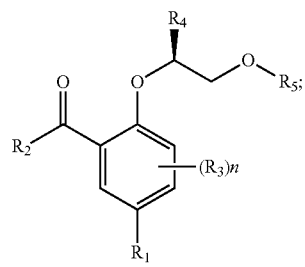

(GM.XII)

b. converting the keto group of product compound of a) into an alkyl-difluoro group;
c. removing the protecting group $R_{10}$ of product compound of b); and
d. reacting the product of c) with an oxidising reagent thus generating a compound as defined herein.

Items
1. A compound of Formula (I):

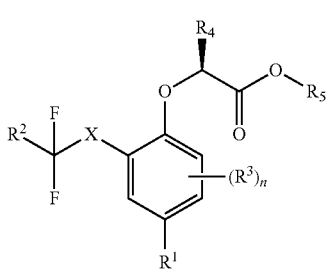

Formula (I)

wherein:
- $R^1$ is selected from the group consisting of $C_{1-2}$ alkyl, $C_2$ alkenyl, $C_2$ alkynyl, CN, $CF_3$, $NO_2$, F, Cl, Br, and I;
- $R^2$ is selected from the group consisting of $C_{1-5}$ alkyl optionally be substituted with one or more, identical or different, substituents $R^6$, $C_{2-5}$ alkenyl optionally be substituted with one or more, identical or different, substituents $R^6$, $C_{2-5}$ alkynyl optionally be substituted with one or more, identical or different, substituents $R^6$, $C_{3-5}$ cycloalkyl optionally substituted with one or more, identical or different, substituents $R^6$, phenyl optionally substituted with one or more, identical or different, substituents $R^9$, and 5-6 membered aromatic heterocycle optionally substituted with one or more, identical or different, substituents $R^7$;
- $R^3$ is selected from the group consisting of deuterium, Cl and F;
- $R^4$ is selected from the group consisting of H, deuterium, $C_{1-5}$ alkyl, $C_{2-5}$ alkenyl, $C_{2-5}$ alkynyl, and $C_{3-5}$ cycloalkyl, each of which may be optionally substituted with one or more, identical or different, substituents $R^7$;
- $R^5$ is selected from the group consisting of H, $C_{1-5}$ alkyl optionally substituted with one or more, identical or different, substituents $R^8$, $C_{2-5}$ alkenyl optionally substituted with one or more, identical or different, substituents $R^8$, $C_{2-5}$ alkynyl optionally substituted with one or more, identical or different, substituents $R^8$, $C_{3-6}$ cycloalkyl optionally substituted with one or more, identical or different, substituents $R^8$, phenyl optionally substituted with one or more, identical or different, substituents $R^9$, and benzyl optionally substituted with one or more, identical or different, substituents $R^9$;
- $R^6$ is independently selected from the group consisting of deuterium, F, —CN, —O—$C_{1-5}$ alkyl, —O—$C_{3-5}$ cycloalkyl, —S—$C_{1-5}$ alkyl, and —S—$C_{3-5}$ cycloalkyl, wherein the —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;
- $R^7$ is independently selected from the group consisting deuterium, F, Cl, —CN, $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, wherein the $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;
- $R^8$ is independently selected from the group consisting of deuterium and F;
- $R^9$ is independently selected from the group consisting of deuterium, methoxy, nitro, cyano, Cl, Br, I, and F;
- X is a bond or selected from the group consisting of —O—, —S—, —$CH_2$—, —$CHR^6$—, and —$C(R^6)_2$—; and
- n is an integer 0, 1, 2, or 3;
or a pharmaceutically acceptable salt, hydrate, polymorph, tautomer, or solvate thereof.

2. The compound according to any one of the preceding items, wherein the compound is of Formula (I):

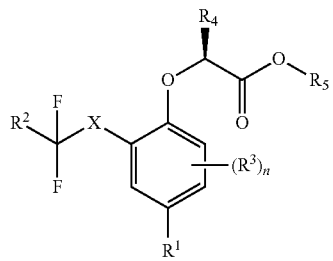

Formula (I)

wherein:
- $R^1$ is selected from the group consisting of F, Cl, Br, and I;
- $R^2$ is selected from the group consisting of $C_{1-5}$ alkyl optionally be substituted with one or more, identical or different, substituents $R^6$, $C_{2-5}$ alkenyl optionally be substituted with one or more, identical or different, substituents $R^6$, $C_{2-5}$ alkynyl optionally be substituted with one or more, identical or different, substituents $R^6$, $C_{3-5}$ cycloalkyl optionally substituted with one or more, identical or different, substituents $R^6$, phenyl optionally substituted with one or more, identical or different, substituents $R^9$, and 5-6 membered aromatic heterocycle optionally substituted with one or more, identical or different, substituents $R^7$;
- $R^3$ is selected from the group consisting of deuterium and F;
- $R^4$ is selected from the group consisting of H, deuterium, $C_{1-5}$ alkyl, $C_{2-5}$ alkenyl, $C_{2-5}$ alkynyl, and $C_{3-5}$ cycloalkyl, each of which may be optionally substituted with one or more, identical or different, substituents $R^7$;
- $R^5$ is selected from the group consisting of H, $O_{1-5}$ alkyl optionally substituted with one or more, identical or different, substituents $R^8$, $C_{2-5}$ alkenyl optionally substituted with one or more, identical or different, substituents $R^8$, $C_{2-5}$ alkynyl optionally substituted with one or more, identical or different, substituents $R^8$, $C_{3-6}$ cycloalkyl optionally substituted with one or more, identical or different, substituents $R^8$, phenyl optionally substituted with one or more, identical or different, substituents $R^9$, and benzyl optionally substituted with one or more, identical or different, substituents $R^9$;
- $R^6$ is independently selected from the group consisting of —O—$C_{1-5}$ alkyl, —O—$C_{3-5}$ cycloalkyl, —S—$C_{1-5}$ alkyl, and —S—$C_{3-5}$ cycloalkyl, each of which may optionally be substituted with one or more, identical or different, substituents $R^8$, deuterium, F and —CN;
- $R^7$ is independently selected from the group consisting $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, each of which may optionally be substituted with one or more, identical or different, substituents $R^8$, of deuterium, F and —CN;
- $R^8$ is independently selected from the group consisting of deuterium and F;
- $R^9$ is independently selected from the group consisting of deuterium, methoxy, nitro, cyano, Cl, Br, I, and F;

X is a bond or selected from the group consisting of —O—, —S—, —CH$_2$—, —CHR$^6$—, and —C(R$^6$)$_2$—; and n is an integer 0, 1, 2, or 3;

or a pharmaceutically acceptable salt, hydrate, polymorph, tautomer, or solvate thereof.

3. The compound according to any one of the preceding items, wherein the compound is of Formula (II):

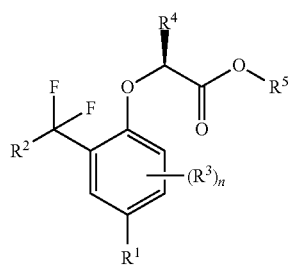

Formula (II)

wherein:
R$^1$ is selected from the group consisting of C$_{1-2}$ alkyl, C$_2$ alkenyl, C$_2$ alkynyl, CN, CF$_3$, NO$_2$, F, Cl, Br, and I;

R$^2$ is selected from the group consisting of C$_{1-5}$ alkyl optionally be substituted with one or more, identical or different, substituents R$^6$, C$_{2-5}$ alkenyl optionally be substituted with one or more, identical or different, substituents R$^6$, C$_{2-5}$ alkynyl optionally be substituted with one or more, identical or different, substituents R$^6$, C$_{3-5}$ cycloalkyl optionally substituted with one or more, identical or different, substituents R$^6$, phenyl optionally substituted with one or more, identical or different, substituents R$^9$, and 5-6 membered aromatic heterocycle optionally substituted with one or more, identical or different, substituents R$^7$;

R$^3$ is selected from the group consisting of deuterium, Cl and F;

R$^4$ is selected from the group consisting of H, deuterium, C$_{1-5}$ alkyl, C$_{2-5}$ alkenyl, C$_{2-5}$ alkynyl, and C$_{3-5}$ cycloalkyl, each of which may be optionally substituted with one or more, identical or different, substituents R$^7$;

R$^5$ is selected from the group consisting of H, C$_{1-5}$ alkyl optionally substituted with one or more, identical or different, substituents R$^8$, C$_{2-5}$ alkenyl optionally substituted with one or more, identical or different, substituents R$^8$, C$_{2-5}$ alkynyl optionally substituted with one or more, identical or different, substituents R$^8$, C$_{3-6}$ cycloalkyl optionally substituted with one or more, identical or different, substituents R$^8$, phenyl optionally substituted with one or more, identical or different, substituents R$^9$, and benzyl optionally substituted with one or more, identical or different, substituents R$^9$;

R$^6$ is independently selected from the group consisting of deuterium, F, —CN, —O—C$_{1-5}$ alkyl, —O—C$_{3-5}$ cycloalkyl, —S—C$_{1-5}$ alkyl, and —S—C$_{3-5}$ cycloalkyl, wherein the —O—C$_{1-5}$ alkyl, —O—C$_{3-5}$ cycloalkyl, —S—C$_{1-5}$ alkyl, and —S—C$_{3-5}$ cycloalkyl may optionally be substituted with one or more, identical or different, substituents R$^8$;

R$^7$ is independently selected from the group consisting deuterium, F, Cl, —CN, C$_{3-5}$ cycloalkyl, —O—C$_{1-5}$ alkyl, —O—C$_{3-5}$ cycloalkyl, —S—C$_{1-5}$ alkyl, and —S—C$_{3-5}$ cycloalkyl, wherein the C$_{3-5}$ cycloalkyl, —O—C$_{1-5}$ alkyl, —O—C$_{3-5}$ cycloalkyl, —S—C$_{1-5}$ alkyl, and —S—C$_{3-5}$ cycloalkyl may optionally be substituted with one or more, identical or different, substituents R$^8$;

R$^8$ is independently selected from the group consisting of deuterium and F;

R$^9$ is independently selected from the group consisting of deuterium, methoxy, nitro, cyano, Cl, Br, I, and F; and n is an integer 0, 1, 2, or 3;

or a pharmaceutically acceptable salt, hydrate, polymorph, tautomer, or solvate thereof.

4. The compound according to any one of the preceding items, wherein the compound is of Formula (II):

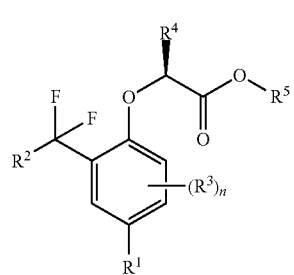

Formula (II)

wherein:
R$^1$ is selected from the group consisting of F, Cl, Br, and I;

R$^2$ is selected from the group consisting of C$_{1-5}$ alkyl optionally be substituted with one or more, identical or different, substituents R$^6$, C$_{2-5}$ alkenyl optionally be substituted with one or more, identical or different, substituents R$^6$, C$_{2-5}$ alkynyl optionally be substituted with one or more, identical or different, substituents R$^6$, C$_{3-5}$ cycloalkyl optionally substituted with one or more, identical or different, substituents R$^6$, phenyl optionally substituted with one or more, identical or different, substituents R$^9$, and 5-6 membered aromatic heterocycle optionally substituted with one or more, identical or different, substituents R$^7$;

R$^3$ is selected from the group consisting of deuterium and F;

R$^4$ is selected from the group consisting of H, deuterium, C$_{1-5}$ alkyl, C$_{2-5}$ alkenyl, C$_{2-5}$ alkynyl, and C$_{3-5}$ cycloalkyl, each of which may be optionally substituted with one or more, identical or different, substituents R$^7$;

R$^5$ is selected from the group consisting of H, C$_{1-5}$ alkyl optionally substituted with one or more, identical or different, substituents R$^8$, C$_{2-5}$ alkenyl optionally substituted with one or more, identical or different, substituents R$^8$, C$_{2-5}$ alkynyl optionally substituted with one or more, identical or different, substituents R$^8$, C$_{3-6}$ cycloalkyl optionally substituted with one or more, identical or different, substituents R$^8$, phenyl optionally substituted with one or more, identical or different, substituents R⁹, and benzyl optionally substituted with one or more, identical or different, substituents R⁹;

R⁶ is independently selected from the group consisting of —O—$C_{1-5}$ alkyl, —O—$C_{3-5}$ cycloalkyl, —S—$C_{1-5}$ alkyl, and —S—$C_{3-5}$ cycloalkyl, each of which may optionally be substituted with one or more, identical or different, substituents R⁸, deuterium, F and —CN;

R⁷ is independently selected from the group consisting $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, each of which may optionally be substituted with one or more, identical or different, substituents R⁸, of deuterium, F and —CN;

R⁸ is independently selected from the group consisting of deuterium and F;

R⁹ is independently selected from the group consisting of deuterium, methoxy, nitro, cyano, Cl, Br, I, and F; and n is an integer 0, 1, 2, or 3;

or a pharmaceutically acceptable salt, hydrate, polymorph, tautomer, or solvate thereof.

5. The compound according to any one of the preceding items, wherein the compound is of Formula (II):

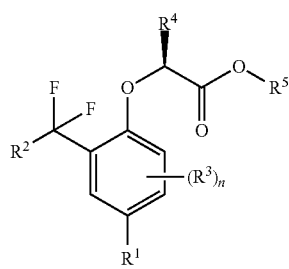

Formula (II)

wherein:
R¹ is selected from the group consisting of $C_2$ alkenyl, $C_2$ alkynyl, NO₂, F, Cl, Br, and I;

R² is $C_{1-5}$ alkyl optionally be substituted with one or more, identical or different, substituents R⁶;

R³ is selected from the group consisting of deuterium, Cl and F;

R⁴ is selected from the group consisting of H, deuterium, $C_{1-5}$ alkyl and $C_{2-5}$ alkynyl each of which may be optionally substituted with one or more, identical or different, substituents R⁷;

R⁵ is H;

R⁶ is independently selected from the group consisting of deuterium, F, —CN, —O—$C_{1-5}$ alkyl, —O—$C_{3-5}$ cycloalkyl, —S—$C_{1-5}$ alkyl, and —S—$C_{3-5}$ cycloalkyl, wherein the —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents R⁸;

R⁷ is independently selected from the group consisting deuterium, F, Cl, —CN, $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, wherein the $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents R⁸;

R⁸ is independently selected from the group consisting of deuterium and F; and n is an integer 0, 1, 2, or 3;

or a pharmaceutically acceptable salt, hydrate, polymorph, tautomer, or solvate thereof.

6. The compound according to any one of the preceding items, wherein the compound is of Formula (III):

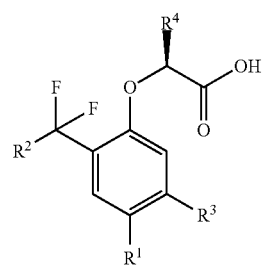

Formula (III)

wherein:
R¹ is selected from the group consisting of $C_2$ alkenyl, $C_2$ alkynyl, NO₂, F, Cl, Br, and I;

R² is $C_{1-5}$ alkyl optionally be substituted with one or more, identical or different, substituents R⁶;

R³ is selected from the group consisting of H, deuterium, Cl and F;

R⁴ is selected from the group consisting of H, deuterium, $C_{1-5}$ alkyl and $C_{2-5}$ alkynyl each of which may be optionally substituted with one or more, identical or different, substituents R⁷;

R⁶ is independently selected from the group consisting of deuterium, F, —CN, —O—$C_{1-5}$ alkyl, —O—$C_{3-5}$ cycloalkyl, —S—$C_{1-5}$ alkyl, and —S—$C_{3-5}$ cycloalkyl, wherein the —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents R⁸;

R⁷ is independently selected from the group consisting deuterium, F, Cl, —CN, $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, wherein the $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents R⁸;

R⁸ is independently selected from the group consisting of deuterium and F;

or a pharmaceutically acceptable salt, hydrate, polymorph, tautomer, or solvate thereof.

7. The compound according to any one of the preceding items, wherein the compound is of Formula (III):

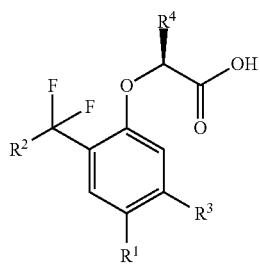

Formula (III)

wherein:
R$^1$ is selected from the group consisting of C$_2$ alkenyl, C$_2$ alkynyl, NO$_2$, F, Cl, Br, and I;
R$^2$ is C$_{1-3}$ alkyl optionally be substituted with one or more, identical or different, substituents R$^8$;
R$^3$ is selected from the group consisting of H, deuterium, Cl and F;
R$^4$ is selected from the group consisting of H, deuterium, C$_{1-3}$ alkyl and C$_{2-3}$ alkynyl each of which may be optionally substituted with one or more, identical or different, substituents R$^8$; and
R$^8$ is independently selected from the group consisting of deuterium and F;
or a pharmaceutically acceptable salt, hydrate, polymorph, tautomer, or solvate thereof.

8. The compound according to any one of the preceding items, wherein R$^1$ is C$_{1-2}$ alkyl.
9. The compound according to any one of the preceding items, wherein R$^1$ is C$_2$ alkenyl.
10. The compound according to any one of the preceding items, wherein R$^1$ is C$_2$ alkynyl.
11. The compound according to any one of the preceding items, wherein R$^1$ is CN.
12. The compound according to any one of the preceding items, wherein R$^1$ is CF$_3$.
13. The compound according to any one of the preceding items, wherein R$^1$ is NO$_2$.
14. The compound according to any one of the preceding items, wherein R$^1$ is Cl or Br.
15. The compound according to any one of the preceding items, wherein R$^1$ is Cl.
16. The compound according to any one of the preceding items, wherein R$^1$ is Br.
17. The compound according to any one of the preceding items, wherein R$^2$ is C$_{1-5}$ alkyl optionally substituted with one or more, identical or different, substituents R$^6$.
18. The compound according to any one of the preceding items, wherein R$^2$ is C$_{1-3}$ alkyl optionally substituted with one or more, identical or different, substituents R$^6$.
19. The compound according to any one of the preceding items, wherein R$^2$ is selected from the group consisting of methyl, ethyl, n-propyl and isopropyl.
20. The compound according to any one of the preceding items, wherein R$^2$ is selected from the group consisting of methyl, ethyl, n-propyl and isopropyl, wherein the methyl, ethyl, n-propyl or isopropyl group is substituted with one or more, identical or different, substituents R$^6$.
21. The compound according to any one of the preceding items, wherein R$^2$ is C$_{2-5}$ alkenyl optionally substituted with one or more, identical or different, substituents R$^6$.
22. The compound according to any one of the preceding items, wherein R$^2$ is C$_{2-5}$ alkynyl optionally substituted with one or more, identical or different, substituents R$^6$.
23. The compound according to any one of the preceding items, wherein R$^2$ is C$_{3-5}$ cycloalkyl optionally substituted with one or more, identical or different, substituents R$^6$.
24. The compound according to any one of the preceding items, wherein R$^2$ is phenyl optionally substituted with one or more, identical or different, substituents R$^9$.
25. The compound according to any one of the preceding items, wherein R$^2$ is 5-6 membered aromatic heterocycle optionally substituted with one or more, identical or different, substituents R$^7$.
26. The compound according to any one of the preceding items, wherein R$^3$ is deuterium.
27. The compound according to any one of the preceding items, wherein R$^3$ is F.
28. The compound according to any one of the preceding items, wherein R$^3$ is Cl.
29. The compound according to any one of the preceding items, wherein R$^4$ is H.
30. The compound according to any one of the preceding items, wherein R$^4$ is C$_{1-5}$ alkyl optionally substituted with one or more, identical or different, substituents R$^7$.
31. The compound according to any one of the preceding items, wherein R$^4$ is selected from the group consisting of methyl, ethyl, n-propyl and isopropyl.
32. The compound according to any one of the preceding items, wherein R$^4$ is Me.
33. The compound according to any one of the preceding items, wherein R$^4$ is —CH$_2$F.
34. The compound according to any one of the preceding items, wherein R$^4$ is selected from the group consisting of methyl, ethyl, n-propyl and isopropyl, wherein the methyl, ethyl, n-propyl or isopropyl group is substituted with one or more, identical or different, substituents R$^7$.
35. The compound according to any one of the preceding items, wherein R$^4$ is —CH$_2$—O—C$_{1-5}$ alkyl optionally substituted with one or more, identical or different, substituents R$^7$.
36. The compound according to any one of the preceding items, wherein R$^4$ is —CH$_2$—S—C$_{1-5}$ alkyl optionally substituted with one or more, identical or different, substituents R$^7$.
37. The compound according to any one of the preceding items, wherein R$^4$ is C$_{2-5}$ alkenyl optionally be substituted with one or more, identical or different, substituents R$^7$.
38. The compound according to any one of the preceding items, wherein R$^4$ is C$_{2-5}$ alkynyl optionally be substituted with one or more, identical or different, substituents R$^7$.
39. The compound according to any one of the preceding items, wherein R$^4$ is —CH$_2$—C$_{2-4}$ alkynyl optionally substituted with one or more, identical or different, substituents R$^7$.
40. The compound according to any one of the preceding items, wherein R$^4$ is C$_{3-5}$ cycloalkyl optionally substituted with one or more, identical or different, substituents R$^7$.
41. The compound according to any one of the preceding items, wherein R$^5$ is H.
42. The compound according to any one of the preceding items, wherein R$^5$ is C$_{1-5}$ alkyl optionally substituted with one or more, identical or different, substituents R$^8$.

43. The compound according to any one of the preceding items, wherein $R^5$ is $C_{3-6}$ cycloalkyl optionally substituted with one or more, identical or different, substituents $R^8$.

44. The compound according to any one of the preceding items, wherein $R^5$ is phenyl optionally substituted with one or more, identical or different, substituents $R^9$.

45. The compound according to any one of the preceding items, wherein $R^5$ is benzyl optionally substituted with one or more, identical or different, substituents $R^9$.

46. The compound according to any one of the preceding items, wherein $R^6$ is deuterium.

47. The compound according to any one of the preceding items, wherein $R^6$ is F.

48. The compound according to any one of the preceding items, wherein $R^6$ is CN.

49. The compound according to any one of the preceding items, wherein $R^6$ is —O—$C_{1-5}$ alkyl optionally substituted with one or more, identical or different, substituents $R^8$.

50. The compound according to any one of the preceding items, wherein $R^6$ is —O—$C_{3-5}$ cycloalkyl optionally substituted with one or more, identical or different, substituents $R^8$.

51. The compound according to any one of the preceding items, wherein $R^6$ is —S—$C_{1-5}$ alkyl optionally substituted with one or more, identical or different, substituents $R^8$.

52. The compound according to any one of the preceding items, wherein $R^6$ is —S—$C_{3-5}$ cycloalkyl optionally substituted with one or more, identical or different, substituents $R^8$.

53. The compound according to any one of the preceding items, wherein $R^7$ is deuterium.

54. The compound according to any one of the preceding items, wherein $R^7$ is F.

55. The compound according to any one of the preceding items, wherein $R^7$ is CN.

56. The compound according to any one of the preceding items, wherein $R^7$ is —O—$C_{1-5}$ alkyl optionally substituted with one or more, identical or different, substituents $R^8$.

57. The compound according to any one of the preceding items, wherein $R^7$ is —O—$C_{3-5}$ cycloalkyl optionally substituted with one or more, identical or different, substituents $R^8$.

58. The compound according to any one of the preceding items, wherein $R^7$ is —S—$C_{1-5}$ alkyl optionally substituted with one or more, identical or different, substituents $R^8$.

59. The compound according to any one of the preceding items, wherein $R^7$ is —S—$C_{3-5}$ cycloalkyl optionally substituted with one or more, identical or different, substituents $R^8$.

60. The compound according to any one of the preceding items, wherein $R^7$ is $C_{3-5}$ cycloalkyl optionally substituted with one or more, identical or different, substituents $R^8$.

61. The compound according to any one of the preceding items, wherein $R^8$ is deuterium.

62. The compound according to any one of the preceding items, wherein $R^8$ is F.

63. The compound according to any one of the preceding items, wherein n is 0.

64. The compound according to any one of the preceding items, wherein n is 1.

65. The compound according to any one of the preceding items, wherein n is 2.

66. The compound according to any one of the preceding items, wherein n is 3.

67. The compound according to any one of the preceding items, wherein X is a bond.

68. The compound according to any one of the preceding items, wherein X is —O—.

69. The compound according to any one of the preceding items, wherein X is —S—.

70. The compound according to any one of the preceding items, wherein X is —$CH_2$—.

71. The compound according to any one of the preceding items, wherein X is —$CHR^6$—

72. The compound according to any one of the preceding items, wherein X is —$C(R^8)_2$—.

73. The compound according to any one of the preceding items, wherein $R^1$ is Cl or Br, $R^2$ is selected from the group consisting of methyl, ethyl, n-propyl, and iso-propyl optionally substituted with one or more, identical or different, substituents $R^7$, and $R^5$ is H.

74. The compound according to any one of the preceding items, wherein, the compound is selected from the list consisting of:

(2S)-2-[4-bromo-2-(1,1-difluoroethyl)phenoxy]-3-cyclopropylpropanoic acid;

(2S)-2-[4-bromo-2-(1,1-difluoroethyl)phenoxy]butanoic acid;

(2S)-2-[4-bromo-2-(1,1-difluoropropyl)phenoxy]propanoic acid;

(2S)-2-[4-bromo-2-(1,1-difluoroethyl)phenoxy]propanoic acid;

(2S)-2-[4-chloro-2-(1,1-difluoropropyl)phenoxy]propanoic acid;

2-[4-bromo-2-(1,1-difluoropropyl)phenoxy]acetic acid;

(2S)-2-[4-bromo-2-(1,1-difluoro-2-methylpropyl)phenoxy]propanoic acid;

(2S)-2-{4-bromo-2-[difluoro(phenyl)methyl]phenoxy}propanoic acid;

(2S)-2-[4-bromo-2-(1,1-difluoroethyl)phenoxy]-2-cyclopropylacetic acid;

(2S)-2-[4-bromo-2-(1,1-difluorobutyl)phenoxy]propanoic acid;

(2R)-2-[4-bromo-2-(1,1-difluoropropyl)phenoxy]-3-fluoropropanoic acid;

(2S)-2-[4-bromo-2-(cyclopropyldifluoromethyl)phenoxy]propanoic acid;

(2S)-2-{4-bromo-2-[difluoro(1,3-thiazol-2-yl)methyl]phenoxy}propanoic acid;

(2S)-2-[4-bromo-2-(1,1-difluoroethyl)phenoxy]pent-4-ynoic acid;

(2S)-2-[4-bromo-2-(cyclobutyldifluoromethyl)phenoxy]propanoic acid;

(2R)-2-[4-bromo-2-(1,1-difluoroethyl)phenoxy]-3-fluoropropanoic acid;

(2R)-2-[4-bromo-2-(1,1-difluoropropyl)phenoxy]-3-chloropropanoic acid;

(2S)-2-[4-bromo-2-(1,1-difluoropropyl)phenoxy]pent-4-ynoic acid;

(2S)-2-[4-chloro-2-(1,1-difluoroethyl)phenoxy]pent-4-ynoic acid;

(2S)-2-[2-(1,1-difluoropropyl)-4-iodophenoxy]propanoic acid;

(2S)-2-[4-bromo-2-(1,1-difluoropropyl)phenoxy]($2$-$^2$H)propanoic acid;

(2R)-2-[4-chloro-2-(1,1-difluoropropyl)phenoxy]-3-fluoropropanoic acid;

(2S)-2-[2-(1,1-difluoropropyl)-4-ethynylphenoxy]propanoic acid;
(2S)-2-[4-bromo-2-(1,1-difluoropropyl)-5-fluorophenoxy]propanoic acid;
(2S)-2-[4-bromo-2-(1,1-difluoropropyl)-6-fluorophenoxy]propanoic acid;
(2S)-2-[4-cyano-2-(1,1-difluoropropyl)phenoxy]propanoic acid;
(2R)-2-[4-chloro-2-(1,1-difluoroethyl)phenoxy]-3-fluoropropanoic acid;
(2S)-2-[4-bromo-2-(1,1-difluoroethyl)-5-fluorophenoxy]propanoic acid;
(2S)-2-[4-bromo-2-(1,1-difluoropropyl)(3,5,6-$^2H_3$)phenoxy]propanoic acid;
2-[4-bromo-2-(1,1-difluoropropyl)-5-fluorophenoxy]acetic acid;
(2S)-2-[4-chloro-2-(1,1-difluoropropyl)-5-fluorophenoxy]propanoic acid;
(2S)-2-[2-(1,1-difluoropropyl)-4-(trifluoromethyl)phenoxy]propanoic acid;
(2R)-2-[4-bromo-2-(1,1-difluoropropyl)-5-fluorophenoxy]-3-fluoropropanoic acid;
(2S)-2-[2-(1,1-difluoropropyl)-4-ethenylphenoxy]propanoic acid;
2-[4-bromo-2-(1,1-difluoroethyl)-5-fluorophenoxy]acetic acid;
(2S)-2-[2-(1,1-difluoropropyl)-4-methylphenoxy]propanoic acid;
2-[4-bromo-2-(1,1-difluoro-2-methylpropyl)phenoxy]acetic acid; 2-[4-chloro-2-(1,1-difluoropropyl)-5-fluorophenoxy]acetic acid;
(2S)-2-[2-(1,1-difluoroethyl)-4-ethynylphenoxy]propanoic acid;
(2R)-2-[4-chloro-2-(1,1-difluoropropyl)-5-fluorophenoxy]-3-fluoropropanoic acid;
(2S)-2-[4,5-dichloro-2-(1,1-difluoropropyl)phenoxy]propanoic acid;
(2R)-2-[4-bromo-2-(1,1-difluoroethyl)-5-fluorophenoxy]-3-fluoropropanoic acid;
(2R)-2-[4,5-dichloro-2-(1,1-difluoroethyl)phenoxy]-3-fluoropropanoic acid;
(2S)-2-[4-bromo-2-(1,1-difluoroethyl)phenoxy]-4-fluorobutanoic acid;
(2S)-2-[4-bromo-2-(1,1-difluoro-2-methylpropyl)phenoxy]butanoic acid;
(2S)-2-[2-(1,1-difluoropropyl)-4-ethenyl-5-fluorophenoxy]propanoic acid;
(2S)-2-[4-bromo-2-(1,1-difluoropropyl)-5-fluorophenoxy]butanoic acid;
(2S)-2-[4-chloro-2-(1,1-difluoropropyl)-5-fluorophenoxy]butanoic acid;
(2R)-2-[5-chloro-2-(1,1-difluoropropyl)-4-fluorophenoxy]-3-fluoropropanoic acid;
(2S)-2-[2-(1,1-difluoropropyl)-4-nitrophenoxy]propanoic acid;
(2S)-2-[5-chloro-2-(1,1-difluoropropyl)-4-fluorophenoxy]propanoic acid;
(2S)-2-[4-bromo-2-(1,1-difluoropropyl)phenoxy]-4-methoxybutanoic acid;
(2R)-2-[2-(1,1-difluoropropyl)-4,5-difluorophenoxy]-3-fluoropropanoic acid;
(2S)-2-[2-(1,1-difluoropropyl)-4,5-difluorophenoxy]propanoic acid; and
(2S)-2-[4-bromo-2-(1,1-difluoro-3-methoxypropyl)phenoxy]propanoic acid.

75. The compound according to any one of the preceding items, wherein the compound has activity on ClC-1 receptor.

76. The compound according to any one of the preceding items, wherein the compound is an inhibitor of the ClC-1 ion channel.

77. The compound according to item 80, wherein the $EC_{50}$<50 µM, for example<40 µM, for example<30 µM, for example<20 µM, for example<15 µM, for example<10 µM, and for example<5 µM.

78. The compound according to any one of the preceding items, wherein the recovery of force in muscles with neuromuscular dysfunction is >5%, for example>10%, for example>15%, for example>20%, for example>25%, for example>30% and for example>35%.

79. The compound according to any one of the preceding items, wherein the compound improves the recovered force in isolated rat soleus muscles after exposure to tubocurarine.

80. A composition comprising the compound according to any one of the preceding items.

81. The composition according to any one of the preceding items, wherein the composition is a pharmaceutical composition.

82. The compound or the composition according to any one of the preceding items, for use as a medicament.

83. The composition according to any one of the preceding items, wherein the composition further comprises a pharmaceutically acceptable carrier.

84. The composition according to any one of the preceding items, wherein the composition further comprises at least one further active agent.

85. The composition according to any one of the preceding items, wherein said further active agent is suitable for treating, preventing or ameliorating said neuromuscular disorder.

86. The composition according to any one of the preceding items, wherein said further active agent is an acetylcholine esterase inhibitor.

87. The composition according to any one of the preceding items, wherein said acetylcholine esterase inhibitor is selected from the group consisting of delta-9-tetrahydrocannabinol, carbamates, physostigmine, neostigmine, pyridostigmine, ambenonium, demecarium, rivastigmine, phenanthrene derivatives, galantamine, piperidines, donepezil, tacrine, edrophonium, huperzine, ladostigil, ungeremine and lactucopicrin.

88. The composition according to any one of the preceding items, wherein said acetylcholine esterase inhibitor is neostigmine or pyridostigmine.

89. The composition according to any one of the preceding items, wherein said further active agent is sugammadex.

90. The composition according to any one of the preceding items, wherein said further active agent is tirasemtiv or CK-2127107.

91. The composition according to any one of the preceding items, wherein said further active agent is 3,4-aminopyridine.

92. A method for manufacturing the compound according to any one of the preceding items, the method comprising the steps of a. reacting a compound having formula (GM.III)

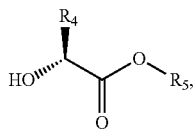
(GM.III)

wherein $R^4$ and $R^5$ are defined in any one of the preceding items with a compound having formula (GM.II) under Mitsunobu or similar reaction conditions

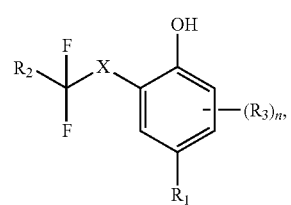
(GM.II)

wherein $R^1$, $R^2$, $R^3$, n and X are as defined in any one of the preceding items to generate a compound having formula (GM.IV)

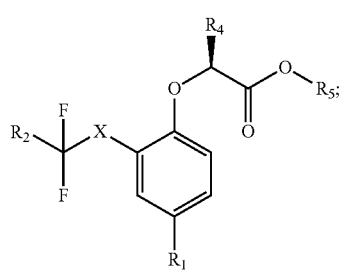
(GM.IV)

and b. reacting the product compound of a) with an ester hydrolysing reagent thus generating a compound according to any one of the preceding items.

93. A method for manufacturing the compound according to any one of the preceding items, the method comprising the steps of a. reacting a compound having formula (GM. VI)

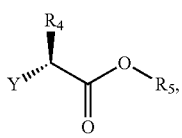
(GM.VI)

wherein $R^4$ and $R^5$ are defined herein and Y is a leaving group (for example a methanesulphonate or a tosylate) with a compound having formula (GM.II) under conditions which involve a suitable base such a sterically hindered amine or an alkali metal carbonate

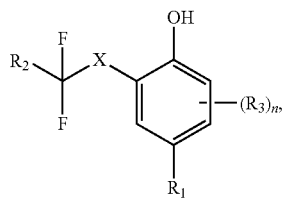
(GM.II)

wherein $R^1$, $R^2$, $R^3$, n and X are as defined in any one of the preceding items to generate a compound having formula (GM.IV)

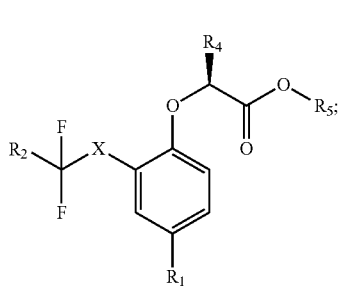
(GM.IV)

and b. reacting the product compound of a) with an ester hydrolysing reagent thus generating a compound according to any one of the preceding items.

94. A method for manufacturing the compound according to any one of the preceding items, the method comprising the steps of a. reacting a compound having formula (GM. VIII)

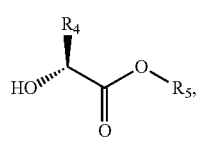
(GM.VIII)

wherein $R^4$ and $R^5$ are defined in any one of the preceding items with a compound having formula (GM.VII)

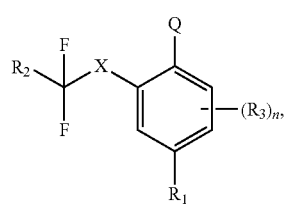
(GM.VII)

wherein $R^1$, $R^2$, $R^3$, n and X are as defined in any one of the preceding items and Q is a suitable leaving group such as a halogen such as fluorine or iodine to generate a compound having formula (GM.IV)

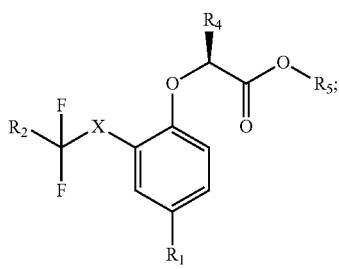

(GM.IV)

and
b. reacting the product compound of a) with an ester hydrolysing reagent thus generating a compound according to any one of the preceding items.
95. A method for manufacturing the compound according to any one of the preceding items, the method comprising the steps of
a. reacting a compound having formula (GM.IX)

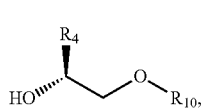

(GM.IX)

wherein $R^4$ is defined in any one of the preceding items and $R_{10}$ is a suitable protecting group, such as a silyl-containing, with a compound having formula (GM.II) under Mitsunobu or similar reaction conditions

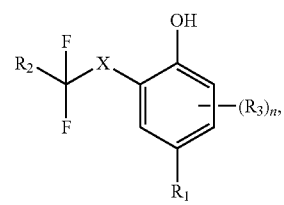

(GM.II)

wherein $R^1$, $R^2$, $R^3$, n and X are as defined in any one of the preceding items to generate a compound having formula (GM.X)

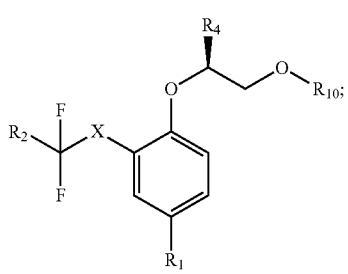

(GM.X)

b. removing the protecting group $R_{10}$ of product compound of a); and
c. reacting the product compound of b) with an oxidising reagent thus generating a compound according to any one of the preceding items.

96. A method for manufacturing the compound according to any one of the preceding items, the method comprising the steps of
a. reacting a compound having formula (GM.III)

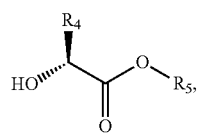

(GM.III)

wherein $R^4$ and $R^5$ are defined in any one of the preceding items with a compound having formula (GM.XI)

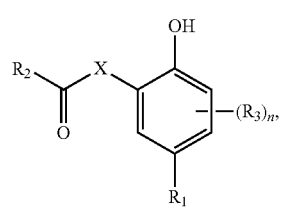

(GM.XI)

wherein $R^1$, $R^2$, $R^3$, n and X are as defined in any one of the preceding items to generate a compound having formula (GM.XII)

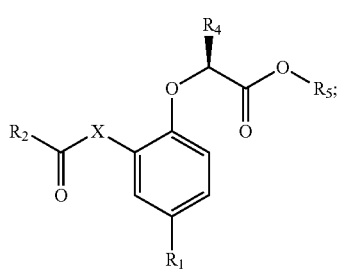

(GM.XII)

and
b. converting the keto group of product compound of a) into an alkyl-difluoro group; and
c. reacting the product compound of b) with an ester hydrolysing reagent thus generating a compound according to any one of the preceding items.

97. A method for manufacturing the compound according to any one of the preceding items, the method comprising the steps of a. reacting a compound having formula (GM. XIII)

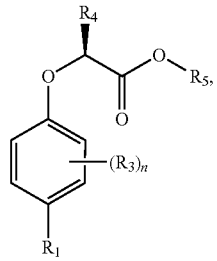
(GM.XIII)

wherein $R^1$, $R^3$, $R^4$, $R^5$ and n are defined in any one of the preceding items under acylating conditions to generate a compound having formula (GM.XII)

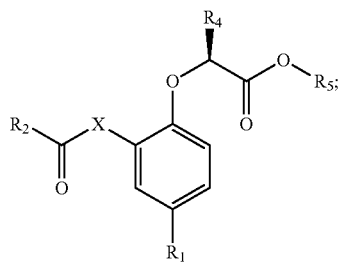
(GM.XII)

b. converting the keto group of product compound of a) into an alkyl-difluoro group wherein X is a bond and $R^2$ is defined in any one of the preceding items; and c. reacting the product compound of b) with an ester hydrolysing reagent thus generating a compound according to any one of the preceding items.

98. A method for manufacturing the compound according to any one of the preceding items, the method comprising the steps of a. reacting a compound having formula (GM.IX)

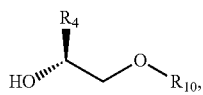
(GM.IX)

wherein $R^4$ and $R^9$ are defined herein with a compound having formula (GM.XV)

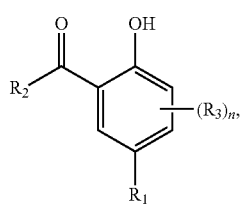
(GM.XV)

wherein $R^1$, $R^2$, $R^3$ and n are defined herein to generate a compound having formula (GM.XIV)

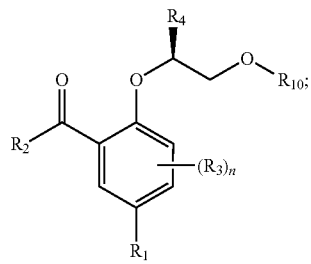
(GM.XVI)

b. converting the keto group of product compound of a) into an alkyl-difluoro group;

c. removing the protecting group $R_{10}$ of product compound of b); and d. reacting the product of c) with an oxidising reagent thus generating a compound as defined herein.

99. The compound according to any one of the preceding items for use in treating, ameliorating and/or preventing a neuromuscular disorder, and/or for use in reversing and/or ameliorating a neuromuscular blockade.

100. The compound for use according to any one of the preceding items wherein the neuromuscular disorder is myasthenia gravis.

101. The compound for use according to any one of the preceding items wherein the neuromuscular disorder is autoimmune myasthenia gravis.

102. The compound for use according to any one of the preceding items wherein the neuromuscular disorder is congenital myasthenia gravis.

103. The compound for use according to any one of the preceding items wherein the neuromuscular disorder is Lambert-Eaton Syndrome.

104. The compound for use according to any one of the preceding items wherein the neuromuscular disorder is critical illness myopathy.

105. The compound for use according to any one of the preceding items wherein the neuromuscular disorder is amyotrophic lateral sclerosis (ALS).

106. The compound for use according to any one of the preceding items wherein the neuromuscular disorder is spinal muscular atrophy (SMA).

107. The compound for use according to any one of the preceding items wherein the neuromuscular disorder is critical illness myopathy (CIM).

108. The compound for use according to any one of the preceding items wherein the neuromuscular disorder is Charcot-Marie tooth disease (CMT).

109. The compound for use according to any one of the preceding items wherein the neuromuscular disorder is sarcopenia.

110. The compound for use according to any one of the preceding items wherein the neuromuscular disorder arises from diabetic polyneuropathy.

111. The compound for use according to any one of the preceding items wherein the neuromuscular disorder is periodic paralysis.

112. The compound for use according to any one of the preceding items wherein the neuromuscular disorder is hypokalemic periodic paralysis or hyperkalemic periodic paralysis.

113. The compound for use according to any one of the preceding items wherein the neuromuscular disorder is myotubular myopathy.

114. The compound for use according to any one of the preceding items wherein the neuromuscular disorder is Duchenne muscular dystrophy.
115. The compound for use according to any one of the preceding items in the treatment of botulism poisoning.
116. The compound for use according to any one of the preceding items in the treatment of snake bites.
117. The compound for use according to any one of the preceding items in the treatment of nerve gas poisoning or prophylactically against nerve gas poisoning.
118. The compound for use according to any one of the preceding items wherein the neuromuscular disorder is selected from the group consisting of Guillain-Barré syndrome, poliomyelitis, post-polio syndrome, chronic fatigue syndrome, and critical illness polyneuropathy.
119. The compound for use according to any one of the preceding items, wherein the compound is for use in the treatment of symptoms of an indication selected from the group consisting of myasthenia gravis (such as autoimmune and congenital myasthenia gravis), Lambert-Eaton Syndrome, critical illness myopathy, amyotrophic lateral sclerosis (ALS), spinal muscular atrophy (SMA), critical illness myopathy (CIM), reversal diabetic polyneuropathy, Guillain-Barré syndrome, poliomyelitis, post-polio syndrome, chronic fatigue syndrome, critical illness polyneuropathy, periodic paralysis, sarcopenia, hypokalemic periodic paralysis, hyperkalemic periodic paralysis, myotubular myopathy and Duchenne muscular dystrophy.
120. The compound for use according to any one of the preceding items wherein the neuromuscular disorder has been induced by a neuromuscular blocking agent.
121. The compound for use according to any one of the preceding items, wherein the neuromuscular blockade is neuromuscular blockade after surgery.
122. The compound for use according to any one of the preceding items, wherein the neuromuscular blockade is drug induced.
123. The compound for use according to any one of the preceding items, wherein the drug is an antibiotic.
124. The compound for use according to any one of the preceding items, wherein the drug is a non-depolarizing neuromuscular blocker.
125. The compound for use according to any one of the preceding items, wherein said compound further has been modified in order to increase its half-life when administered to a patient, in particular its plasma half-life.
126. The compound for use according to any one of the preceding items, wherein said compound further comprises a moiety conjugated to said compound, thus generating a moiety-conjugated compound.
127. The compound for use according to any one of the preceding items, wherein the moiety-conjugated compound has a plasma and/or serum half-life being longer than the plasma and/or serum half-life of the non-moiety conjugated compound.
128. The compound for use according to any one of the preceding items, wherein the moiety conjugated to the compound is one or more type(s) of moieties selected from the group consisting of albumin, fatty acids, polyethylene glycol (PEG), acylation groups, antibodies and antibody fragments.
129. The compound for use according to any one of the preceding items, wherein said compound is comprised in a composition.
130. The compound for use according to any one of the preceding items, wherein the composition is a pharmaceutical composition.
131. The compound for use according to any one of the preceding items, wherein the composition further comprises a pharmaceutically acceptable carrier.
132. The compound for use according to any one of items, wherein the composition further comprises at least one further active agent.
133. The compound for use according to any one of the preceding items, wherein said further active agent is suitable for treating, preventing or ameliorating said neuromuscular disorder.
134. The compound for use according to any one of the preceding items, wherein said further active agent is an acetylcholine esterase inhibitor.
135. The compound for use according to any one of the preceding items, wherein said acetylcholine esterase inhibitor is selected from the group consisting of delta-9-tetrahydrocannabinol, carbamates, physostigmine, neostigmine, pyridostigmine, ambenonium, demecarium, rivastigmine, phenanthrene derivatives, galantamine, piperidines, donepezil, tacrine, edrophonium, huperzine, ladostigil, ungeremine and lactucopicrin.
136. The compound for use according to any one of the preceding items, wherein said acetylcholine esterase inhibitor is neostigmine or pyridostigmine.
137. The compound for use according to any one of the preceding items, wherein said further active agent is sugammadex.
138. The compound for use according to any one of the preceding items, wherein said further active agent is tirasemtiv.
139. The compound for use according to any one of the preceding items, wherein said further active agent is 3,4-aminopyridine.
140. A method of treating, preventing and/or ameliorating a neuromuscular disorder, said method comprising administering a therapeutically effective amount of the compound as defined in any one of the preceding items to a person in need thereof.
141. Use of a compound as defined in any one of the preceding items, for the manufacture of a medicament for the treatment, prevention and/or amelioration of a neuromuscular disorder, and/or for reversing and/or ameliorating of a neuromuscular blockade.
142. A method of reversing and/or ameliorating a neuromuscular blockade, said method comprising administering a therapeutically effective amount of the compound as defined in any one of the preceding items to a person in need thereof.
143. A method for recovery of neuromuscular transmission, said method comprising administering a therapeutically effective amount of the compound as defined in any one of the preceding items to a person in need thereof.
144. A method for recovering neuromuscular transmission, the method comprising administering a compound as defined in any one of the preceding items to an individual in need thereof.

EXAMPLES

Materials and Methods

Chemicals

Compounds for testing were obtained from different suppliers including Enamine, Vitas, and CanAm Bioresearch. For synthesis of particular compounds please see below.

NMR Spectra $^1$H-NMR and $^{19}$F-NMR spectra were recorded on a Bruker AM-300 spectrometer and were calibrated using residual nondeuterated solvent as internal reference. Spectra were processed using Spinworks version 4.0 (developed by Dr. Kirk Marat, Department of Chemistry, University of Manitoba), or on a Bruker 400 MHZ Ultrashield plus equipped with probe BBO 400 MHz S1 5 mm with Z gradient probe or a Bruker 500 MHz Avance III HD spectrometer, equipped with a Bruker 5 mm SmartProbe™, calibrated using residual non-deuterated solvent as internal reference and spectra processed using topspin version 3.2.7.

LC/MS System

Samples were analysed by direct inject on a Waters Acquity QDa Mass Detector with a Waters 2695 HPLC and a WATERS Micromass with a WATERS 2795 HPLC. Mass spectra was processed using WATERS Masslynx software. Mass spectra were recorded in ESI scan mode (negative/positive).

HPLC Method

The product was analysed by Waters 2695 HPLC consisting of a Waters 996 photodiode array detector, Kromasil Eternity C18, 5 μm, 4.6×150 mm column. Flow rate: 1 mL/minute, run time 20 minutes. Chromatograms were processed using WATERS Empower software.

Method 1A: Solvent A: methanol; solvent B: 0.1% formic acid in water. Gradient 0-100% Solvent B over 15 minutes with monitoring at 280 nm.

Method 1A: Solvent C: Acetonitrile; solvent D: 0.1% formic acid in water. Gradient 10-100% Solvent C vs D over 15 minutes with monitoring at 280 nm.

Acidic 2-Minute Method

LCMS analysis was carried out with a Waters Acquity UPLC system consist of a Acquity I Class Sample Manager-FL, an Acquity I Class Binary Solvent Manager and an Acquity UPLC Column Manager. UV detection was afforded with an Acquity UPLC PDA detector (scanning from 210 nm to 400 nm) and mass detection was afforded with an Acquity QDa detector (mass scanning from 100-1250 Da; positive and negative modes simultaneously). A Waters Acquity UPLC BEH C18 column (2.1×50 mm 1.7 mm) was used to achieve separation of analytes.

Samples were prepared by dissolving (with or without sonication) into 1 mL of 50% v/v MeCN in water. These solutions were filtered with 0.45 mm syringe filter before submitting for analysis. All solvents (including formic acid) used were HPLC grade. Conditions: 0.1% v/v Formic acid in water [Eluent A]; 0.1% v/v Formic acid in MeCN [Eluent B]; Flow rate 0.8 mL/min; injection volume 2 mL and 1.5 min equilibration time between samples.

Gradient:

| Time (min) | Eluent A (%) | Eluent B (%) |
| --- | --- | --- |
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Basic 2-Minute Method

Samples were prepared by dissolving (with or without sonication) into 1 mL of 50% v/v MeCN in water. These solutions were filtered with 0.45 mm syringe filter before submitting for analysis. All solvents (and ammonium bicarbonate) used (including 35% ammonia solution) were HPLC grade.

Conditions: 10 mM Ammonium Bicarbonate+0.1% v/v 35% ammonia solution [Eluent A]; 0.1% v/v 35% ammonia solution in MeCN [Eluent B]; Flow rate 0.8 mL/min; injection volume 2 mL and 1.5 min equilibration time between samples.

Gradient:

| Time (min) | Eluent A (%) | Eluent B (%) |
| --- | --- | --- |
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Acidic 4-Minute Method

Samples were prepared by dissolving (with or without sonication) into 1 mL of 50% v/v MeCN in water. These solutions were filtered with 0.45 mm syringe filter before submitting for analysis. All solvents (including formic acid) used were HPLC grade.

Conditions: 0.1% v/v formic acid in water [Eluent A]; 0.1% v/v formic acid in MeCN [Eluent B]; Flow rate 0.8 mL/min; injection volume 2 mL and 1.5 min equilibration time between samples.

Gradient:

| Time (min) | Eluent A (%) | Eluent B (%) |
| --- | --- | --- |
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Basic 4-Minute Method

Samples were prepared by dissolving (with or without sonication) into 1 mL of 50% v/v MeCN in water. These solutions were filtered with 0.45 mm syringe filter before submitting for analysis. All solvents (including 36% ammonia solution) used were HPLC grade.

Conditions: 0.1% ammonia in water [Eluent A]; 0.1% ammonia in MeCN [Eluent B]; Flow rate 0.8 mL/min; injection volume 2 mL and 1.5 min equilibration time between samples.

Gradient:

| Time (min) | Eluent A (%) | Eluent B (%) |
| --- | --- | --- |
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Chiral SCF Method 1

Compounds were analysed using a Waters ACQUITY ultra-performance convergence chromatography (UPC2) system equipped with a binary solvent delivery pump, an auto-sampler, a column oven (CM-30S), a back pressure regulator, and a diode array detector.

Column: Lux A1 (4.6 mm×250 mm, 5 μm).

Conditions: 40° C., 4 mL/min, isocratic 10:90 EtOH:CO$_2$ (0.1% v/v TFA), 125 BarG.

Chiral HPLC

HPLC instrument equipped with Agilent 1200 binary pump, Agilent 1200 variable wavelength detector (UV-vis detector) and a Shodex 150×4.5 mm, 3 μm chiral column. Flow rate 0.5 mL/minute. Solvent A: 0.05% CH$_3$COOH and 0.2 M NaCl in water. Solvent B: acetonitrile. Chiral HPLC analysis was performed in isocratic conditions (75% of solvent-A and 25% of solvent-B) at 280 nm wavelength. Chromatograms were processed using Agilent ChemStation software.

General Synthetic Strategies

Compounds of formula (I) may be synthesized by the following general methods:

General Method A

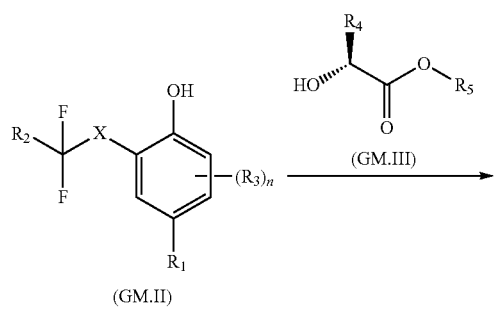

(GM.II)    (GM.III)

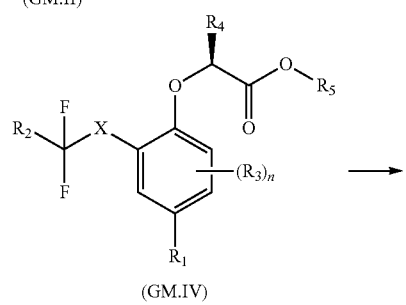

(GM.IV)

-continued

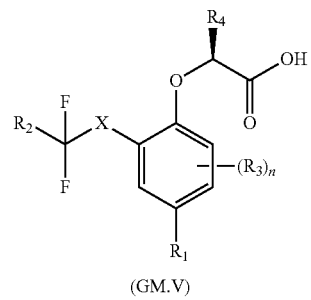

(GM.V)

Method A involves the synthesis of compound (GM.V), which is an aryloxy substituted acetic acid derivative, wherein $R^1$ to $R^9$, n and X are as defined in Formula (I) above. Compound (GM.II) is available either commercially or synthetically, and can be converted into an ether (GM.IV) by methods which include variations on Mitsunobu reaction conditions. This ether contains an ester functionality —CO$_2$R$^5$, which can be hydrolysed under a range of standard conditions, involving acid or base, to provide the carboxylic acid structure (GM.V). These standard conditions can also for example involve an enzymic hydrolysis, employing for example an esterase or lipase. If an ester molecule (GM.IV) includes for example a (CH$_3$)$_3$SiCH$_2$CH$_2$O— group as —O—R$^5$, then a fluoride ion source such as tetra-n-butylammonium fluoride can be employed to convert (GM.IV) into the corresponding carboxylic acid (GM.V).

Substituted phenols of general formula (GM.II), can be prepared by a variety of standard methods, for example by an ester rearrangement in the Fries rearrangement, by a rearrangement of N-phenylhydroxylamines in the Bamberger rearrangement, by hydrolysis of phenolic esters or ethers, by reduction of quinones, by replacement of an aromatic amine or by a hydroxyl group with water and sodium bisulfide in the Bucherer reaction. Other methods include hydrolysis of diazonium salts, by rearrangement reaction of dienones in the dienone phenol rearrangement, by the oxidation of aryl silanes, by the Hock process.

Phenols of formula (GM.II), wherein X is a bond, can be prepared by Grignard reaction of a suitable Grignard reagent to 2-hydroxybenzonitrile derivatives.

General Method B

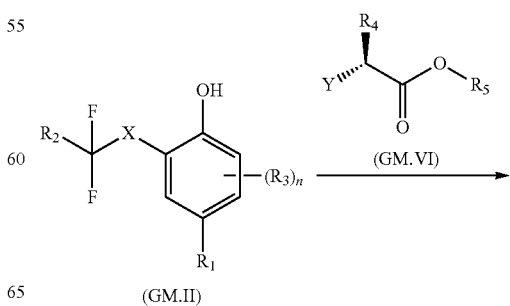

(GM.II)    (GM.VI)

-continued

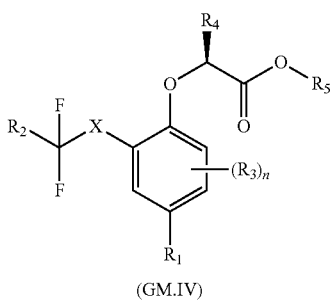

(GM.IV)

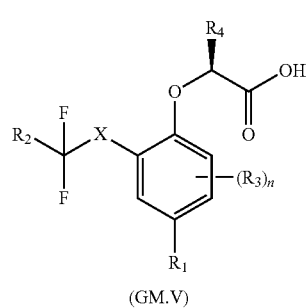

(GM.V)

Method B involves the synthesis of compound (GM.V), an aryloxy substituted acetic acid derivative, wherein $R^1$ to $R^9$, n and X are as defined in Formula (I) above, and is related to Method A. Compound (GM.II) is available either commercially or synthetically, and can be converted into an ether (GM.IV) by displacement of an appropriate leaving group Y, for example a methanesulphonate or a tosylate, under conditions which involve a suitable base such a sterically hindered amine or an alkali metal carbonate.

General Method C

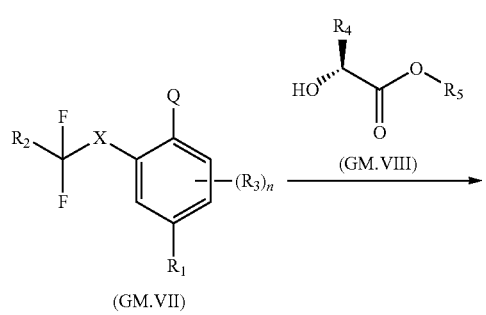

(GM.VII)

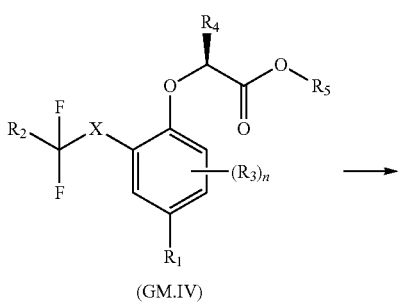

(GM.IV)

-continued

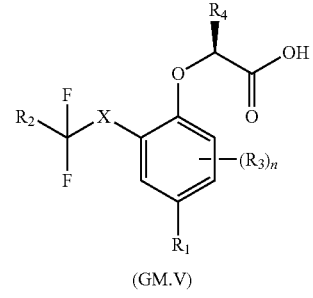

(GM.V)

Carboxylic acids of general formula (GM.V) can additionally be prepared by the procedure illustrated in General Method C. A phenolic ether of formula (GM.IV) can be prepared by displacement of a suitable leaving group Q in (GM.VII). Q can for example be a halogen such as fluorine or iodine, and the ether product of formula (GM.IV) can be converted into the carboxylic acid derivative (GM.V) by one of a range of methods outlined in Method A, involving hydrolysis of the ester functionality.

General Method D

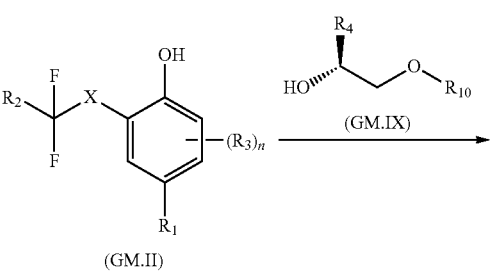

(GM.II)        (GM.X)

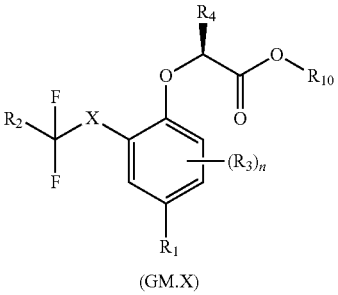

(GM.V)

Carboxylic acids of general formula (GM.V) can be prepared by the procedure illustrated as General Method D. A phenolic ether of formula (GM.II) can be prepared by utilising e.g. Mitsunobu conditions on the phenol structure (GM.II), and (GM.IX) is a suitable secondary alcohol wherein $R^1$ to $R^9$, n and X are as defined in Formula (I) above and —$R_{10}$ is a suitable protecting group, such as a silyl-containing moiety. On removal of the protecting group —$R_{10}$, the deprotection step, primary alcohol (GM.X) can be oxidised to a carboxylic acid under standard conditions involving potassium permanganate, Jones oxidation conditions, the Heyns oxidation, ruthenium tetroxide or TEMPO.

General Method E

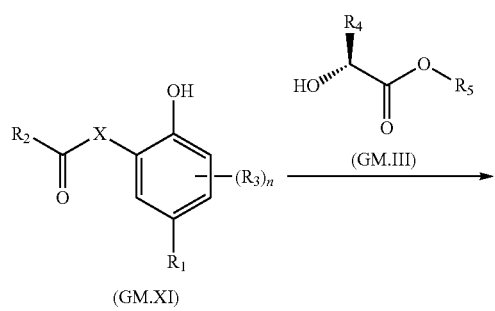

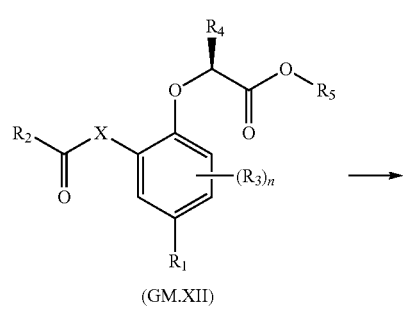

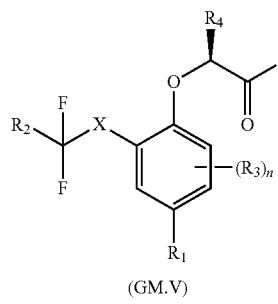

Carboxylic acids of general formula (GM.V) wherein $R^1$ to $R^9$, n and X are as defined in Formula (I) above can be prepared by the procedure illustrated as General Method E. The phenol (GM.XI), is available either commercially or synthetically, and can be converted into an ether (GM.XII) by methods which include variations on Mitsunobu reaction conditions. The acyl group in the ether (GM.XII) can be converted into an alkyl-difluoro derivative by a range of fluorination conditions, including utilisation of deoxofluor as a reagent, to provide after ester hydrolysis compound (GM.V).

General Method F

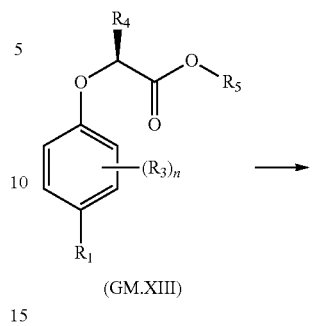

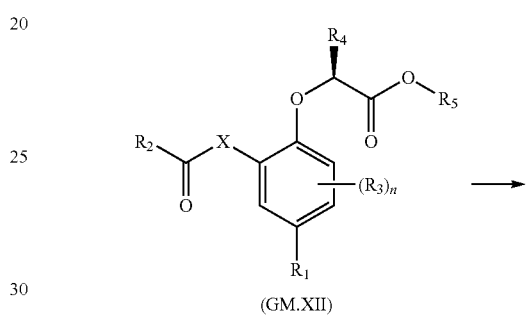

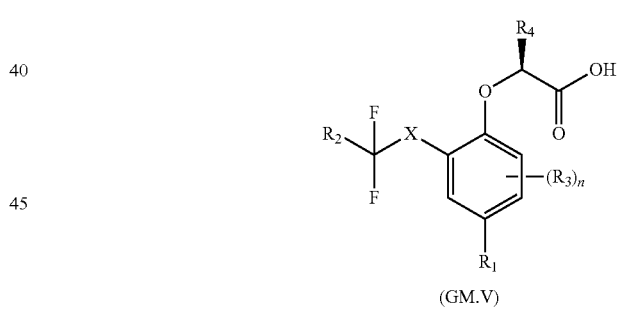

Carboxylic acids of general formula (V) wherein $R^1$ to $R^9$ and n are as defined in Formula (I) above and X is a bond can be prepared by the procedure illustrated as General Method E. The phenyl ether (GM.XIII), prepared by methods analogous to those illustrated above, can be converted into an ether (GM.XII) by methods which include the classical Friedel Crafts aromatic acylation reaction, one well known variation of which proceeds via an alkanoic acid chloride in the presence of a Lewis Acid. The acyl group in the resultant ether (GM.XII) can be converted into an alkyl-difluoro derivative by a range of fluorination conditions, including utilisation of deoxofluor as a reagent, to provide after ester hydrolysis compound (GM.V). An alternative procedure is to perform the acylation on a protected primary alcohol derivative, and to oxidise the deprotected alcohol as described in General Method D above.

General Method G

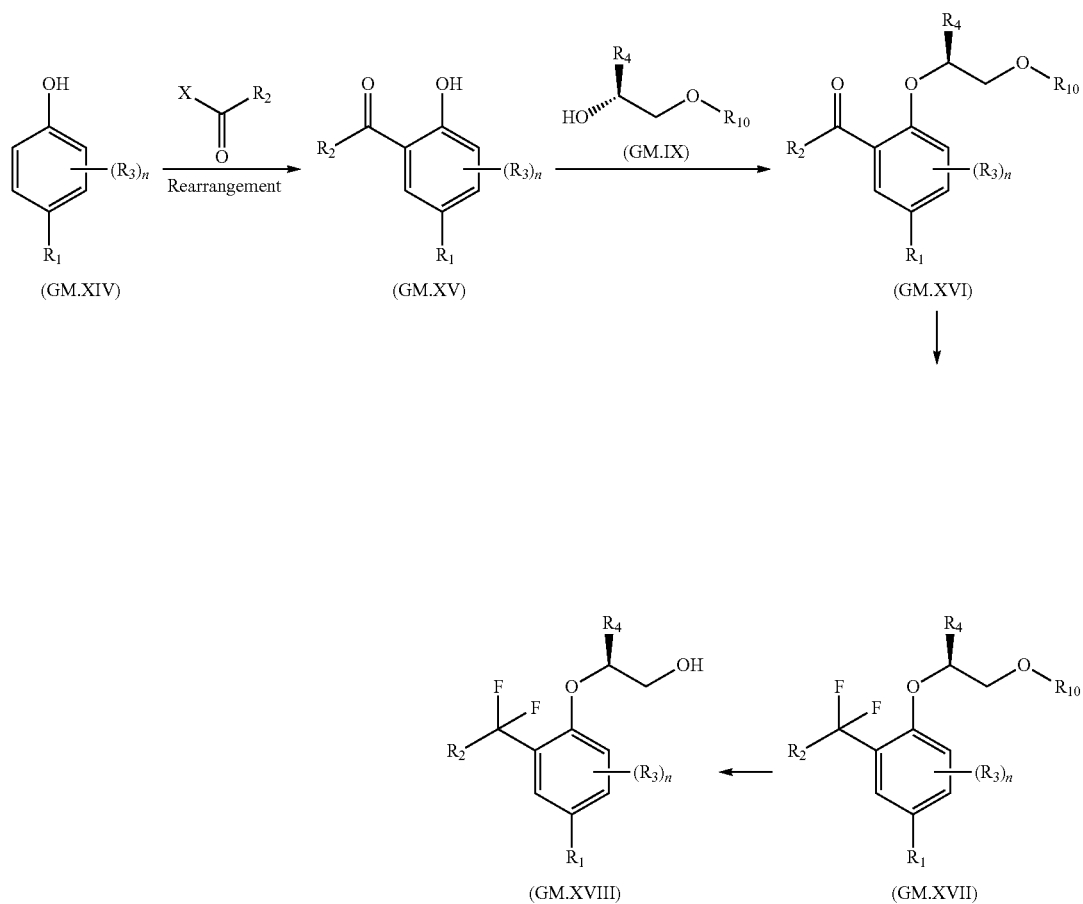

Carboxylic acids of general formula (XVIII) wherein $R^1$ to $R^9$ and n are as defined in Formula (I), Formula (II) and Formula (III) above can be prepared by the procedure illustrated as General Method G. Phenol (GM.XV) is available commercially or can be prepared from phenol (GM.XIV) via reaction with for example an acyl halide followed by rearrangement using e.g. $AlCl_3$. Phenol (GM.XV) is then converted into ether (GM.XVI) by methods which include variations on Mitsunobu reaction conditions. In some cases, it may be necessary to change protecting group —$R_{10}$ before the acyl group in ether (GM.XVI) is converted into alkyl-difluoro derivative (GM.XVII) by a range of fluorination conditions, including utilisation of deoxofluor as a reagent. On removal of protecting group —$R_{10}$, the primary alcohol can be oxidised to carboxylic acid (GM.XVIII) under standard conditions involving potassium permanganate, Jones oxidation conditions, the Heyns oxidation, ruthenium tetroxide or TEMPO.

General Method H

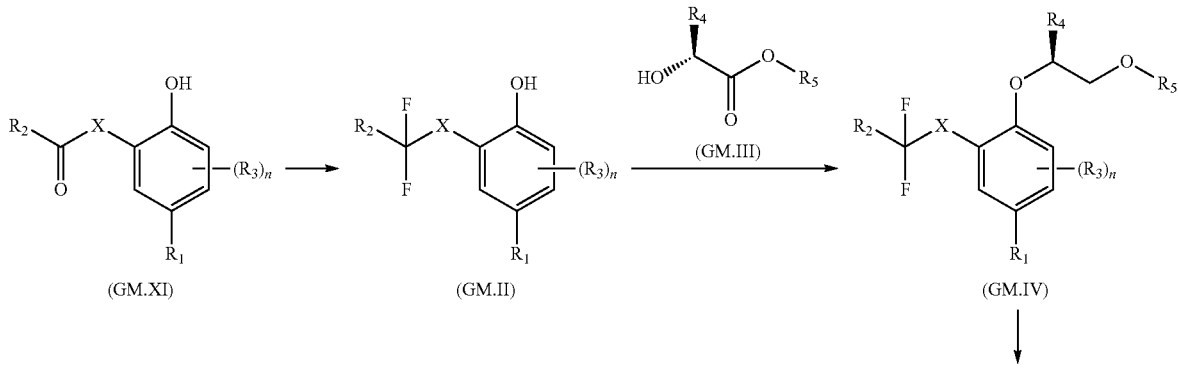

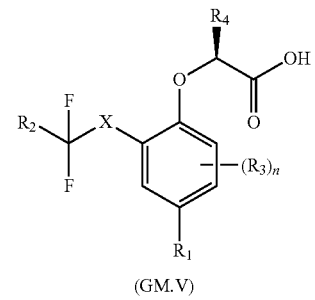

(GM.V)

Carboxylic acids of general formula (GM.V) wherein $R^1$ to $R^9$, n and X are as defined in Formula (I) above can be prepared by the procedure illustrated as General Method G. The phenol (GM.XI), which is available commercially or can be prepared as described in General Method G, can be converted into alkyl-difluoro derivative (GM.II) by a range of fluorination conditions, including utilisation of deoxofluor as a reagent. The alkyl-difluoro derivative (GM.II) is then coupled with ester (GM.III) using methods which include variations on Mitsunobu reaction conditions to give ester (GM.IV). Ester (GM.IV) can undergo further functional group modifications, for example on the aromatic ring, before being hydrolysed to carboxylic acids (GM.V).

Exemplified Compounds

Table 1 below illustrates Example compounds defined by the general Formula (I) which were prepared in >95% purity.

TABLE 1

Illustrative Examples of the Disclosure

| Cpd Number | IUPAC name | Spectroscopic data | Synthesis method |
|---|---|---|---|
| A-1 | (2S)-2-[4-bromo-2-(1,1-difluoroethyl)phenoxy]-3-cyclopropylpropanoic acid | $^1$H NMR (300 MHz, CDCl$_3$) δ 10.63-9.51 (br s, 1H), 7.66 (d, 1H), 7.44 (dd, 1H), 6.69 (d, 1H), 4.80 (dd, 1H), 2.14-1.93 (m, 4H), 1.90-1.77 (m, 1H), 1.05-0.85 (m, 1H), 0.61-0.44 (m, 2H), 0.26-0.10 (m, 2H) MS (ES-): m/z 347.2 (M − H)$^-$ HPLC retention time: 13.15 min | E |
| A-2 | (2S)-2-[4-bromo-2-(1,1-difluoroethyl)phenoxy] butanoic acid | $^1$H NMR (300 MHz, CDCl$_3$) δ 10.87-10.58 (br, 1H); 7.49 (d, 1H); 7.28 (dd, 1H); 6.50 (d, 1H); 4.53 (t, 1H); 2.01-1.73 (m, 5H), 0.95 (t, 3H); $^{19}$F NMR (300 MHz, CDCl$_3$) δ −85.78, −89.42 MS (ES-): m/z 322 (M − H)$^-$ HPLC retention time: 11.90 min | E |
| A-3 | (2S)-2-[4-bromo-2-(1,1-difluoropropyl)phenoxy] propanoic acid | 1H NMR (300 MHz, CDCl3) δ 9.69 (br s, 1H), 7.45 (dd, 1H), 7.27 (dd, 1H), 6.52 (d, 1H), 4.63 (q, 1 H), 2.9-2.05 (m, 2 H), 1.50 (d, 3H), 0.74 (t, 3H) HPLC retention time: 13.56 min Chiral SCF method 1: 1.17 mins | E |
| A-4 | (2S)-2-[4-bromo-2-(1,1-difluoroethyl)phenoxy] propanoic acid | $^1$H NMR (300 MHz, CDCl$_3$) δ 7.56 (d, 1H); 7.46 (dd, 1H); 6.87 (d, 1H); 4.51 (q, 1H); 2.09 (d, 3H); 1.60 (d, 3H) HPLC retention time: 11.16 min Chiral SCF method 1: 09 mins | E |
| A-5 | (2S)-2-[4-chloro-2-(1,1-difluoropropyl)phenoxy] propanoic acid | $^1$H NMR (300 MHz, CD$_3$OD) δ 9.40 (d, 1H), 7.32 (dd, 1H), 6.92 (d, 1H), 4.49 (q, 1H), 2.58-2.36 (m, 2H), 1.57 (d, 3H), 0.95 (t, 3H). $^{19}$F NMR (300 MHz, CDCl$_3$) δ −95.80, −99.29 MS (ES-): m/z 277 (M − H)$^-$ HPLC retention time: 11.65 min | E |
| A-6 | 2-[4-bromo-2-(1,1-difluoropropyl)phenoxy] acetic acid | $^1$H NMR (300 MHz, CDCl$_3$) δ 9.74-9.16 (br s, 1H), 7.71 (d, 1H), 7.54 (dd, 1H), 6.80 (d, 1H), 4.77 (s, 2H), 2.54-2.30 (m, 2H), 1.00 (t, 3H). $^{19}$F NMR (300 MHz, CDCl$_3$) δ −96.44. MS (ES-): m/z 308 (M − H)$^-$ HPLC retention time: 11.25 min | E |
| A-7 | (2S)-2-[4-bromo-2-(1,1-difluoro-2-methylpropyl)phenoxy] propanoic acid | $^1$H NMR (300 MHz, MeOD) δ 7.47 (d, 1H); 7.43 (dd, 1H); 6.84 (d, 1H); 4.43 (q, 1H); 3.18-2.95(m, 1H); 1.54 (d, 3H); 1.01 (d, 3H); 0.92 (d, 3H) $^{19}$F NMR (300 MHz, CDCl$_3$) δ −99.17, −106.6 MS (ES-): m/z 336 (M − H)$^-$ HPLC retention time: 12.42 min | E |

TABLE 1-continued

Illustrative Examples of the Disclosure

| Cpd Number | IUPAC name | Spectroscopic data | Synthesis method |
|---|---|---|---|
| A-8 | (2S)-2-{4-bromo-2-[difluoro(phenyl)methyl]phenoxy}propanoic acid | $^1$H NMR (300 MHz, CDCl$_3$) δ 7.93 (d, 1H), 7.59-7.50 (m, 3H), 7.48-7.39 (m, 3H), 6.70 (d, 1H), 4.64 (q, 1H), 1.34 (d, 3H) $^{19}$F NMR (300 MHz, CDCl$_3$) δ −88.51, −91.65 MS (ES−): m/z 371 (M − H)$^-$ HPLC retention time: 12.39 min | E |
| A-9 | (2S)-2-[4-bromo-2-(1,1-difluoroethyl)]-2-cyclopropylacetic acid | $^1$H NMR (300 MHz, CDCl$_3$) δ 8.38-7.65 (br, 1H), 7.49 (d, 1H), 7.26 (dd, 1H), 6.49 (d, 1H), 4.13 (d, 1H), 1.86 (t, 3H), 1.36-1.99 (m, 1H), 0.62-0.37 (m, 4H). $^{19}$F NMR (300 MHz, CDCl$_3$) δ −86.25, −88.75 ppm. MS (ES−): m/z 333.3 (M − H) HPLC retention time: 11.87 min. | E |
| A-10 | (2S)-2-[4-bromo-2-(1,1-difluorobutyl)phenoxy]propanoic acid | $^1$H NMR (300 MHz, MeOD) δ 7.51 (d, 1H); 7.44 (dd, 1H); 6.85 (d, 1H); 4.46 (q, 1H); 2.52-2.28 (m, 2H); 1.57 (d, 3H); 1.40 (p, 2H); 0.95 (t, 3H); (ES−): m/z 336 (M − H). $^{19}$F NMR (300 MHz, CDCl$_3$) δ −96.55, −93.80. HPLC retention time: 12.526 min | E |
| A-11 | (2R)-2-[4-bromo-2-(1,1-difluoropropyl)phenoxy]-3-fluoropropanoic acid | See Example 3 | G |
| A-12 | (2S)-2-[4-bromo-2-(cyclopropyldifluoromethyl)phenoxy]propanoic acid | $^1$H NMR (300 MHz, CDCl$_3$) δ 8.65-8.02 (br, 1H); 7.64 (d, 1H); 7.52 (dd, 1H); 6.79 (d, 1H); 4.89 (q, 1H); 1.76 (t, 3H); 0.95-0.56 (m, 4H); (ES−): m/z 334 (M − H). $^{19}$F NMR (300 MHz, CDCl$_3$) δ −102.66, −95.95 HPLC retention time: 11.799 min | E |
| A-13 | (2S)-2-{4-bromo-2-[difluoro(1,3-thiazol-2-yl)methyl]phenoxy}propanoic acid | See Example 9 | H |
| A-14 | (2S)-2-[4-bromo-2-(1,1-difluoroethyl)phenoxy]pent-4-ynoic acid | $^1$H NMR (300 MHz, CDCl$_3$) δ 9.22-8.65 (br, 1H); 7.72 (d, 1H); 7.53 (dd, 1H); 6.80 (d, 1H); 4.91 (t, 1H); 2.58-2.33 (m, 2H); 2.17 (t, 1H); 0.99 (t, 3H); (ES−): m/z 346 (M − H). $^{19}$F NMR (300 MHz, CDCl$_3$) δ −88.16, −86.27. HPLC retention time: 11.871 min | A |
| A-15 | (2S)-2-[4-bromo-2-(cyclobutyldifluoromethyl)phenoxy]propanoic acid | See Example 10 | H |
| A-16 | (2R)-2-[4-bromo-2-(1,1-difluoroethyl)phenoxy]-3-fluoropropanoic acid | See Example 4 | G |
| A-17 | (2R)-2-[4-bromo-2-(1,1-difluoropropyl)phenoxy]-3-chloropropanoic acid | $^1$H NMR (300 MHz, CDCl$_3$) δ 7.73 (d, 1H), 7.54 (dd, 1H), 6.82 (d, 1H), 5.86-5.36 (br s, 1H), 5.06 (t, 1H), 4.09 (d, 2H), 2.56-2.35 (m, 2H), 1.01 (t, 3H). $^{19}$F NMR (300 MHz, CDCl$_3$) δ −94.90, −97.58 ppm. HPLC retention time: 12.04 min. | G |
| A-18 | (2S)-2-[4-bromo-2-(1,1-difluoropropyl)phenoxy]pent-4-ynoic acid | $^1$H NMR (300 MHz, CDCl$_3$) δ 9.22-8.65 (br, 1H); 7.72 (d, 1H); 7.53 (dd, 1H); 6.80 (d, 1H); 4.91 (t, 1H); 3.06-2.96 (m, 2H); 2.58-2.33 (m, 2H); 2.17 (t, 1H); 0.99 (t, 3H) (ES−): m/z 346 (M − H) $^{19}$F NMR (300 MHz, CDCl$_3$) δ −97.57, −94.98 HPLC retention time: 11.871 | A |
| A-19 | (2S)-2-[4-chloro-2-(1,1-difluoroethyl)phenoxy]pent-4-ynoic acid | $^1$H NMR (300 MHz, CDCl$_3$) δ 9.73-9.40 (br, 1H), 7.60 (d, 1H), 7.38 (dd, 1H), 6.86 (d, 1H), 4.93 (t, 1H), 3.02 (dd, 2H), 2.21-2.02 (m, 4H) MS (ES−): m/z 286.94 (M − H) $^{19}$F NMR (300 MHz, CDCl$_3$) δ −86.23, −88.28 ppm HPLC retention time: 11.10 min Chiral HPLC: 7.20 mins, 99.2% e.e. | A |
| A-20 | (2S)-2-[2-(1,1-difluoropropyl)-4-iodophenoxy]propanoic acid | $^1$H NMR (300 MHz, CDCl$_3$) δ 9.81-9.08 (br, 1H); 7.87 (d, 1H); 7.70 (dd, 1H); 6.65 (d, 1H); 4.87 (q, 1H); 1.74 (t, 3H); 0.99 (t, 3H) (ES−): m/z 369 (M − H) $^{19}$F NMR (300 MHz, CDCl$_3$) δ −98.35, −94.33 HPLC retention time: 12.116 min | E |
| A-21 | (2S)-2-[4-bromo-2-(1,1-difluoropropyl)phenoxy](2-$^2$H) propanoic acid | $^1$H NMR (DMSO-d$_6$) δ: 7.49 (dd, J = 2.1, 8.9 Hz, 1H), 7.41 (d, J = 2.5 Hz, 1H), 6.82 (d, J = 8.8 Hz, 1H), 2.48-2.35 (m, 2H), 1.35 (s, 3H), 0.86 (t, J = 7.5 Hz, 3H) | E + chiral separation |

TABLE 1-continued

Illustrative Examples of the Disclosure

| Cpd Number | IUPAC name | Spectroscopic data | Synthesis method |
|---|---|---|---|
| A-22 | (2R)-2-[4-chloro-2-(1,1-difluoropropyl)phenoxy]-3-fluoropropanoic acid | $^{19}$F NMR (376 MHz, DMSO-$d_6$) δ −97.24 (d, J = 241.1 Hz), −91.68 (d, J = 241.0 Hz) UPLC-MS: acidic 4-minute run MS (ES−): m/z 322.0/324.0 (M − H)$^-$; retention time: 1.87 min; purity: 84%. $^1$H NMR (300 MHz, CDCl$_3$) δ 8.12-7.70 (br s, 1H), 7.59 (d, 1H), 7.40 (dd, 1H), 6.87 (d, 1H), 5.09-4.87 (m, 3H), 2.53-2.32 (m, 2H), 1.00 (t, 3H) MS (ES−): m/z 295.3 (M − H) $^{19}$F NMR (300 MHz, CDCl$_3$) δ −94.83, −97.70, −228.74 ppm HPLC retention time: 11.39 min | G |
| A-23 | (2S)-2-[2-(1,1-difluoropropyl)-4-ethynylphenoxy]propanoic acid | $^1$H NMR (300 MHz, CDCl$_3$) δ 7.66 (d, 1H); 7.48 (dd, 1H); 6.76 (d, 1H); 4.86 (q, 1H); 3.03 (s, 1H); 2.47-2.24 (m, 2H); 2.47-2.24 (m, 2H); 1.69 (d, 3H); 0.93 (t, 3H); (ES−): m/z 267 (M − H). $^{19}$F NMR (300 MHz, CDCl$_3$) δ −98.47, −94.46. HPLC retention time: 11.161 | E |
| A-24 | (2S)-2-[4-bromo-2-(1,1-difluoropropyl)-5-fluorophenoxy]propanoic acid | See Example 5 | E |
| A-25 | (2S)-2-[4-bromo-2-(1,1-difluoropropyl)-6-fluorophenoxy]propanoic acid | See Example 11 | E |
| A-26 | (2S)-2-[2-(1,1-difluoropropyl)-4,5-difluorophenoxy]propanoic acid | See Example 13 | H |
| A-27 | (2S)-2-[4-cyano-2-(1,1-difluoropropyl)phenoxy]propanoic acid | See Example 12 | |
| A-28 | (2R)-2-[4-chloro-2-(1,1-difluoroethyl)phenoxy]-3-fluoropropanoic acid | $^1$H NMR (300 MHz, CDCl$_3$) δ 10.46-9.91 (br, 1H); 7.49 (d, 1H); 7.27 (dd, 1H); 6.74 (d, 1H); 4.98-4.84 (m, 2H); 4.77 (d, 1H); 1.97 (t, 3H); (ES−): m/z 281 (M − H) $^{19}$F NMR (300 MHz, CDCl$_3$) δ −228.74, −88.42, −86.25 HPLC retention time: 10.792 min | G |
| A-29 | (2S)-2-[4-bromo-2-(1,1-difluoroethyl)-5-fluorophenoxy]propanoic acid | $^1$H NMR (300 MHz, CDCl$_3$) δ 11.62-11.24 (br, 1H); 7.78 (d, 1H); 6.69 (d, 1H); 4.87 (q, 1H); 2.07 (t, 3H); 1.78 (t, 3H) $^{19}$F NMR (300 MHz, CDCl$_3$) δ −101.59, −87.96, −85.07 (ES−): m/z 326 (M − H) HPLC retention time: 11.596 min | E |
| A-30 | (2S)-2-[4-bromo-2-(1,1-difluoropropyl)(3,5,6-$^2$H$_3$)phenoxy]propanoic acid | $^1$H NMR (300 MHz, CDCl$_3$) δ 10.68-8.63 (br s, 1H), 4.87 (q, 1H), 2.52-2.31 (m, 2H), 1.74 (d, 3H), 0.99 (t, 3H) MS (ES−): m/z 333.85 (M − H) $^{19}$F NMR (300 MHz, CDCl$_3$) δ −94.31, −98.38 ppm HPLC retention time: 12.02 min Chiral HPLC: 9.33 mins, 99.5% e.e. | E |
| A-31 | 2-[4-bromo-2-(1,1-difluoropropyl)-5-fluorophenoxy]acetic acid | $^1$H NMR (300 MHz, CDCl$_3$) δ 10.60-9.89 (br, 1H), 7.77 (d, 1H), 6.72 (d, 1H), 4.78 (s, 2H), 2.52-2.27 (m, 2H), 1.00 (t, 3H) MS (ES−): m/z 324.86 (M − H) $^{19}$F NMR (300 MHz, CDCl$_3$) δ −95.54, −101.45 ppm HPLC retention time: 11.71 min | B |
| A-32 | (2S)-2-[4-chloro-2-(1,1-difluoropropyl)-5-fluorophenoxy]propanoic acid | $^1$H NMR (400 MHz, DMSO-$d_6$) δ 0.86 (t, J = 7.5 Hz, 3H), 1.36 (d, J = 6.6 Hz, 3H), 2.30-2.49 m, 2H), 4.32 (q, J = 6.6 Hz, 1H), 6.86 (d, J = 11.9 Hz, 1H), 7.43 (dd, J = 8.7, 1.1 Hz, 1H) $^{19}$F NMR (376 MHz, DMSO-$d_6$) δ −112.39 (d, J = 2.6 Hz), −96.33 (d, J = 241.3 Hz), −90.88 (dd, J = 241.5, 3.4 Hz) UPLC-MS (acidic, 4 mins), RT = 1.88 mins, m/z (ES−) 295.0, purity 100% | E |

TABLE 1-continued

Illustrative Examples of the Disclosure

| Cpd Number | IUPAC name | Spectroscopic data | Synthesis method |
|---|---|---|---|
| A-33 | (2S)-2-[2-(1,1-difluoropropyl)-4-(trifluoromethyl)phenoxy]propanoic acid | $^1$H NMR (300 MHz, CDCl$_3$) δ 9.35-8.23 (br, 1H), 7.79 (s, 1H), 7.62 (d, 1H), 6.87 (d, 1H), 4.92 (q, 1H), 2.52-2.22 (m, 2H), 1.72 (d, 3H), 0.94 (t, 3H)<br>MS (ES−): m/z 311.11 (M − H)<br>$^{19}$F NMR (300 MHz, CDCl$_3$) δ −61.86, −94.53, −98.83 ppm<br>HPLC retention time: 12.08 min<br>Chiral HPLC: 6.42 mins, 96.0% e.e. | A |
| A-34 | (2R)-2-[4-bromo-2-(1,1-difluoropropyl)-5-fluorophenoxy]-3-fluoropropanoic acid | See Example 6 | G |
| A-35 | (2S)-2-[2-(1,1-difluoropropyl)-4-ethenylphenoxy]propanoic acid | See Example 14 | H |
| A-36 | 2-[4-bromo-2-(1,1-difluoroethyl)-5-fluorophenoxy]acetic acid | $^1$H NMR (300 MHz, CDCl$_3$) δ 8.56-7.90 (br s, 1H), 7.80 (d, 1H), 6.73 (d, 1H), 4.79 (s, 2H), 2.08 (t, 3H)<br>$^{19}$F NMR (300 MHz, CDCl$_3$) δ −86.36, −101.55 ppm.<br>MS (ES−): m/z 310.99 (M − H)<br>HPLC retention time: 11.02 min. | B |
| A-37 | (2S)-2-[2-(1,1-difluoropropyl)-4-methylphenoxy]propanoic acid | See Example 15 | H |
| A-38 | 2-[4-bromo-2-(1,1-difluoro-2-methylpropyl)phenoxy]acetic acid | $^1$H NMR (300 MHz, CDCl$_3$) δ 10.85-10.16 (br, 1H); 7.69 (d, 1H); 7.54 (dd, 1H); 6.81 (d, 1H); 4,77 (s, 2H); 1.04 (d, 6H)<br>$^{19}$F NMR (300 MHz, CDCl$_3$) δ −105.26<br>(ES−): m/z 322 (M − H)<br>HPLC retention time: 12.034 min | B |
| A-39 | 2-[4-chloro-2-(1,1-difluoropropyl)-5-fluorophenoxy]acetic acid | $^1$H NMR (300 MHz, CDCl$_3$) δ 7.64 (d, 1H), 7.75 (d, 1H), 4.77 (s, 2H), 2.50-2.31 (m, 2H), 1.00 (t, 3H). MS (ES−): m/z 280.82 (M − H)<br>$^{19}$F NMR (300 MHz, CDCl$_3$) δ −95.51, −19.34 ppm<br>HPLC retention time: 11.64 min | B |
| A-40 | (2S)-2-[2-(1,1-difluoroethyl)-4-ethynylphenoxy]propanoic acid | See Example 16 | H |
| A-41 | (2R)-2-[4-chloro-2-(1,1-difluoropropyl)-5-fluorophenoxy]-3-fluoropropanoic acid | See Example 7 | G |
| A-42 | (2S)-2-[4,5-dichloro-2-(1,1-difluoropropyl)phenoxy]propanoic acid | $^1$H NMR (300 MHz, CDCl$_3$) δ 10.01-8.67 (br, 1H); 7.65 (s, 1H); 6.98 (s, 1H); 2.54-2.27 (m, 2H); 1.77 (d, 3H); 0.99 (t, 3H); (ES−): m/z 270 (M − H)<br>$^{19}$F NMR (300 MHz, CDCl$_3$) δ −98.51, −93.68<br>HPLC retention time: 12.597 min<br>Chiral HPLC: 13.55 mins, 99.8% e.e. | H |
| A-43 | (2R)-2-[4-bromo-2-(1,1-difluoroethyl)-5-fluorophenoxy]-3-fluoropropanoic acid | See Example 8 | G |
| A-44 | (2R)-2-[4,5-dichloro-2-(1,1-difluoroethyl)phenoxy]-3-fluoropropanoic acid | $^1$H NMR (300 MHz, CDCl$_3$) δ 9.91-9.17 (br s, 1H), 7.64 (s, 1H), 6.95 (s, 1H), 5.05-4.89 (m, 2H), 4.84 (d, 1H), 2.02 (t, 2H).<br>MS (ES−): m/z 315.3 (M − H)<br>$^{19}$F NMR (300 MHz, CDCl$_3$) δ −86.08, −88.18, −228.53 ppm<br>HPLC retention time: 11.61 min<br>Chiral HPLC: 14.0 mins, 99.8% e.e. | G |
| A-45 | (2S)-2-[4-bromo-2-(1,1-difluoroethyl)phenoxy]-4-fluorobutanoic acid | $^1$H NMR (300 MHz, CDCl$_3$) δ 11.47-11.04 (br, 1H); 7.48 (d, 1H); 7.27 (d, 1H); 6.52 (d, 1H); 4,66-4.49 (m, 1H); 4,51-4.34 (m, 1H); 2.40-2.04 (m, 2H); 1.82 (t, 3H)<br>$^{19}$F NMR (300 MHz, CDCl$_3$) δ −222.51, −89.77, −85.74<br>MS (ES−): m/z 340 (M − H)<br>HPLC retention time: 12.327 min<br>Chiral HPLC: 8.56 mins, 85.4% e.e. | A |

TABLE 1-continued

Illustrative Examples of the Disclosure

| Cpd Number | IUPAC name | Spectroscopic data | Synthesis method |
|---|---|---|---|
| A-46 | (2S)-2-[4-bromo-2-(1,1-difluoro-2-methylpropyl)phenoxy]butanoic acid | $^1$H NMR (DMSO-$d_6$) δ 7.60 (dd, J = 8.8, 2.6 Hz, 1H), 7.47 (d, J = 2.5 Hz, 1H), 6.91 (d, J = 8.9 Hz, 1H), 4.87 (t, J = 5.6 Hz, 1H), 3.08-2.83 (m, 1H), 2.01-1.78 (m, 2H), 1.08-0.92 (m, 6H), 0.84 (d, J = 6.9 Hz, 3H) $^{19}$F NMR (376 MHz, DMSO-$d_6$) δ −99.27 (d, J = 243.0 Hz), −109.11 (dd, J = 243.0, 21.3 Hz) UPLC-MS (acidic, 4 mins), RT = 2.12 mins, m/z (ES−) 349.0/351.0, purity 100% | A |
| A-47 | (2S)-2-[2-(1,1-difluoropropyl)-4-ethenyl-5-fluorophenoxy]propanoic acid | See Example 17 | H |
| A-48 | (2S)-2-[4-bromo-2-(1,1-difluoropropyl)-5-fluorophenoxy]butanoic acid | See Example 18 | H |
| A-49 | (2S)-2-[4-chloro-2-(1,1-difluoropropyl)-5-fluorophenoxy]butanoic acid | See Example 19 | H |
| A-50 | (2R)-2-[5-chloro-2-(1,1-difluoropropyl)-4-fluorophenoxy]-3-fluoropropanoic acid | $^1$H NMR (300 MHz, CDCl$_3$) δ 8.15-7.44 (br s, 1H), 7.35 (d, 1H), 6.94 (d, 1H), 5.00-4.82 (m, 3H), 2.47-2.25 (m, 2H), 0.93 (t, 3H) $^{19}$F NMR (300 MHz, CDCl$_3$) δ −94.37, −97.38, −121.99, −228.75 ppm MS (ES−): m/z 313.3 (M − H) HPLC retention time: 11.63 min Chiral HPLC: 10.39 mins, 99.6% e.e. | G |
| A-51 | (2S)-2-[2-(1,1-difluoropropyl)-4-nitrophenoxy]propanoic acid | See Example 20 | H |
| A-52 | (2S)-2-[5-chloro-2-(1,1-difluoropropyl)-4-fluorophenoxy]propanoic acid | See Example 21 | H |
| A-53 | (2S)-2-[4-bromo-2-(1,1-difluoropropyl)phenoxy]-4-methoxybutanoic acid | $^1$H NMR (300 MHz, CDCl$_3$) δ 10.03-9.43 (br, 1H); 7.46 (d, 1H); 7.27 (d, 1H); 6.53 (d, 1H); 4.79-4.64 (m, 1H); 3.43 (t, 2H); 3.14 (s, 3H); 2.29-1.9 (m, 2H); 0.77 (t, 3H) $^{19}$F NMR (300 MHz, CDCl$_3$) δ −99.56, −93.60 MS (ES−): m/z 365 (M − H) HPLC retention time: 11.835 min Chiral HPLC: 8.56 mins, 99.7% e.e. | E |
| A-54 | (2R)-2-[2-(1,1-difluoropropyl)-4,5-difluorophenoxy]-3-fluoropropanoic acid | $^1$H NMR (300 MHz, CDCl$_3$) δ 10.97-10.67 (br, 1H), 7.26 (t, 1H), 6.62 (dd, 1H), 4.85 (d, 1H), 4.82-4.62 (m, 1H), 2.37-2.06 (m, 2H), 0.80 (t, 3H) $^{19}$F NMR (300 MHz, CDCl$_3$) δ −93.44, −97.03, −131.74, −144.39, −228.85 ppm MS (ES−): m/z 297.4 (M − H) HPLC retention time: 11.10 min Chiral HPLC: 8.80 mins, 98.1% e.e. | G |
| A-55 | (2S)-2-[2-(1,1-difluoropropyl)-4,5-difluorophenoxy]propanoic acid | See Example 13 | H |

Example 1: Synthesis of (2S)-2-[4-bromo-2-(1,1-difluoroethyl)phenoxy]propanoic acid

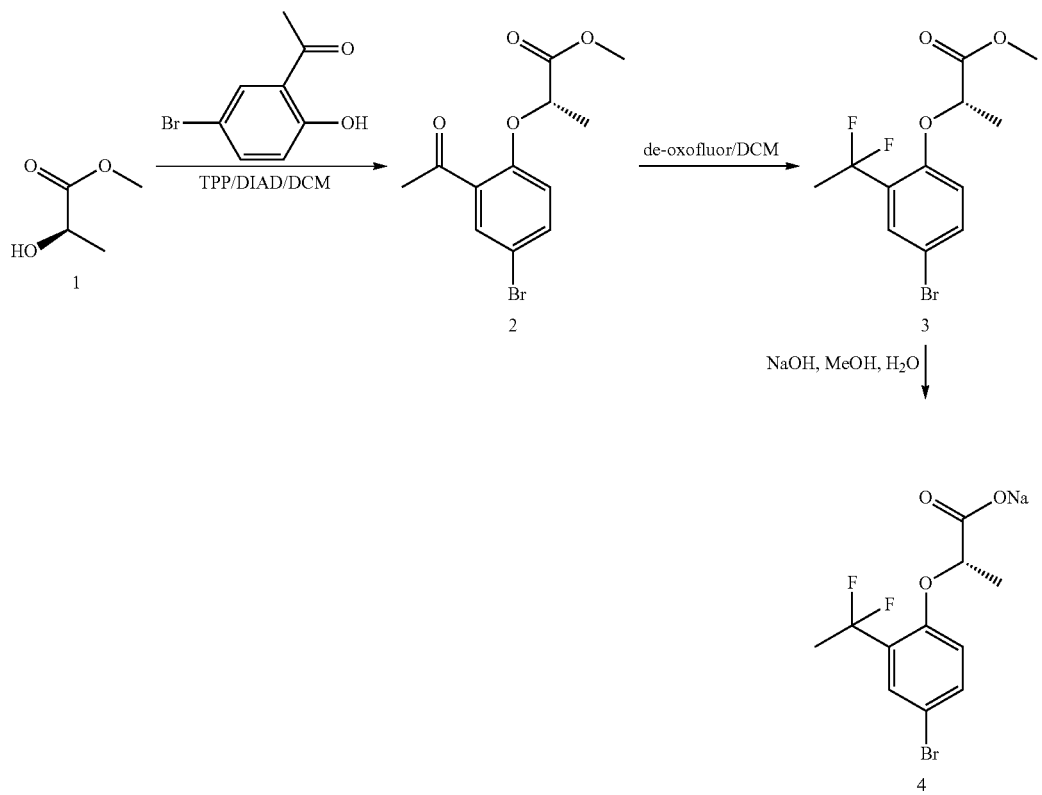

Step 1: Synthesis of (S)-methyl 2-(2-acetyl-4-bromophenoxy) propanoate 2

To a solution of (R)-methyl 2-hydroxypropanoate 1 (3.07 g, 29.44 mmol), 1-(5-bromo-2-hydroxy phenyl)ethanone (6.33 g, 29.44 mmol) and TPP (9.28 g, 35.38 mmol) in 150 mL DCM previously cooled to 0° C. was slowly added a DIAD (6.96 mL) with stirring. The ice bath was then removed, and the mixture stirred at room temperature overnight and then concentrated under reduced pressure. After removal of the solvent, the residue was passed through a short silica gel column (hexane-EtOAc, 25:1, 10:1) to give desired product 2 (7.9 g, 89%) as a light yellow oil.

$^1$H NMR (300 MHz, CDCl$_3$) δ 7.83 (d, 1H); 7.48 (dd, 1H); 6.67 (d, 1H); 4.87 (q, 1H); 3.75 (s, 3H); 2.67 (s, 3H); 1.68 (d, 3H).

Step 2: Synthesis of (S)-methyl 2-(4-bromo-2-(1,1-difluoroethyl)phenoxy) propanoate 3

To a solution of (S)-methyl 2-(2-acetyl-4-bromophenoxy) propanoate 2 (3.99 g, 13.3 mmol) in dry CH$_2$Cl$_2$ (40 mL) in a seal tube was added de-oxofluor (24.5 ml, 133 mmol, 10 eq) and flush with argon and seal the cap. The resulting mixture was stirred at 40° C. for 7-8 days until the starting material completely consumed. After completion of the reaction, the reaction mixture was poured into ice-cold saturated aqueous sodium bicarbonate and stirred for 20 to 30 minutes. The aqueous layer was extracted with ethyl acetate (2×100 mL). The combined organic extracts were washed with brine and dried (Na$_2$SO$_4$). After removal of the solvent, the residue was passed through a short silica gel column (hexane-EtOAc, 25:1, 5:1) to give desired product 3 (3.55 g, 83%) as a colourless oil.

$^1$H NMR (300 MHz, CDCl$_3$) δ 7.65 (d, 1H); 7.42 (dd, 1H); 6.66 (d, 1H); 4.79 (q, 1H); 3.75 (s, 3H); 2.04 (d, 3H); 1.64 (d, 3H); F$^{19}$ NMR (300 MHz, CDCl$_3$) δ −85.67, −89.11.

Step 3: Synthesis of sodium (S)-2-(4-bromo-2-(1,1-difluoroethyl)phenoxy) propanoate 4

To a solution of (S)-methyl 2-(4-bromo-2-(1,1-difluoroethyl)phenoxy) propanoate 3 (1.62 g, 5.01 mmol) in MeOH (32 mL) and water (8 mL) at <10° C., solid NaOH (200 mg, 5.01 mmol) was added and the resulting mixture was stirred at room temperature for 1-2 h (reaction monitored by TLC). After completion of the reaction, the volatiles were removed, and the reaction mixture was diluted with water (30 mL). The aqueous layer was washed with DCM (2×20 mL) to remove impurities and unreacted ester. The aqueous layer was separated, the water was removed under reduced pressure and the product 4 dried under vacuum to give the desired product 4 as a light yellow solid (1.54 g, 99%).

$^1$H NMR (300 MHz, CDCl$_3$) δ 7.56 (d, 1H); 7.46 (dd, 1H); 6.87 (d, 1H); 4.51 (q, 1H); 2.09 (d, 3H); 1.60 (d, 3H). F$^{19}$ NMR (300 MHz, CDCl$_3$) δ−86.77, −89.58.

MS (ES−): m/z 307.0 (M−H)$^−$. HPLC retention time: 11.16 min Chiral SCF method 1: 1.17 mins (>99% e.e.). (R)-enantiomer at 1.43 mins.

Example 2: Synthesis of (S)-2-(4-bromo-2-(1,1-difluoropropyl)phenoxy)propanoic acid The compound was prepared as described in example 1.

(S)-Methyl 2-(4-bromo-2-propionylphenoxy)propanoate

1H NMR (300 MHz, CDCl$_3$) δ 7.84 (d, 1H), 7.52 (dd, 1H), 6.72 (d, 1H), 4.91 (q, 1H), 3.82 (s, 3H), 3.16-3.07 (m, 2H), 1.73 (d, 3H), 1.23 (t, 3H).

(S)-Methyl 2-(4-bromo-2-(1,1-difluoropropyl)phenoxy)propanoate

1H NMR (300 MHz, CDCl$_3$) δ 7.48 (dd, 1H), 7.27 (dd, 1H), 6.50 (d, 1H), 4.63 (q, 1H), 3.59 (s, 3H), 3.34-3.14 (m, 2H), 1.48 (d, 3H), 0.79 (t, 3H). $^{19}$F NMR (300 MHz, CDCl3) δ −93.5 and −99 ppm.

(S)-2-(4-Bromo-2-(1,1-difluoropropyl)phenoxy)propanoic acid

1H NMR (300 MHz, CDCl$_3$) δ 9.69 (br s, 1H), 7.45 (dd, 1H), 7.27 (dd, 1H), 6.52 (d, 1H), 4.63 (q, 1H), 2.9-2.05 (m, 2H), 1.50 (d, 3H), 0.74 (t, 3H). $^{19}$F NMR (300 MHz, CDCl$_3$) δ −94 and −98 ppm.

MS (ES−): m/z 321.2 (M−H)⁻. HPLC retention time: 13.56 min

Chiral SCF method 1: 1.09 mins (>97.2% e.e.). (R)-enantiomer at 1.25 mins.

Example 3: Synthesis of (R)-2-(4-bromo-2-(1,1-difluoropropyl)phenoxy)-3-fluoropropanoic acid

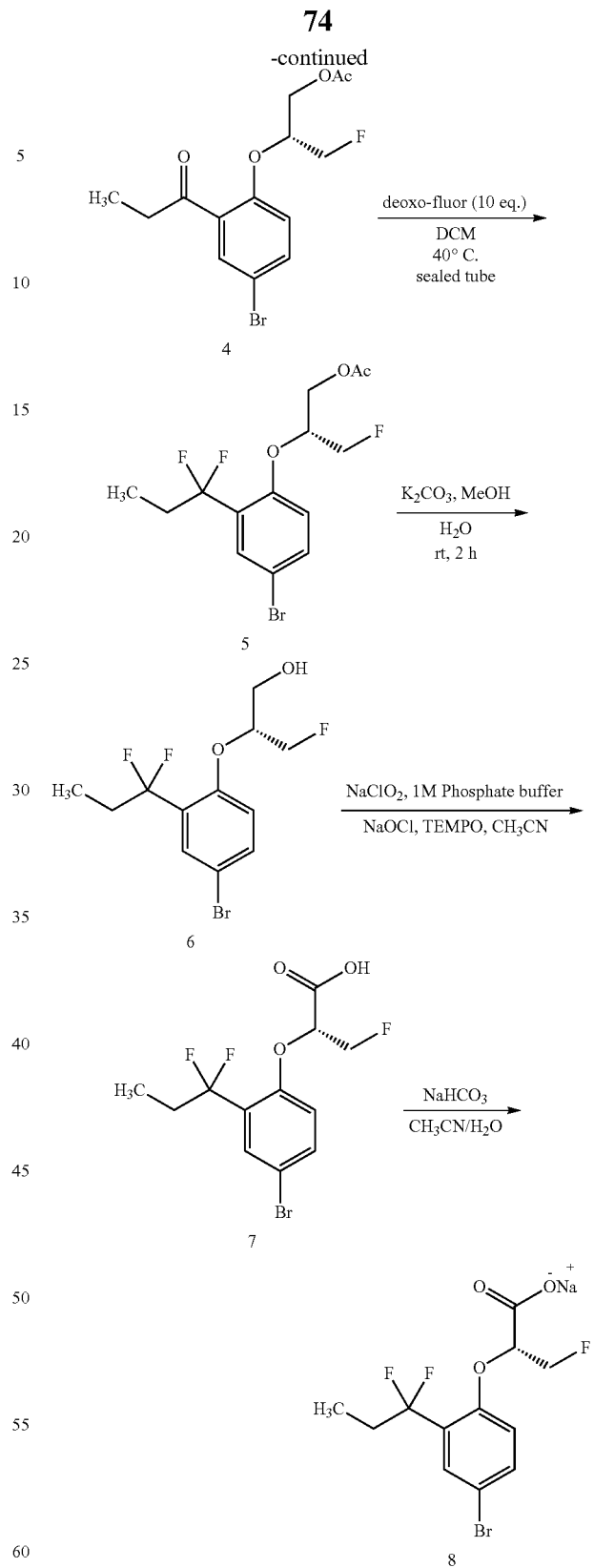

Synthesis of (S)-1-(benzyloxy)-3-fluoropropan-2-ol (R)-Benzyl glycidyl ether (200 g, 1.22 mol, 1.0 eq.), CsF (191 g, 1.26 mol, 1.0 eq.), and KHF$_2$ (99 g, 1.27 mol, 1.0 eq.)

were added to a flask at RT under N₂. 1 M TBAF in THF (3.91 L, 3.2 eq.) was added [no exotherm] and the reaction was stirred at RT under N₂. The reaction was heated to 65° C. over 1 h 30 mins and stirred at 65° C. for 21 h, at which point, LC indicated 76% product. The reaction was cooled to 25° C. and KHF₂ (9.9 g, 0.13 mol, 0.1 eq) and CsF (19.1 g, 0.13 mol, 0.1 eq) were added. The reaction was heated to 65° C. and for 18 h, at which point, LC indicated 77% product. The reaction was cooled to RT and H₂O (3.90 L) was added over 5 mins [mild exotherm]. The aqueous was extracted with toluene (3×1.00 L). The combined organic extracts were washed with 20% K₂CO₃(aq) (1.90 L) and H₂O (2×1.90 L) and then reduced in vacuo to give 315 g of crude product at a purity of 87% by LC. The material was purified via column chromatography (2.0 Kg, 10 eq. SiO₂, 5→15% EtOAc in heptane) and the product was eluted as two portions that were reduced in vacuo. The first portion gave 19 g (8% yield) of product at 91% by LC and the second gave 163 g (73% yield) at 97% by LC and >95% by ¹H NMR.

Step 1: Synthesis of (R)-1-(2-(1-(benzyloxy)-3-fluoropropan-2-yloxy)-5-bromophenyl)propan-1-one 2

To a stirred solution of 1-(5-bromo-2-hydroxyphenyl)propan-1-one (4.0 g, 17.5 mmol), (S)-1-(benzyloxy)-3-fluoropropan-2-ol (3.85 g, 21.0 mmol), and triphenylphosphine (5.5 g, 21.0 mmol) in 60 mL of dichloromethane previously cooled to 0° C. was slowly added DIAD (4.25 g, 21.0 mmol). The ice bath was then removed and the reaction mixture was stirred at room temperature overnight, then concentrated under reduced pressure.

After removal of the solvent, the residue was purified by silica gel column chromatography using 0-30% ethyl acetate/hexane to get desired product 2 (5.0 g, 72.5%) as a light-yellow oil.

¹H NMR (300 MHz, CDCl₃) δ 7.82 (d, 1H), 7.53 (dd, 1H), 7.45-7.32 (m, 5H), 6.95 (d, 1H), 4.83-4.56 (m, 5H), 3.78 (dd, 2H), 3.02 (q, 2H), 1.19 (t, 3H).

¹⁹F NMR (300 MHz, CDCl₃) δ–230.69 ppm.

Step 2: Synthesis of (R)-1-(5-bromo-2-(1-fluoro-3-hydroxypropan-2-yloxy)phenyl)propan-1-one 3

To (R)-1-(2-(1-(benzyloxy)-3-fluoropropan-2-yloxy)-5-bromophenyl)propan-1-one (5.0 g, 12.7 mmol) in a 250 mL of round bottom flask was added pyridine.HCl (36.65 g, 31.7 mmol). The reaction mixture was heated at 180° C. for 90 minutes. The reaction mixture was cooled then quenched with H₂O (50 mL), and the product extracted with ethyl acetate (2×100 mL), washed with H₂O (2×30 mL), brine (25 mL), dried over sodium sulphate and concentrated under reduced pressure. The residue was passed through a silica gel column (EtOAc/hexane, 0-50%) to give desired product 3 (2.84 g, 73.5%) as a white solid.

¹H NMR (300 MHz, CDCl₃) δ 7.74 (d, 1H), 7.59 (dd, 1H), 7.07 (d, 1H), 4.80 (d, 1H), 4.71-4.59 (m, 2H), 3.96-3.81 (m, 2H), 3.50 (t, 1H), 3.12-2.85 (m, 2H), 1.24 (t, 3H).

¹⁹F NMR (300 MHz, CDCl₃) δ–229.52 ppm.

Step 3: Synthesis of (R)-2-(4-bromo-2-propionylphenoxy)-3-fluoropropyl acetate 4

To a stirred solution of (R)-1-(5-bromo-2-(1-fluoro-3-hydroxypropan-2-yloxy)phenyl)propan-1-one (1.95 g, 6.4 mmol) in 25 mL of dichloromethane at 0° C. was added triethylamine (0.97 g, 9.6 mmol), followed by dropwise addition of acetyl chloride (0.55 g, 7.05 mmol). The reaction mixture was stirred at room temperature for 1 h. The product was extracted with DCM (2×50 mL), washed with H₂O (3×20 mL), brine (20 mL), dried over sodium sulphate and concentrated to give the crude product 4 (2.21 g, quantitative), which was used for the next step without further purification.

¹H NMR (300 MHz, CDCl₃) δ 7.81 (d, 1H), 7.58 (dd, 1H), 7.01 (d, 1H), 4.88-4.75 (m, 2H), 4.64 (m, 1H), 4.50-4.34 (m, 2H), 3.01 (q, 2H), 2.13 (s, 3H), 1.21 (t, 3H).

Step 4: Synthesis of (R)-2-(4-bromo-2-(1,1-difluoropropyl)phenoxy)-3-fluoropropyl acetate 5

To a solution of (R)-2-(4-bromo-2-propionylphenoxy)-3-fluoropropyl acetate (2.21 g, 6.4 mmol) in dry CH₂Cl₂ (1 mL) in a seal tube was added deoxo-fluor (14.15 ml, 64.0 mmol) and flush with argon and the cap sealed. The resulting mixture was stirred at 40° C. for 5-7 days. The reaction mixture was poured into ice-cold water (20 mL) and saturated aqueous sodium carbonate was added cautiously and the mixture was stirred for 20 to 30 min. The aqueous layer was extracted with ethyl acetate (2×50 mL). The combined organic extracts were washed with brine (25 mL), dried (Na₂SO₄). After removal of the solvent, the residue was purified by silica gel column chromatography using 0-30% ethyl acetate/hexane to get desired product 5 (1.3 g, 55.2%) as a light-yellow oil.

¹H NMR (300 MHz, CDCl₃) δ 7.62 (d, 1H), 7.48 (dd, 1H), 6.95 (d, 1H), 4.74-4.64 (m, 2H), 4.56 (m, 1H), 4.40-4.28 (m, 2H), 2.38-2.19 (m, 2H), 2.07 (s, 3H), 0.92 (t, 3H).

¹⁹F NMR (300 MHz, CDCl₃) δ–96.31, –96.58, –230.69 ppm.

Step 5: Synthesis of (R)-2-(4-bromo-2-(1,1-difluoropropyl)phenoxy)-3-fluoropropan-1-ol 6

To a solution of (R)-2-(4-bromo-2-(1,1-difluoropropyl)phenoxy)-3-fluoropropyl acetate (1.3 g, 3.5 mmol) in MeOH/H₂O (20/10 mL) was added K₂CO₃ (0.975 g, 7.0 mmol) and stirred at room temperature for 2 h. The reaction mixture was concentrated and passed through a short silica gel column (EtOAc/hexane, 1-40%) to give the desired product 6 (1.0 g, 87.6%) as a white solid.

¹H NMR (300 MHz, CDCl₃) δ 7.67 (m, 1H), 7.55 (dd, 1H), 7.02 (d, 1H), 4.81 (m, 1H), 4.73-4.61 (m, 2H), 4.01-3.84 (m, 2H), 2.47-2.27 (m, 2H), 2.05 (m, 1H), 1.00 (t, 3H).

¹⁹F NMR (300 MHz, CDCl₃) δ–94.10, –98.99, –230.30 ppm.

Step 6: Synthesis of (R)-2-(4-bromo-2-(1,1-difluoropropyl)phenoxy)-3-fluoropropanoic acid 7

To a stirred solution of (R)-2-(4-bromo-2-(1,1-difluoropropyl)phenoxy)-3-fluoropropan-1-ol (1.0 g, 3.06 mmol), sodium chlorite (0.7 g, 7.66 mmol) in acetonitrile (26 mL) and 1M sodium phosphate buffer (pH6, 26 mL) was added sodium hypochlorite (10 drops, 4-4.99M solution) followed by TEMPO (0.024 g, 0.153 mmol). The reaction mixture was stirred at room temperature for 2 hours. Extra sodium hypochlorite (4 drops, 4-4.99M solution) and TEMPO (0.024 g, 0.153 mmol) were added and the addition of sodium hypochlorite and TEMPO was repeated three more times at 8 h intervals. After completion of the reaction, the mixture was cooled to 0° C. and 1M NaOH solution was added to adjust pH ~13 and the product washed with DCM (40 mL). The water layer was separated, cooled again to 0° C., and acidified with 1M HCl to pH ~1. The product was extracted with ethyl acetate (2×50 mL), washed with water (2×10 mL), brine (10 mL), dried over sodium sulphate, filtered and concentrated to give 7 as a white solid (1.0 g, 96.1%).

$^1$H NMR (300 MHz, CDCl$_3$) δ 9.62-8.91 (br s, 1H), 7.72 (d, 1H), 7.54 (dd, 1H), 6.80 (d, 1H), 5.06-4.87 (m, 3H), 2.52-2.32 (m, 2H), 2.05 (m, 1H), 1.00 (t, 3H).

$^{19}$F NMR (300 MHz, CDCl$_3$) δ −94.61, −97.86, −228.93 ppm.

Step 7: Synthesis of sodium (R)-2-(4-bromo-2-(1,1-difluoropropyl)phenoxy)-3-fluoropropanoate 8

To a stirred solution of (R)-2-(4-bromo-2-(1,1-difluoropropyl)phenoxy)-3-fluoropropanoic acid (1.0 g, 2.94 mmol) in acetonitrile (15 mL) at 0° C. was added NaHCO$_3$ (0.247 g, 2.94 mmol) in 5 mL of water. The reaction mixture was stirred at room temperature for 30 min. Acetonitrile was removed in situ and the aqueous solution was lyophilized to give 8 as a white solid (1.0 g, 94%).

1H NMR (300 MHz, CD$_3$OD) δ 7.55 (d, 1H), 7.49 (dd, 1H), 6.87 (d, 1H), 4.89-4.84 (m, 1H), 4.76-4.63 (m, 2H), 2.57-2.37 (m, 2H), 0.94 (t, 3H).

$^{19}$F NMR (300 MHz, CDCl$_3$) δ −96.91, −97.92, −226.21 ppm.

MS (ES−): m/z 339.4 (M−H), HPLC retention time: 11.68 min

Example 4: Synthesis of (R)-2-(4-bromo-2-(1,1-difluoroethyl)phenoxy)-3-fluoropropanoic acid

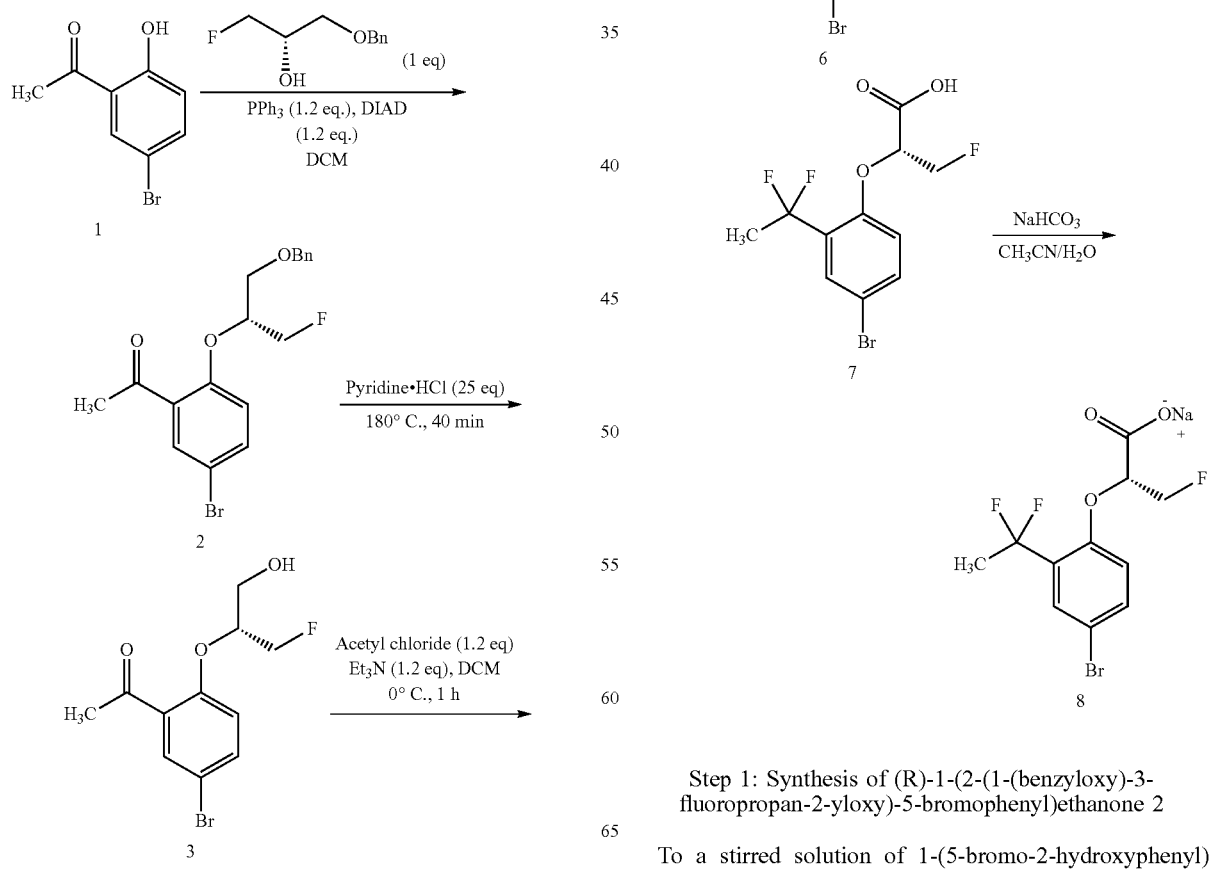

Step 1: Synthesis of (R)-1-(2-(1-(benzyloxy)-3-fluoropropan-2-yloxy)-5-bromophenyl)ethanone 2

To a stirred solution of 1-(5-bromo-2-hydroxyphenyl)ethanone (1.18 g, 4.98 mmol), (S)-1-(benzyloxy)-3-fluoropropan-2-ol (0.92 g, 4.99 mmol), and triphenylphosphine (1.57 g, 5.98 mmol) in 60 mL of dichloromethane previously cooled to 0° C. was slowly added DIAD (1.21 g, 5.98 mmol). The ice bath was then removed and the reaction mixture was stirred at room temperature overnight then concentrated under reduced pressure. After removal of the solvent, the residue was purified by silica gel column chromatography using 0-30% ethyl acetate/hexane to get desired product 2 (1.1 g, 57.7%) as a light-yellow oil.

1H NMR (300 MHz, CDCl$_3$) δ 7.89 (d, 1H), 7.56 (dd, 1H), 7.46-7.30 (m, 5H), 6.96 (d, 1H), 4.87-4.64 (m, 3H), 4.60 (d, 2H), 3.80 (dd, 2H), 2.66 (s, 3H).

$^{19}$F NMR (300 MHz, CDCl$_3$) δ–230.48 ppm.

Step 2: Synthesis of (R)-1-(5-bromo-2-(1-fluoro-3-hydroxypropan-2-yloxy)phenyl)ethanone 3

To (R)-1-(2-(1-(benzyloxy)-3-fluoropropan-2-yloxy)-5-bromophenyl)ethanone (1.1 g, 2.88 mmol) in a 100 mL of round bottom flask was added pyridine.HCl (8.33 g, 72.1 mmol). The reaction mixture was heated at 180° C. for 90 min. then cooled. The reaction mixture was quenched with H$_2$O (30 mL), and the product extracted with ethyl acetate (2×50 mL), washed with H$_2$O (2×30 mL), brine (25 mL), dried over sodium sulphate and concentrated under reduced pressure. The residue was passed through a silica gel column (EtOAc/hexane, 0-50%) to give desired product 3 (0.8 g, 95.2%) as a colourless liquid.

1H NMR (300 MHz, CDCl$_3$) δ 7.81 (d, 1H), 7.59 (dd, 1H), 7.05 (d, 1H), 4.81 (d, 1H), 4.76-4.49 (m, 2H), 4.02-3.72 (m, 2H), 3.38 (t, 1H), 2.65 (s, 3H).

$^{19}$F NMR (300 MHz, CDCl$_3$) δ–229.93 ppm.

Step 3: Synthesis of (R)-2-(2-acetyl-4-bromophenoxy)-3-fluoropropyl acetate 4

To a stirred solution of (R)-1-(5-bromo-2-(1-fluoro-3-hydroxypropan-2-yloxy)phenyl)ethanone (0.8 g, 2.75 mmol) in 25 mL of dichloromethane at 0° C. was added triethylamine (0.333 g, 3.29 mmol), followed by dropwise addition of acetyl chloride (0.259 g, 3.29 mmol). The reaction mixture was stirred at room temperature for 1 h. The product was extracted with DCM (2×50 mL), washed with H$_2$O (3×30 mL), brine (30 mL), dried over sodium sulphate and concentrated to get the crude product 4 (0.92 g, quantitative), which was used for the next step without further purification. 1H NMR (300 MHz, CDCl$_3$) δ 7.88 (d, 1H), 7.60 (dd, 1H), 7.03 (d, 1H), 4.92-4.74 (m, 2H), 4.73-4.58 (m, 1H), 4.54-4.32 (m, 2H), 2.66 (s, 3H), 2.13 (s, 3H).

$^{19}$F NMR (300 MHz, CDCl$_3$) δ–231.06 ppm.

Step 4: Synthesis of (R)-2-(4-bromo-2-(1,1-difluoroethyl)phenoxy)-3-fluoropropyl acetate 5

To a solution of (R)-2-(2-acetyl-4-bromophenoxy)-3-fluoropropyl acetate (0.92 g, 2.76 mmol) in dry CH$_2$Cl$_2$ (1 mL) in a seal tube was added deoxo-fluor (5.09 ml, 27.6 mmol) and flush with argon and the cap sealed. The resulting mixture was stirred at 40° C. for 5-7 days. The reaction mixture was poured into ice-cold water (20 mL), saturated aqueous sodium carbonate was added cautiously and the mixture was stirred for 20 to 30 min. The aqueous layer was extracted with ethyl acetate (2×30 mL). The combined organic extracts were washed with brine (25 mL), dried (Na$_2$SO$_4$). After removal of the solvent, the residue was purified by silica gel column chromatography using 0-30% ethyl acetate/hexane to get desired product 5 (0.69 g, 70.3%) as a light-yellow oil. 1H NMR (300 MHz, CDCl$_3$) δ 7.71 (d, 1H), 7.54 (dd, 1H), 7.02 (d, 1H), 4.86-4.69 (m, 2H), 4.68-4.56 (m, 1H), 4.50-4.32 (m, 2H), 2.13 (s, 3H), 2.03 (t, 3H).

$^{19}$F NMR (300 MHz, CDCl$_3$) δ–86.97, –87.97, –230.69 ppm.

Step 5: Synthesis of (R)-2-(4-bromo-2-(1,1-difluoroethyl)phenoxy)-3-fluoropropan-1-ol 6

To a solution of (R)-2-(4-bromo-2-(1,1-difluoroethyl)phenoxy)-3-fluoropropyl acetate (0.69 g, 1.94 mmol) in MeOH/H$_2$O (40/4 mL) was added K$_2$CO$_3$ (0.536 g, 3.88 mmol). The reaction was stirred at room temperature for 2 h, then concentrated and passed through a short silica gel column (EtOAc/hexane, 1-40%) to give a desired product 6 (0.55 g, 90.4%) as a white solid. 1H NMR (300 MHz, CDCl$_3$) δ 7.70 (d, 1H), 7.55 (dd, 1H), 7.02 (d, 1H), 4.82 (dd, 1H), 4.76-4.61 (m, 2H), 4.02-3.85 (m, 2H), 2.06 (t, 3H).

$^{19}$F NMR (300 MHz, CDCl$_3$) δ–86.08, –88.97, –230.49 ppm.

Step 6: Synthesis of (R)-2-(4-bromo-2-(1,1-difluoroethyl)phenoxy)-3-fluoropropanoic acid 7

To a stirred solution of (R)-2-(4-bromo-2-(1,1-difluoroethyl)phenoxy)-3-fluoropropan-1-ol (0.55 g, 1.76 mmol), sodium chlorite (0.397 g, 4.39 mmol) in acetonitrile (15 mL) and 1M sodium phosphate buffer (pH-6, 15 mL) was added sodium hypochlorite (5 drops, 4-4.99M solution) followed by TEMPO (13.7 mg, 0.088 mmol). The reaction mixture was stirred at room temperature for 2 hours, Extra sodium hypochlorite (5 drops, 4-4.99M solution) and TEMPO (0.024 g, 0.153 mmol) were added and the addition of sodium hypochlorite and TEMPO was repeated three more times at 8 h intervals. After completion of the reaction, the mixture was cooled to 0° C. and 1M NaOH solution was added to adjust pH ~13 and the product washed with DCM (40 mL). The water layer was separated, cooled again to 0° C., and acidified with 1M HCl to pH ~1. The product was extracted with ethyl acetate (2×50 mL), washed with water (2×20 mL), brine (20 mL), dried over sodium sulphate, filtered and concentrated to get product 7 as a white solid (0.53 g, 92.2%).

$^1$H NMR (300 MHz, CDCl$_3$) δ 10.46-9.91 (br, 1H); 7.72 (d, 1H); 7.49 (dd, 1H); 6.78 (d, 1H); 5.04-4.88 (m, 2H); 4.84 (d, 1H); 2.09 (t, 3H);

$^{19}$F NMR (300 MHz, CDCl$_3$) δ–228.15, –88.33, –86.24; ES-MS: 326 [M−1].

HPLC Retention Time: 10.852 min, 99.45% purity @ 280 nm.

Example 5: Synthesis of (S)-2-(4-bromo-2-(1,1-difluoropropyl)-5-fluorophenoxy)propanoic acid

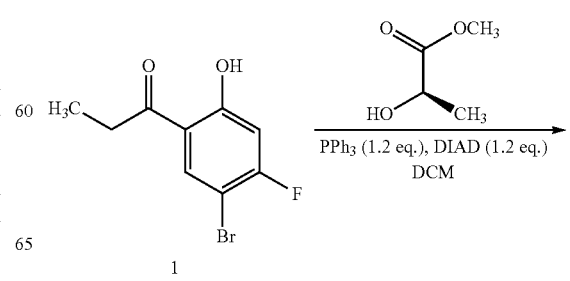

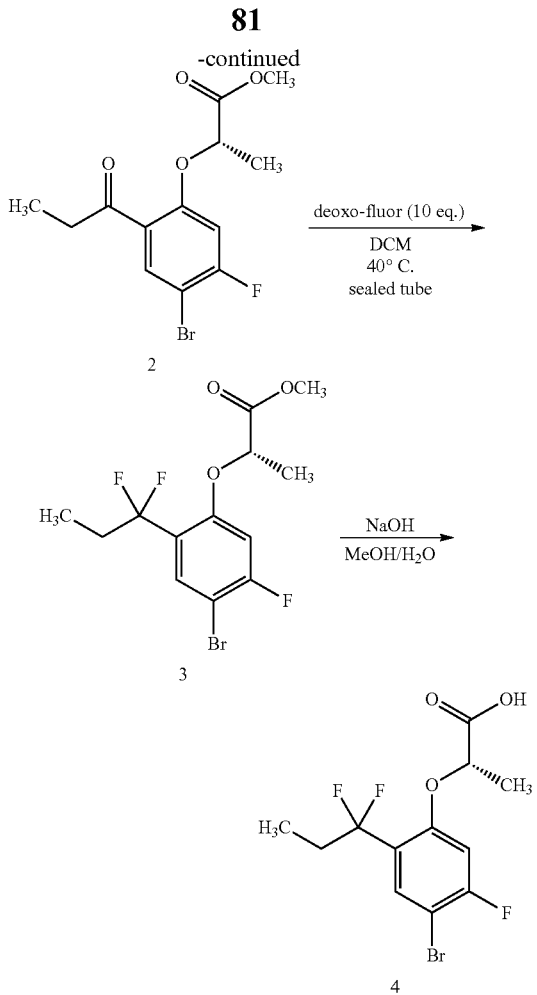

Step 1: Synthesis of (S)-methyl 2-(4-bromo-5-fluoro-2-propionylphenoxy)propanoate 2

To a stirred solution of 1-(5-bromo-4-fluoro-2-hydroxyphenyl)propan-1-one (0.613 g, 2.49 mmol), (R)-methyl 2-hydroxypropanoate (0.311 g, 2.99 mmol), and triphenylphosphine (0.784 g, 2.99 mmol) in 20 mL of dichloromethane previously cooled to 0° C. was slowly added DIAD (0.605 g, 2.99 mmol). The ice bath was then removed and the reaction mixture was stirred at room temperature overnight, then concentrated under reduced pressure. After removal of the solvent, the residue was purified by silica gel column chromatography using 0-20% ethyl acetate/hexane to give the desired product 2 (0.52 g, 62.9%) as a light-yellow oil.

$^1$H NMR (300 MHz, CDCl$_3$) δ 8.02 (d, 1H), 6.62 (d, 1H), 4.89 (q, 1H), 3.85 (s, 3H), 3.20-3.00 (m, 2H), 1.76 (d, 3H), 1.24 (t, 3H).

$^{19}$F NMR (300 MHz, CDCl$_3$) δ−98.44 ppm.

Step 2: Synthesis of (S)-methyl 2-(4-bromo-2-(1,1-difluoropropyl)-5-fluorophenoxy)propanoate 3

To a solution of (S)-methyl 2-(4-bromo-5-fluoro-2-propionylphenoxy)propanoate (0.52 g, 1.57 mmol) in dry CH$_2$Cl$_2$ (0.5 mL) in a seal tube was added deoxo-fluor (2.9 ml, 15.7 mmol) and flush with argon and the cap sealed. The resulting mixture was stirred at 40° C. for 5-7 days. The reaction mixture was poured into ice-cold water (10 mL) and saturated aqueous sodium carbonate was added cautiously and the mixture stirred for 20 to 30 min. The aqueous layer was extracted with ethyl acetate (2×30 mL). The combined organic extracts were washed with brine (15 mL), dried (Na$_2$SO$_4$). After removal of the solvent, the residue was purified by silica gel column chromatography using 0-20% ethyl acetate/hexane to give the desired product 3 (0.45 g, 81.0%) as a light-yellow oil.

$^1$H NMR (300 MHz, CDCl$_3$) δ 7.68 (dd, 1H), 6.57 (d, 1H), 4.74 (q, 1H), 3.77 (s, 3H), 2.47-2.27 (m, 2H), 1.64 (d, 3H), 0.93 (t, 3H).

$^{19}$F NMR (300 MHz, CDCl$_3$) δ−92.58, −98.20, −102.00 ppm.

Step 3: Synthesis of (S)-2-(4-bromo-2-(1,1-difluoropropyl)-5-fluorophenoxy)propanoic acid 4

To a stirred solution of (S)-methyl 2-(4-bromo-2-(1,1-difluoropropyl)-5-fluorophenoxy)propanoate (0.45 g, 1.27 mmol) in MeOH/H$_2$O (20/5 mL) was added NaOH (0.061 g, 1.53 mmol) at 0° C. The reaction mixture was stirred at room temperature for 1-2 h. The reaction mixture was concentrated, and 10 mL of H$_2$O was added. The mixture was cooled to 0° C. and acidified with 1M HCl to pH 2. The product was extracted with EtOAc (2×10 mL), washed with H$_2$O (5 ml), brine (5 mL), dried over Na$_2$SO$_4$, filtered and concentrated to give compound 4 (0.4 g, 92.6%) as a white solid.

$^1$H NMR (300 MHz, CDCl$_3$) δ 9.57-8.08 (br s, 1H), 7.69 (dd, 1H), 6.62 (d, 1H), 4.78 (q, 1H), 2.43-2.23 (m, 2H), 1.70 (d, 3H), 0.92 (t, 3H).

$^{19}$F NMR (300 MHz, CDCl$_3$) δ−93.27, −97.65, −101.65 ppm.

MS (ES−): m/z 339.3 (M−H), HPLC retention time: 12.04 min

Example 6: Synthesis of (R)-2-(4-bromo-2-(1,1-difluoropropyl)-5-fluorophenoxy)-3-fluoropropanoic acid

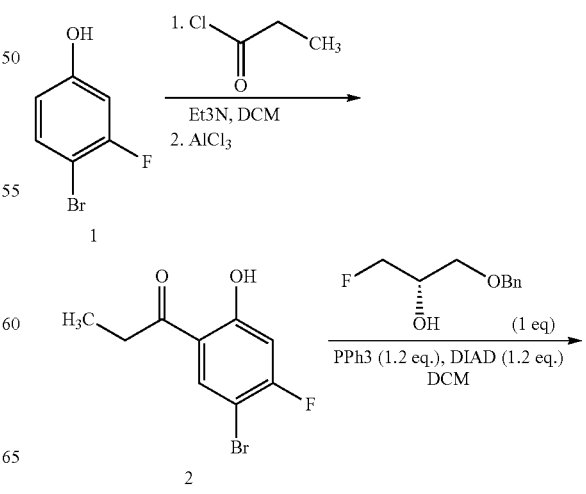

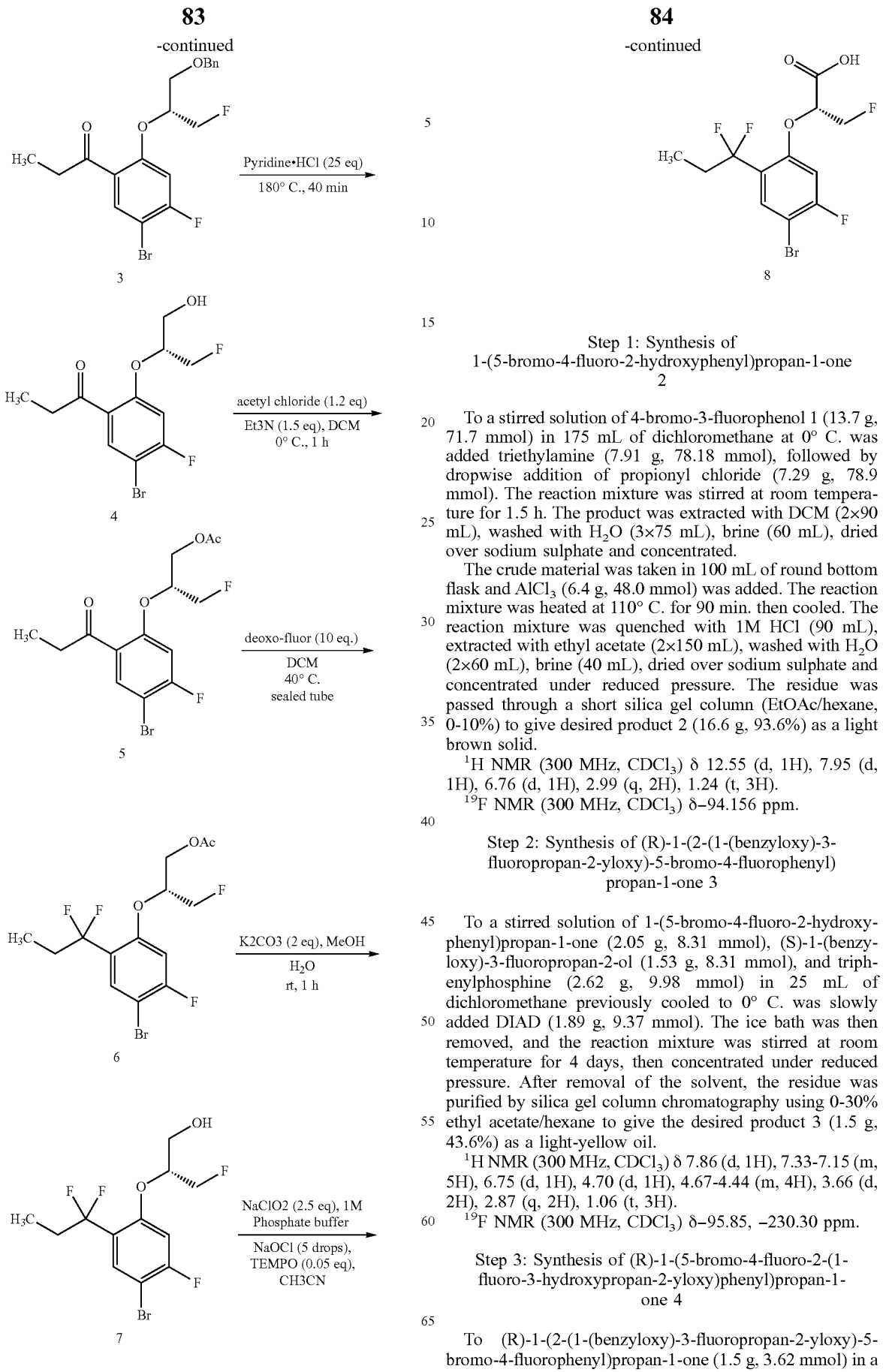

Step 1: Synthesis of 1-(5-bromo-4-fluoro-2-hydroxyphenyl)propan-1-one 2

To a stirred solution of 4-bromo-3-fluorophenol 1 (13.7 g, 71.7 mmol) in 175 mL of dichloromethane at 0° C. was added triethylamine (7.91 g, 78.18 mmol), followed by dropwise addition of propionyl chloride (7.29 g, 78.9 mmol). The reaction mixture was stirred at room temperature for 1.5 h. The product was extracted with DCM (2×90 mL), washed with H$_2$O (3×75 mL), brine (60 mL), dried over sodium sulphate and concentrated.

The crude material was taken in 100 mL of round bottom flask and AlCl$_3$ (6.4 g, 48.0 mmol) was added. The reaction mixture was heated at 110° C. for 90 min. then cooled. The reaction mixture was quenched with 1M HCl (90 mL), extracted with ethyl acetate (2×150 mL), washed with H$_2$O (2×60 mL), brine (40 mL), dried over sodium sulphate and concentrated under reduced pressure. The residue was passed through a short silica gel column (EtOAc/hexane, 0-10%) to give desired product 2 (16.6 g, 93.6%) as a light brown solid.

$^1$H NMR (300 MHz, CDCl$_3$) δ 12.55 (d, 1H), 7.95 (d, 1H), 6.76 (d, 1H), 2.99 (q, 2H), 1.24 (t, 3H).
$^{19}$F NMR (300 MHz, CDCl$_3$) δ −94.156 ppm.

Step 2: Synthesis of (R)-1-(2-(1-(benzyloxy)-3-fluoropropan-2-yloxy)-5-bromo-4-fluorophenyl)propan-1-one 3

To a stirred solution of 1-(5-bromo-4-fluoro-2-hydroxyphenyl)propan-1-one (2.05 g, 8.31 mmol), (S)-1-(benzyloxy)-3-fluoropropan-2-ol (1.53 g, 8.31 mmol), and triphenylphosphine (2.62 g, 9.98 mmol) in 25 mL of dichloromethane previously cooled to 0° C. was slowly added DIAD (1.89 g, 9.37 mmol). The ice bath was then removed, and the reaction mixture was stirred at room temperature for 4 days, then concentrated under reduced pressure. After removal of the solvent, the residue was purified by silica gel column chromatography using 0-30% ethyl acetate/hexane to give the desired product 3 (1.5 g, 43.6%) as a light-yellow oil.

$^1$H NMR (300 MHz, CDCl$_3$) δ 7.86 (d, 1H), 7.33-7.15 (m, 5H), 6.75 (d, 1H), 4.70 (d, 1H), 4.67-4.44 (m, 4H), 3.66 (d, 2H), 2.87 (q, 2H), 1.06 (t, 3H).
$^{19}$F NMR (300 MHz, CDCl$_3$) δ −95.85, −230.30 ppm.

Step 3: Synthesis of (R)-1-(5-bromo-4-fluoro-2-(1-fluoro-3-hydroxypropan-2-yloxy)phenyl)propan-1-one 4

To (R)-1-(2-(1-(benzyloxy)-3-fluoropropan-2-yloxy)-5-bromo-4-fluorophenyl)propan-1-one (1.5 g, 3.62 mmol) in a 250 mL of round bottom flask was added pyridine·HCl (10.5 g, 90.7 mmol). The reaction mixture was heated at 180° C. for 90 minutes. The reaction mixture was cooled, quenched with H$_2$O (30 mL), and the product extracted with ethyl acetate (2×50 mL), washed with H$_2$O (2×20 mL), brine (15 mL), dried over sodium sulphate and concentrated under reduced pressure. The residue was passed through a short silica gel column (EtOAc/hexane, 0-50%) to give desired product 4 (1.08 g, 92.1%) as a white solid.

$^1$H NMR (300 MHz, CDCl$_3$) δ 7.83 (d, 1H), 6.92 (d, 1H), 4.75 (d, 1H), 4.66-4.50 (m, 2H), 3.92-3.77 (m, 2H), 3.38 (t, 1H), 3.07-2.79 (m, 2H), 1.16 (t, 3H).

$^{19}$F NMR (300 MHz, CDCl$_3$) δ −97.68, −229.52 ppm.

Step 4: Synthesis of (R)-2-(4-bromo-5-fluoro-2-propionylphenoxy)-3-fluoropropyl acetate 5

To a stirred solution of (R)-1-(5-bromo-4-fluoro-2-(1-fluoro-3-hydroxypropan-2-yloxy)phenyl)propan-1-one (1.08 g, 3.34 mmol) in 20 mL of dichloromethane at 0° C. was added triethylamine (0.40 g, 4.0 mmol), followed by dropwise addition of acetyl chloride (0.31 g, 4.0 mmol). The reaction mixture was stirred at room temperature for 1 h. The product was extracted with DCM (2×30 mL), washed with H$_2$O (2×30 mL), brine (20 mL), dried over sodium sulphate and concentrated to get the crude product 5 (1.21 g, quantitative), which was used for the next step without further purification.

$^1$H NMR (300 MHz, CDCl$_3$) δ 7.93 (d, 1H), 6.89 (d, 1H), 4.84-4.53 (m, 3H), 4.46-4.27 (m, 2H), 2.94 (q, 2H), 2.08 (s, 3H), 1.15 (t, 3H).

$^{19}$F NMR (300 MHz, CDCl$_3$) δ −98.26, −230.88 ppm.

Step 5: Synthesis of (R)-2-(4-bromo-2-(1,1-difluoropropyl)-5-fluorophenoxy)-3-fluoropropyl acetate 6

To a solution of (R)-2-(4-bromo-5-fluoro-2-propionylphenoxy)-3-fluoropropyl acetate (1.21 g, 3.31 mmol) in dry CH$_2$Cl$_2$ (10.8 mL) in a seal tube was added deoxo-fluor (5.1 ml, 33.1 mmol) and flush with argon and the cap sealed. The resulting mixture was stirred at 40° C. for 5-7 days. The reaction mixture was poured into ice-cold water (20 mL) and saturated aqueous sodium carbonate was added cautiously and the mixture stirred for 20 to 30 min. The aqueous layer was extracted with ethyl acetate (2×40 mL).

The combined organic extracts were washed with brine (20 mL), dried (Na$_2$SO$_4$). After removal of the solvent, the residue was purified by silica gel column chromatography using 0-30% ethyl acetate/hexane to give the desired product 6 (0.68 g, 53.0%) as an oil.

$^1$H NMR (300 MHz, CDCl$_3$) δ 7.67 (d, 1H), 6.89 (d, 1H), 4.78-4.49 (m, 3H), 4.41-4.26 (m, 2H), 2.38-2.15 (m, 2H), 2.07 (s, 3H), 0.91 (t, 3H).

$^{19}$F NMR (300 MHz, CDCl$_3$) δ −94.91 and, −96.02, −101.74, −230.49 ppm.

Step 6: Synthesis of (R)-2-(4-bromo-2-(1,1-difluoropropyl)-5-fluorophenoxy)-3-fluoropropan-1-ol 7

To a stirred solution of (R)-2-(4-bromo-2-(1,1-difluoropropyl)-5-fluorophenoxy)-3-fluoropropyl acetate (0.68 g, 1.75 mmol) in MeOH/H$_2$O (40/4 mL) was added K$_2$CO$_3$ (0.485 g, 3.51 mmol). The mixture was stirred at room temperature for 2 h, concentrated and passed through a short silica gel column (EtOAc/hexane, 1-40%) to give desired product 7 (0.59 g, 97.3%) as a white solid.

$^1$H NMR (300 MHz, CDCl$_3$) δ 7.67 (d, 1H), 6.89 (d, 1H), 4.81-4.68 (m, 1H), 4.66-4.49 (m, 2H), 3.94-3.78 (m, 2H), 2.40-2.17 (m, 2H), 2.04 (m, 1H), 0.94 (t, 3H).

$^{19}$F NMR (300 MHz, CDCl$_3$) δ −93.29, −97.91, −101.56, −230.10 ppm.

Step 7: Synthesis of (R)-2-(4-bromo-2-(1,1-difluoropropyl)-5-fluorophenoxy)-3-fluoropropanoic acid 8

To a stirred solution of (R)-2-(4-bromo-2-(1,1-difluoropropyl)-5-fluorophenoxy)-3-fluoropropan-1-ol (0.59 g, 1.70 mmol) and sodium chlorite (386 mg, 4.27 mmol) in acetonitrile (15.5 mL) and 1M sodium phosphate buffer (pH-6, 15.5 mL) was added sodium hypochlorite (5 drops, 4-4.99M solution) followed by TEMPO (13.3 mg, 0.08 mmol). The reaction mixture was stirred at room temperature for 2 hours. Extra sodium hypochlorite (4 drops, 4-4.99M solution) and TEMPO (6.24 mg, 0.04 mmol) were added and the addition of sodium hypochlorite and TEMPO was repeated three more times at 8 h intervals. After completion of the reaction, the mixture was cooled to 0° C. and 1M NaOH solution was added to adjust pH ~13 and washed with DCM (30 mL). The water layer was separated and cooled again to 0° C., then acidified with 1M HCl to pH ~1. The product was extracted with ethyl acetate (2×30 mL), washed with water (20 mL), brine (20 mL), dried over sodium sulphate, filtered and concentrated to give product 8 as a white solid (0.56 g, 91.2%).

$^1$H NMR (300 MHz, CDCl$_3$) δ 8.74-7.98 (br s, 1H), 7.73 (d, 1H), 6.68 (d, 1H), 5.03-4.79 (m, 3H), 2.47-2.21 (m, 2H), 0.94 (t, 3H).

$^{19}$F NMR (300 MHz, CDCl$_3$) δ −93.66, −97.02, −101.25, −228.55 ppm. MS (ES−): m/z 358 (M−H)

HPLC Retention Time: 11.816 min, 98.19% purity @ 280 nm.

Example 7: Synthesis of (R)-2-(4-chloro-2-(1,1-difluoropropyl)-5-fluorophenoxy)-3-fluoropropanoic acid

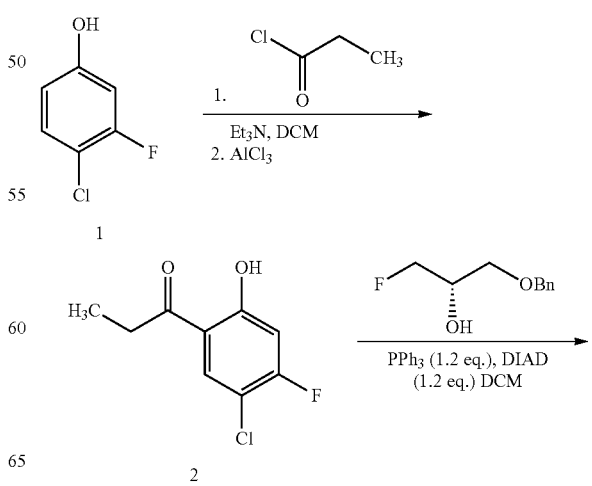

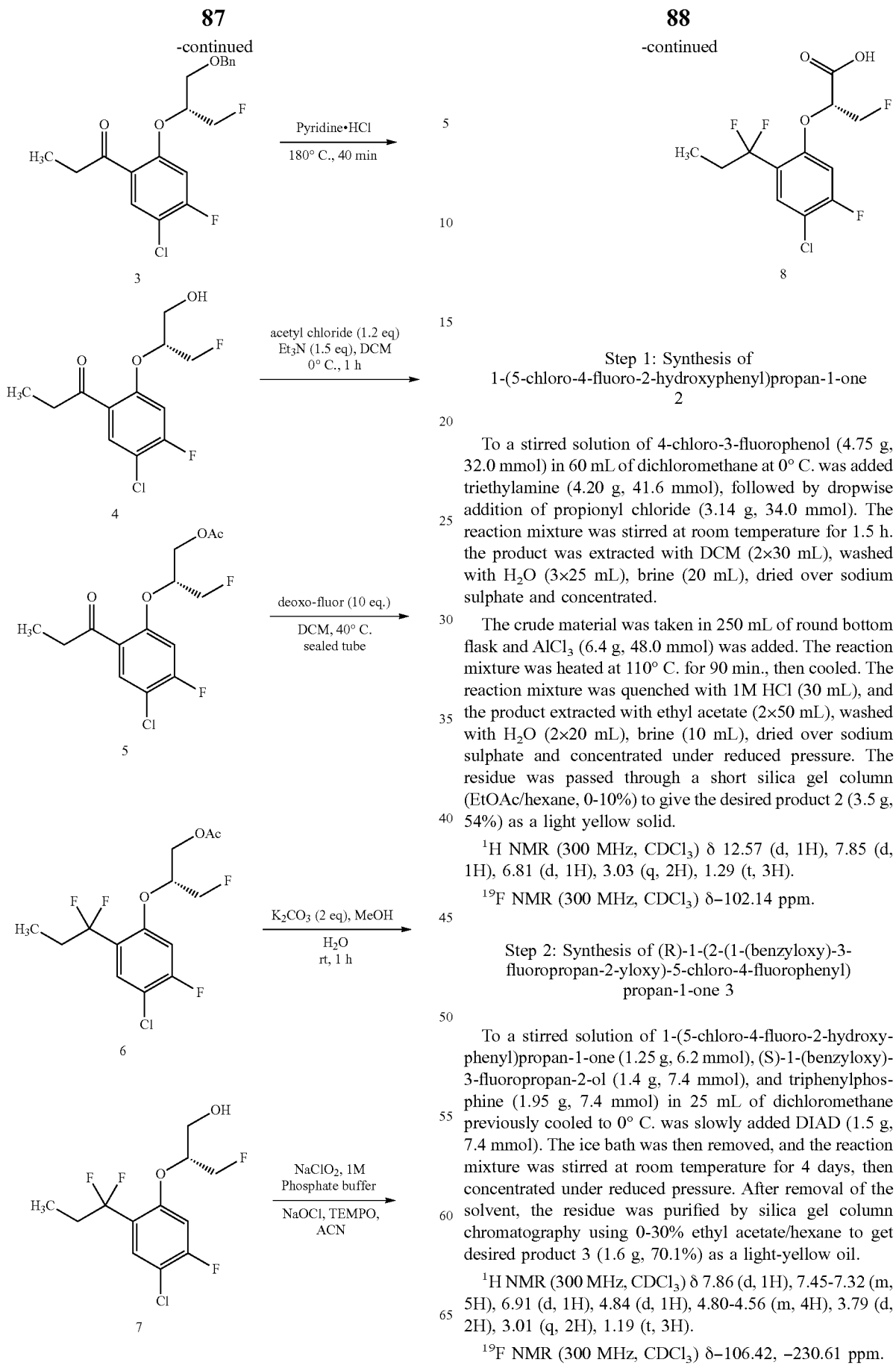

Step 1: Synthesis of 1-(5-chloro-4-fluoro-2-hydroxyphenyl)propan-1-one 2

To a stirred solution of 4-chloro-3-fluorophenol (4.75 g, 32.0 mmol) in 60 mL of dichloromethane at 0° C. was added triethylamine (4.20 g, 41.6 mmol), followed by dropwise addition of propionyl chloride (3.14 g, 34.0 mmol). The reaction mixture was stirred at room temperature for 1.5 h. the product was extracted with DCM (2×30 mL), washed with H₂O (3×25 mL), brine (20 mL), dried over sodium sulphate and concentrated.

The crude material was taken in 250 mL of round bottom flask and AlCl₃ (6.4 g, 48.0 mmol) was added. The reaction mixture was heated at 110° C. for 90 min., then cooled. The reaction mixture was quenched with 1M HCl (30 mL), and the product extracted with ethyl acetate (2×50 mL), washed with H₂O (2×20 mL), brine (10 mL), dried over sodium sulphate and concentrated under reduced pressure. The residue was passed through a short silica gel column (EtOAc/hexane, 0-10%) to give the desired product 2 (3.5 g, 54%) as a light yellow solid.

$^1$H NMR (300 MHz, CDCl₃) δ 12.57 (d, 1H), 7.85 (d, 1H), 6.81 (d, 1H), 3.03 (q, 2H), 1.29 (t, 3H).

$^{19}$F NMR (300 MHz, CDCl₃) δ−102.14 ppm.

Step 2: Synthesis of (R)-1-(2-(1-(benzyloxy)-3-fluoropropan-2-yloxy)-5-chloro-4-fluorophenyl)propan-1-one 3

To a stirred solution of 1-(5-chloro-4-fluoro-2-hydroxyphenyl)propan-1-one (1.25 g, 6.2 mmol), (S)-1-(benzyloxy)-3-fluoropropan-2-ol (1.4 g, 7.4 mmol), and triphenylphosphine (1.95 g, 7.4 mmol) in 25 mL of dichloromethane previously cooled to 0° C. was slowly added DIAD (1.5 g, 7.4 mmol). The ice bath was then removed, and the reaction mixture was stirred at room temperature for 4 days, then concentrated under reduced pressure. After removal of the solvent, the residue was purified by silica gel column chromatography using 0-30% ethyl acetate/hexane to get desired product 3 (1.6 g, 70.1%) as a light-yellow oil.

$^1$H NMR (300 MHz, CDCl₃) δ 7.86 (d, 1H), 7.45-7.32 (m, 5H), 6.91 (d, 1H), 4.84 (d, 1H), 4.80-4.56 (m, 4H), 3.79 (d, 2H), 3.01 (q, 2H), 1.19 (t, 3H).

$^{19}$F NMR (300 MHz, CDCl₃) δ−106.42, −230.61 ppm.

Step 3: Synthesis of (R)-1-(5-chloro-4-fluoro-2-(1-fluoro-3-hydroxypropan-2-yloxy)phenyl)propan-1-one 4

To (R)-1-(2-(1-(benzyloxy)-3-fluoropropan-2-yloxy)-5-chloro-4-fluorophenyl)propan-1-one (1.6 g, 4.35 mmol) in a 250 mL of round bottom flask was added pyridine·HCl (12.5 g, 108.7 mmol). The reaction mixture was heated at 180° C. for 90 min. then cooled. The reaction mixture was quenched with H$_2$O (30 mL), and the product extracted with ethyl acetate (2×50 mL), washed with H$_2$O (2×20 mL), brine (15 mL), dried over sodium sulphate and concentrated under reduced pressure. The residue was passed through a short silica gel column (EtOAc/hexane, 0-50%) to give desired product 4 (0.78 g, 64.4%) as a white solid.

$^1$H NMR (300 MHz, CDCl$_3$) δ 7.76 (d, 1H), 7.01 (d, 1H), 4.82 (d, 1H), 4.70-4.58 (m, 2H), 3.95-3.87 (m, 2H), 3.36 (t, 1H), 3.11-2.86 (m, 2H), 1.24 (t, 3H).

$^{19}$F NMR (300 MHz, CDCl$_3$) δ −105.66, −229.13 ppm.

Step 4: Synthesis of (R)-2-(4-chloro-5-fluoro-2-propionylphenoxy)-3-fluoropropyl acetate 5

To a stirred solution of (R)-1-(5-chloro-4-fluoro-2-(1-fluoro-3-hydroxypropan-2-yloxy)phenyl)propan-1-one (0.77 g, 2.77 mmol) in 20 mL of dichloromethane at 0° C. was added triethylamine (0.42 g, 4.16 mmol), followed by dropwise addition of acetyl chloride (0.261 g, 3.32 mmol). The reaction mixture was stirred at room temperature for 1 h. The product was extracted with DCM (2×20 mL), washed with H$_2$O (2×20 mL), brine (10 mL), dried over sodium sulphate and concentrated to get the crude product 5 (0.887 g, quantitative), which was used for the next step without further purification.

$^1$H NMR (300 MHz, CDCl$_3$) δ 7.86 (d, 1H), 6.97 (d, 1H), 4.83-4.65 (m, 3H), 4.51-4.36 (m, 2H), 3.01 (q, 2H), 2.14 (s, 3H), 1.22 (t, 3H).

$^{19}$F NMR (300 MHz, CDCl$_3$) δ −106.05, −230.88 ppm.

Step 5: Synthesis of (R)-2-(4-chloro-2-(1,1-difluoropropyl)-5-fluorophenoxy)-3-fluoropropyl acetate 6

To a solution of (R)-2-(4-chloro-5-fluoro-2-propionylphenoxy)-3-fluoropropyl acetate (0.887 g, 2.77 mmol) in dry CH$_2$Cl$_2$ (1 mL) in a seal tube was added deoxo-fluor (5.1 ml, 27.7 mmol) and flush with argon and the cap sealed. The resulting mixture was stirred at 40° C. for 5-7 days. The reaction mixture was poured into ice-cold water (20 mL), saturated aqueous sodium carbonate was added cautiously and the mixture stirred for 20 to 30 min. The aqueous layer was extracted with ethyl acetate (2×30 mL). The combined organic extracts were washed with brine (15 mL), dried (Na$_2$SO$_4$). After removal of the solvent, the residue was purified by silica gel column chromatography using 0-30% ethyl acetate/hexane to get desired product 6 (0.59 g, 62.2%) as a light-yellow oil.

$^1$H NMR (300 MHz, CDCl$_3$) δ 7.60 (d, 1H), 6.98 (d, 1H), 4.81-4.59 (m, 3H), 4.45-4.34 (m, 2H), 2.43-2.23 (m, 2H), 2.14 (s, 3H), 0.98 (t, 3H).

$^{19}$F NMR (300 MHz, CDCl$_3$) δ−95.31 and, −95.71, −109.63, −230.30 ppm.

Step 6: Synthesis of (R)-2-(4-chloro-2-(1,1-difluoropropyl)-5-fluorophenoxy)-3-fluoropropan-1-ol 7

To a stirred solution of (R)-2-(4-chloro-2-(1,1-difluoropropyl)-5-fluorophenoxy)-3-fluoropropyl acetate (0.44 g, 1.29 mmol) in MeOH/H$_2$O (10/2 mL) was added K$_2$CO$_3$ (0.391 g, 2.83 mmol) and the mixture was stirred at room temperature for 2 h. The reaction mixture was concentrated and passed through a short silica gel column (EtOAc/hexane, 1-40%) to give desired product 7 (0.37 g, 95.6%) as a white solid.

$^1$H NMR (300 MHz, CDCl$_3$) δ 7.59 (d, 1H), 6.98 (d, 1H), 4.85-4.79 (m, 1H), 4.69-4.57 (m, 2H), 4.01-3.87 (m, 2H), 2.47-2.25 (m, 2H), 2.00 (m, 1H), 1.00 (t, 3H).

$^{19}$F NMR (300 MHz, CDCl$_3$) δ−93.30, −98.05, −109.44, −230.10 ppm.

Step 7: Synthesis of (R)-2-(4-chloro-2-(1,1-difluoropropyl)-5-fluorophenoxy)-3-fluoropropanoic acid 8

To a stirred solution of (R)-2-(4-chloro-2-(1,1-difluoropropyl)-5-fluorophenoxy)-3-fluoropropan-1-ol (0.24 g, 0.799 mmol) and sodium chlorite (181 mg, 2.0 mmol) in acetonitrile (7 mL) and 1M sodium phosphate buffer (pH6, 7 mL) was added sodium hypochlorite (4 drops, 4-4.99M solution) followed by TEMPO (6.24 mg, 0.04 mmol). The reaction mixture was stirred at room temperature for 2 hours. Extra sodium hypochlorite (4 drops, 4-4.99M solution) and TEMPO (6.24 mg, 0.04 mmol) were added and the addition of sodium hypochlorite and TEMPO was repeated three more times at 8 h intervals. After completion of the reaction, the mixture was cooled to 0° C., 1M NaOH solution was added to adjust pH ~13 and washed with DCM (15 mL). The water layer was separated and cooled again to 0° C. The aqueous layer was acidified with 1M HCl to pH ~1, and the product extracted with ethyl acetate (2×15 mL), washed with water (10 mL), brine (10 mL), dried over sodium sulphate, filtered and concentrated to give product 8 as a white solid (0.23 g, 91.6%).

$^1$H NMR (300 MHz, CDCl$_3$) δ 8.30-7.67 (br s, 1H), 7.58 (d, 1H), 6.70 (d, 1H), 5.01-4.82 (m, 3H), 2.46-2.23 (m, 2H), 0.93 (t, 3H).

$^{19}$F NMR (300 MHz, CDCl$_3$) δ−93.75, −97.08, −109.14, −228.60 ppm.

MS (ES−): m/z 313 (M−H), HPLC retention time: 11.76 min Chiral H PLC: 7.62 mins, 99.4% e.e.

Example 8: Synthesis of (R)-2-[4-bromo-2-(1,1-difluoroethyl)-5-fluorophenoxy]-3-fluoropropionic acid

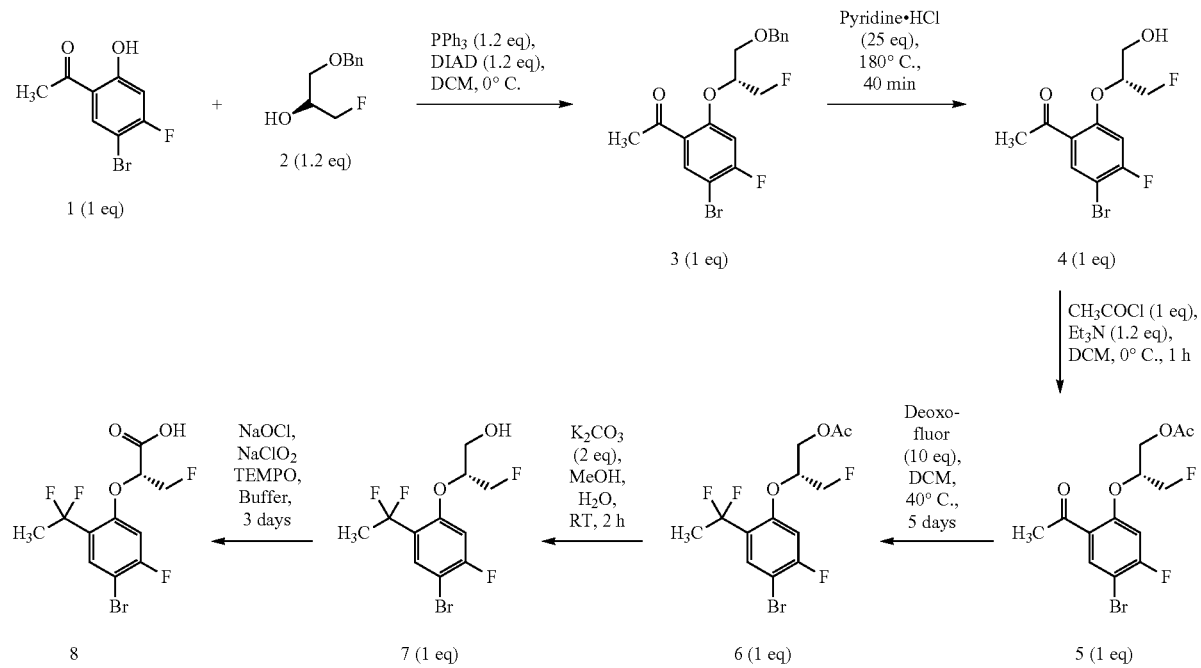

Step 1: Synthesis of 1-{2-[(R)-2-(benzyloxy)-1-(fluoromethyl)ethoxy]-5-bromo-4-fluorophenyl}-1-ethanone 3

To a stirred solution of 1-(5-bromo-4-fluoro-2-hydroxyphenyl)-1-ethanone (1.0 g, 4.29 mmol), (S)-1-(benzyloxy)-3-fluoropropan-2-ol (0.79 g, 4.29 mmol), and triphenylphosphine (1.35 g, 5.15 mmol) in 25 mL of dichloromethane previously cooled to 0° C. was slowly added DIAD (1.04 g, 5.15 mmol). The ice bath was then removed, and the reaction mixture was stirred at room temperature for 5 days, then concentrated under reduced pressure. After removal of the solvent, the residue was purified by silica gel column chromatography using 0-30% ethyl acetate/hexane to get desired product 3 (0.94 g, 54.8%) as a light-yellow oil.

$^1$H NMR (300 MHz, CDCl$_3$) δ 7.91 (d, 1H), 7.32-7.16 (m, 5H), 6.77 (d, 1H), 4.72 (d, 1H), 4.69-4.42 (m, 4H), 3.68 (d, 2H), 2.51 (s, 3H).

$^{19}$F NMR (300 MHz, CDCl$_3$) δ−97.82, −230.10 ppm.

Step 2: Synthesis of 1-{2-[(R)-1-(fluoromethyl)-2-hydroxyethoxy]-5-bromo-4-fluorophenyl}-1-ethanone 4

To 1-{2-[(R)-2-(benzyloxy)-1-(fluoromethyl)ethoxy]-5-bromo-4-fluorophenyl}-1-ethanone (0.94 g, 2.35 mmol) in a 250 mL of round bottom flask was added pyridine·HCl (6.8 g, 58.86 mmol). The reaction mixture was heated at 180° C. for 40 minutes. The reaction mixture was cooled, quenched with H$_2$O (30 mL), and the product extracted with ethyl acetate (2×50 mL), washed with H$_2$O (2×20 mL), brine (15 mL), dried over sodium sulphate and concentrated under reduced pressure. The residue was passed through a short silica gel column (EtOAc/hexane, 0-50%) to give desired product 4 (0.41 g, 56.3%) as a white solid.

$^1$H NMR (300 MHz, CDCl$_3$) δ 7.84 (d, 1H), 6.88 (d, 1H), 4.75 (d, 1H), 4.68-4.50 (m, 2H), 3.93-3.78 (br, 2H), 3.60 (t, 1H), 2.55 (s, 3H).

$^{19}$F NMR (300 MHz, CDCl$_3$) δ−97.01, −230.07 ppm.

Step 3: Synthesis of (R)-2-(2-acetyl-4-bromo-5-fluorophenoxy)-3-fluoropropyl acetate 5

To a stirred solution of 1-{2-[(R)-1-(fluoromethyl)-2-hydroxyethoxy]-5-bromo-4-fluorophenyl}-1-ethanone (0.41 g, 1.32 mmol) in 10 mL of dichloromethane at 0° C. was added triethylamine (0.20 g, 1.98 mmol), followed by the dropwise addition of acetyl chloride (0.125 g, 1.59 mmol). The reaction mixture was stirred at room temperature for 1 h. The product was extracted with DCM (2×20 mL), washed with H$_2$O (2×20 mL), brine (10 mL), dried over sodium sulphate and concentrated to get the crude product 5 (0.46 g, quantitative), which was used for the next step without further purification.

$^1$H NMR (300 MHz, CDCl$_3$) δ 7.93 (d, 1H), 6.89 (d, 1H), 4.85-4.53 (m, 3H), 4.46-4.23 (m, 2H), 2.55 (s, 3H), 2.05 (s, 3H).

$^{19}$F NMR (300 MHz, CDCl$_3$) δ−97.53, −230.98 ppm.

Step 4: Synthesis of (R)-2-[4-bromo-2-(1,1-difluoroethyl)-5-fluorophenoxy]-3-fluoropropyl acetate 6

To a solution of (R)-2-(2-acetyl-4-bromo-5-fluorophenoxy)-3-fluoropropyl acetate (0.46 g, 1.31 mmol) in dry CH$_2$Cl$_2$ (1 mL) in a seal tube was added deoxo-fluor (2.41 ml, 13.1 mmol) and flush with argon and the cap sealed. The resulting mixture was stirred at 40° C. for 5 days. The reaction mixture was poured into ice-cold water (20 mL) and saturated aqueous sodium carbonate was added cautiously. The mixture was stirred for 20 to 30 min. The aqueous layer was extracted with ethyl acetate (2×30 mL). The combined organic extracts were washed with brine (15 mL), dried (Na$_2$SO$_4$). After removal of the solvent, the residue was purified by silica gel column chromatography using 0-30% ethyl acetate/hexane to get desired product 6 (0.286 g, 58.5%) as a light-yellow oil.

$^1$H NMR (300 MHz, CDCl$_3$) δ 7.69 (d, 1H), 6.90 (d, 1H), 4.79-4.50 (m, 3H), 4.42-4.26 (m, 2H), 2.07 (s, 3H), 1.94 (t, 3H).

$^{19}$F NMR (300 MHz, CDCl$_3$) δ−86.01 and, −87.05, −101.67, −230.38 ppm.

Step 5: Synthesis of (R)-2-[4-bromo-2-(1,1-difluoroethyl)-5-fluorophenoxy]-3-fluoropropanol 7

To a stirred solution of (R)-2-[4-bromo-2-(1,1-difluoroethyl)-5-fluorophenoxy]-3-fluoropropyl acetate (0.20 g, 0.54 mmol) in MeOH/H$_2$O (10/2 mL) was added K$_2$CO$_3$ (0.15 g, 1.07 mmol) and the reaction was stirred at room temperature for 2 h. The reaction mixture was concentrated and passed through a short silica gel column (EtOAc/hexane, 1-40%) to give desired product 7 (0.16 g, 90.15%) as a white solid.

$^1$H NMR (300 MHz, CDCl$_3$) δ 7.75 (dd, 1H), 6.95 (d, 1H), 4.88-4.76 (m, 1H), 4.72-4.55 (m, 2H), 4.03-3.84 (m, 2H), 2.24-2.13 (br, H), 2.04 (t, 3H).

$^{19}$F NMR (300 MHz, CDCl$_3$) δ−85.22, −88.01, −101.49, −230.16 ppm.

Step 6: Synthesis of (R)-2-[4-bromo-2-(1,1-difluoroethyl)-5-fluorophenoxy]-3-fluoropropionic acid 8

To a stirred solution of (R)-2-[4-bromo-2-(1,1-difluoroethyl)-5-fluorophenoxy]-3-fluoropropanol (0.15 g, 0.453 mmol), sodium chlorite (102.4 mg, 1.13 mmol) in acetonitrile (3.9 mL) and 1M sodium phosphate buffer (pH6, 3.9 mL) was added sodium hypochlorite (9 drops, 4-4.99M solution) followed by TEMPO (3.54 mg, 0.023 mmol). The reaction mixture was stirred at room temperature for 2 hours. Extra sodium hypochlorite (9 drops, 4-4.99M solution) and TEMPO (3.54 mg, 0.023 mmol) were added and the addition of sodium hypochlorite and TEMPO was repeated three more times at 8 h intervals. After completion, the reaction was cooled to 0° C. 1M NaOH solution was added to adjust pH ~13 and the mixture washed with DCM (15 mL). The water layer was separated and cooled again to 0° C., then acidify with 1M HCl to pH ~1. The product was extracted with ethyl acetate (2×15 mL), washed with water (10 mL), brine (10 mL), dried over sodium sulphate, filtered and concentrated to give product 8 as a white solid (0.151 g, 96.9%).

$^1$H NMR (300 MHz, CDCl$_3$) δ 7.75 (d, 1H), 6.67 (d, 1H), 6.60-6.01 (br, 1H), 5.07-4.88 (m, 2H), 4.85 (d, 1H), 2.02 (t, 3H).

$^{19}$F NMR (300 MHz, CDCl$_3$) δ−85.37, −87.48, −101.10, −228.46 ppm.

MS (ES−): m/z 343 (M−H).

HPLC retention time: 11.37 min.

Chiral HPLC: 14.12 mins, 99.5% e.e.

Example 9: Synthesis of sodium (S)-2-(4-bromo-2-(difluoro(thiazol-2-yl)methyl)phenoxy)propanoate

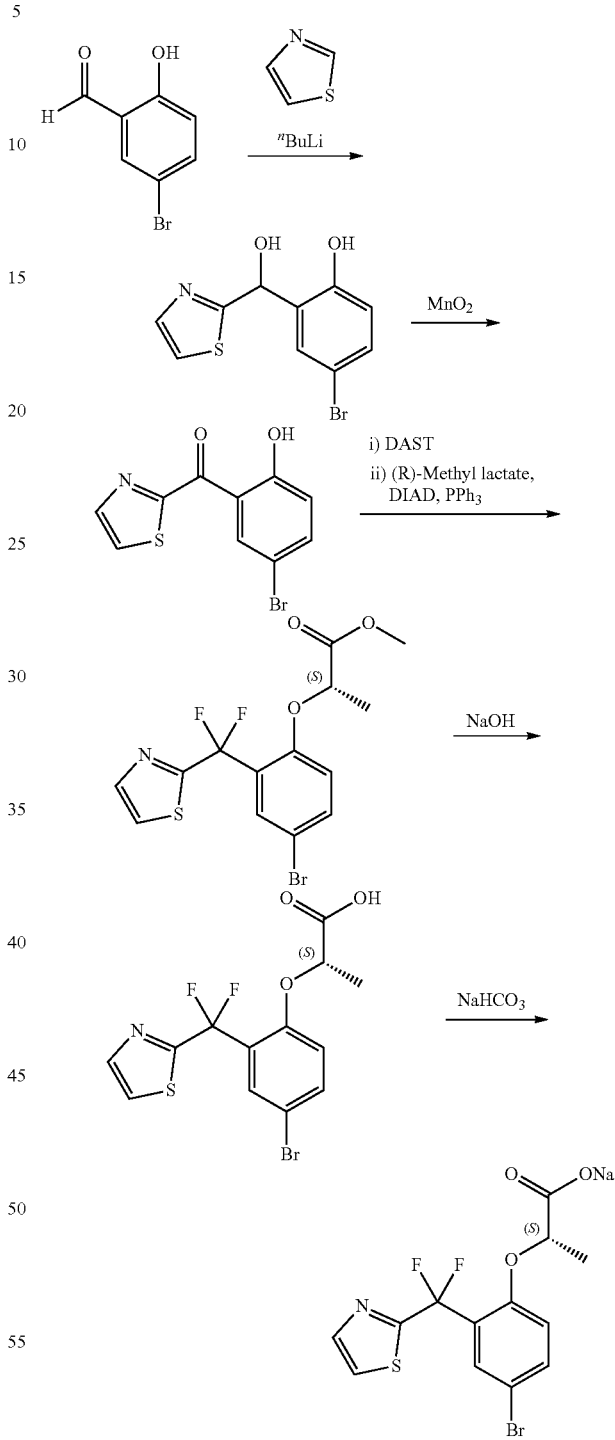

Step 1: Synthesis of 4-bromo-2-(hydroxy(thiazol-2-yl)methyl)phenol

To a cooled (−78° C.) solution of 1,3-thiazole (2.8 mL, 40 mmol, 2.0 eq.) in THF (22.6 mL) was added dropwise n-butyl lithium (2.7 M in heptanes, 14.7 mL, 40 mmol, 2.0 eq.) and the reaction mixture was subsequently allowed to slowly warm to room temperature over 1 h. The reaction mixture was re-cooled to −78° C. for the dropwise addition of a solution of 5-bromo-2-hydroxybenzaldehyde (4.0 g, 20 mmol, 1.0 eq.) in THF (12 mL), then allowed to warm to room temperature slowly and stirred for 18 h. The reaction mixture was quenched by the addition of saturated aqueous ammonium chloride solution (20 mL) and extracted with EtOAc (3×50 mL). The combined organic layers were washed with brine (50 mL), dried over sodium sulphate and concentrated under reduced pressure. The crude material was purified by flash column chromatography (Si, 0-30% EtOAc in hexanes) to give the title compound (2.64 g, 9.2 mmol, 46%) as a beige solid.

UPLC-MS: acidic 2-minute run MS (ES−): m/z 284.0/286.0 (M−H)−; retention time: 0.95 min; purity: 67%. $^1$H NMR (400 MHz, Chloroform-d) δ 7.73 (d, J=3.3 Hz, 1H), 7.53 (d, J=2.4 Hz, 1H), 7.36-7.27 (m, 2H), 6.85 (d, J=8.6 Hz, 1H), 6.26 (s, 1H).

Step 2: Synthesis of (5-bromo-2-hydroxyphenyl)(thiazol-2-yl)methanone

To a solution of 4-bromo-2-(hydroxy(thiazol-2-yl)methyl)phenol (540 mg, 1.9 mmol, 1.0 eq.) in DCM (9.4 mL) was added manganese (IV) oxide (820 mg, 9.4 mmol, 5.0 eq.) and the reaction stirred at room temperature overnight. The reaction mixture was filtered through a pad of Celite and the pad washed with DCM (2×5 mL). The filtrate was concentrated under reduced pressure to give the title compound (488 mg, 1.7 mmol, 91%) as a dark yellow solid which was used in the subsequent reaction without additional purification.

UPLC-MS: acidic 2-minute run MS (ES+): no m/z; retention time: 1.26 min; purity: 86%.

$^1$H NMR (400 MHz, Chloroform-d) 512.15 (s, 1H), 9.31 (d, J=2.5 Hz, 1H), 8.08 (d, J=3.0 Hz, 1H), 7.72 (d, J=3.0 Hz, 1H), 7.55 (dd, J=9.0, 2.5 Hz, 1H), 6.88 (d, J=8.9 Hz, 1H).

Step 3: Synthesis of methyl (S)-2-(4-bromo-2-(difluoro(thiazol-2-yl)methyl) phenoxy)propanoate To a cooled (0° C.) solution of (5-bromo-2-hydroxyphenyl)(thiazol-2-yl)methanone (488 mg, 1.7 mmol, 1.0 eq.) in DCM (8.6 mL) was added DAST (2.3 mL, 17 mmol, 10.0 eq.), the reaction vial was sealed and the mixture was allowed to slowly warm to room-temperature overnight. The reaction mixture was poured into ice-water (50 mL) and extracted with DCM (2×50 mL). The combined organic extracts were washed sequentially with saturated aqueous sodium hydrogen carbonate (50 mL) and brine (50 mL), dried over sodium sulphate and the solvent concentrated under reduced pressure to ca. 10 mL. The resultant solution was immediately re-cooled to 0° C., diluted with THF (8.6 mL) and treated sequentially with (R)-methyl lactate (0.17 mL, 1.8 mmol, 1.05 eq.), triphenylphosphine (496 mg, 1.9 mmol, 1.1 eq.) and DIAD (0.37 mL, 1.9 mmol, 1.1 eq.). The reaction mixture was allowed to warm to room temperature slowly overnight. The reaction was concentrated under reduced pressure and the crude product purified twice by flash column chromatography (Si, 5-30% EtOAc in hexanes, followed by 10-50% DCM in hexanes) to give the title compound (142 mg, 0.36 mmol, 21%) as a colourless oil.

UPLC-MS: acidic 2-minute run MS (ES+): m/z 392/394 (M+H)+; retention time: 1.23 min; purity: 93%. $^1$H NMR (400 MHz, Chloroform-d) δ 7.96 (d, J=2.5 Hz, 1H), 7.82 (dt, J=3.3, 1.7 Hz, 1H), 7.57-7.48 (m, 2H), 6.64 (d, J=8.8 Hz, 1H), 4.60 (q, J=6.8 Hz, 1H), 3.67 (s, 3H), 1.27 (d, J=6.7 Hz, 3H).

Step 4: Synthesis of (S)-2-(4-bromo-2-(difluoro(thiazol-2-yl)methyl)phenoxy)propanoic acid A solution of methyl (S)-2-(4-bromo-2-(difluoro(thiazol-2-yl)methyl)phenoxy)propanoate (142 mg, 0.36 mmol, 1.0 eq.) in THF (2.2 mL) was treated with 1M aqueous sodium hydroxide solution (2.2 mL, 2.2 mmol, 6.0 eq.). The reaction mixture was allowed to stand at room temperature for 30 min. The reaction mixture was washed with EtOAc (3 mL). The aqueous layer was acidified to ~pH 3 with 1M aqueous hydrochloric acid solution and extracted with EtOAc (2×10 mL). The combined secondary organic extracts were washed with brine (15 mL), dried over sodium sulphate and concentrated under reduced pressure to give the title compound (101 mg, 0.27 mmol, 73%) as a colourless oil.

UPLC-MS: acidic 4-minute run MS (ES−): m/z 376.0/378.0 (M−H)−; retention time: 1.72 min; purity: 100%. $^1$H NMR (400 MHz, DMSO-d6) δ 13.16 (s, 1H), 8.00 (d, J=3.1 Hz, 1H), 7.94-7.84 (m, 1H), 7.81 (d, J=2.5 Hz, 1H), 7.71 (dd, J=8.9, 2.5 Hz, 1H), 6.90 (d, J=9.0 Hz, 1H), 4.71 (q, J=6.6 Hz, 1H), 1.09 (d, J=6.8 Hz, 3H). $^{19}$F NMR (376 MHz, DMSO-d6) δ−85.27.

Step 5: Synthesis of sodium (S)-2-(4-bromo-2-(difluoro(thiazol-2-yl)methyl) phenoxy)propanoate To a solution of (S)-2-(4-bromo-2-(difluoro(thiazol-2-yl)methyl)phenoxy)propanoic acid (101 mg, 0.27 mmol, 1.0 eq.) in water (11.4 mL) and MeCN (22.9 mL) was added 1M aqueous sodium hydrogen carbonate solution (0.28 mL, 0.28 mmol, 1.05 eq.) and the reaction stirred at room temperature for 30 min. The mixture was concentrated under reduced pressure and dried in a vacuum oven at 40° C. overnight to give the title compound (105 mg, 0.26 mmol, 98%) as an off-white powder.

UPLC-MS: acidic 2-minute run MS (ES+): m/z 378.0/380.0 (M+H)+; retention time: 0.85 min; purity: 100%. $^1$H NMR (DMSO-d6) δ: 7.97 (d, J=3.2 Hz, 1H), 7.86 (dt, J=3.2, 1.6 Hz, 1H), 7.71 (d, J=2.5 Hz, 1H), 7.60 (dd, J=8.9, 2.6 Hz, 1H), 6.80 (d, J=8.9 Hz, 1H), 3.89 (q, J=6.7 Hz, 1H), 0.91 (d, J=6.7 Hz, 3H). $^{19}$F NMR (376 MHz, DMSO-d6) δ −85.01 (d, J=2.0 Hz).

Example 10: Synthesis of sodium (S)-2-(4-bromo-2-(cyclobutyldifluoromethyl)phenoxy)propanoate

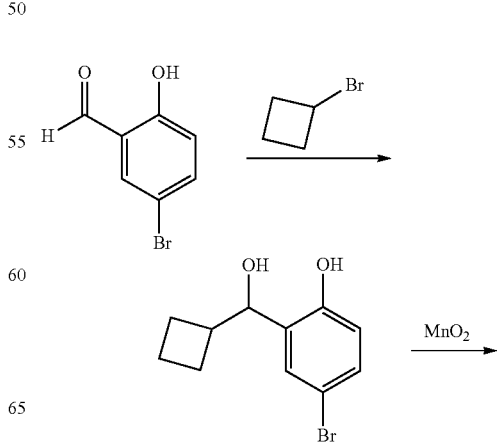

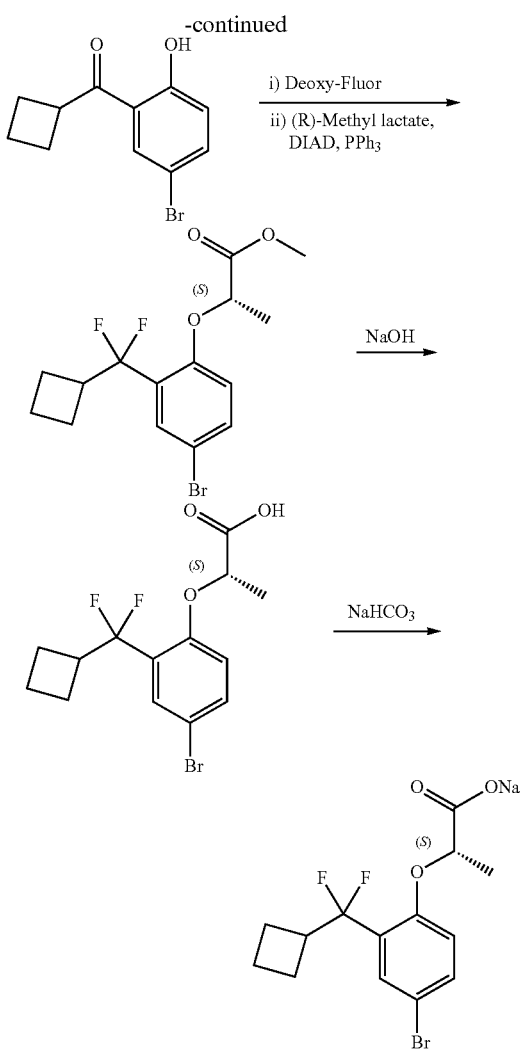

Step 1: Synthesis of 4-bromo-2-(cyclobutyl(hydroxy)methyl)phenol

To a cooled (0° C.) solution of 5-bromosalicylaldehyde (1.0 g, 5.0 mmol, 1.0 eq.) in THF (40 mL) was added dropwise freshly prepared cyclobutyl magnesium bromide (14.9 mL, 14.9 mmol, 3.0 eq.) and the reaction was slowly warmed to room temperature and stirred overnight. The reaction mixture was poured into saturated aqueous ammonium chloride solution (150 mL) and extracted with EtOAc (3×80 mL). The combined organic extracts were dried over sodium sulphate, concentrated under reduced pressure and the resultant crude material was purified by flash column chromatography (Si, 0-100% DCM in hexanes) to give the title compound (1.01 g, 79%) as a yellow crystalline solid.

UPLC-MS: basic 2-minute run MS (ES−): m/z 255.0/257.0 (M−H)⁻; retention time: 1.09 min; purity: 100%. $^1$H NMR (Chloroform-d) δ 8.09 (s, 1H), 7.41-7.29 (m, 1H), 7.13 (d, J=2.5 Hz, 1H), 6.82 (d, J=8.6 Hz, 1H), 4.75 (d, J=8.5 Hz, 1H), 2.93-2.82 (m, 1H), 2.78 (s, 1H), 2.31-2.12 (m, 1H), 2.09-1.82 (m, 5H).

Step 2: Synthesis of (5-bromo-2-hydroxyphenyl)(cyclobutyl)methanone

To a solution of 4-bromo-2-(cyclobutyl(hydroxy)methyl)phenol (1.14 g, 4.98 mmol, 1.0 eq.) in DCM (22 mL) was added manganese (IV) oxide (2.16 g, 24.9 mmol, 5.0 eq.) and the mixture stirred at room temperature overnight. The mixture was filtered through a pad of Celite and the filtrate concentrated under reduced pressure giving a viscous brown oil which was stored in the freezer over the weekend. The oil was subsequently re-dissolved in DCM (25 mL) and fresh manganese (IV) oxide (8.81 g, 101 mmol, 20.0 eq.) was added. The resulting mixture was stirred at room temperature for 24 h. The reaction mixture was filtered through a pad of Celite and the filtrate concentrated under reduced pressure to give the crude title compound (3.52 g) which was used in the next step without further purification.

UPLC-MS: basic 2-minute run MS (ES−): m/z 253.0/255.0 (M−H)⁻; retention time: 1.31 min; purity: 77%.

Step 3: Synthesis of methyl (S)-2-(4-bromo-2-(cyclobutyldifluoromethyl)phenoxy)propanoate To a cooled (0° C.) solution of (5-bromo-2-hydroxyphenyl)(cyclobutyl)methanone (750 mg, 2.9 mmol, 1.0 eq.) in DCM (14.7 mL) was added with DAST (3.9 mL, 29.0 mmol, 10.0 eq.), the reaction vial was sealed and the mixture was allowed to slowly warm to room-temperature over 1 h. The reaction mixture was poured into ice-water (50 mL) and extracted with DCM (2×50 mL). The combined organic extracts were washed sequentially with saturated aqueous sodium hydrogen carbonate (50 mL) and brine (50 mL), dried over sodium sulphate and the solvent concentrated under reduced pressure to ca. 10 mL. The resultant solution was immediately re-cooled to 0° C., diluted with THF (14.7 mL), and treated sequentially with (R)-methyl lactate (0.30 mL, 3.1 mol, 1.05 eq.), triphenylphosphine (848 mg, 3.2 mol, 1.1 eq.) and DIAD (0.64 mL, 3.2 mol, 1.1 eq.). The reaction mixture was allowed to warm to room temperature slowly overnight. The reaction was concentrated under reduced pressure and the crude product purified twice by flash column chromatography (Si, 0-50% DCM in hexanes, followed by 5-20% DCM in hexanes) to give the title compound (158 mg, 0.44 mmol, 15%) as a colourless oil.

UPLC-MS: acidic 2-minute run MS (ES−): m/z 361.0/363.0 (M−H)⁻; retention time: 1.37 min; purity: 100%. $^1$H NMR (400 MHz, Chloroform-d) δ 7.55 (dd, J=2.5, 1.1 Hz, 1H), 7.33 (ddd, J=8.8, 2.5, 0.9 Hz, 1H), 6.57 (d, J=8.8 Hz, 1H), 4.68 (q, J=6.8 Hz, 1H), 3.68 (s, 3H), 3.50-3.33 (m, 1H), 2.25-2.11 (m, 1H), 2.03-1.87 (m, 2H), 1.87-1.69 (m, 3H), 1.57 (d, J=6.8 Hz, 3H).

Step 4: Synthesis of (S)-2-(4-bromo-2-(cyclobutyldifluoromethyl)phenoxy)propanoic acid A solution of methyl (S)-2-(4-bromo-2-(cyclobutyldifluoromethyl)phenoxy)propanoate (158 mg, 0.44 mmol, 1.0 eq.) in water (5.2 mL), THF (7.8 mL) and MeOH (2.6 mL) was treated with 1M aqueous sodium hydroxide solution (2.6 mL, 2.6 mmol, 6.0 eq.). After 1 h, the reaction mixture was partitioned between water (25 mL) and EtOAc (25 mL), the aqueous layer acidified with 1M aqueous hydrochloric acid solution and re-extracted with EtOAc (2×25 mL). The combined secondary organic extracts were washed with brine (20 mL), dried over sodium sulphate and concentrated under reduced pressure to give the title compound (142 mg, 0.41 mmol, 93%) as a colourless oil which solidified upon standing.

UPLC-MS: acidic 2-minute run MS (ES−): m/z 347.0/349.0 (M−H)⁻; retention time: 1.20 min; purity: 90%. $^1$H NMR (400 MHz, Chloroform-d) δ 7.55 (d, J=2.5 Hz, 1H), 7.37 (dd, J=8.8, 2.5 Hz, 1H), 6.64 (d, J=8.8 Hz, 1H), 4.73 (q, J=6.8 Hz, 1H), 3.45-3.24 (m, 1H), 2.15 (dq, J=11.4, 8.8 Hz, 1H), 2.01 (s, 1H), 1.93-1.70 (m, 4H), 1.62 (d, J=6.8 Hz, 3H). $^{19}$F NMR (376 MHz, Chloroform-d) δ−101.99 (d, J=248.2 Hz), −106.98 (d, J=248.2 Hz).

Step 5: Synthesis of sodium (S)-2-(4-bromo-2-(cyclobutyldifluoromethyl)phenoxy)propanoate A solution of (S)-2-(4-bromo-2-(cyclobutyldifluoromethyl)phenoxy)propanoic acid (142 mg, 0.41 mmol, 1.0 eq.) in MeCN (10 mL) and water (5 mL) was treated with 1M aqueous sodium bicarbonate solution (0.43 mL, 0.43 mmol, 1.05 eq.). After 30 min, the reaction was concentrated under reduced pressure and the resulting solid was dried in a vacuum oven at 40° C. overnight to give the title compound (146 mg, 0.39 mmol, 97%) as an off-white solid.

UPLC-MS: acidic 4-minute run MS (ES−): m/z 347.0/349.0 (M−H)$^-$; retention time: 2.06 min; purity: 86%. $^1$H NMR (DMSO-d$_6$) δ: 7.50-7.40 (m, 2H), 6.83 (d, J=8.9 Hz, 1H), 4.36 (q, J=6.7 Hz, 1H), 3.72 (m, 1H), 2.10 (m, 1H), 2.01-1.70 (m, 5H), 1.40 (d, J=6.6 Hz, 3H). $^{19}$F NMR (376 MHz, DMSO-d$_6$) δ: −99.92 (d, J=242.7 Hz), −105.96 (d, J=242.6 Hz).

Example 11: Synthesis of sodium (S)-2-(4-bromo-2-(1,1-difluoropropyl)-6-fluorophenoxy)propanoate

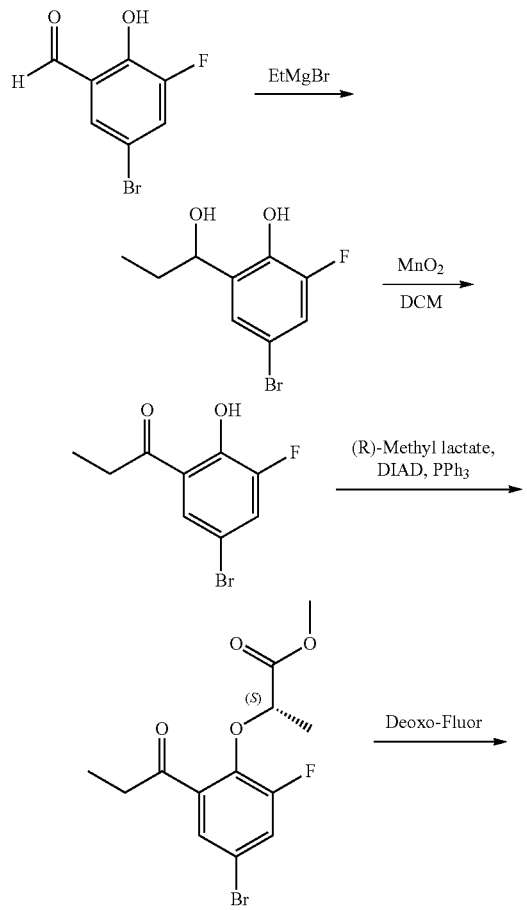

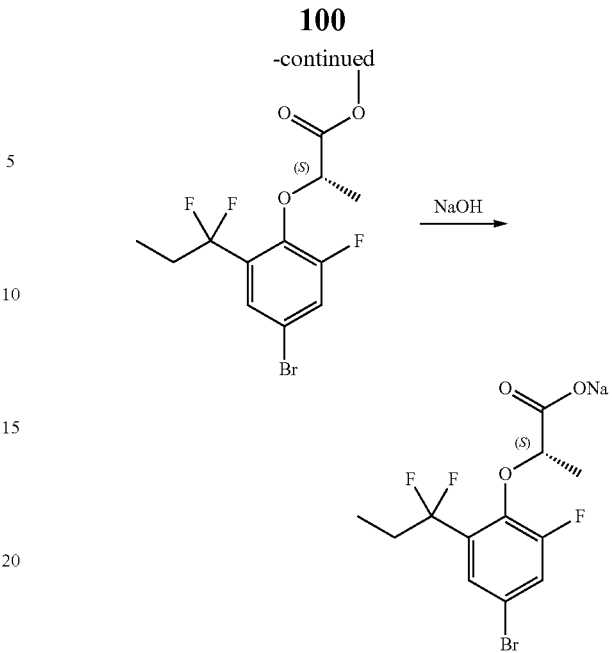

Step 1: Synthesis of 4-bromo-2-fluoro-6-(1-hydroxypropyl)phenol

To a cooled (0° C.) solution of 5-bromo-3-fluoro-2-hydroxybenzaldehyde (3.0 g, 13.7 mmol, 1.0 eq.) in THF (150 mL) was added dropwise ethylmagnesium bromide (14 mL, 3.0 M in diethyl ether, 41.1 mmol, 3.0 eq.) and the reaction was stirred for 1 h. The reaction mixture was subsequently poured into saturated aqueous ammonium chloride solution (200 mL) and extracted with EtOAc (3×100 mL). The combined organic extracts were dried over sodium sulphate and concentrated under reduced pressure to give the title compound (3.84 g, 13.7 mmol, 97%) as a viscous yellow oil which was used in the next step without further purification.

UPLC-MS: acidic 2-minute run MS (ES−): m/z 247.0/249.0 (M−H)$^-$; retention time: 1.02 min; purity: 86%. $^1$H NMR (Chloroform-d) δ: 7.71 (s, 1H), 7.12 (dd, J=9.9, 2.3 Hz, 1H), 6.99-6.93 (m, 1H), 4.77 (dd, J=7.4, 5.9 Hz, 1H), 3.22 (s, 1H), 1.93-1.70 (m, 2H), 0.95 (t, J=7.4 Hz, 3H).

Step 2: Synthesis of 1-(5-bromo-3-fluoro-2-hydroxyphenyl)propan-1-one

To a solution of 4-bromo-2-fluoro-6-(1-hydroxypropyl)phenol (3.84 g, 13.7 mmol, 1.0 eq.) in DCM (70 mL) was added manganese (IV) oxide (6.70 g, 77.1 mmol, 5.6 eq.) and the mixture stirred at room temperature for 24 h. The reaction mixture was filtered through Celite and the filter cake was washed with DCM (20 mL). The filtrate was treated with manganese (IV) oxide (6.70 g, 77.1 mmol, 5.6 eq.) and the mixture stirred at room temperature for 5 h. The reaction mixture was filtered through Celite, the filtrate concentrated under reduced pressure and the crude material purified by flash column chromatography (Si, 0-100% DCM in hexanes) to give the title compound (511 mg, 2.0 mmol, 13%) as a bright yellow crystalline solid.

UPLC-MS: basic 2-minute run MS (ES−): m/z 245.0/247.0 (M−H)$^-$; retention time: 1.06 min; purity: 97%. $^1$H NMR (400 MHz, Chloroform-d) δ 1.25 (t, J=7.2 Hz, 3H), 3.03 (q, J=7.2 Hz, 2H), 7.42 (ddd, J=9.8, 2.3, 0.6 Hz, 1H), 7.68 (t, J=2.0 Hz, 1H), 12.30 (d, J=0.6 Hz, 1H).

Step 3: Synthesis of methyl (S)-2-(4-bromo-2-fluoro-6-propionylphenoxy)propanoate To a cooled (0° C.) solution of 1-(5-bromo-3-fluoro-2-hydroxyphenyl)propan-1-one) (501 mg, 2.03 mmol, 1.0 eq.) in THF (7.5 mL) was added sequentially methyl (2R)-2-hydroxypropanoate (211 mg, 2.03 mmol, 1.0 eq.), triphenylphosphine (585 mg, 2.23 mmol, 1.1 eq.) and diisopropyl azodicarboxylate (0.44 mL, 2.23 mmol, 1.1 eq.). The reaction was allowed to warm slowly to room temperature overnight. The reaction mixture was concentrated under reduced pressure and the crude product purified by flash column chromatography (Si, 0-40% EtOAc in hexanes) to give the title compound (480 mg, 1.44 mmol, 67%) as a colourless oil.

UPLC-MS: acidic 4-minute run MS (ES-): m/z 333.0/335.0 (M-H)$^-$; retention time: 2.06 min; purity: 97%. $^1$H NMR (400 MHz, Chloroform-d) δ 7.45 (dd, J=2.5, 1.6 Hz, 1H), 7.33 (dd, J=11.0, 2.4 Hz, 1H), 4.89 (qd, J=6.8, 0.7 Hz, 1H), 3.69 (s, 3H), 3.16 (dq, J=18.2, 7.3 Hz, 1H), 2.93 (dq, J=18.2, 7.2 Hz, 1H), 1.63 (dd, J=6.9, 0.8 Hz, 3H), 1.16 (t, J=7.2 Hz, 3H).

Step 4: Synthesis of methyl (S)-2-(4-bromo-2-(1,1-difluoropropyl)-6-fluorophenoxy)propanoate A mixture of methyl (S)-2-(4-bromo-2-fluoro-6-propionylphenoxy)propanoate (470 mg, 1.41 mmol, 1.0 eq.) and Deoxo-Fluor solution (50% in THF, 6 mL, 14.1 mmol, 10 eq.) was stirred at room temperature for 72 h, then heated to 40° C. for 7 days. The reaction mixture was allowed to cool to room temperature before being poured into a cooled (0° C.) saturated aqueous sodium bicarbonate solution (50 mL). The aqueous mixture was extracted with DCM (3×25 mL) and the combined organic extracts washed with brine (30 mL), dried over sodium sulphate and concentrated under reduced pressure. The crude dark oil was purified by flash column chromatography (Si, 0-60% EtOAc in hexanes) to give the title compound (135 mg, 0.36 mmol, 26%) as a yellow/brown semi-solid.

UPLC-MS: acidic 2-minute run MS (ES-): no m/z; retention time: 1.34 min; purity: 95%.

$^1$H NMR (Chloroform-d) δ 7.43 (qd, J=1.0, 1.5 Hz, 1H), 7.31 (ddd, J=0.8, 2.5, 11.1 Hz, 1H), 4.84 (qd, J=1.6, 6.8 Hz, 1H), 3.77 (s, 3H), 2.44-2.25 (m, 2H), 1.59-1.53 (m, 3H), 0.94 (t, J=7.5 Hz, 3H). $^{19}$F NMR (376 MHz, Chloroform-d) δ-93.67 (d, J=246.9 Hz), -97.26 (dd, J=2.9, 247.0 Hz), -125.43 (d, J=2.7 Hz).

Step 5: Synthesis of sodium (S)-2-(4-bromo-2-(1,1-difluoropropyl)-6-fluorophenoxy)propanoate To a solution of methyl (S)-2-[4-bromo-2-(1,1-difluoropropyl)-6-fluorophenoxy]propanoate (106 mg, 0.29 mmol, 1.0 eq.) in MeOH (2.1 mL) was added 1M aqueous sodium hydroxide solution (0.31 mL, 0.31 mmol, 1.06 eq.) and the mixture stirred at room temperature for 4 h. The mixture was then concentrated under reduced pressure and the resultant solid dried in a vacuum oven at 45° C. overnight to give the title compound (96 mg, 0.26 mmol, 89%) as a peach coloured solid.

UPLC-MS: acidic 4-minute run MS (ES-): m/z 339.0/341.0 (M-H)$^-$; retention time: 1.93 min; purity: 100%. $^1$H NMR (DMSO-d$_6$) δ: 7.50 (ddd, J=12.6, 2.5, 0.9 Hz, 1H), 7.24 (dt, J=2.6, 1.3 Hz, 1H), 4.80 (qd, J=6.8, 4.5 Hz, 1H), 2.50 (m, 2H), 1.34 (dd, J=6.8, 1.0 Hz, 3H), 0.87 (t, J=7.5 Hz, 3H). $^{19}$F NMR (376 MHz, DMSO-d$_6$) δ-124.78 (d, J=3.9 Hz), -96.92 (dd, J=240.6, 3.9 Hz), -89.00 (d, J=240.7 Hz).

Example 12: Synthesis of (S)-2-(4-cyano-2-(1,1-difluoropropyl)phenoxy)propanoic acid

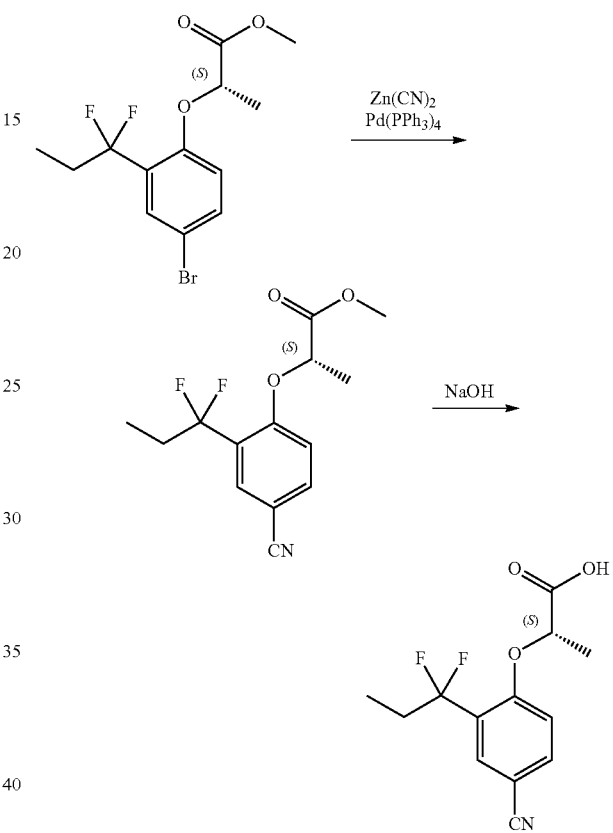

Step 1: Synthesis of methyl (S)-2-(4-cyano-2-(1,1-difluoropropyl)phenoxy)propanoate A degassed solution of methyl (2S)-2-[4-bromo-2-(1,1-difluoropropyl)phenoxy]propanoate (100 mg, 0.24 mmol, 1.0 eq.), zincdicarbonitrile (24 mg, 0.20 mmol, 0.85 eq.) and tetrakis(triphenylphosphane) palladium (27 mg, 0.02 mmol, 0.10 eq.) in NMP (0.8 mL) was heated under microwave irradiation at 150° C. for 15 min. The reaction was filtered, diluted with EtOAc (20 mL) and washed sequentially with saturated aqueous sodium bicarbonate solution (2×20 mL), water (20 mL), and brine (20 mL). The organic phase was concentrated under reduced pressure and purified by flash chromatography (Si, 0-40% EtOAc in hexanes) to give the title compound (35 mg, 0.10 mmol, 42%) as a colourless oil.

UPLC-MS: acidic 2-minute run MS (ES-): m/z 282.1 (M-H)$^-$; retention time: 1.16 min; purity: 72%. $^1$H NMR (400 MHz, Chloroform-d) δ 7.86-7.79 (m, 1H), 7.64 (dd, J=8.7, 2.0 Hz, 1H), 6.81 (d, J=8.7 Hz, 1H), 4.90 (q, J=6.8 Hz, 1H), 3.76 (s, 3H), 2.54-2.27 (m, 2H), 1.68 (d, J=6.8 Hz, 3H), 0.94 (t, J=7.5 Hz, 3H). $^{19}$F NMR (376 MHz, Chloroform-d) δ-93.51--100.37 (m).

Step 2: Synthesis of (S)-2-(4-cyano-2-(1,1-difluoropropyl)phenoxy)propanoic acid To a stirred solution of methyl (2S)-2-[4-cyano-2-(1,1-difluoropropyl)phenoxy]propanoate (35 mg, 0.10 mmol, 1.0 eq.) in MeOH (0.9 mL) was added 1M aqueous sodium hydroxide solution (0.12 mL, 0.12 mmol, 1.2 eq.) and the mixture stirred at room temperature for 1 h. The mixture was concentrated under reduced pressure and the residue purified by reverse-phase column chromatography (C18, 5-95% MeCN in water+0.1% formic acid) to give the title compound (14 mg, 0.05 mmol, 53%) as a colourless oil.

UPLC-MS: acidic 4-minute run MS (ES−): m/z 268.0 (M−H)⁻; retention time: 1.54 min; purity: 100%. $^1$H NMR (400 MHz, MeOH-d$_4$) δ 7.80-7.71 (m, 2H), 7.07 (d, J=8.5 Hz, 1H), 4.96 (q, J=6.8 Hz, 1H), 2.63-2.28 (m, 2H), 1.63 (d, J=6.8 Hz, 3H), 0.92 (t, J=7.5 Hz, 3H). $^{19}$F NMR (376 MHz, MeOH-d$_4$) δ−89.28−−109.92 (m).

Example 13: Synthesis of (S)-2-(2-(1,1-difluoropropyl)-4,5-difluorophenoxy)propanoic acid

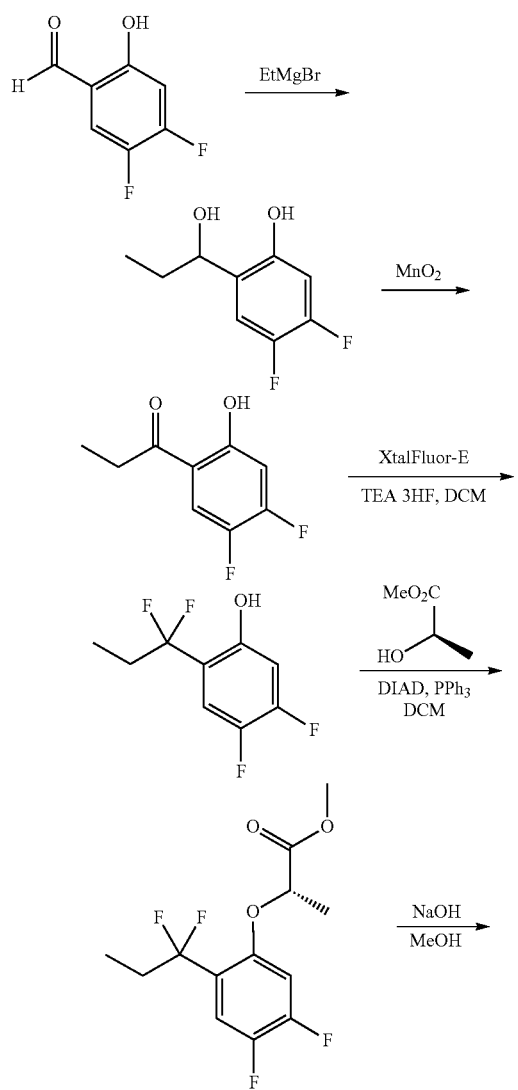

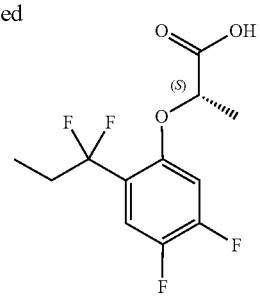

Step 1: Synthesis of 4,5-difluoro-2-(1-hydroxypropyl)phenol

To a cooled (0° C.) solution of 4,5-difluoro-2-hydroxybenzaldehyde (2.5 g, 15.8 mmol, 1.0 eq.) in THF (110 mL) was added dropwise ethylmagnesium bromide (11.1 mL, 3.0 M in diethyl ether, 33.3 mmol, 2.1 eq.) and the reaction was allowed to warm slowly to room temperature and stirred overnight. The reaction mixture was subsequently poured into saturated aqueous ammonium chloride solution (200 mL) and extracted with EtOAc (3×100 mL). The combined organic extracts were dried over sodium sulphate and concentrated under reduced pressure to give the title compound (3.27 g, 16.3 mmol, quant.) as an amber oil which was used in the next step without further purification.

UPLC-MS: acidic 2-minute run MS (ES−): m/z 187.1 (M−H)⁻; retention time: 0.95 min; purity: 94%. $^1$H NMR (400 MHz, Chloroform-d) δ 8.02 (s, 1H), 6.74 (dd, J=10.6, 8.7 Hz, 1H), 6.67 (dd, J=11.6, 6.9 Hz, 1H), 4.70 (td, J=6.8, 2.8 Hz, 1H), 2.55 (d, J=3.4 Hz, 1H), 1.98-1.73 (m, 2H), 0.97 (t, J=7.4 Hz, 3H). $^{19}$F NMR (376 MHz, Chloroform-d) δ−137.56 (ddd, J=8.7, 11.6, 22.3 Hz), −149.62 (ddd, J=7.4, 10.9, 22.4 Hz).

Step 2: Synthesis of 1-(4,5-difluoro-2-hydroxyphenyl)propan-1-one

To a solution of 4,5-difluoro-2-(1-hydroxypropyl)phenol (3.27 g, 16.3 mmol, 1.0 eq.) in 1,4-dioxane (22 mL) was added manganese (IV) oxide (6.67 g, 76.7 mmol, 4.4 eq.) and the reaction stirred at reflux for 4.5 h. The reaction mixture was cooled to room temperature, filtered through a pad of Celite and the filter cake washed with 4:1 EtOAc:MeOH (2×100 mL). The filtrate was concentrated under reduced pressure and the crude product purified by flash column chromatography (Si, 0-20% EtOAc in hexanes) to give the title compound (1.37 g, 7.4 mmol, 35%) as a yellow solid which was used in subsequent reaction without additional purification.

UPLC-MS: acidic 2-minute run MS (ES−): m/z 185.1 (M−H)⁻; retention time: 1.15 min; purity: 83%. $^1$H NMR (400 MHz, Chloroform-d) δ12.41 (s, 1H), 7.55 (dd, J=8.8, 10.6 Hz, 1H), 6.77 (dd, J=6.7, 11.5 Hz, 1H), 2.95 (q, J=7.3 Hz, 2H), 1.24 (td, J=0.8, 7.2 Hz, 3H). $^{19}$F NMR (376 MHz, Chloroform-d) δ−123.00−−124.00 (m), −147.67 (ddd, J=22.4, 10.6, 6.8 Hz).

Steps 3+4: Synthesis of methyl (S)-2-(2-(1,1-difluoropropyl)-4,5-difluorophenoxy)propanoate To a solution of triethylamine trihydrofluoride (0.88 mL, 5.4 mmol, 2.0 eq.) in DCM (7.7 mL) was successively added XtalFluor-E (2.46 g, 10.7 mmol, 4.0 eq.) and 1-(4,5-difluoro-2-hydroxyphenyl)propan-1-one (500 mg, 2.7 mmol, 1.0 eq.) and the reaction was stirred at room temperature overnight. The reaction mixture was poured onto ice, and the resulting mixture was extracted with DCM (2×20 mL). The combined organic phases were washed with water (3×25 mL), dried over magnesium sulphate and concentrated under reduced pressure to ¼ volume. The remaining solution was directly purified by flash column chromatography (Si, DCM eluent), the appropriate fractions were collected, concentrated under reduced pressure to approximately 10 mL. This solution was cooled to 0° C., then treated sequentially with methyl (2R)-2-hydroxypropanoate (280 mg, 2.7 mmol, 1.0 eq.), triphenylphosphine (775 mg, 3.0 mol, 1.1 eq.) and DIAD (0.58 mL, 3.0 mol, 1.1 eq.) and stirred at room temperature for 72 h. The mixture was concentrated under reduced pressure and purified by flash column chromatography (Si, 0-20% EtOAc in hexanes) to give the title compound (654 mg, 1.8 mmol, 68%) as a yellow oil.

UPLC-MS: acidic 2-minute run MS (ES-): m/z 293.0 (M-H)-; retention time: 1.26 min; purity: 82%. $^1$H NMR (400 MHz, Chloroform-d) δ 7.42-7.31 (m, 1H), 6.64 (dd, J=6.3, 11.6 Hz, 1H), 4.70 (q, J=6.8 Hz, 1H), 3.77 (s, 3H), 2.51-2.24 (m, 2H), 1.63 (d, J=6.8 Hz, 3H), 0.93 (t, J=7.5 Hz, 3H). $^{19}$F NMR (376 MHz, Chloroform-d) δ-92.61 (dddd, J=245.8, 15.5, 12.3, 3.2 Hz), -98.04 (dt, J=245.9, 20.6 Hz), -131.77--133.21 (m), -146.19 (ddd, J=22.1, 10.9, 6.4 Hz).

Step 5: Synthesis of (S)-2-(2-(1,1-difluoropropyl)-4,5-difluorophenoxy)propanoic acid A solution of methyl (2S)-2-[2-(1,1-difluoropropyl)-4,5-difluorophenoxy]propanoate (100 mg, 0.34 mmol, 1.0 eq.) in MeOH (2 mL) was treated with 1M aqueous sodium hydroxide solution (0.36 mL, 0.36 mmol, 1.05 eq.) and the reaction was stirred at room temperature for 18 h. The reaction mixture was concentrated under reduced pressure and the residue purified by prep-HPLC chromatography (5-95% MeCN in water+0.1% ammonium hydroxide) to give the title compound (69 mg, 0.25 mmol, 73%) as a colourless gum.

UPLC-MS: acidic 4-minute run MS (ES-): m/z 279.1 (M-H)-; retention time: 1.79 min; purity: 100%. $^1$H NMR (400 MHz, DMSO-$d_6$) 57.42 (dd, J=11.2, 9.1 Hz, 1H), 7.07 (dd, J=12.9, 6.7 Hz, 1H), 4.78 (q, J=6.7 Hz, 1H), 2.49-2.25 (m, 2H), 1.43 (d, J=6.7 Hz, 3H), 0.85 (t, J=7.4 Hz, 3H). $^{19}$F NMR (376 MHz, DMSO-$d_6$) δ-90.73 (dddd, J=242.5, 16.1, 12.5, 3.1 Hz), -95.87 (dt, J=242.3, 19.9 Hz), -133.94 (dt, J=22.9, 10.4 Hz), -148.62--149.79 (m).

Example 14: Synthesis of (S)-2-(2-(1,1-difluoropropyl)-4-vinylphenoxy)propanoic acid

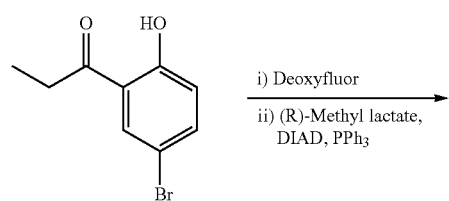

i) Deoxyfluor
ii) (R)-Methyl lactate, DIAD, PPh$_3$

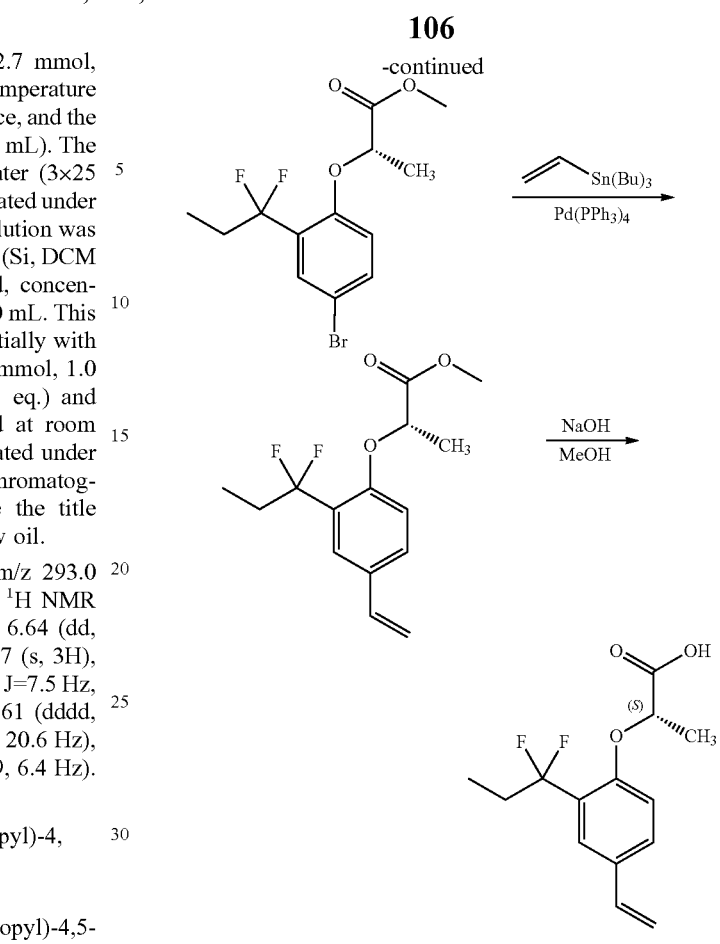

Step 1: Synthesis of methyl (S)-2-(4-bromo-2-(1,1-difluoropropyl)phenoxy)propanoate To a solution of triethylamine trihydrofluoride (2.1 mL, 13.1 mmol, 2.0 eq.) in DCM (19 mL) was successively added XtalFluor-E (6.0 g, 26.2 mmol, 4.0 eq.) and 1-(5-bromo-2-hydroxyphenyl)propan-1-one (1.5 g, 6.5 mmol, 1.0 eq.) and the reaction was stirred at room temperature overnight. The reaction mixture was poured onto ice, and the resulting mixture was extracted with DCM (2×20 mL). The combined organic phases were washed with water (3×25 mL), dried over magnesium sulphate and concentrated under reduced pressure to ¼ volume. The remaining solution was directly purified by flash column chromatography (Si, DCM eluent), the appropriate fractions were collected, concentrated under reduced pressure to approximately 20 mL. This solution was cooled to 0° C., then treated sequentially with methyl (2R)-2-hydroxypropanoate (0.69 mL, 7.2 mmol, 1.1 eq.), triphenylphosphine (1.89 g, 7.2 mol, 1.1 eq.) and DIAD (1.4 mL, 7.2 mol, 1.1 eq.) and stirred at room temperature for 1 h. The mixture was concentrated under reduced pressure and purified twice by flash column chromatography (Si, 0-10% EtOAc in hexanes, followed by 5-60% EtOAc in hexanes) to give the title compound (1.52 g, 4.5 mmol, 69%) as a yellow oil.

UPLC-MS: acidic 2-minute run MS (ES-): m/z 335.0/337.0 (M-H)-; retention time: 1.31 min; purity: 85%. $^1$H NMR (400 MHz, Chloroform-d) δ 7.65 (dd, J=2.5, 1.1 Hz, 1H), 7.48-7.41 (m, 1H), 6.68 (d, J=8.8 Hz, 1H), 4.80 (q, J=6.8 Hz, 1H), 3.77 (s, 3H), 2.53-2.30 (m, 2H), 1.65 (d, J=6.8 Hz, 3H), 0.96 (t, J=7.5 Hz, 3H). $^{19}$F NMR (376 MHz, Chloroform-d) δ −85.67--−106.78 (m).

Step 2: Synthesis of methyl (S)-2-(2-(1,1-difluoropropyl)-4-vinylphenoxy)propanoate To a degassed solution of methyl (2S)-2-[4-bromo-2-(1,1-difluoropropyl)phenoxy]propanoate (239 mg, 0.71 mmol, 1.0 eq.) and tributyl(ethenyl)stannane (0.41 mL, 1.42 mmol, 2.0 eq.) in 1,4-dioxane (2.8 mL) was added tetrakis(triphenylphosphane) palladium (41.0 mg, 0.035 mmol, 0.05 eq.) and the reaction was heated at 100° C. for 4 h. The mixture was filtered through Celite and purified by flash column chromatography (Si, 0-10% EtOAc in hexanes) to give the title compound (144 mg, 0.25 mmol, 36%) as a colourless oil which was used in the following step without further purification.

UPLC-MS: basic 2-minute run MS (ES−): m/z 283.2 (M−H)⁻; retention time: 1.29 min; purity: 57%. $^1$H NMR (400 MHz, Chloroform-d) δ 7.62-7.55 (m, 1H), 7.38 (dd, J=8.6, 1.8 Hz, 1H), 6.75 (d, J=8.5 Hz, 1H), 6.68 (m, 1H), 5.68 (dd, J=17.6, 0.7 Hz, 1H), 5.21 (d, J=11.5 Hz, 1H), 4.84 (m, 1H), 3.77 (s, 3H), 2.64-2.22 (m, 2H), 1.66 (d, J=6.8 Hz, 3H), 1.03-0.91 (m, 3H). $^{19}$F NMR (376 MHz, Chloroform-d) δ −92.76--−93.37 (m), −99.10 (dtd, J=245.7, 19.8, 4.1 Hz).

Step 3: Synthesis of (S)-2-(2-(1,1-difluoropropyl)-4-vinylphenoxy)propanoic acid To a stirred solution of methyl (2S)-2-[2-(1,1-difluoropropyl)-4-ethenylphenoxy]propanoate (137 mg, 0.48 mmol, 1.0 eq.) in MeOH (2.6 mL) was added 1M aqueous sodium hydroxide solution (0.51 mL, 0.51 mmol, 1.05 eq.) and the reaction was stirred at room temperature overnight. The mixture was concentrated under reduced pressure and the residue purified by prep-HPLC chromatography (5-95% MeCN in water+0.1% ammonium hydroxide) to give the title compound (23 mg, 0.085 mmol, 18%) as a white solid.

UPLC-MS: acidic 4-minute run MS (ES−): m/z 269.1 (M−H)⁻; retention time: 1.85 min; purity: 99%. $^1$H NMR (400 MHz, DMSO-d$_6$) δ 13.23 (s, 1H), 7.58-7.52 (m, 1H), 7.50 (s, 1H), 6.94 (d, J=8.6 Hz, 1H), 6.72 (dd, J=17.7, 11.0 Hz, 1H), 5.72 (d, J=17.0 Hz, 1H), 5.19 (d, J=11.6 Hz, 1H), 4.97 (q, J=6.8 Hz, 1H), 2.48-2.20 (m, 2H), 1.51 (d, J=6.7 Hz, 3H), 0.86 (t, J=7.5 Hz, 3H). $^{19}$F NMR (376 MHz, DMSO-d$_6$) δ −83.76--−106.49 (m).

Example 15: Synthesis of sodium (S)-2-(2-(1,1-difluoropropyl)-4-methyl phenoxy)propanoate

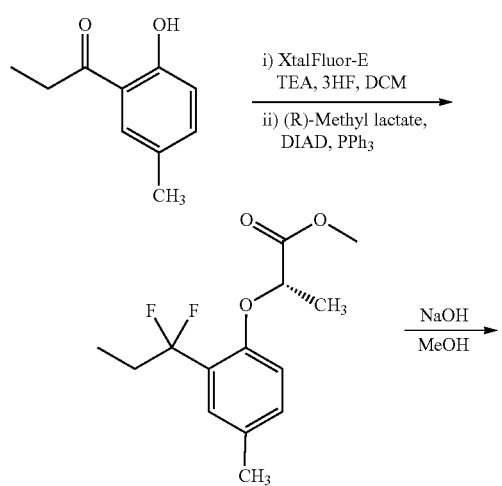

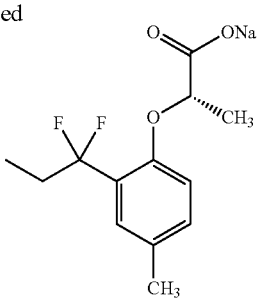

Step 1: Synthesis of methyl (S)-2-(2-(1,1-difluoropropyl)-4-methylphenoxy)propanoate To a solution of triethylamine trihydrofluoride (0.99 mL, 6.09 mmol, 2.0 eq.) in DCM (8.7 mL) was successively added XtalFluor-E (2.79 g, 12.2 mmol, 4.0 eq.) and 1-(2-hydroxy-5-methylphenyl)propan-1-one (0.47 mL, 3.05 mmol, 1.0 eq.) and the reaction was stirred at room temperature overnight. The reaction mixture was poured onto ice, and the resulting mixture was extracted with DCM (2×20 mL). The combined organic phases were washed with water (3×25 mL), dried over magnesium sulphate and concentrated under reduced pressure to ¼ volume. The remaining solution was directly purified by flash column chromatography (Si, DCM eluent), the appropriate fractions were collected, concentrated under reduced pressure to approximately 12 mL. This solution was cooled to 0° C., then treated sequentially with methyl (2R)-2-hydroxypropanoate (0.32 mL, 3.3 mmol, 1.1 eq.), triphenylphosphine (879 mg, 3.3 mol, 1.1 eq.) and DIAD (0.66 mL, 3.3 mol, 1.1 eq.) and stirred at room temperature for 1 h. The mixture was concentrated under reduced pressure and purified by flash column chromatography (Si, 0-10% EtOAc in hexanes) to give the title compound (286 mg, 0.85 mmol, 35%) as a colourless oil.

UPLC-MS: acidic 2-minute run MS (ES+): no m/z; retention time: 1.27 min; purity: 91%. $^1$H NMR (400 MHz, Chloroform-d) δ 7.34 (s, 1H), 7.13 (d, J=8.3 Hz, 1H), 6.70 (d, J=8.3 Hz, 1H), 4.79 (q, J=6.8 Hz, 1H), 3.77 (s, 3H), 2.55-2.34 (m, 2H), 2.32 (s, 3H), 1.64 (d, J=6.8 Hz, 3H), 0.96 (t, J=7.5 Hz, 3H). $^{19}$F NMR (376 MHz, Chloroform-d) δ −86.24--−107.45 (m).

Step 2: Synthesis of sodium (S)-2-(2-(1,1-difluoropropyl)-4-methylphenoxy)propanoate To a solution of methyl (2S)-2-[2-(1,1-difluoropropyl)-4-methylphenoxy]propanoate (213 mg, 0.78 mmol, 1.0 eq.) in MeOH (4.2 mL) was added 1M aqueous sodium hydroxide solution (0.82 mL, 0.82 mmol, 1.05 eq.) and the mixture was stirred at room temperature for 3 h. The mixture was concentrated under reduced pressure, taken up in water (2 mL) and freeze-dried to give the title compound (219 mg, 0.78 mmol, quant.) as a white solid.

UPLC-MS: acidic 4-minute run MS (ES+): m/z 257.0 (M+H)⁺; retention time: 1.81 min; purity: 100%. $^1$H NMR (400 MHz, DMSO-d$_6$) δ 7.14 (s, 1H), 7.09 (d, J=8.4 Hz, 1H), 6.77 (d, J=8.4 Hz, 1H), 4.22 (q, J=6.6 Hz, 1H), 2.50-2.32 (m, 2H), 2.23 (s, 3H), 1.33 (d, J=6.7 Hz, 3H), 0.85 (t, J=7.5 Hz, 3H). $^{19}$F NMR (376 MHz, DMSO-d$_6$) δ −86.62--−107.16 (m).

Example 16: Synthesis of (S)-2-(2-(1,1-difluoro-ethyl)-4-ethynylphenoxy)propanoic acid

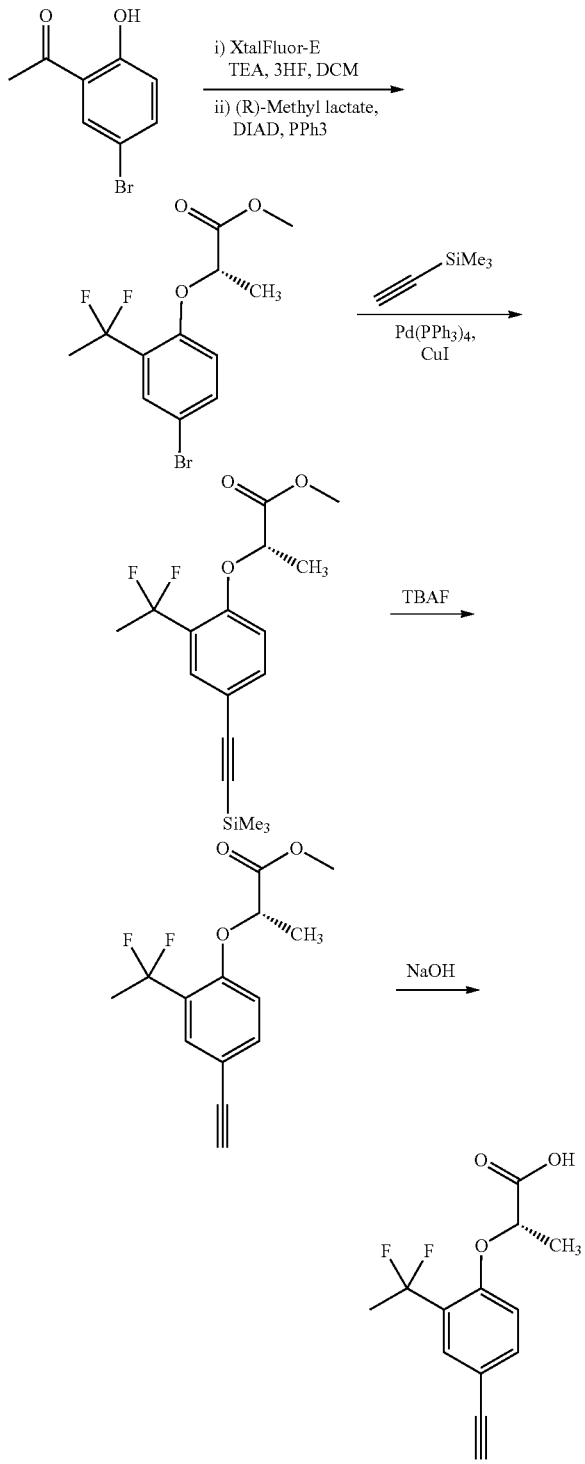

Step 1: Synthesis of methyl (S)-2-(4-bromo-2-(1,1-difluoroethyl)phenoxy)propanoate To a solution of triethylamine trihydrofluoride (0.76 mL, 4.7 mmol, 2.0 eq.) in DCM (6.7 mL) was successively added XtalFluor-E (2.13 g, 9.3 mmol, 4.0 eq.) and 1-(5-bromo-2-hydroxyphenyl)ethan-1-one (500 mg, 2.3 mmol, 1.0 eq.) and the reaction was stirred at room temperature overnight. The reaction mixture was poured onto ice, and the resulting mixture was extracted with DCM (2×20 mL). The combined organic phases were washed with water (3×25 mL), dried over magnesium sulphate and concentrated under reduced pressure to ¼ volume. The remaining solution was directly purified by flash column chromatography (Si, DCM eluent), the appropriate fractions were collected, concentrated under reduced pressure to approximately 12 mL. This solution was cooled to 0° C., then treated sequentially with methyl (2R)-2-hydroxypropanoate (0.22 mL, 2.3 mmol, 1.0 eq.), triphenylphosphine (671 mg, 2.6 mol, 1.1 eq.) and DIAD (0.50 mL, 2.6 mol, 1.1 eq.) and stirred at room temperature for 1 h. The mixture was concentrated under reduced pressure and purified by flash column chromatography (Si, 0-10% EtOAc in hexanes) to give the title compound (425 mg, 1.3 mmol, 50%) as a colourless oil.

UPLC-MS: acidic 2-minute run MS (ES−): m/z 321.0/323.0 (M−H)⁻; retention time: 1.26 min; purity: 89%. $^1$H NMR (400 MHz, Chloroform-d) δ 7.66 (dd, J=2.5, 1.0 Hz, 1H), 7.42 (dd, J=8.8, 2.5 Hz, 1H), 6.66 (d, J=8.8 Hz, 1H), 4.80 (q, J=6.8 Hz, 1H), 3.75 (s, 3H), 2.04 (dd, J=19.3, 18.3 Hz, 3H), 1.64 (d, J=6.8 Hz, 3H). 95% purity. $^{19}$F NMR (376 MHz, Chloroform-d) δ−84.43--−91.12 (m).

Step 2: Synthesis of methyl (S)-2-(2-(1,1-difluoro-ethyl)-4-((trimethylsilyl)ethynyl)phenoxy)propano-ate To a degassed mixture of methyl (2S)-2-[4-bromo-2-(1,1-difluoroethyl)phenoxy]propanoate (200 mg, 0.62 mmol, 1.0 eq.), ethynyltrimethylsilane (0.18 mL, 1.2 mmol, 2.0 eq.), copper (I) iodide (12 mg, 0.06 mmol, 0.1 eq.) and triethylamine (0.13 mL, 0.93 mmol, 1.5 eq.) in toluene (1.8 mL) was added bis(triphenylphosphine)dichloropalladium (43 mg, 0.06 mmol, 0.1 eq.) and the mixture was stirred at 100° C. for 1 h. The reaction was filtered through Celite and the filtrate concentrated under reduced pressure to give the title compound (325 mg, 0.62 mmol, quant.) as a crude dark oil which was used in the following step without further purification.

UPLC-MS: acidic 2-minute run MS (ES+): no m/z; retention time: 1.42 min; purity: 68%.

$^1$H NMR (400 MHz, Chloroform-d) δ 7.47 (s, 1H), 7.31-7.17 (m, 1H), 6.50 (d, J=8.6 Hz, 1H), 4.65 (q, J=6.8 Hz, 1H), 3.55 (s, 3H), 1.84 (t, J=18.9 Hz, 3H), 1.46 (d, J=6.8 Hz, 3H), 0.05 (s, 9H). $^{19}$F NMR (376 MHz, Chloroform-d) δ−81.29--−92.61 (m).

Step 3: Synthesis of methyl (S)-2-(2-(1,1-difluoro-ethyl)-4-ethynylphenoxy)propanoate To a solution of methyl (S)-2-(2-(1,1-difluoroethyl)-4-((trimethylsilyl)ethynyl)phenoxy)propanoate (215 mg, 0.62 mmol, 1.0 eq.) in THF (2 mL) was added tetrabutylammonium fluoride (1.0M in THF, 1.9 mL, 1.9 mmol, 3.0 eq.) and the mixture was stirred at room temperature for 3 h. 1M aqueous hydrochloric acid solution (1 mL) was added and the mixture was stirred at room temperature for 30 min. The reaction mixture was concentrated under reduced pressure and the residue was purified by flash column chromatography (Si, 0-20% EtOAc in hexanes) to give the title compound (84 mg, 0.31 mmol, 37%) as a brown oil.

UPLC-MS: acidic 2-minute run MS (ES+): m/z 269.2 (M+H)⁺; retention time: 1.20 min; purity: 75%. $^1$H NMR (400 MHz, Chloroform-d) δ 7.68 (s, 1H), 7.45 (d, J=6.8 Hz, 1H), 6.71 (d, J=8.5 Hz, 1H), 4.85 (q, J=6.7 Hz, 1H), 3.75 (s, 3H), 3.01 (s, 1H), 2.04 (dd, J=19.4, 18.2 Hz, 3H), 1.66 (d, J=6.8 Hz, 3H). $^{19}$F NMR (376 MHz, Chloroform-d) δ −87.80−−89.94 (m).

Step 4: Synthesis of (S)-2-(2-(1,1-difluoroethyl)-4-ethynylphenoxy)propanoic acid To a solution of methyl (2S)-2-[2-(1,1-difluoroethyl)-4-ethynylphenoxy]propanoate (84 mg, 0.31 mmol, 1.0 eq.) in MeOH (1.7 mL) was added 1M aqueous sodium hydroxide solution (0.33 mL, 0.33 mmol, 1.05 eq.) and the reaction was stirred at room temperature overnight. The reaction mixture was concentrated under reduced pressure and the residue purified by prep-HPLC chromatography (5-95% MeCN in water+0.1% formic acid) to give the title compound (22 mg, 0.09 mmol, 28%) as an off-white solid. UPLC-MS: acidic 4-minute run MS (ES+): m/z 255.1 (M+H)$^+$; retention time: 1.54 min; purity: 100%. $^1$H NMR (400 MHz, DMSO-d$_6$) δ7.48 (dd, J=8.3, 2.2 Hz, 1H), 7.44 (d, J=2.2 Hz, 1H), 6.91 (d, J=8.5 Hz, 1H), 4.63 (q, J=6.6, 6.1 Hz, 1H), 4.05 (s, 1H), 2.05 (dd, J=19.9, 18.6 Hz, 3H), 1.44 (d, J=6.7 Hz, 3H). $^{19}$F NMR (376 MHz, DMSO-d$_6$) δ−83.53 (dq, J=242.5, 18.8 Hz), −87.25 (dq, J=241.8, 19.7 Hz).

Example 17: Synthesis of ammonium (S)-2-(2-(1,1-difluoropropyl)-5-fluoro-4-vinylphenoxy)propanoate

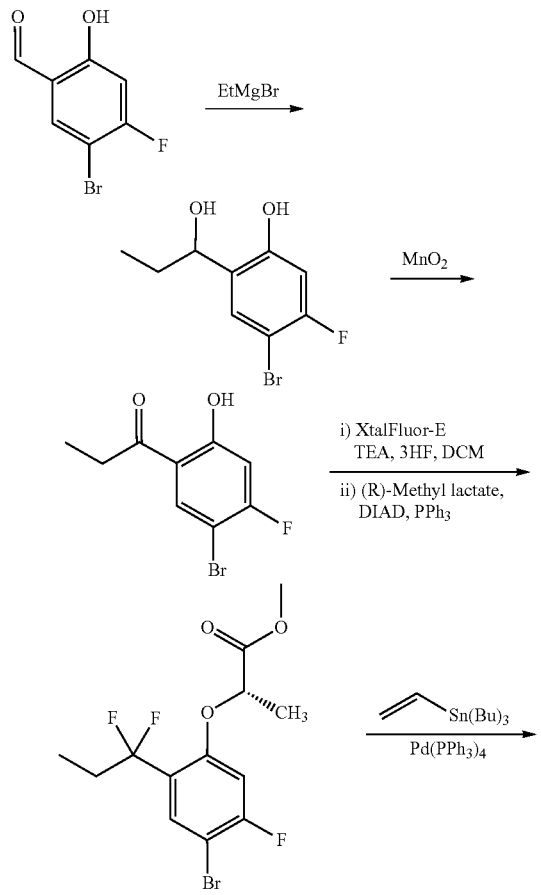

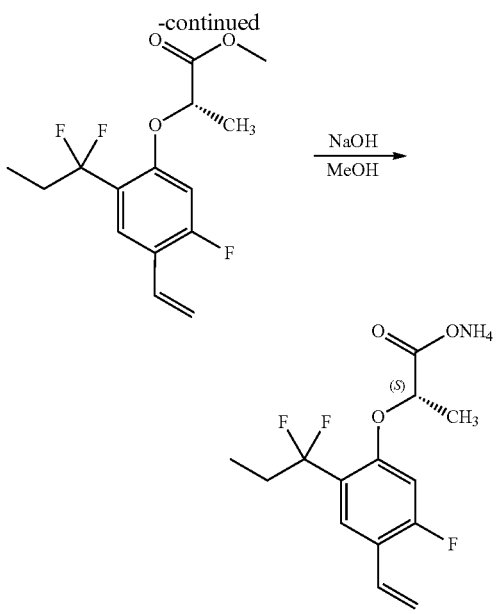

Step 1: Synthesis of 4-bromo-5-fluoro-2-(1-hydroxypropyl)phenol

To a cooled (0° C.) solution of 5-bromo-4-fluoro-2-hydroxybenzaldehyde (5.0 g, 22.8 mmol, 1.0 eq.) in THF (228 mL) was added dropwise ethylmagnesium bromide (22.8 mL, 3.0 M in diethyl ether, 68.5 mmol, 3.0 eq.) and the reaction was stirred for 1 h. The reaction mixture was subsequently poured into saturated aqueous ammonium chloride solution (200 mL) and extracted with EtOAc (3×100 mL). The combined organic extracts were washed with brine (2×100 mL), dried over sodium sulphate and concentrated under reduced pressure to give the title compound (6.14 g, 24.7 mmol, quant.) as a colourless oil which was used in the next step without further purification. UPLC-MS: basic 2-minute run MS (ES−): m/z 247.0/249.0 (M−H)$^−$; retention time: 1.03 min; purity: 97%. $^1$H NMR (400 MHz, Chloroform-d) δ 8.31 (s, 1H), 7.07 (d, J=7.6 Hz, 1H), 6.66 (d, J=9.9 Hz, 1H), 4.73 (t, J=6.6 Hz, 1H), 2.68 (s, 1H), 1.97-1.74 (m, 2H), 0.97 (t, J=7.4 Hz, 3H). $^{19}$F NMR (376 MHz, Chloroform-d) δ−107.57 (dd, J=9.7, 7.8 Hz).

Step 2: Synthesis of 1-(5-bromo-4-fluoro-2-hydroxyphenyl)propan-1-one

To a solution of 4-bromo-5-fluoro-2-(1-hydroxypropyl)phenol (6.14 g, 24.7 mmol, 1.0 eq.) in 1,4-dioxane (25 mL) was added manganese (IV) oxide (8.57 g, 98.6 mmol, 4.0 eq.) and the reaction heated at reflux for 2.5 h. The reaction mixture was cooled, filtered through a pad of Celite and the pad washed with EtOAc (100 mL), then MeOH (30 mL). The filtrate was concentrated under reduced pressure and the crude product purified by flash column chromatography (Si, 0-20% EtOAc in hexanes) to give the title compound (3.20 g, 13.0 mmol, 53%) as a yellow solid.

UPLC-MS: basic 2-minute run MS (ES−): m/z 245.0/247.0 (M−H)$^−$; retention time: 1.24 min; purity: 100%. $^1$H NMR (400 MHz, Chloroform-d) δ12.55 (d, J=1.5 Hz, 1H), 7.95 (d, J=7.6 Hz, 1H), 6.76 (d, J=10.0 Hz, 1H), 2.99 (q, J=7.2 Hz, 2H), 1.24 (t, J=7.2 Hz, 3H). $^{19}$F NMR (376 MHz, Chloroform-d) δ−91.85−−98.32 (m).

Step 3: Synthesis of methyl (S)-2-(4-bromo-2-(1,1-difluoropropyl)-5-fluorophenoxy)propanoate To a solution of triethylamine trihydrofluoride (0.66 mL, 4.04 mmol, 2.0 eq.) in DCM (6 mL) was successively added XtalFluor-E (1.85 g, 8.10 mmol, 4.0 eq.) and 1-(5-bromo-4-fluoro-2-hydroxyphenyl)propan-1-one) (500 mg, 2.02 mmol, 1.0 eq.) and the reaction was stirred at room temperature overnight. The reaction mixture was poured onto ice, and the resulting mixture was extracted with DCM (2×20 mL). The combined organic phases were washed with water (3×25 mL), dried over magnesium sulphate and concentrated under reduced pressure to ¼ volume. The remaining solution was directly purified by flash column chromatography (Si, DCM eluent), the appropriate fractions were collected, concentrated under reduced pressure to approximately 12 mL. This solution was cooled to 0° C., then treated sequentially with methyl (2R)-2-hydroxypropanoate (0.21 mL, 2.22 mmol, 1.1 eq.), triphenylphosphine (584 mg, 2.22 mol, 1.1 eq.) and DIAD (0.44 mL, 2.22 mol, 1.1 eq.) and stirred at room temperature for 2 h. The mixture was concentrated under reduced pressure and purified by flash column chromatography (Si, 5-20% EtOAc in hexanes) to give the title compound (390 mg, 1.45 mmol, 54%) as a colourless oil.

UPLC-MS: acidic 2-minute run MS (ES-): m/z 353.0/355.0 (M-H)$^-$; retention time: 1.32 min; purity: 90%. $^1$H NMR (400 MHz, Chloroform-d) δ 7.68 (d, J=7.8 Hz, 1H), 6.58 (d, J=9.9 Hz, 1H), 4.75 (q, J=6.8 Hz, 1H), 3.77 (s, 3H), 2.48-2.27 (m, 2H), 1.65 (d, J=6.8 Hz, 3H), 0.94 (t, J=7.5 Hz, 3H). $^{19}$F NMR (376 MHz, Chloroform-d) δ-89.65--99.10 (m), -101.34--103.92 (m).

Step 4: Synthesis of methyl (S)-2-(2-(1,1-difluoropropyl)-5-fluoro-4-vinylphenoxy)propanoate To a degassed solution of methyl (2S)-2-[4-bromo-2-(1,1-difluoropropyl)-5-fluorophenoxy]propanoate (200 mg, 0.56 mmol, 1.0 eq.) and tributyl(vinyl)tin (0.33 mL, 1.13 mmol, 1.1 eq.) in 1,4-dioxane (2.3 mL) was added Pd(PPh$_3$)$_4$ (33 mg, 0.03 mmol, 0.05 eq.) and the mixture heated in a sealed tube at 100° C. for 4 h. The reaction mixture was cooled to room temperature, diluted with EtOAc (25 mL) and filtered through Celite. The filtrate was concentrated under reduced pressure and purified by flash column chromatography (Si, 0-10% EtOAc in hexanes) to give the title compound (69 mg, 0.23 mmol, 41%) as a colourless oil.

UPLC-MS: basic 2-minute run MS (ES-): m/z 301.1 (M-H)$^-$; retention time: 1.32 min; purity: 100%. $^1$H NMR (DMSO-d$_6$) δ 7.63 (d, J=8.6 Hz, 1H), 6.99 (d, J=12.7 Hz, 1H), 6.75 (dd, J=17.8, 11.3 Hz, 1H), 5.82 (d, J=17.8 Hz, 1H), 5.36 (d, J=11.4 Hz, 1H), 5.25 (q, J=6.7 Hz, 1H), 3.69 (s, 3H), 2.36 (tdd, J=17.0, 14.1, 7.4 Hz, 2H), 1.52 (d, J=6.7 Hz, 3H), 0.87 (q, J=7.2 Hz, 3H). $^{19}$F NMR (376 MHz, DMSO-d$_6$) δ-90.86 (dd, J=242.8, 3.0 Hz), -95.77 (dd, J=242.8, 2.2 Hz), -113.48 (t, J=2.6 Hz).

Step 5: Synthesis of ammonium (S)-2-(2-(1,1-difluoropropyl)-5-fluoro-4-vinylphenoxy)propanoate A solution of methyl (2S)-2-[2-(1,1-difluoropropyl)-4-ethenyl-5-fluorophenoxy]propanoate (47 mg, 0.16 mmol, 1.0 eq.) in MeOH (1.1 mL) was treated with 1M aqueous sodium hydroxide solution (0.16 mL, 0.16 mmol, 1.0 eq.) and the reaction was stirred at room temperature for 2 h. The reaction mixture was concentrated under reduced pressure and the crude product purified by prep-HPLC chromatography (5-95% MeCN in water+0.1% ammonium hydroxide) to give the title compound (18 mg, 0.06 mmol, 38%) as an off-white powder.

UPLC-MS: acidic 4-minute run MS (ES-): m/z 287.1 (M-H)$^-$; retention time: 1.91 min; purity: 100%. $^1$H NMR (DMSO-d$_6$) δ 7.53 (d, J=8.8 Hz, 1H), 6.79-6.60 (m, 2H), 5.74 (d, J=17.7 Hz, 1H), 5.27 (d, J=11.4 Hz, 1H), 4.34 (q, J=6.8 Hz, 1H), 2.40 (ddq, J=7.7, 15.4, 22.7 Hz, 2H), 1.38 (d, J=6.6 Hz, 3H), 0.86 (t, J=6.9 Hz, 3H). $^{19}$F NMR (376 MHz, DMSO-d$_6$) δ-90.64 (dd, J=240.6, 3.2 Hz), -96.20 (d, J=240.7 Hz), -114.94 (d, J=3.1 Hz).

Example 18: Synthesis of (S)-2-(4-bromo-2-(1,1-difluoropropyl)-5-fluorophenoxy)butanoic acid

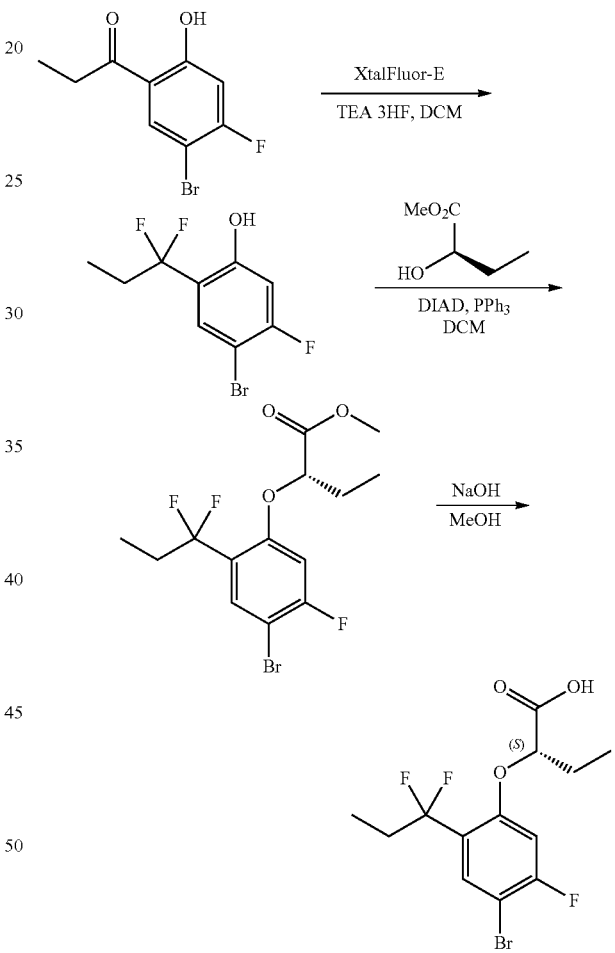

Step 1+2: Synthesis of methyl (S)-2-(4-bromo-2-(1,1-difluoropropyl)-5-fluorophenoxy)butanoate To a solution of triethylamine trihydrofluoride (0.66 mL, 4.05 mmol, 2.0 eq.) in DCM (6 mL) was successively added XtalFluor-E (1.85 g, 8.10 mmol, 4.0 eq.) and 1-(5-bromo-4-fluoro-2-hydroxyphenyl)propan-1-one (500 mg, 2.02 mmol, 1.0 eq.) and the reaction was stirred at room temperature for 2 days. The reaction mixture was poured onto ice, and the resulting mixture was extracted with DCM (2×20 mL). The combined organic phases were washed with water (3×25 mL), dried over sodium sulphate and concentrated under reduced pressure to ¼ volume. The remaining solution was directly purified by flash column chromatography (Si, DCM eluent), the appropriate fractions were collected, concentrated under reduced pressure to approximately 10 mL. This solution was cooled to 0° C., then treated sequentially with methyl (2R)-2-hydroxypropanoate (239 mg, 2.02 mmol, 1.0 eq.), triphenylphosphine (583 mg, 2.22 mol, 1.1 eq.) and DIAD (0.44 mL, 2.22 mol, 1.1 eq.) and stirred at room temperature for 72 h. The mixture was concentrated under reduced pressure and purified by flash column chromatography (Si, 0-20% EtOAc in hexanes) to give the title compound (424 mg, 0.75 mmol, 37%) as a yellow oil.

UPLC-MS: acidic 2-minute run MS (ES+): no m/z; retention time: 1.37 min; purity: 76%.

$^1$H NMR (400 MHz, Chloroform-d) δ 7.68 (dd, J=7.8, 1.3 Hz, 1H), 6.53 (d, J=10.0 Hz, 1H), 4.61 (t, J=5.9 Hz, 1H), 3.76 (s, 3H), 2.48-2.21 (m, 2H), 2.12-1.95 (m, 2H), 1.07 (t, J=7.4 Hz, 3H), 0.95 (t, J=7.5 Hz, 3H). $^{19}$F NMR (376 MHz, Chloroform-d) δ−92.46 (dtd, J=245.7, 13.9, 3.2 Hz), −98.85 (dt, J=245.8, 20.3 Hz), −102.12 (ddd, J=10.2, 7.6, 2.9 Hz).

Step 3: Synthesis of (S)-2-(4-bromo-2-(1,1-difluoropropyl)-5-fluorophenoxy)butanoic acid A solution of methyl (2S)-2-[4-bromo-2-(1,1-difluoropropyl)-5-fluorophenoxy]butanoate (150 mg, 0.26 mmol, 1.0 eq.) in MeOH (1.4 mL) was treated with 1M aqueous sodium hydroxide solution (0.28 mL, 0.28 mmol, 1.05 eq.) and the reaction was stirred at room temperature for 72 h. The reaction mixture was concentrated under reduced pressure to give the title compound (139 mg, 0.39 mmol, 99%) as a pale-yellow gum.

UPLC-MS: basic 4-minute run MS (ES−): m/z 353.0/355.0 (M−H)$^-$; retention time: 1.41 min; purity: 97%. $^1$H NMR (400 MHz, DMSO-d$_6$) δ7.61 (d, J=7.9 Hz, 1H), 7.07 (d, J=11.0 Hz, 1H), 4.87 (dd, J=6.4, 4.6 Hz, 1H), 2.43-2.30 (m, 2H), 2.01-1.78 (m, 2H), 0.95 (t, J=7.4 Hz, 3H), 0.86 (t, J=7.5 Hz, 3H). $^{19}$F NMR (376 MHz, DMSO-d$_6$) δ −91.09 (dt, J=242.4, 14.3 Hz), −97.00 (dt, J=242.4, 20.6 Hz), −103.42 (t, J=9.5 Hz).

Example 19: Synthesis of (S)-2-(4-chloro-2-(1,1-difluoropropyl)-5-fluorophenoxy)butanoic acid

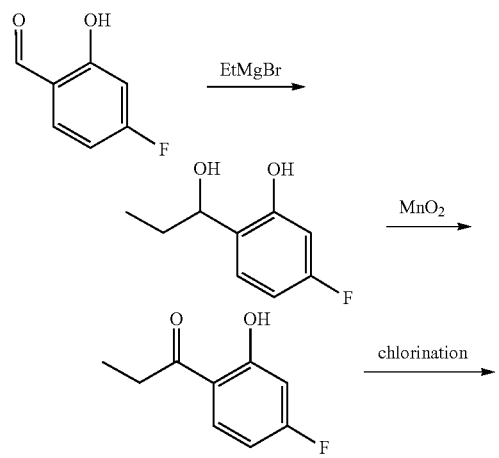

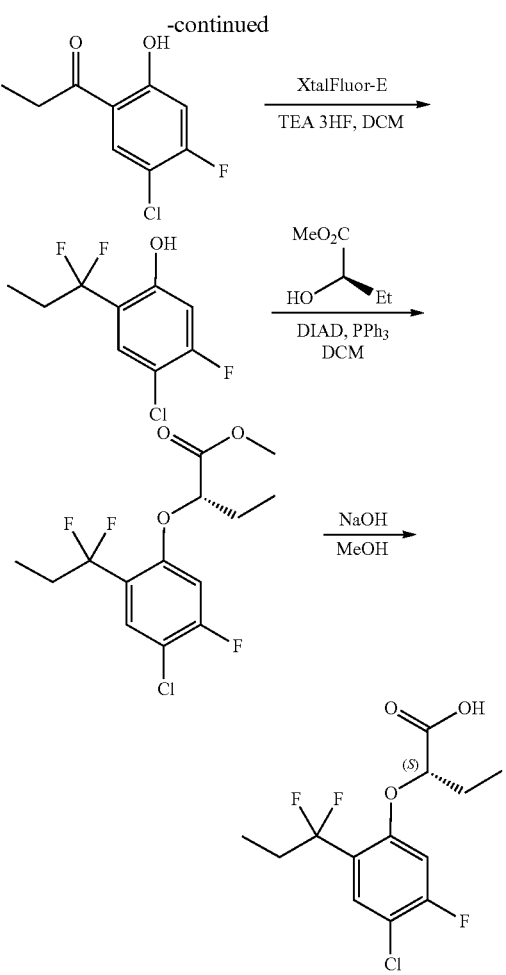

Step 1: Synthesis of 5-fluoro-2-(1-hydroxypropyl)phenol

To a cooled (−40° C.) solution of 4-fluoro-2-hydroxybenzaldehyde (5.0 g, 35.7 mmol, 1.0 eq.) in THF (250 mL) was added dropwise ethylmagnesium bromide (25 mL, 3.0 M in diethyl ether, 75.0 mmol, 3.1 eq.) and the reaction was allowed to warm slowly to room temperature and stirred for 3 h. The reaction mixture was poured into saturated aqueous ammonium chloride solution (200 mL) and extracted with EtOAc (3×100 mL). The combined organic extracts were dried over sodium sulphate and concentrated under reduced pressure to give the title compound (6.70 g, 39.4 mmol, quant.) as a light amber oil which was used in the next step without further purification.

UPLC-MS: acidic 2-minute run MS (ES−): m/z 169.1 (M−H)$^-$; retention time: 0.91 min; purity: 87%. $^1$H NMR (400 MHz, chloroform-d) δ 8.28 (bs, 1H), 6.86 (dd, J=8.4, 6.4 Hz, 1H), 6.67-6.44 (m, 2H), 4.74 (t, J=6.8 Hz, 1H), 2.69 (bs, 1H), 1.98-1.70 (m, 2H), 0.95 (t, J=7.4 Hz, 3H). $^{19}$F NMR (376 MHz, Chloroform-d) −113.64 (ddd, J=10.4, 8.3, 6.3 Hz).

Step 2: Synthesis of 1-(4-fluoro-2-hydroxyphenyl)propan-1-one

To a solution of 5-fluoro-2-(1-hydroxypropyl)phenol (6.07 g, 35.7 mmol, 1.0 eq.) in 1,4-dioxane (50 mL) was added manganese (IV) oxide (13.7 g, 157 mmol, 4.4 eq.) and the reaction stirred at reflux for 2.5 h. The reaction mixture was cooled to room temperature, filtered through a pad of Celite and the filter cake washed with 4:1 EtOAc: MeOH (2×250 mL). The filtrate was concentrated under reduced pressure and the crude material purified by flash column chromatography (Si, 5-20% EtOAc in hexanes) to give the title compound (4.15 g, 24.7 mmol, 63%) as a yellow oil which crystallised upon standing.

UPLC-MS: acidic 2-minute run MS (ES+): m/z 169.1 (M+H)$^+$; retention time: 1.13 min; purity: 95%. $^1$H NMR (400 MHz, chloroform-d) δ 12.68 (s, 1H), 7.77 (dd, J=6.4, 8.9 Hz, 1H), 6.77-6.48 (m, 2H), 3.00 (q, J=7.3 Hz, 2H), 1.24 (t, J=7.3 Hz, 3H). $^{19}$F NMR (376 MHz, Chloroform-d) δ−99.76−−99.87 (m).

Step 3: Synthesis of 1-(5-chloro-4-fluoro-2-hydroxyphenyl)propan-1-one

To a solution of 1-(4-fluoro-2-hydroxyphenyl)propan-1-one (400 mg, 2.38 mmol, 1.0 eq.) in DCM (7.0 mL) was added benzyltrimethylazanium tetrachloro-λ$^3$-iodanuide (997 mg, 2.38 mmol, 1.0 eq.) and the resulting mixture stirred at room temperature in the dark for 4 days. The mixture was concentrated under reduced pressure and purified by flash column chromatography (Si, 0-15% EtOAc in hexanes) to give the title compound (454 mg, 2.24 mmol, 94%) as a yellow oil.

UPLC-MS: acidic 2-minute run MS (ES−): m/z 201.1/ 203.1 (M−H)$^-$; retention time: 1.22 min; purity: 75%. $^1$H NMR (400 MHz, chloroform-d) δ 12.53 (s, 1H), 7.81 (d, J=8.2 Hz, 1H), 6.77 (d, J=10.2 Hz, 1H), 2.99 (m, 2H), 1.24 (t, J=7.2 Hz, 3H). $^{19}$F NMR (376 MHz, Chloroform-d) δ−102.04 (dd, J=10.2, 8.3 Hz).

Step 4+5: Synthesis of methyl (S)-2-(4-chloro-2-(1, 1-difluoropropyl)-5-fluorophenoxy)butanoate To a solution of triethylamine trihydrofluoride (0.72 mL, 4.44 mmol, 2.0 eq.) in DCM (6.4 mL) was successively added XtalFluor-E (2.03 g, 8.88 mmol, 4.0 eq.) and 1-(5-chloro-4-fluoro-2-hydroxyphenyl)propan-1-one (450 mg, 2.22 mmol, 1.0 eq.) and the reaction was stirred at room temperature overnight. The reaction mixture was poured onto ice, and the resulting mixture was extracted with DCM (2×20 mL). The combined organic phases were washed with water (3×25 mL), dried over magnesium sulphate and concentrated under reduced pressure to ¼ volume. The remaining solution was directly purified by flash column chromatography (Si, DCM eluent), the appropriate fractions were collected, concentrated under reduced pressure to approximately 10 mL. This solution was cooled to 0° C., then treated sequentially with methyl (2R)-2-hydroxypropanoate (262 mg, 2.22 mmol, 1.0 eq.), triphenylphosphine (641 mg, 2.44 mol, 1.1 eq.) and DIAD (0.48 mL, 2.44 mol, 1.1 eq.) and stirred at room temperature for 72 h. The mixture was concentrated under reduced pressure and purified by flash column chromatography (Si, 0-20% EtOAc in hexanes) to give the title compound (208 mg, 0.49 mmol, 22%) as a yellow oil which was used in the next step without further purification.

UPLC-MS: acidic 2-minute run MS (ES+): m/z 348.3/ 350.3 (M+Na)$^+$; retention time: 1.36 min; purity: 76%. $^1$H NMR (400 MHz, chloroform-d) δ 7.55 (dd, J=8.4, 1.3 Hz, 1H), 6.55 (d, J=10.5 Hz, 1H), 4.61 (t, J=5.9 Hz, 1H), 3.76 (s, 3H), 2.49-2.22 (m, 2H), 2.12-1.94 (m, 2H), 1.07 (t, J=7.4 Hz, 3H), 0.94 (t, J=7.5 Hz, 3H). $^{19}$F NMR (376 MHz, Chloroform-d) δ−91.91−−93.10 (m), −98.84 (dt, J=246.0, 20.6 Hz), −110.05 (td, J=9.5, 8.2, 2.6 Hz).

Step 6: Synthesis of (S)-2-(4-chloro-2-(1,1-difluoropropyl)-5-fluorophenoxy)butanoic acid A solution of methyl (2S)-2-[4-chloro-2-(1,1-difluoropropyl)-5-fluorophenoxy]butanoate (200 mg, 0.40 mmol, 1.0 eq.) in MeOH (2.1 mL) was treated with 1M aqueous sodium hydroxide solution (0.42 mL, 0.42 mmol, 1.05 eq.) and the reaction was stirred at room temperature for 18 h. The reaction mixture was concentrated under reduced pressure and the crude material purified by prep-HPLC chromatography (5-95% MeCN in water+0.1% formic acid) to give the title compound (29 mg, 0.09 mmol, 23%) as an off-white solid.

UPLC-MS: acidic 4-minute run MS (ES−): m/z 309.0/ 311.0 (M−H)$^-$; retention time: 2.00 min; purity: 100%. $^1$H NMR (400 MHz, DMSO-d$_6$) δ 13.58 (bs, 1H), 7.53 (d, J=8.4 Hz, 1H), 7.14 (d, J=11.5 Hz, 1H), 4.97 (m, 1H), 2.49-2.23 (m, 2H), 2.04-1.80 (m, 2H), 0.96 (t, J=7.4 Hz, 3H), 0.86 (t, J=7.4 Hz, 3H). $^{19}$F NMR (376 MHz, DMSO-d$_6$) δ −90.89 (t, J=14.2 Hz), −91.46−−91.62 (m), −96.55 (t, J=20.3 Hz), −97.20 (t, J=20.4 Hz), −111.16 (t, J=10.1 Hz).

Example 20: Synthesis of sodium (S)-2-(2-(1,1-difluoropropyl)-4-nitrophenoxy)propanoate

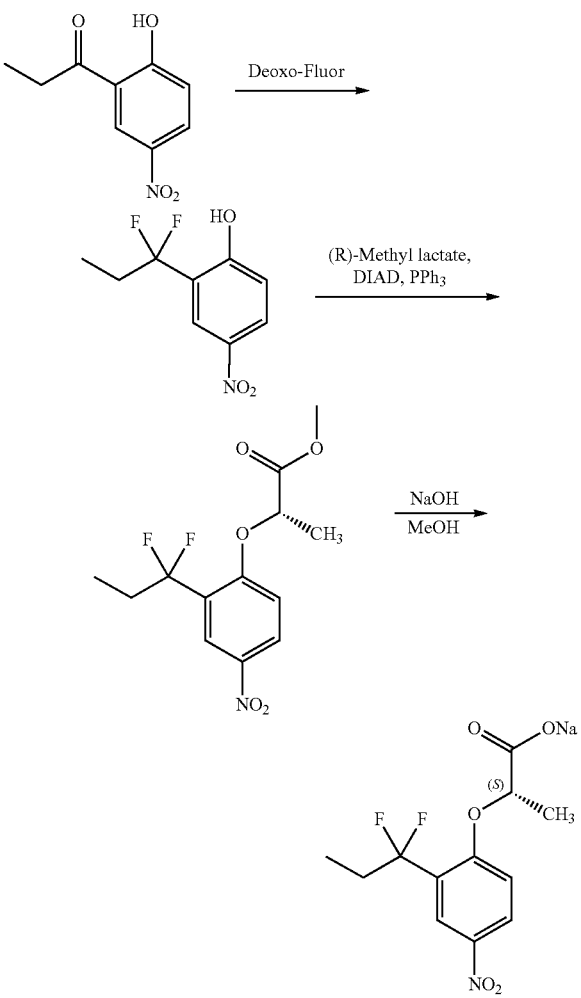

Steps 1+2: Synthesis of methyl (S)-2-(2-(1,1-difluoropropyl)-4-nitrophenoxy)propanoate To a solution of triethylamine trihydrofluoride (0.84 mL, 5.12 mmol, 2.0 eq.) in DCM (7.3 mL) was successively added XtalFluor-E (2.35 g, 10.2 mmol, 4.0 eq.) and 1-(2-Hydroxy-5-nitrophenyl)propan-1-one (500 mg, 2.56 mmol, 1.0 eq.) and the reaction was stirred at room temperature overnight. The reaction mixture was poured onto ice, and the resulting mixture was extracted with DCM (2×20 mL). The combined organic phases were washed with water (3×25 mL), dried over magnesium sulphate and concentrated under reduced pressure to ¼ volume. The remaining solution was directly purified by flash column chromatography (Si, DCM eluent), the appropriate fractions were collected, concentrated under reduced pressure to approximately 10 mL. This solution was cooled to 0° C., then treated sequentially with methyl (2R)-2-hydroxypropanoate (0.25 mL, 2.56 mmol, 1.0 eq.), triphenylphosphine (739 mg, 2.82 mmol, 1.1 eq.) and DIAD (0.55 mL, 2.82 mol, 1.1 eq.) and stirred at room temperature for 18 h. The mixture was concentrated under reduced pressure and purified by flash column chromatography (Si, 0-20% EtOAc in hexanes) to give the title compound (616 mg, 2.03 mmol, 79%) as a light yellow oil.

UPLC-MS: acidic 2-minute run MS (ES+): no m/z; retention time: 1.21 min; purity: 100%. $^1$H NMR (400 MHz, Chloroform-d) δ 8.45 (m, 1H), 8.26 (m, 1H), 6.84 (m, 1H), 4.96 (m, 1H), 3.87-3.64 (m, 3H), 2.41 (m, 2H), 1.83-1.62 (m, 3H), 0.97 (m, 3H). $^{19}$F NMR (376 MHz, Chloroform-d) δ−94.30 (d, J=247.5 Hz), −99.15 (d, J=247.7 Hz).

Step 3: Synthesis of sodium (S)-2-(2-(1,1-difluoropropyl)-4-nitrophenoxy)propanoate A solution of methyl (2S)-2-[2-(1,1-difluoropropyl)-4-nitrophenoxy]propanoate (32 mg, 0.11 mmol, 1.0 eq.) in MeOH (0.6 mL) was treated with 1M aqueous sodium hydroxide solution (0.16 mL, 0.16 mmol, 1.5 eq.) and the reaction was stirred at room temperature for 18 h. The reaction mixture was concentrated under reduced pressure to give the title compound (30 mg, 0.10 mmol, 91%) as a yellow solid.

UPLC-MS: acidic 4-minute run MS (ES−): m/z 288.1 (M−H)$^-$; retention time: 1.62 min; purity: 100%. $^1$H NMR (400 MHz, DMSO-d$_6$) δ 8.26 (dd, J=2.9, 9.2 Hz, 1H), 8.16 (d, J=2.9 Hz, 1H), 7.03 (d, J=9.3 Hz, 1H), 4.55 (q, J=6.7 Hz, 1H), 2.44 (m, 2H), 1.44 (d, J=6.7 Hz, 3H), 0.88 (t, J=7.4 Hz, 3H). $^{19}$F NMR (376 MHz, DMSO-d$_6$) δ−92.29 (dt, J=242.3, 14.4 Hz), −97.91 (dt, J=242.4, 20.5 Hz).

Example 21: Synthesis of sodium (S)-2-(5-chloro-2-(1,1-difluoropropyl)-4-fluorophenoxy)propanoate

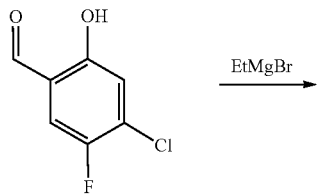

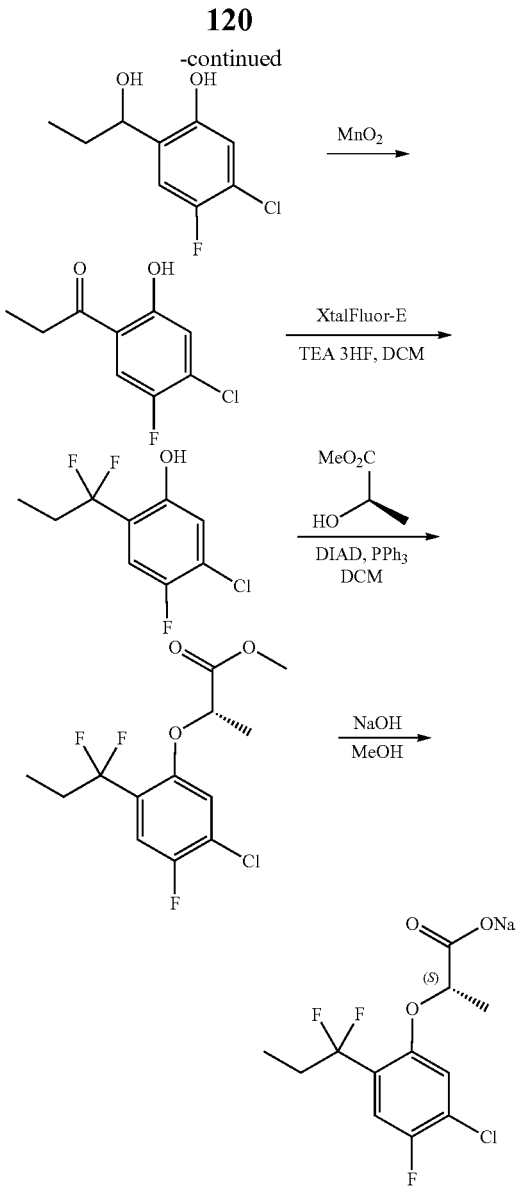

Step 1: Synthesis of 5-chloro-4-fluoro-2-(1-hydroxypropyl)phenol

To a cooled (−40° C.) solution of 4-chloro-5-fluoro-2-hydroxybenzaldehyde (2.5 g, 14.3 mmol, 1.0 eq.) in THF (100 mL) was added dropwise ethylmagnesium bromide (10 mL, 3.0 M in diethyl ether, 30.0 mmol, 3.0 eq.) and the reaction was allowed to warm slowly to room temperature and stirred overnight. The reaction mixture was subsequently poured into saturated aqueous ammonium chloride solution (200 mL) and extracted with EtOAc (3×100 mL). The combined organic extracts were dried over sodium sulphate and concentrated under reduced pressure to give the title compound (3.20 g, 12.8 mmol, 90%) as an amber oil which was used in the next step without further purification.

UPLC-MS: acidic 2-minute run MS (ES−): m/z 203.1/205.1 (M−H)$^-$; retention time: 1.01 min; purity: 92%. $^1$H NMR (400 MHz, Chloroform-d) δ 7.92 (s, 1H), 7.02-6.81 (m, 1H), 6.74 (m, 1H), 4.79-4.61 (m, 1H), 1.97-1.71 (m, 2H), 0.98 (m, 3H). $^{19}$F NMR (376 MHz, Chloroform-d) δ−127.80--127.99 (m).

Step 2: Synthesis of 1-(4-chloro-5-fluoro-2-hydroxyphenyl)propan-1-one

To a solution of 5-chloro-4-fluoro-2-(1-hydroxypropyl) phenol (2.93 g, 14.3 mmol, 1.0 eq.) in 1,4-dioxane (18 mL) was added manganese (IV) oxide (5.50 g, 63.2 mmol, 4.4 eq.) and the reaction stirred at reflux for 6 h. The reaction mixture was cooled to room temperature, filtered through a pad of Celite and the filter cake washed with 4:1 EtOAc:MeOH (2×250 mL). The filtrate was concentrated under reduced pressure and the crude product purified by flash column chromatography (Si, 0-20% EtOAc in hexanes) to give the title compound (1.02 g, 5.0 mmol, 35%) as a yellow solid.

UPLC-MS: acidic 2-minute run MS (ES−): m/z 201.1/203.1 (M−H)⁻; retention time: 1.21 min; purity: 92%. $^1$H NMR (400 MHz, Chloroform-d) 512.15 (s, 1H), 7.50 (d, J=9.2 Hz, 1H), 7.05 (d, J=6.3 Hz, 1H), 2.97 (q, J=7.2 Hz, 2H), 1.24 (t, J=7.2 Hz, 3H). $^{19}$F NMR (376 MHz, Chloroform-d) δ−126.77 (dd, J=6.1, 8.9 Hz), −126.83 (dd, J=3.4, 6.4 Hz).

Step 3+4: Synthesis of methyl (S)-2-(5-chloro-2-(1,1-difluoropropyl)-4-fluorophenoxy)propanoate To a solution of triethylamine trihydrofluoride (0.81 mL, 4.94 mmol, 2.0 eq.) in DCM (7.1 mL) was successively added XtalFluor-E (2.26 g, 9.87 mmol, 4.0 eq.) and 1-(4-chloro-5-fluoro-2-hydroxyphenyl)propan-1-one (500 mg, 2.47 mmol, 1.0 eq.) and the reaction was stirred at room temperature overnight. The reaction mixture was poured onto ice, and the resulting mixture was extracted with DCM (2×20 mL). The combined organic phases were washed with water (3×25 mL), dried over magnesium sulphate and concentrated under reduced pressure to ¼ volume. The remaining solution was directly purified by flash column chromatography (Si, DCM eluent), the appropriate fractions were collected, concentrated under reduced pressure to approximately 20 mL. This solution was cooled to 0° C., then treated sequentially with methyl (2R)-2-hydroxypropanoate (257 mg, 2.47 mmol, 1.0 eq.), triphenylphosphine (712 mg, 2.71 mmol, 1.1 eq.) and DIAD (0.53 mL, 2.71 mol, 1.1 eq.) and stirred at room temperature overnight. The mixture was concentrated under reduced pressure and purified by flash column chromatography (Si, 0-20% EtOAc in hexanes) to give the title compound (697 mg, 1.91 mmol, 77%) as a yellow solid.

UPLC-MS: acidic 2-minute run MS (ES−): m/z 309.0/311.0 (M−H)⁻; retention time: 1.30 min; purity: 85%. $^1$H NMR (400 MHz, Chloroform-d) δ 7.32 (dd, J=9.3, 1.1 Hz, 1H), 6.82 (d, J=5.8 Hz, 1H), 4.73 (q, J=6.8 Hz, 1H), 3.78 (s, 3H), 2.50-2.26 (m, 2H), 1.63 (d, J=6.8 Hz, 3H), 0.93 (t, J=7.5 Hz, 3H). $^{19}$F NMR (376 MHz, Chloroform-d) δ−93.38 (ddd, J=246.3, 15.4, 13.0 Hz), −98.67 (dt, J=246.2, 19.9 Hz), −123.90 (dd, J=9.3, 5.7 Hz).

Step 5: Synthesis of sodium (S)-2-(5-chloro-2-(1,1-difluoropropyl)-4-fluorophenoxy)propanoate A solution of methyl (2S)-2-[5-chloro-2-(1,1-difluoropropyl)-4-fluorophenoxy]propanoate (100 mg, 0.21 mmol, 1.0 eq.) in MeOH (1.1 mL) was treated with 1M aqueous sodium hydroxide solution (0.22 mL, 0.22 mmol, 1.05 eq.) and the reaction was stirred at room temperature for 24 h. The reaction mixture was concentrated under reduced pressure to give the title compound (100 mg, 0.31 mmol, 98%) as an off-white solid.

UPLC-MS: acidic 4-minute run MS (ES−): m/z 295.0/297.0 (M−H)⁻; retention time: 1.86 min; purity: 100%. $^1$H NMR (400 MHz, DMSO-d$_6$) δ 7.33 (d, J=9.9 Hz, 1H), 6.99 (d, J=6.2 Hz, 1H), 4.33 (q, J=6.6 Hz, 1H), 2.48-2.33 (m, 2H), 1.37 (d, J=6.6 Hz, 3H), 0.86 (t, J=7.5 Hz, 3H). $^{19}$F NMR (376 MHz, DMSO-d$_6$) δ−91.66 (dt, J=241.4, 14.5 Hz), −96.69 (dt, J=241.6, 20.3 Hz), −128.48 (dd, J=9.7, 6.2 Hz).

Example 22: Electrophysiological Measurement of Compound Inhibition of ClC-1 in Rat Muscle The investigatory goal of these experiments was to evaluate whether compounds inhibit ClC-1 channels in native tissue of rat skeletal muscle fibres. Apparent ClC-1 affinity was reported by the concentration of compound at which 50% of the compound's full inhibition of ClC-1 was observed (EC$_{50}$).

ClC-1 Cl⁻ ion channels generate around 80% of the total membrane conductance ($G_m$) in resting skeletal muscle fibres of most animals including rat and human (Bretag, A H. Muscle chloride channels. Physiological Reviews, 1987, 67, 618-724). Other ion channels that contribute to $G_m$ can therefore be considered negligible, and it is possible to evaluate whether a compound inhibits ClC-1 in rat muscle by comparing $G_m$ measurements before and after exposure to a compound. ClC-1 inhibition would in such recordings be reflected by a reduction of $G_m$.

Experimentally, $G_m$ was measured in individual fibres of whole rat soleus muscles using a three micro-electrodes technique described in this example and in full detail elsewhere (Riisager et al., Determination of cable parameters in skeletal muscle fibres during repetitive firing of action potentials. Journal of Physiology, 2014, 592, 4417-4429). Briefly, intact rat soleus muscles were dissected out from 12-14 week old Wistar rats and placed in an experimental chamber that was perfused with a standard Krebs Ringer solution containing 122 mM NaCl, 25 mM NaHCO$_3$, 2.8 mM KCl, 1.2 mM KH$_2$PO$_4$, 1.2 mM MgSO$_4$, 1.3 mM CaCl$_2$, 5.0 mM D-glucose. During experiments, the solution was kept at approx. 30° C. and continuously equilibrated with a mixture of 95% O$_2$ and 5% CO$_2$, pH ~7.4. The experimental chamber was placed in Nikon upright microscope that was used to visualize individual muscle fibres and the three electrodes (glass pipettes filled with 2 M potassium citrate). For $G_m$ measurements, the electrodes were inserted into the same fibre with known inter-electrode distances of 0.35-0.5 mm (V1-V2, X1) and 1.1-1.5 mm (V1-V3, X3) (FIG. 1A). The membrane potential of the impaled muscle fibre was recorded by all electrodes. Two of the electrodes were furthermore used to inject 50 ms current pulses of −30 nA. Given the positions of the electrodes, three different inter-electrode distances could be identified (X1-X2, X1-X3, X2-X3) and hence the membrane potential responses to the current injections could be obtained at three distances from the point of current injection. The steady state voltage deflection at each distance was divided by the magnitude of current injected (−30 nA) and the resulting transfer resistances were plotted against inter-electrode distance and the data was fitted to a mono-exponential function from which $G_m$ could be calculated using linear cable theory (FIG. 1B).

To establish a dose response relationship, $G_m$ was first determined in 10 muscle fibres in the absence of compound and then at four increasing compound concentrations with $G_m$ determinations in 5-10 fibres at each concentration. The average $G_m$ values at each concentration were plotted against compound concentration and the data was fitted to sigmoidal function to obtain an EC$_{50}$ value (FIG. 10). Table 2 shows the $EC_{50}$ values for a range of compounds with n values referring to number of experiments that each reflect recordings from around 50 fibres.

TABLE 2

Inhibition of CIC-1 ion channel using compounds of the disclosure

| Compound investigated | $EC_{50}$ (µM) |
|---|---|
| Compound A-3 | 3.5 ± 0.4 (n = 2) |
| Compound A-5 | 4.0 ± 2.1 (n = 3) |
| Compound A-6 | 7.5 ± 2.9 (n = 3) |
| Compound A-7 | 3.5 ± 0.7 (n = 2) |
| Compound A-11 | 1.6 ± 0.2 (n = 5) |
| Compound A-14 | 6.2 ± 0.3 (n = 3) |
| Compound A-16 | 3.2 ± 0.8 (n = 4) |
| Compound A-18 | 4.8 ± 1.1 (n = 2) |
| Compound A-20 | 1.9 (n = 1) |
| Compound A-21 | 2.6 (n = 1) |
| Compound A-22 | 3.3 ± 1.2 (n = 3) |
| Compound A-23 | 6.1 ± 1.1 (n = 3) |
| Compound A-24 | 0.9 ± 0.2 (n = 3) |
| Compound A-29 | 5.5 ± 1.7 (n = 3) |
| Compound A-31 | 5.5 ± 0.2 (n = 3) |
| Compound A-32 | 2.3 ± 0.6 (n = 3) |
| Compound A-34 | 1.1 ± 0.2 (n = 4) |
| Compound A-38 | 7.4 (n = 1) |
| Compound A-39 | 7.9 ± 3.1 (n = 4) |
| Compound A-41 | 1.1 ± 0.4 (n = 3) |
| Compound A-42 | 2.5 ± 0.3 (n = 2) |
| Compound A-43 | 2.9 ± 0.9 (n = 4) |
| Compound A-48 | 2.0 ± 0 (n = 2) |

Example 23: Measurement of Force in an In Vitro Model

The current disclosure relates to compounds that inhibit CIC-1 ion channels and increase muscle excitability and thereby improve muscle function in clinical conditions where muscle activation is failing. Such conditions result in loss of contractile function of skeletal muscle, weakness and excessive fatigue. In this series of experiments the compounds were tested for their ability to restore contractile function of isolated rat muscle when the neuromuscular transmission had been compromised akin to neuromuscular disorders.

Experimentally, soleus muscles from 4-5 wk old rats were isolated with the motor nerve remaining attached. The nerve-muscle preparations were mounted in experimental setups that enabled electrical stimulation of the motor nerve. Stimulation of the motor nerve led to activation of the muscle fibres and ensuing force production that was recorded. The nerve-muscle preparations were also in these experiments incubated in the standard Krebs Ringer (see example 5) and the solution was heated to 30° C. and continuously equilibrated with a mixture of 95% $O_2$ and 5% $CO_2$, pH ~7.4.

Figure 2:
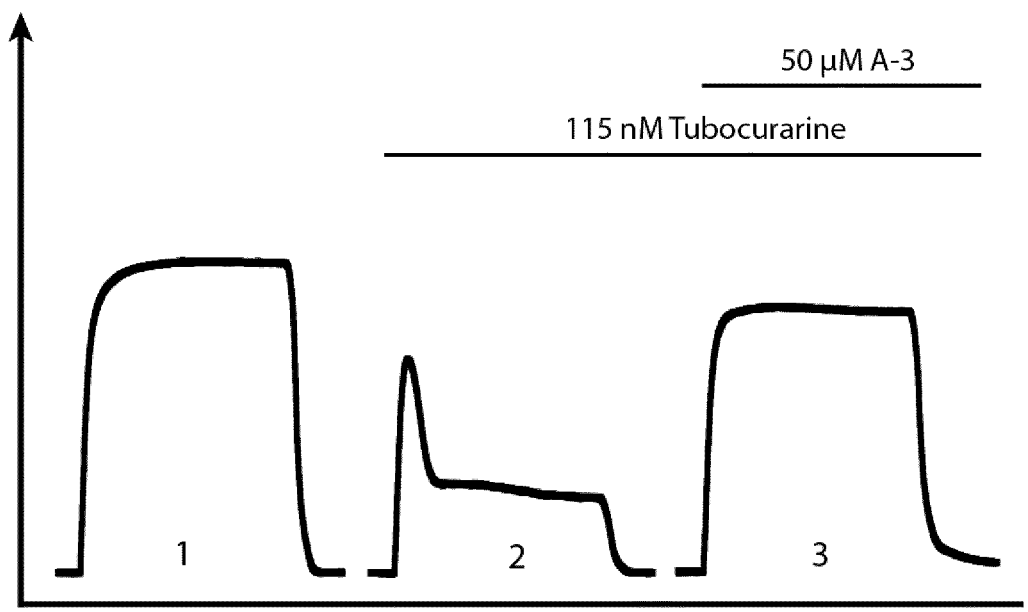
FIG. 2. Panel A shows representative force traces before and after exposure to compound A-3. Force traces from a representative muscle stimulated to contract in 1) control condition before addition of neuromuscular blocking agent, 2) the force response to stimulation after 90 minutes incubation with Tubocurarine. Here the muscle displays severe neuromuscular transmission impediment, and 3) The muscle force response after addition of 50 μM compound A-3. Panel B shows average force (AUC) from 3 muscles relative to their initial force. The traces presented in panel A (1, 2, 3), correspond to the dotted lines in panel B, respectively. Thus, force is lost due to 90 min incubation in tubocurarine and is subsequently recovered when compound A-3 is added.
Figure 2:
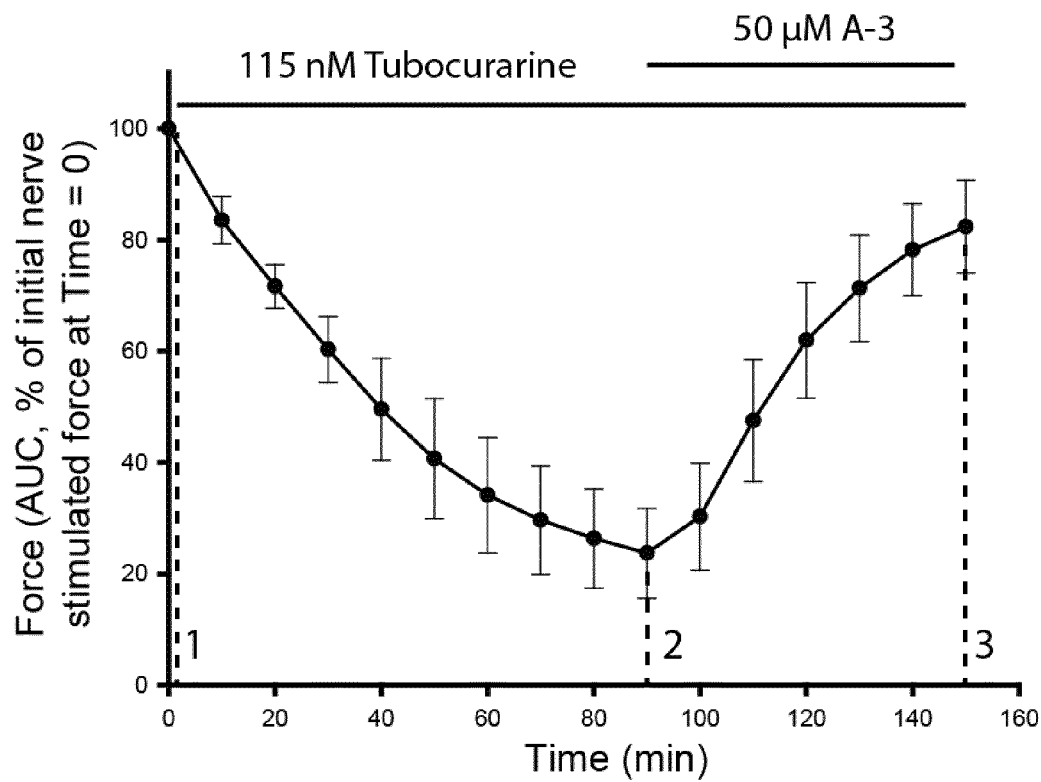

After mounting the nerve-muscle preparation in the experimental setup, the contractile function of the muscle was initially assessed under the control conditions (FIG. 2A). Sub-maximal concentration of tubocurarine (115 nM), an acetylcholine receptors antagonist, was then added to the experimental bath to impose partial inhibition of the ability of the motor nerve to activate the muscle fibres. The experimental condition mimics the failing neuromuscular transmission in a range of neuromuscular disorders. After addition of tubocurarine the contractile force declined over the next 90 mins to 10-50% of the control force. 50 µM of the test compound was then added and the contractile force recovered despite the continued presence of tubocurarine. To quantify the ability of the compound to restore force the percentage of the initial force that was restored was determined after 40 mins of compound exposure (FIG. 2B) and the point increase is reported in Table 3.

TABLE 3

Percentage increase of initial force that was restored

| Compound investigated | Point increase (%) |
|---|---|
| Compound A-3 | 54% |
| Compound A-4 | 34% |
| Compound A-5 | 53% |
| Compound A-6 | 35% |
| Compound A-7 | 42% |
| Compound A-14 | 38% |
| Compound A-17 | 48% |
| Compound A-18 | 31% |
| Compound A-19 | 27% |
| Compound A-20 | 44% |
| Compound A-21 | 44% |
| Compound A-22 | 65% |
| Compound A-23 | 37% |
| Compound A-29 | 46% |
| Compound A-30 | 44% |
| Compound A-31 | 43% |
| Compound A-32 | 41% |
| Compound A-35 | 20% |
| Compound A-39 | 37% |
| Compound A-42 | 30% |
| Compound A-44 | 24% |
| Compound A-47 | 31% |
| Compound A-49 | 24% |
| Compound A-51 | 37% |
| Compound A-54 | 36% |

In conclusion, this example demonstrates that the compounds of the present disclosure are able to increase muscle excitability and thereby improve muscle function in clinical conditions.

Example 24: Measurement of In Situ Muscle Contractile Characteristics

Isometric hindlimb force was measured in 12-week old female Lewis rats in the presence and absence of compound.

Rats were placed under anesthesia with isoflurane (2-4%), intubated and subsequently connected to a micro ventilator (Microvent 1, Hallowell EMC, US). Two stimulation electrodes were inserted through the skin to stimulate the sciatic nerve. A small incision was made proximal to the ankle, to expose the Achilles tendon, which was tied by cotton string, and connected to a force transducer (Fort250, World Precision Instruments) with adjustable position (Vernier control). The Achilles tendon was then cut distal to the attached cotton string. The rat was placed on a heated pad, and to prevent movement artefacts from contraction of the ankle dorsiflexors, the foot was fixated by tape on a footplate.

Muscle contractile properties were assessed by applying an electrical current (under supramaximal voltage conditions) to the nerve and recording the force generated by the muscle. The muscle was stretched until maximal force was obtained, when assessed by 2 Hz stimulation. Isometric force was measured every 30 seconds at 12 Hz (Twitch), 10 pulses, and at every 5 minutes at 80 Hz (Tetanic) for 1 second (80 pulses). This stimulation pattern was employed throughout the experiment, expect in few cases where 80 Hz stimulation was replaced by 12 Hz (10 pulses). Neuromuscular transmission was partially inhibited by constant infusion of Cisatracurium (Nimbex, GlaxoSmithKline) at a concentration of 0.1 mg/kg at an adjustable infusion speed, adjusted individually for each animal to obtain a level of inhibition of ca. 50% of the forced generated at 12 Hz stimulation on the 4$^{th}$ pulse. When the level of neuromuscular inhibition was stable, the test article was injected i.v. at the chosen concentration. The effect of test article was assessed on its ability to increase force generated from the stimulation pattern applied. The effect was assessed in the ability to increase force per se (tetanic, 80 Hz, stimulation), and the ratio between individual twitch peaks (12 Hz stimulation). The effect was monitored for at least 1 hour after injection of test article. In addition, the time from injection of test article to maximal effect on force (both twitch and tetanic) was noted and the time for the effect to disappear (return to baseline), if possible. When appropriate the infusion of neuromuscular blocking agent was ceased, with the stimulation pattern continued, and the return of force to control levels was monitored. Animals were sacrificed by cervical dislocation while still fully sedated.

Compound A-3 was dosed 17.5 mg/kg i.v. resulting in an increase in tetanic force of 64%. Compound A-4 was dosed 21.6 mg/kg i.v. resulting in an increase in tetanic force of 34%. Compound A-5 was dosed 10.5 mg/kg i.v. resulting in an increase in tetanic force of 47%. Compound A-7 was dosed 25.1 mg/kg i.v. resulting in an increase in tetanic force of 64%. Compound A-32 was dosed 11.2 mg/kg i.v. resulting in an increase in tetanic force of 75%. Compound A-31 was dosed 11.4 mg/kg i.v. resulting in an increase in tetanic force of 14%. Compound A-29 was dosed 22.9 mg/kg i.v. resulting in an increase in tetanic force of 76%. Compound A-23 was dosed 18.8 mg/kg i.v. resulting in an increase in tetanic force of 40%. Compound A-22 was dosed 10.4 mg/kg i.v. resulting in an increase in tetanic force of 57%. Compound A-16 was dosed 22.9 mg/kg i.v. resulting in an increase in tetanic force of 46%. Compound A-11 was dosed 17.6 mg/kg i.v. resulting in an increase in tetanic force of 44%. This demonstrates that compounds of the disclosure, such as Compounds A-3, A-4, A-5, A-7, A-32, A-31, A-29, A-23, A-22, A-16 and A-11 can restore force to muscles in vivo which have been partially inhibited by a neuromuscular blocker.

The invention claimed is:

1. A compound of Formula (I):

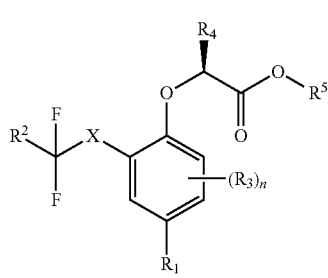

Formula (I)

wherein:
R$^1$ is selected from the group consisting of C$_{1-2}$ alkyl, C$_2$ alkenyl, C$_2$ alkynyl, CN, CF$_3$, NO$_2$, F, Cl, Br, and I;
R$^2$ is selected from the group consisting of C$_{1-5}$ alkyl optionally be substituted with one or more, identical or different, substituents R$^6$, C$_{2-5}$ alkenyl optionally be substituted with one or more, identical or different, substituents R$^6$, C$_{2-5}$ alkynyl optionally be substituted with one or more, identical or different, substituents R$^6$, C$_{3-5}$ cycloalkyl optionally substituted with one or more, identical or different, substituents R$^6$, phenyl optionally substituted with one or more, identical or different, substituents R$^9$, and 5-6 membered aromatic heterocycle optionally substituted with one or more, identical or different, substituents R$^7$;
R$^3$ is selected from the group consisting of deuterium, Cl and F;
R$^4$ is selected from the group consisting of H, deuterium, C$_{1-5}$ alkyl, C$_{2-5}$ alkenyl, C$_{2-5}$ alkynyl, and C$_{3-5}$ cycloalkyl, each of which may be optionally substituted with one or more, identical or different, substituents R$^7$;
R$^5$ is selected from the group consisting of H, C$_{1-5}$ alkyl optionally substituted with one or more, identical or different, substituents R$^8$, C$_{2-5}$ alkenyl optionally substituted with one or more, identical or different, substituents R$^8$, C$_{2-5}$ alkynyl optionally substituted with one or more, identical or different, substituents R$^8$, C$_{3-6}$ cycloalkyl optionally substituted with one or more, identical or different, substituents R$^8$, phenyl optionally substituted with one or more, identical or different, substituents R$^9$, and benzyl optionally substituted with one or more, identical or different, substituents R$^9$;
R$^6$ is independently selected from the group consisting of deuterium, F, —CN, —O—C$_{1-5}$ alkyl, —O—C$_{3-5}$ cycloalkyl, —S—C$_{1-5}$ alkyl, and —S—C$_{3-5}$ cycloalkyl, wherein the —O—C$_{1-5}$ alkyl, —O—C$_{3-5}$ cycloalkyl, —S—C$_{1-5}$ alkyl, and —S—C$_{3-5}$ cycloalkyl may optionally be substituted with one or more, identical or different, substituents R$^8$;
R$^7$ is independently selected from the group consisting deuterium, F, C$_1$, —CN, C$_{3-5}$ cycloalkyl, —O—C$_{1-5}$ alkyl, —O—C$_{3-5}$ cycloalkyl, —S—C$_{1-5}$ alkyl, and —S—C$_{3-5}$ cycloalkyl, wherein the C$_{3-5}$ cycloalkyl, —O—C$_{1-5}$ alkyl, —O—C$_{3-5}$ cycloalkyl, —S—C$_{1-5}$ alkyl, and —S—C$_{3-5}$ cycloalkyl may optionally be substituted with one or more, identical or different, substituents R$^8$;
R$^8$ is independently selected from the group consisting of deuterium and F;
R$^9$ is independently selected from the group consisting of deuterium, methoxy, nitro, cyano, Cl, Br, I, and F;
X is a bond or selected from the group consisting of —O—, —S—, —CH$_2$—, —CHR$^6$—, and —C(R$^6$)$_2$—; and
n is an integer 0, 1, 2, or 3;
or a pharmaceutically acceptable salt, hydrate, polymorph, tautomer, or solvate thereof.

2. The compound according to claim 1, wherein the compound is of Formula (II)

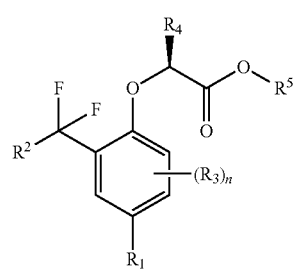

Formula (II)

wherein:
- $R^1$ is selected from the group consisting of $C_{1-2}$ alkyl, $C_2$ alkenyl, $C_2$ alkynyl, CN, $CF_3$, $NO_2$, F, Cl, Br, and I;
- $R^2$ is selected from the group consisting of $C_{1-5}$ alkyl optionally be substituted with one or more, identical or different, substituents $R^6$, $C_{2-5}$ alkenyl optionally be substituted with one or more, identical or different, substituents $R^6$, $C_{2-5}$ alkynyl optionally be substituted with one or more, identical or different, substituents $R^6$, $C_{3-5}$ cycloalkyl optionally substituted with one or more, identical or different, substituents $R^6$, phenyl optionally substituted with one or more, identical or different, substituents $R^9$, and 5-6 membered aromatic heterocycle optionally substituted with one or more, identical or different, substituents $R^7$;
- $R^3$ is selected from the group consisting of deuterium, Cl and F;
- $R^4$ is selected from the group consisting of H, deuterium, $C_{1-5}$ alkyl, $C_{2-5}$ alkenyl, $C_{2-5}$ alkynyl, and $C_{3-5}$ cycloalkyl, each of which may be optionally substituted with one or more, identical or different, substituents $R^7$;
- $R^5$ is selected from the group consisting of H, $C_{1-5}$ alkyl optionally substituted with one or more, identical or different, substituents $R^8$, $C_{2-5}$ alkenyl optionally substituted with one or more, identical or different, substituents $R^8$, $C_{2-5}$ alkynyl optionally substituted with one or more, identical or different, substituents $R^8$, $C_{3-6}$ cycloalkyl optionally substituted with one or more, identical or different, substituents $R^8$, phenyl optionally substituted with one or more, identical or different, substituents $R^9$, and benzyl optionally substituted with one or more, identical or different, substituents $R^9$;
- $R^6$ is independently selected from the group consisting of deuterium, F, —CN, —O—$C_{1-5}$ alkyl, —O—$C_{3-5}$ cycloalkyl, —S—$C_{1-5}$ alkyl, and —S—$C_{3-5}$ cycloalkyl, wherein the —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;
- $R^7$ is independently selected from the group consisting deuterium, F, Cl, —CN, $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl, wherein the $C_{3-5}$ cycloalkyl, —O—$C_{1-5}$ alkyl, —O—$C_{3-5}$ cycloalkyl, —S—$C_{1-5}$ alkyl, and —S—$C_{3-5}$ cycloalkyl may optionally be substituted with one or more, identical or different, substituents $R^8$;
- $R^8$ is independently selected from the group consisting of deuterium and F;
- $R^9$ is independently selected from the group consisting of deuterium, methoxy, nitro, cyano, Cl, Br, I, and F; and
- n is an integer 0, 1, 2, or 3;

or a pharmaceutically acceptable salt, hydrate, polymorph, tautomer, or solvate thereof.

3. The compound according to claim 2, wherein $R^1$ is Cl or Br.

4. The compound according to claim 2, wherein $R_2$ is $C_{1-3}$ alkyl optionally substituted with one or more, identical or different, substituents $R_6$.

5. The compound according to claim 2, wherein $R^3$ is F and n is 1.

6. The compound according to claim 2, wherein $R^4$ is $C_{1-5}$ alkyl optionally substituted with one or more, identical or different, substituents $R^6$.

7. The compound according to claim 2, wherein $R^4$ is $CH_2F$.

8. The compound according to claim 2, wherein $R^4$ is $C_{2-5}$ alkynyl optionally substituted with one or more, identical or different, substituents $R^6$.

9. The compound according to claim 2, wherein $R^5$ is H.

10. The compound according to claim 1, wherein the compound is selected from the group consisting of:
- (2S)-2-[4-bromo-2-(1,1-difluoroethyl) phenoxy]-3-cyclopropylpropanoic acid;
- (2S)-2-[4-bromo-2-(1,1-difluoroethyl) phenoxy]butanoic acid;
- (2S)-2-[4-bromo-2-(1,1-difluoropropyl) phenoxy]propanoic acid;
- (2S)-2-[4-bromo-2-(1,1-difluoroethyl) phenoxy]propanoic acid;
- (2S)-2-[4-chloro-2-(1,1-difluoropropyl) phenoxy]propanoic acid;
- 2-[4-bromo-2-(1,1-difluoropropyl) phenoxy]acetic acid;
- (2S)-2-[4-bromo-2-(1,1-difluoro-2-methylpropyl) phenoxy]propanoic acid;
- (2S)-2-{4-bromo-2-[difluoro (phenyl)methyl] phenoxy}propanoic acid;
- (2S)-2-[4-bromo-2-(1,1-difluoroethyl) phenoxy]-2-cyclopropylacetic acid;
- (2S)-2-[4-bromo-2-(1,1-difluorobutyl) phenoxy]propanoic acid;
- (2R)-2-[4-bromo-2-(1,1-difluoropropyl) phenoxy]-3-fluoropropanoic acid;
- (2S)-2-[4-bromo-2-(cyclopropyldifluoromethyl) phenoxy]propanoic acid;
- (2S)-2-{4-bromo-2-[difluoro (1,3-thiazol-2-yl)methyl] phenoxy}propanoic acid;
- (2S)-2-[4-bromo-2-(1,1-difluoroethyl) phenoxy]pent-4-ynoic acid;
- (2S)-2-[4-bromo-2-(cyclobutyldifluoromethyl) phenoxy] propanoic acid;
- (2R)-2-[4-bromo-2-(1,1-difluoroethyl) phenoxy]-3-fluoropropanoic acid;
- (2R)-2-[4-bromo-2-(1,1-difluoropropyl) phenoxy]-3-chloropropanoic acid;
- (2S)-2-[4-bromo-2-(1,1-difluoropropyl) phenoxy]pent-4-ynoic acid;
- (2S)-2-[4-chloro-2-(1,1-difluoroethyl) phenoxy]pent-4-ynoic acid;
- (2S)-2-[2-(1,1-difluoropropyl)-4-iodophenoxy]propanoic acid;
- (2S)-2-[4-bromo-2-(1,1-difluoropropyl) phenoxy](2-2H) propanoic acid;
- (2R)-2-[4-chloro-2-(1,1-difluoropropyl) phenoxy]-3-fluoropropanoic acid;
- (2S)-2-[2-(1,1-difluoropropyl)-4-ethynylphenoxy]propanoic acid;
- (2S)-2-[4-bromo-2-(1,1-difluoropropyl)-5-fluorophenoxy]propanoic acid;
- (2S)-2-[4-bromo-2-(1,1-difluoropropyl)-6-fluorophenoxy]propanoic acid;
- (2S)-2-[4-cyano-2-(1,1-difluoropropyl) phenoxy]propanoic acid;
- (2R)-2-[4-chloro-2-(1,1-difluoroethyl) phenoxy]-3-fluoropropanoic acid;
- (2S)-2-[4-bromo-2-(1,1-difluoroethyl)-5-fluorophenoxy] propanoic acid;

(2S)-2-[4-bromo-2-(1,1-difluoropropyl) (3,5,6-$^2$H$_3$) phenoxy]propanoic acid;
2-[4-bromo-2-(1,1-difluoropropyl)-5-fluorophenoxy]acetic acid;
(2S)-2-[4-chloro-2-(1,1-difluoropropyl)-5-fluorophenoxy]propanoic acid;
(2S)-2-[2-(1,1-difluoropropyl)-4-(trifluoromethyl) phenoxy]propanoic acid;
(2R)-2-[4-bromo-2-(1,1-difluoropropyl)-5-fluorophenoxy]-3-fluoropropanoic acid;
(2S)-2-[2-(1,1-difluoropropyl)-4-ethenylphenoxy]propanoic acid;
2-[4-bromo-2-(1,1-difluoroethyl)-5-fluorophenoxy]acetic acid;
(2S)-2-[2-(1,1-difluoropropyl)-4-methylphenoxy]propanoic acid;
2-[4-bromo-2-(1,1-difluoro-2-methylpropyl) phenoxy]acetic acid;
2-[4-chloro-2-(1,1-difluoropropyl)-5-fluorophenoxy]acetic acid;
(2S)-2-[2-(1,1-difluoroethyl)-4-ethynylphenoxy]propanoic acid;
(2R)-2-[4-chloro-2-(1,1-difluoropropyl)-5-fluorophenoxy]-3-fluoropropanoic acid;
(2S)-2-[4,5-dichloro-2-(1,1-difluoropropyl) phenoxy]propanoic acid;
(2R)-2-[4-bromo-2-(1,1-difluoroethyl)-5-fluorophenoxy]-3-fluoropropanoic acid;
(2R)-2-[4,5-dichloro-2-(1,1-difluoroethyl) phenoxy]-3-fluoropropanoic acid;
(2S)-2-[4-bromo-2-(1,1-difluoroethyl) phenoxy]-4-fluorobutanoic acid;
(2S)-2-[4-bromo-2-(1,1-difluoro-2-methylpropyl) phenoxy]butanoic acid;
(2S)-2-[2-(1,1-difluoropropyl)-4-ethenyl-5-fluorophenoxy]propanoic acid;
(2S)-2-[4-bromo-2-(1,1-difluoropropyl)-5-fluorophenoxy]butanoic acid;
(2S)-2-[4-chloro-2-(1,1-difluoropropyl)-5-fluorophenoxy]butanoic acid;
(2R)-2-[5-chloro-2-(1,1-difluoropropyl)-4-fluorophenoxy]-3-fluoropropanoic acid;
(2S)-2-[2-(1,1-difluoropropyl)-4-nitrophenoxy]propanoic acid;
(2S)-2-[5-chloro-2-(1,1-difluoropropyl)-4-fluorophenoxy]propanoic acid;
(2S)-2-[4-bromo-2-(1,1-difluoropropyl) phenoxy]-4-methoxybutanoic acid;
(2R)-2-[2-(1,1-difluoropropyl)-4,5-difluorophenoxy]-3-fluoropropanoic acid;
(2S)-2-[2-(1,1-difluoropropyl)-4,5-difluorophenoxy]propanoic acid; and
(2S)-2-[4-bromo-2-(1,1-difluoro-3-methoxypropyl) phenoxy]propanoic acid.

11. The compound according to claim 2, wherein the compound is an inhibitor of the ClC-1 ion channel.

12. A composition comprising the compound according to claim 1.

13. A method of treating a patient comprising administering to a patient a therapeutically effective amount of the compound according to claim 2,
for use in the treatment of symptoms of an indication selected from the group consisting of myasthenia gravis, Lambert-Eaton Syndrome, critical illness myopathy, amyotrophic lateral sclerosis (ALS), spinal muscular atrophy (SMA), critical illness myopathy (CIM), reversal diabetic polyneuropathy, Guillain-Barre syndrome, poliomyelitis, post-polio syndrome, chronic fatigue syndrome, critical illness polyneuropathy, periodic paralysis, sarcopenia, hypokalemic periodic paralysis, hyperkalemic periodic paralysis, myotubular myopathy and Duchenne muscular dystrophy.

14. A method of reversing and/or ameliorating a neuromuscular blockade in a patient comprising administering to a patient a therapeutically effective amount of the compound according to claim 2.

15. A method of claim 13 wherein in Formula (I), $R^3$ is F and n is 1.

16. A method of claim 14 wherein in Formula (II), $R^3$ is F and n is 1.

17. The method of claim 13 wherein in Formula (I), $R^1$ is $C_1$ or Br.

18. The method of claim 13 wherein in Formula (I), $R^2$ is $C_{1-3}$ alkyl optionally substituted with one or more, identical or different, substituents $R^6$.

19. The method of claim 14 wherein in Formula (II), $R^1$ is Cl or Br.

* * * * *